United States Patent
Winssinger et al.

(10) Patent No.: US 9,051,302 B2
(45) Date of Patent: *Jun. 9, 2015

(54) SYNTHESIS OF RESORCYLIC ACID LACTONES USEFUL AS THERAPEUTIC AGENTS

(75) Inventors: Nicolas Winssinger, Strasbourg (FR); Sofia Barluenga, Strasbourg (FR); Martin Karplus, Cambridge, MA (US)

(73) Assignee: UNIVERSITE DE STRASBOURG, Strasbourg (FR)

( * ) Notice: Subject to any disclaimer, the term of this patent is extended or adjusted under 35 U.S.C. 154(b) by 1016 days.

This patent is subject to a terminal disclaimer.

(21) Appl. No.: 12/863,123

(22) PCT Filed: Jan. 15, 2009

(86) PCT No.: PCT/US2009/031149
§ 371 (c)(1),
(2), (4) Date: May 23, 2011

(87) PCT Pub. No.: WO2009/091921
PCT Pub. Date: Jul. 23, 2009

(65) Prior Publication Data
US 2011/0217335 A1    Sep. 8, 2011

Related U.S. Application Data

(60) Provisional application No. 61/011,163, filed on Jan. 15, 2008.

(51) Int. Cl.
| | |
|---|---|
| C07D 211/14 | (2006.01) |
| C07D 225/06 | (2006.01) |
| C07D 313/00 | (2006.01) |
| C07D 405/12 | (2006.01) |
| C07D 405/14 | (2006.01) |
| A61K 31/435 | (2006.01) |
| A61K 31/4453 | (2006.01) |
| A61K 31/335 | (2006.01) |

(52) U.S. Cl.
CPC ............ C07D 405/12 (2013.01); A61K 31/435 (2013.01); C07D 211/14 (2013.01); C07D 225/06 (2013.01); A61K 31/4453 (2013.01); A61K 31/335 (2013.01); C07D 313/00 (2013.01); C07D 405/14 (2013.01)

(58) Field of Classification Search
CPC .. C07D 311/14; C07D 225/06; C07D 313/00; A61K 31/335; A61K 31/435; A61K 31/4453
See application file for complete search history.

(56) References Cited

U.S. PATENT DOCUMENTS

| | | | |
|---|---|---|---|
| 5,977,165 | A | 11/1999 | Agatsuma et al. |
| 6,239,168 | B1 * | 5/2001 | Ino et al. ................. 514/450 |
| 7,115,651 | B2 | 10/2006 | Danishefsky et al. |

FOREIGN PATENT DOCUMENTS

EP    1 813 270    8/2007
WO    WO 2008021213 A1 *  2/2008

OTHER PUBLICATIONS

International Search Report for International Application No. PCT/US2009/031149, mailed on Feb. 26, 2009.
Written Opinion for International Application No. PCT/US2009/031149, mailed on Feb. 26, 2009.
International Preliminary Report on Patentability for International Application No. PCT/US2009/031149, dated Feb. 19, 2009.
Supplementary European Search Report for European Application No. EP 09702521, dated Sep. 28, 2011.
Barluenga et al., "Divergent synthesis of a pochonin library targeting HSP90 and in vivo efficacy of an identified inhibitor," *Angewandte Chemie International Ed Engl.*, 47(23):4432-4435 (2008).
Moulin et al., "Design, synthesis, and biological evaluation of HSP90 inhibitors based on conformational analysis of radicicol and its analogues," *J Am Chem Soc*, 127(19):6999-7004 (2005).
Office Action for Australian Application No. 2009206097, dated Jul. 1, 2013.
Office Action for Chinese Application No. 200980109146.7, dated Dec. 5, 2012.
Office Action for Chinese Application No. 200980109146.7, dated Oct. 28, 2013.
Office Action for European Application No. 09702521.7, mailed Mar. 12, 2013.
Office Action for Japanese Application No. 2010-543254, mailed Aug. 27, 2013.
Prolsy, N. et al., "Inhibition of Hsp90 with synthetic macrolactones: synthesis and structural and biological evaluation of ring and conformational analogs of radicicol," *Chemistry & Biology*, 13(11):1203-1215 (2006).
Moulin, E. et al., "Diversity-oriented synthesis of pochonins and biological evaluation against a panel of kinases," *Chemisty A European Journal*, 12(34):8819-8834 (2006).
Soga, S. et al., "KF25706, a novel oxime derivative of radicicol, exhibits in vivo antitumor activity via selective depletion of Hsp90 binding signaling molecules," *Cancer Research*, 59:2931-2938 (1999).
Office Action for Russian Application No. 2010133979, dated Jun. 6, 2013.
Office Action for Russian Application No. 2010133979, dated Nov. 16, 2012.

* cited by examiner

*Primary Examiner* — Sarah Pihonak
(74) *Attorney, Agent, or Firm* — Cooley LLP

(57) ABSTRACT

Disclosed are macrocyclic compounds of formulae I, I', II, II', III, III', IV, and V, which are analogs of the pochonin resorcylic acid lactones, pharmaceutical compositions comprising the compounds, and methods and uses comprising the compounds for the treatment of diseases mediated by kinases and Heat Shock Protein 90 HSP90.

2 Claims, 4 Drawing Sheets

Figure 1

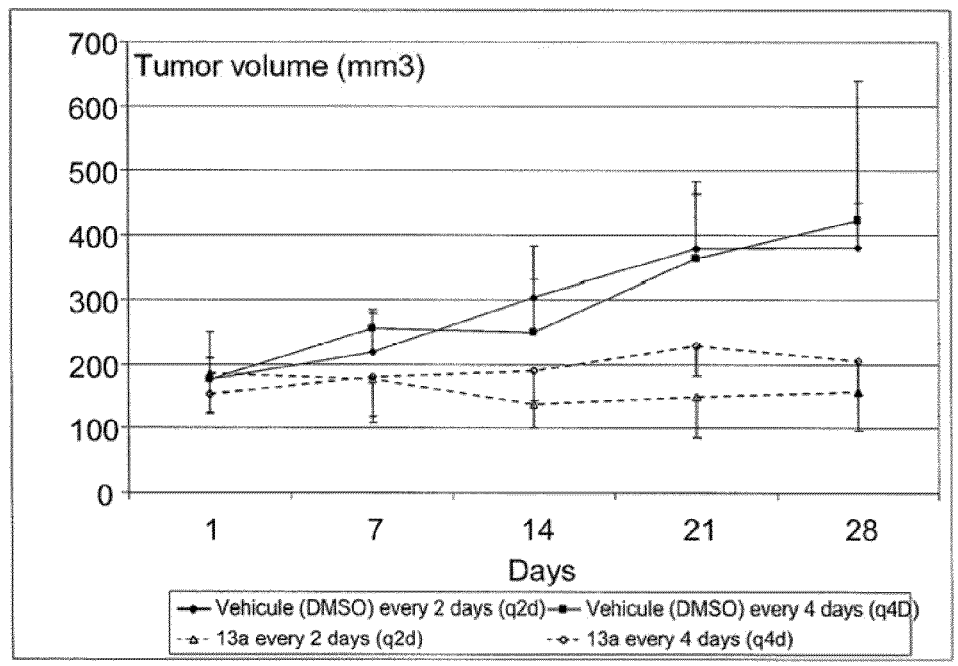

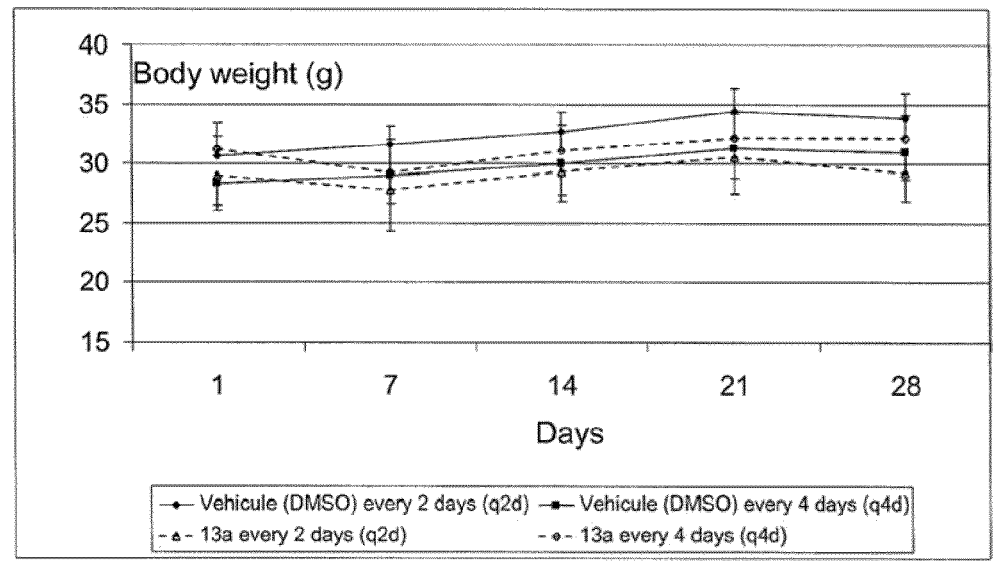

Tumor volume (BT474) and animal weight following treatment with compound 13a or control vehicle. Each point represents the mean of measurements from 5 (for vehicle) or 6 (for 13a) animals. The experiment was carried out for 28 days and tumor volumes were determined weekly by caliper measurement. Student's t-test was used to determine the statistical analysis of the difference between tumor volumes of vehicle-treated and drug-treated animals. Individual body weights were also determined weekly. Statistical significance was achieved (comparing tumor volumes in vehicle-treated and drug-treated animals) at day 21 for the q4d schedule ($p = 0.0497$). In comparison, on the q2d schedule increasing statistical significance was achieved on days 14, 21, and 28, when comparing tumor volume of vehicle-treated and drug-treated animals ($p = 0.012$, $p = 0.007$, and $p = 0.0002$, respectively).

Figure 2

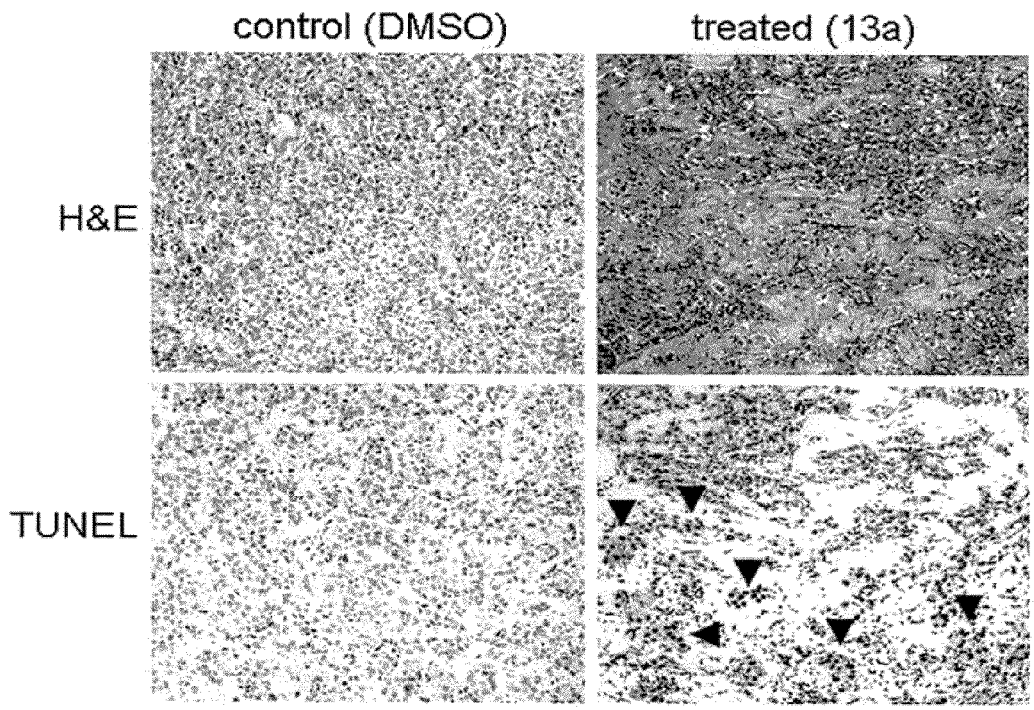

Tumor histology and apoptosis in mock- and drug-treated animals. Top panels represent hematoxylin & eosin (H & E) stained paraffin sections. Nuclei appear blue in color. The dark blue condensed nuclei in drug-treated tumors (right) are consistent with apoptotic cells. A dramatic loss of celularity in drug-treated tumors can also be clearly seen. Bottom panels represent TUNEL (terminal deoxynucleotidyl transferase-mediated dUTP-biotin nick end labeling)-stained paraffin sections. The high preponderance of reddish-pink nuclei (positive for TUNEL staining) in the drug-treated tumors reflects DNA fragmentation which is characteristic of apoptosis. Blue arrowheads point to characteristic TUNEL positive nuclei.

Wire-frame representation of crystal structure of compound 13a

Wire-frame representation of crystal structure of compound 13b

Wire-frame representation of the Z-isomer of compound 13c

SYNTHESIS OF RESORCYLIC ACID LACTONES USEFUL AS THERAPEUTIC AGENTS

CROSS REFERENCE TO RELATED APPLICATIONS

This application is a U.S. National Stage application of International Application number PCT/US2009/031149, filed on Jan. 15, 2009 and Entitled "SYNTHESIS OF REDORCYLIC ACID LACTONES USEFUL AS THERAPEUTIC AGENTS", which claims priority to U.S. provisional application Ser. No. 61/011,163, filed Jan. 15, 2008, each of which is incorporated by reference herein in its entirety for all purpose.

FIELD OF THE INVENTION

The present invention is directed to novel derivatives, analogs and intermediates of the natural products radicicol and the pochonins, and to their syntheses. The present invention is further directed to use of these compounds as inhibitors of kinases and of the enzyme family known as heat shock protein 90 (HSP90).

BACKGROUND OF THE INVENTION

The invention claimed herein was made by or behalf of Universite de Srasbourg, Le Center national De La Recherche Scientifique, and NexGenix Pharmaceuticals Inc., who are parties to a joint research agreement signed on Jul. 1, 2007 and related to marcrolcyclic compounds, such as radicicol and its derivatives, which are useful as kinase and HSP90 inhibitors.

In the mid-1950's, it was discovered that phosphorylation can reversibly alter the function of enzymes by means of protein kinases which catalyze phosphorylation, or by protein phosphatases which are involved in the dephosphorylation step. These reactions play an essential role in regulating many cellular processes, especially signaling transduction pathways. In the late 1970's, the Rous sarcoma virus (v-Src)'s transforming factor was discovered to be a protein kinase, and also tumor-promoting phorbol esters were found to be potent activators of protein kinase C, revealing the first known connection between disease and abnormal protein phosphorylation. Since then transduction mechanistic defects have been found to cause numerous oncogenic processes and to have a role in diabetes, inflammatory disorders, and cardiovascular diseases. (T. Hunter, *Cell,* 100:113-127 (2000); P. Cohen, *Nat. Rev. Drug Discov.,* 1:309 (2002)). Thus selective kinase and phosphatase inhibitors have emerged as important drug targets, and inhibition of kinase phosphorylation activity is one of the most promising strategies for chemotherapy.

Macrocyclic resorcylic acid lactones such as radicicol and the related pochonins, are a structurally related group of secondary metabolites isolated from cultures of the clavicipitaceous hyphomycete *Pochonia* genus, such as *Pochonia chlamydosporia* var. catenulate strain P0297. See, e.g., V. Hellwig et al., *J. Natural Prod.,* 66(6):829-837 (2003). These compounds and analogs or derivatives of the compounds have been evaluated as kinase inhibitors or inhibitors of HSP90. Halohydrin and oxime derivatives of radicicol were prepared and evaluated for their v-src tyrosine kinase inhibitory, antiproliferative, and antitumor in vitro activity (T. Agatsuma et al., *Bioorg. & Med. Chem.,* 10(11):3445-3454 (2002).

Like kinases, heat shock proteins (HSPs) interact with ATP and are important targets for controlling disease, however they have a different mechanistic effect. Immediately after exposure to a stress such as heat, hypoxia or acidosis, cells in most tissues rapidly escalate production rate of the HSPs. It is now believed that heat HSPs are molecular chaperones, i.e., they prevent improper associations and assist in the correct folding of other cellular proteins collectively termed clients and substrates. HSP's are also found in association with tumors and other pathophysiological conditions. In fact, chaperone proteins facilitate the survival of tumor cells in stressful environments by facilitating tolerance of alterations inside the cell. HSPs are ubiquitous, highly conserved among the species, and usually classified by molecular weight to the following major families: HSP100, HSP90, HSP70, HSP60 and small HSPs. These families have structural and functional differences, but work cooperatively at different stages of protein folding. HSP90 has attracted particular attention due to its association with many types of signaling molecules such as v-Src and Raf that play a critical role in malignant transformation and metastasis development. Thus, HSP90 inhibitors are desired for designing chemotherapies, and also for elucidating the interplay in complex signaling networks.

Heat Shock Protein 90's (Hsp90s) are ubiquitous chaperone proteins that maintain the proper conformation of many "client" proteins (see Kamal et. al. *Trends Mol. Med.* 2004, 10, 283-290; Dymock et. al. *Expert Opin. Ther. Patents* 2004, 14, 837-847; Isaacs et. al. *Cancer Cell,* 2003, 3, 213; Maloney et. al. *Expert Opin. Biol. Ther.* 2002, 2, 3-24 and Richter et. al. *J. Cell. Physiol.* 2001, 188, 281-290), and are involved in folding, activation and assembly of a wide range of proteins, including key proteins involved in signal transduction, cell cycle control and transcriptional regulation. Researchers have reported that HSP90 chaperone proteins are associated with important signaling proteins, such as steroid hormone receptors and protein kinases, including, e.g., Raf-1, EGFR, v-Src family kinases, Cdk4, and ErbB-2 (Buchner, *TIBS,* 1999, 24, 136-141; Stepanova et. al., *Genes Dev.* 1996, 10, 1491-502; Dai et. al., *J. Biol. Chem.* 1996, 271, 22030-4). Studies further indicate that certain co-chaperones, e.g., Hsp70, p60/Hop/Sti1, Hip, Bag1, HSP40/Hdj2/Hsj1, immunophilins, p23, and p50, may assist HSP90 in its function (see for example Caplan, *Trends in Cell Biol.,* 1999, 9, 262-268). Inhibition of Hsp90 causes these client proteins to adopt aberrant conformations, and these abnormally folded proteins are rapidly eliminated by the cell via ubiquitinylation and proteasome degradation. Interestingly, the list of Hsp90 client proteins includes a series of notorious oncogenes. Four of them are clinically validated cancer targets: HER-2/neu (Herceptin® (trastuzumab)), Bcr-Abl (Gleevec® (imatinib mesylate)), the estrogen receptor (tamoxifen), and the androgen receptor (Casodex® (bicalutamide)), while the others play a critical role in the development of cancer. Some of the most sensitive Hsp90 clients are involved in growth signaling (Raf-1, Akt, cdk4, Src, Bcr-Abl, etc). In contrast, few tumor suppressor genes, if any, seem to be clients of Hsp90 (for lists of client proteins see Pratt et. al. *Exp. Biol. Med.* 2003, 228, 111-133; Workman et. al. *Cancer Lett.* 2004, 206, 149-157 and Zhang et. al. *J. Mol. Med.* 2004, 82, 488-499), and consequently, inhibition of Hsp90 has an overall anti-proliferative effect. In addition, some client proteins are involved in other fundamental processes of tumorigenesis, namely apoptosis evasion (e.g. Apaf-1, RIP, Akt), immortality (e.g. hTert), angiogenesis (e.g. VEGFR, Flt-3, FAK, HIF-1), and metastasis (c-Met).

The numerous client proteins of HSP90 play a crucial role in growth control, cell survival and development processes, and those clients are known to include receptor tyrosine kinases, serine/threonine kinases, steroid hormone receptors, transcription factors and telomerase.

In addition to anti-cancer and antitumorgenic activity, HSP90 inhibitors have also been implicated in a wide variety of other utilities, including use as anti-inflammation agents, anti-infectious disease agents, agents for treating autoimmunity, agents for treating ischemia, and agents useful in treating neurodegenerative diseases and in promoting nerve regeneration (see M. Waza et al, *Nature Med.* 11:1088 (2005); Rosen et al., WO 02/09696; PCT/US01/23640; Degranco et al., WO 99/51223; PCT/US99/07242; Gold, U.S. Pat. No. 6,210,974 B1). There are reports in the literature that fibrogenetic disorders including but not limited to scleroderma, polymyositis, systemic lupus, rheumatoid arthritis, liver cirrhosis, keloid formation, interstitial nephritis, and pulmonary fibrosis may be treatable. (Strehlow, WO 02/02123; PCT/US01/20578).

Some resorcylic acid lactones have been found to inhibit HSP90, thus natural products radicicol and geldanamycin (P. Delmotte and J. Delmotte-Plaquee, *Nature* (London), 171: 344 (1953); and C. DeBoer et al., *J Antibiot* (Tokyo), 23:442 (1970), respectively) were shown to suppress the transformed phenotype of cell expressing activated Src (H. J. Kwon et al., *Cancer Research,* 52:6926 (1992); Y. Uehara et al., *Virology,* 164:294 (1988)). Related compounds such as herbimycin have been reported to have similar effects (S. Omura et al., *J Antibiot* (Tokyo), 32:255 (1979).

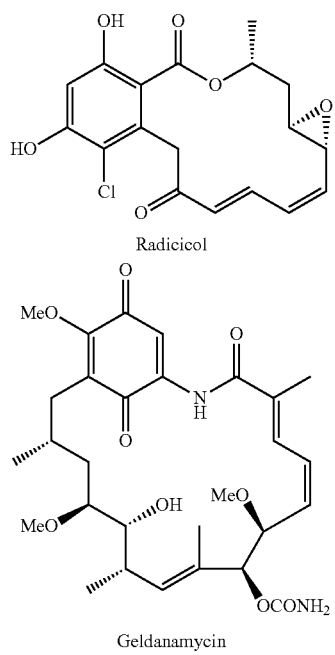

Other resorcylic acid lactones (RALs) studied in this respect include 17-allylamino-17-demethoxygeldanamycin (17AAG) (D. B. Solit et al., *Clin. Cancer Res.,* 8:986 (2002); L. R. Kelland et al., *J. Natl. Cancer Inst.,* 91:1940 (1999)); 17DMAG (J. L. Eiseman et al., *Cancer Chemother. Pharmacol.,* 55:21-32 (2005)); IPI-504 (J. Ge et al., *J. Med. Chem.,* 49:4606 (2006); oxime derivatives such as KF25706 (S. Soga, et al., *Cancer Res.,* 59:2931 (1999)) and KF55823 (S. Soga et al., *Cancer Chemotherapy and Pharmacology,* 48:435 (2001)); and Danishefsky et al.'s cycloproparadicicol (A. Rivkin et al., *Ibid.,* 44:2838 (2005)). Structurally related variants include chimeric inhibitors having radicicol's car- boxyresorcinol and the geldanamycin's benzoquinone (R. C. Clevenger and B. S. Blagg, *Org. Lett.,* 6:4459 (2004); G. Shen and B. S. Blagg, *Ibid.* 7:2157 (2004); G. Shen et al., *J. Org. Chem.,* 71:7618 (2006)).

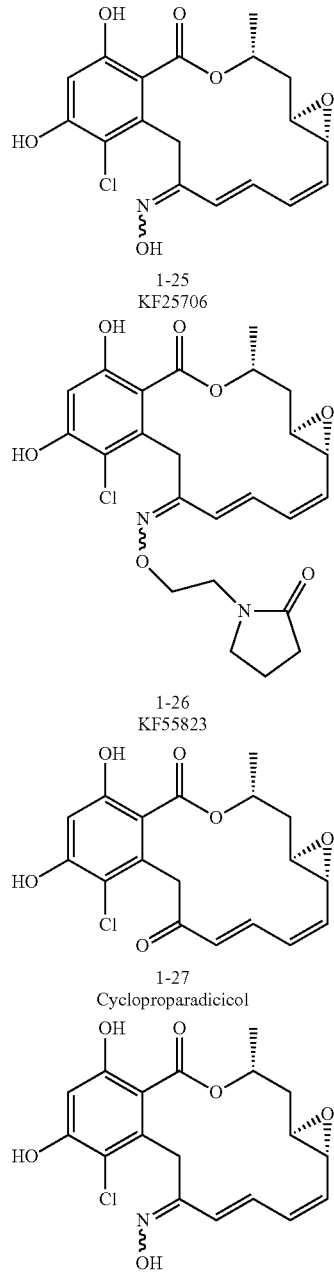

Radicicol-Based HSP90 Inhibitors

Considerable interest in radicicol's medicinal applications has followed the initial findings. (See U.S. Pat. No. 6,946, 456; and U.S. Patent Application Publication Nos. 2003-0211469, 2004-0102458, 2005-0074457, 2005-0261263, 2005-0267087, 2006-0073151, 2006-0251574, 2006-0269618, 2007-0004674, and 2007-0010432).

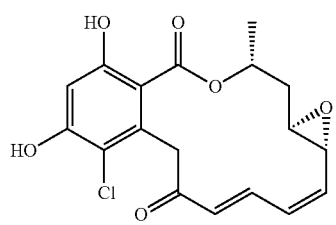

radicicol
HSP-90 inhibitor (20 nM)
cocrystal structure

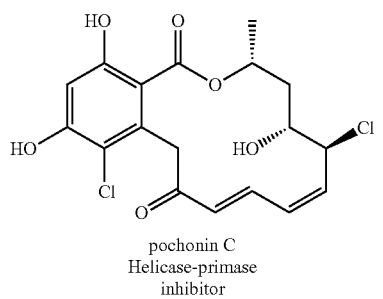

pochonin C
Helicase-primase
inhibitor

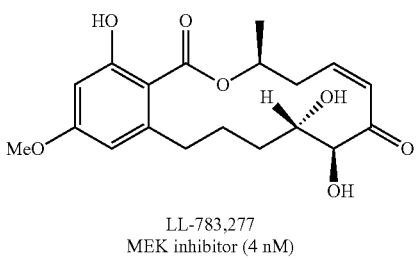

LL-783,277
MEK inhibitor (4 nM)

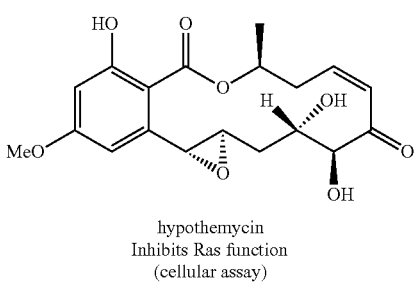

hypothemycin
Inhibits Ras function
(cellular assay)

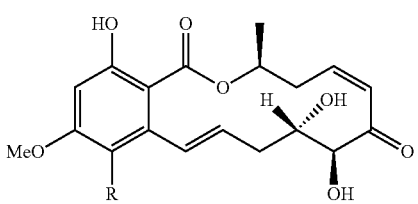

LL-Z1640-2: R = H;
TAK-1 inhibitor (8.1 nM)
F87-2509.04: R = OMe;
Promotes degradation of
ARE-containing genes
(cellular assay)

-continued

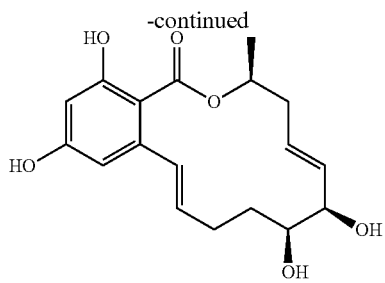

aigialomycin D
CDK1/cyclin B (5.7 mM)
CDK5/p25 (5.8 mM)

Strikingly, some resorcylic macrolides that are close analogs of radicicol are known to inhibit kinases but not HSP90. Indeed, LL-Z1640-2 was found to be a potent and selective inhibitor of TAK1 kinase for which radicicol and other resorcylides were not active. (J. Ninomiya-Tsuji et al., *J. Biol. Chem.*, 278:18485 (2003); P. Rawlins et al., *Int. J. Immunopharma.*, 21:799 (1999); K. Takehana et al., *Biochem. Biophys. Res. Comm.*, 257:19 (1999); A. Zhao et al., *J. Antibiotics*, 52:1086 (1999)). Closely related LL-783,227, where one of the olefins has been reduced, is a potent inhibitor of MEK kinase. (A. Zhao et al., *J. Antibiotics* 52:1086 (1999)). Compound F87-2509.04 was found to induce degradation of mRNA containing AU-rich elements (ARE) (T. Kastelic et al., *Cytokine*, 8:751 (1996)) and hypothemycin was found to inhibit the Ras-mediated cellular signaling. (H. Tanaka et al., *Jap. J. Cancer Res.*, 90:1139 (1999)). It has been shown that aigialomycin D is a CDK inhibitor. (S. Barluenga et al., *Angew. Chem., Int. Ed.*, 46(24):3951 (2006)).

Other close analogs of radicicol do inhibit HSP90. Pochonin D is a potent inhibitor of HSP90. (E. Moulin et al., *J. Am. Chem. Soc.*, 127(19):6999 (2005)). And pochonin A has been reported to be a 90 nM inhibitor of HSP90. Pochonin C was found to be an inhibitor of herpes' helicase-primase, which is an ATPase rather than a kinase. (V. Hellwig et al., *J. Nat. Prod.*, 66:829 (2003)). Although radicicol and pochonin C are structurally very similar, they have very different conformations in solution, and different biological activities. (S. Barluenga et al., *Chem. Eur. J.*, 11:4935 (2005). Thus it appears the "floppiness" of the macrocyclic may play an essential role in inhibitory differences among resorcylic acid macrolides, and in any case makes those effects difficult to predict by theoretical methods.

Some resorcylic acid macrolides had been known as kinase or phosphatase inhibitors (U.S. Pat. Nos. 5,674,892; 5,728,726; 5,731,343; and 5,795,910), or to inhibit other enzymes (U.S. Pat. No. 5,710,174 inhibiting FXIIIa catalysis of fibrin cross-linking). Resorcylic acid macrolides were also employed for other medical indications (U.S. Pat. Nos. 3,453,367; 3,965,275; 4,035,504; 4,670,249; 4,778,821; 4,902,711; and 6,635,671).

Radicicol and the pochonins are natural products; intermediates for synthesizing some of their analogues of them may be obtained by fermentation, however relying only upon those natural products or their fermentation derivatives severely limits the range of compounds. Thus a number of novel resorcylic acid macrolides have been synthesized. Many of these are zearalane and related compounds in which the macrocyclic ring contains no carbon-carbon double bond other than between carbons of the phenyl ring. (U.S. Pat. Nos. 3,373,038; 3,586,701; 3,621,036; 3,631,179; 3,687,982; 3,704,249; 3,751,431; 3,764,614; 3,810,918; 3,836,544;

3,852,307; 3,860,616; 3,901,921; 3,901,922; 3,903,115; 3,957,825; 4,042,602; 4,751,239; 4,849,447; and 2005-0256183). Syntheses have also been reported for resorcylic acid macrolides characterized by one double bond between ring carbons outside the phenyl ring. (U.S. Pat. Nos. 3,196, 019; 3,551,454; 3,758,511; 3,887,583; 3,925,423; 3,954,805; and 4,088,658). Most of those are 14-member macrocycles, but syntheses have also been reported for the 12-member macrocycle analogs. (U.S. Pat. Ser. Nos. 5,710,174; 6,617, 348; and 2004-0063778. and PCT publication no. WO 02/48135)

Syntheses have also been reported for radicicol-related compounds having two non-aromatic double bonds and either a halide or a 1,2-oxo group (i.e., an epoxide) on the macrocyclic ring. (U.S. Pat. Nos. 4,228,079; 5,597,846; 5,650,430; 5,977,165; 7,115,651; and Japanese patent document nos. JP 6-279279A, JP 6-298764A, JP 9-202781A, JP 10-265381A2; and JP 2000-236984). Syntheses of oximes of radicicol-related compounds are disclosed in U.S. Pat. Nos. 5,977,165; 6,239,168; 6,316,491; 6,635,662; 2001-0027208; 2004-0053990; Japanese patent document no. JP 2003-113183A2; and PCT publication no. WO 99/55689 Synthesis of cyclopropa-analogs of radicicol is disclosed in U.S. Pat. No. 7,115,651 and PCT Publication No. WO 05/061481. Syntheses of some other resorcylic acid macrolide analogs are disclosed in U.S. patent publication no. 2006-0247448 and in PCT publication no. WO 02/48135. Radicicol as well as Pochonins A and C have also been synthesized. (S. Barluenga et al., *Angew. Chemie*, 43(26):3467-3470 (2004); S. Barluenga et al., *Chemistry—A European Journal*, 11(17): 4935-4952 (Aug. 19, 2005); E. Moulin et al., et al., *Organic Letters*, 7(25):5637-5639 (Dec. 8, 2005).

U.S. Pat. No. 7,115,651 to Danishefsky et al., which is incorporated by reference herein in its entirety, describes derivatives of radicicol, including cyclopropyl analogs; and the use of these compounds as therapeutic agents.

International Publication No. WO 2008/021213 to Winssinger et al., which is incorporated by reference herein in its entirety, describes certain analogs and derivatives of radicicol and pochonins useful as inhibitors of HSP90, including pharmaceutical compositions comprising the compounds and methods for the treatment of various diseases mediated by HSP90.

International Publication No. WO 2008/150302 to Nexgenix Pharmaceuticals, which is incorporated by reference herein in its entirety, describes uses and methods for the treatment of neurofibromatosis with analogs and derivatives of radicicol and pochonins.

Despite the progress described above, chemical biologists continue to suffer from a limited ability to knock out specific kinase activity in order to deconvolute the role of specific kinases within complex signaling networks. Small molecules that can permeate cells have promise for solving this problem. And it has become increasingly apparent that the biological function of kinases is often regulated by their conformation, which is in turn dictated by their phosphorylation level and by intra- and inter-molecular associations. Small molecule inhibitors also have the potential to discriminate between different conformations of a given kinase, thus small molecules offer a means to dissect the respective functions of those conformation. Unfortunately the portfolio of known kinase inhibitors cannot yet support the full range of work to be done in parsing the roles of the various members of the kinome. This is not a merely academic pursuit, because the rationality of drug design will continue to suffer until kinase mechanisms and their selectivity is understood.

Thus there is an ongoing need for kinase inhibitors and HSP90 inhibitors that have improved potency and selectivity. Moreover, the design and synthesis of such inhibitors and of targeted libraries of inhibitors remains challenging, thus there is an ongoing need for improved synthetic methods.

SUMMARY OF THE INVENTION

Novel analogs of the pochonin macrolides of formulae I, I', II, II', III, III', IV and V, tautomers thereof, pharmaceutically acceptable salts, solvates, esters or prodrugs thereof, and pharmaceutical compositions comprising the compounds for the treatment of kinase-mediated or HSP90-mediated disorders are provided. Also presented are methods for the treatment of kinase-mediated or HSP90-mediated disorders using the compounds. In another embodiment, the invention provides the use of the compounds of formulae I, I', II, II', III, III', IV and V, in the treatment of a kinase-mediated or HSP90-mediated disorder or in the manufacture of a medicament for the treatment of a kinase-mediated or HSP90-mediated disorder in a patient. The compounds of the invention are active as kinase inhibitors and inhibitors of HSP90. In addition, improved processes for the preparation of the compounds are provided.

In one embodiment, the invention provides a compound of formula I or I', or a tautomer thereof, or a pharmaceutically acceptable salt, solvate, ester or prodrug thereof:
wherein:

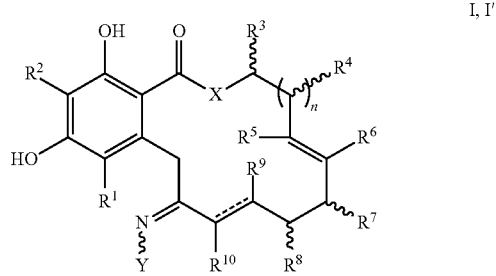

I, I'

X is O, S or NR;

Y is —OR, —O—$(CH_2)_m$COOR, —O—$(CH_2)_m$CON$(R)_2$, —N$(R)_2$, —N(R)SOR or —N(R)SO$_2$R, wherein the groups bound to the nitrogen atom may be in Z- or E-configuration;

$R^1$ and $R^2$ are independently hydrogen, halogen, OR, N$(R)_2$, SR, azido, nitro, cyano, aliphatic, aryl, alkylaryl, arylalkyl, heterocyclyl, heteroaryl, —S(O)R, —S(O)$_2$R, —SO$_2$N$(R)_2$, —N(R)SO$_2$R, —N(CO)R, —N(CO)N$(R)_2$, —N(CO)OR, —O(CO)R, —(CO)R, —(CO)OR, —(CO)N$(R)_2$, —O(CO)OR, or —O(CO)N$(R)_2$;

$R^3$, $R^4$, $R^5$, $R^6$, $R^7$, $R^8$, $R^9$ and $R^{10}$ are independently hydrogen, halogen, azido, nitro, cyano, aliphatic, alkylaryl, aralkyl, aryl, heteroalkyl, alkylheteroaryl, heterocyclyl, heteroaryl, OR, N$(R)_2$, SR, —O$(CH_2)_m$N(R)C(O)$(CH_2)_p$R, —O$(CH_2)_m$OC(O)$(CH_2)_p$R, —O$(CH_2)_m$C(O)$(CH_2)_p$N$(R)_2$, —O$(CH_2)_m$C(O)$(CH_2)_p$OR, —O$(CH_2)_m$N(R)C(O)$(CH_2)_p$OR, —O$(CH_2)_m$N(R)C(O)$(CH_2)_p$N$(R)_2$, —O$(CH_2)_m$OC(O)$(CH_2)_p$OR, —O$(CH_2)_m$OC(O)$(CH_2)_p$N$(R)_2$, —NR$(CH_2)_m$N(R)C(O)$(CH_2)_p$R, —NR$(CH_2)_m$OC(O)$(CH_2)_p$R, —NR$(CH_2)_m$C(O)$(CH_2)_p$N$(R)_2$, —NR$(CH_2)_m$C(O)$(CH_2)_p$OR, —NR$(CH_2)_m$N(R)C(O)$(CH_2)_p$OR, —NR$(CH_2)_m$N(R)C(O)$(CH_2)_p$N$(R)_2$, —NR$(CH_2)_m$OC(O)$(CH_2)_p$OR, —NR$(CH_2)_m$OC(O)$(CH_2)_p$N$(R)_2$, —$(CH_2)_m$N(R)C(O)$(CH_2)_p$R, —$(CH_2)_m$OC(O)$(CH_2)_p$R, —$(CH_2)_m$C(O)$(CH_2)_p$N$(R)_2$, —(CH$_2$)$_m$C(O)(CH$_2$)$_p$OR, —(CH$_2$)$_m$N(R)C(O)(CH$_2$)$_p$OR, —(CH$_2$)$_m$N(R)C(O)(CH$_2$)$_p$N(R)$_2$, —(CH$_2$)$_m$OC(O)(CH$_2$)$_p$OR, —(CH$_2$)$_m$OC(O)(CH$_2$)$_p$N(R)$_2$, —(CH$_2$)$_m$N$_3$, —O(CH$_2$)$_m$N$_3$—(CH$_2$)$_m$N(R)$_2$, —(CH$_2$)$_m$OR, —(CH$_2$)$_m$S(O)(CH$_2$)$_p$R, —(CH$_2$)$_m$S(O)$_2$(CH$_2$)$_p$R, —(CH$_2$)$_m$SO$_2$(CH$_2$)$_p$N(R)$_2$, or —(CH$_2$)$_m$N(R)SO$_2$(CH$_2$)$_p$R; and each R is independently R$^{11}$, hydrogen, aliphatic, amino, azido, cyano, nitro, alkylamino, dialkylamino, OH, alkoxy, carbonylamino, aminocarbonyl, alkoxycarbonyl, carbonyloxy, carboxy, acyl, aryl, alkaryl, arylalkyl including benzyl, heteroalkyl, heteroaryl, heterocyclyl, or a protecting group; or two R on the same nitrogen are taken together with the nitrogen to form a 5-8 membered heterocyclic or heteroaryl ring; wherein where a group contains more than one R substituent; wherein R is optionally substituted, and each R can be the same or different;

R$^{11}$ is the group:

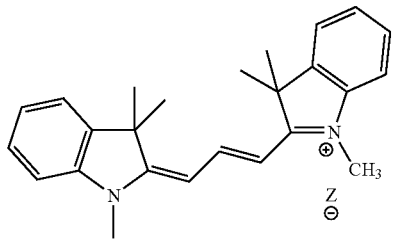

where Z is an inorganic or organic counterion;
n is 0, 1 or 2;
m and p are independently 0, 1, 2, 3, 4 or 5; and the dashed lines indicate either a single or a double bond, where the valence requirements are fulfilled by additional hydrogen atoms;

wherein in formula I', when n is 1, and X is O and a double bond is present between the carbon atoms bearing R$^9$ and R$^{10}$, then at least one of R$^5$, R$^6$, R$^7$, R$^8$, R$^9$ or R$^{10}$ is not hydrogen; and wherein in formula I', when n is 1 and X is O and the bond between the carbon atoms bearing R$^9$ and R$^{10}$ is a single bond, then at least one of R$^5$, R$^6$, R$^7$ or R$^8$ is not hydrogen.

In one embodiment of formulae I or I', R$^1$ and R$^2$ are independently hydrogen or halogen. In another embodiment of formulae I or I', X is O or NR. In still another embodiment of formulae I or I', X is O, S or NR; Y is —OR, —O—(CH$_2$)$_m$COOR, —O—(CH$_2$)$_m$CON(R)$_2$, In another embodiment, a compound of formula II or II', or a tautomer, pharmaceutically acceptable salt, solvate, ester or prodrug thereof, is provided:

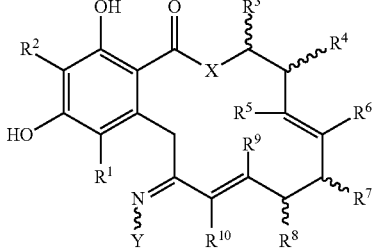

where the variables X, Y, R$^1$, R$^2$, R$^3$, R$^4$, R$^5$, R$^6$, R$^7$, R$^8$, R$^9$, R$^{10}$, R, m and p are as defined for formula I; and wherein in formula II', when X is O, then at least one of R$^5$, R$^6$, R$^7$, R$^8$, R$^9$ or R$^{10}$ is not hydrogen.

In one embodiment of formulae II or II', R$^1$ and R$^2$ are independently hydrogen or halogen. In another embodiment, R$^3$ and are R$^4$ are independently alkyl or hydrogen. In still another embodiment of formulae II or II', variables R$^9$ and R$^{10}$ are independently hydrogen or aliphatic.

In another embodiment of formulae II or II', X is O; Y is —O—(CH$_2$)$_m$COOR or —O—(CH$_2$)$_m$CON(R)$_2$, wherein the groups bound to the nitrogen atom may be in the Z- or E-configuration; R$^1$, R$^2$ are independently hydrogen or halogen; and R$^9$ and R$^{10}$ are independently hydrogen or aliphatic.

In another embodiment, the invention provides a compound of formulae III or III', or a tautomer, pharmaceutically acceptable salt, solvate, ester or prodrug thereof:

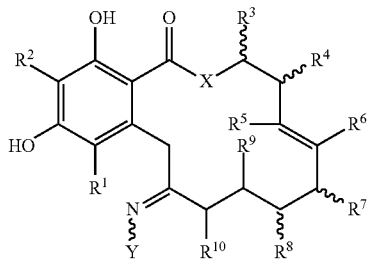

where the variables X, Y, R$^1$, R$^2$, R$^3$, R$^4$, R$^5$, R$^6$, R$^7$, R$^8$, R$^9$, R$^{10}$, R, m and p are as defined for formula I, and wherein in formula III', when X is O, then at least one of R$^5$, R$^6$, R$^7$ or R$^8$ is not hydrogen.

In one embodiment of formulae III or III', X is O or NR. In another embodiment, Y is —O—(CH$_2$)$_m$COOR or —O—(CH$_2$)$_m$CON(R)$_2$, wherein the groups bound to the nitrogen atom may be in the Z- or E-configuration. In still another embodiment of formulae III or III', X is O, Y is —O—(CH$_2$)$_m$COOR or —O—(CH$_2$)$_m$CON(R)$_2$, wherein the groups bound to the nitrogen atom may be in the Z- or E-configuration; R$^1$ and R$^2$ are independently hydrogen or halogen; and R$^9$ and R$^{10}$ are hydrogen.

In another aspect, the invention provides a compound of formula IV, or a tautomer thereof, or a pharmaceutically acceptable salt, solvate, ester or prodrug thereof:

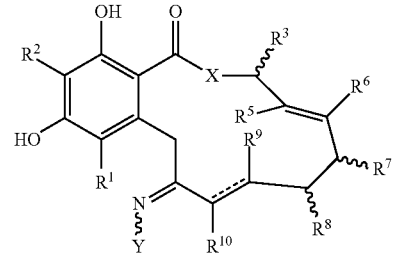

where the variables X, Y, R$^1$, R$^2$, R$^3$, R$^5$, R$^6$, R$^8$, R$^9$, R$^{10}$, R, m and p are as defined for formula I above, and the dashed lines represents a single or double bond.

In yet another aspect, the invention provides a compound of formula V, or a tautomer thereof, or a pharmaceutically acceptable salt, solvate, ester or prodrug thereof:

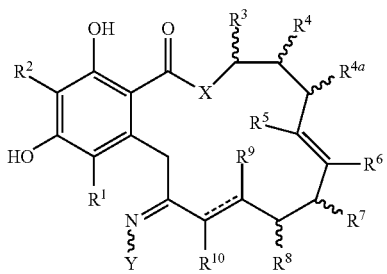

where the variables X, Y, R$^1$, R$^2$, R$^3$, R$^4$, R$^5$, R$^6$, R$^7$, R$^8$R$^9$, R$^{10}$, R, m and p are as defined for formula I; R$^{4a}$ has the same definition as R$^4$ in formula I above; and the dashed lines represents a single or double bond.

In various other embodiments, the invention provides the macrocyclic compounds shown in Table 1 below, or tautomers thereof, or pharmaceutically acceptable salts, solvates, esters or prodrugs thereof.

Pharmaceutical compositions comprising an effective HSP 90-inhibiting amount of a compound of formulae I, I', II, II', III, III', IV or V, in combination with a pharmaceutically acceptable carrier are provided for the treatment of a disorder mediated by HSP 90. Also provided are pharmaceutical composition comprising an effective kinase-inhibiting amount of a compound of the invention, in combination with a pharmaceutically acceptable carrier. In some embodiments, the pharmaceutical compositions comprise particles that are less than about 2 microns average particle size. In other embodiments, the invention provides pharmaceutical compositions wherein the carrier is suitable for oral, parenteral, intravenous, inhalation, topical, or intradermal administration. In addition, pharmaceutical compositions comprising the compounds of the invention in combination with other active agents and pharmaceutically acceptable carriers are provided.

In another aspect of the invention, a method of treating a patient with a disease comprising administering to the patient an effective amount of a compound of formulae I, I', II, II', III, III', IV or V is provided, wherein the disease may be an autoimmune disease, an inflammatory disease, a neurological or neurodegenerative disease, cancer, a cardiovascular disease, an allergy, asthma, or a hormone-related disease. In one embodiment, the patient is a human patient. In another embodiment, use of the compounds in the manufacture of a medicament for the treatment of the diseases is provided.

In one embodiment, the disease to be treated is cancer. The cancers that may be treated with the compounds include, but are not limited to, a solid tumor, blood borne tumor, breast, ovary, cervix, prostate, testis, genitourinary tract, esophagus, larynx, glioblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity, pharynx, lip, tongue, mouth, pharynx, small intestine, colon-rectum, large intestine, rectum, brain and central nervous system, or leukemia.

In another embodiment, the method provided is for treating an inflammatory disease with the compounds of the invention. In various embodiments, the inflammatory disease may be excessive or abnormal stimulation of endothelial cells, atherosclerosis, vascular malfunctions, abnormal wound healing, inflammatory and immune disorders, Bechet's disease, gout or gouty arthritis, abnormal angiogenesis accompanying rheumatoid arthritis, skin diseases, psoriasis, diabetic retinopathy, retinopathy of prematurity, retrolental fibroplasia, macular degeneration, corneal graft rejection, neovascular glaucoma or Osler Weber syndrome.

BRIEF DESCRIPTION OF THE FIGURES

FIG. 1 depicts the tumor volume and animal weight change following treatment with compound 13a or control vehicle.

FIG. 2 shows the tumor histology in animals treated with compound 13a and animals treated with control vehicle.

FIG. 3 shows a Wire-frame representation of the crystal structure of compound 13a.

DETAILED DESCRIPTION OF THE INVENTION

Figure 3:
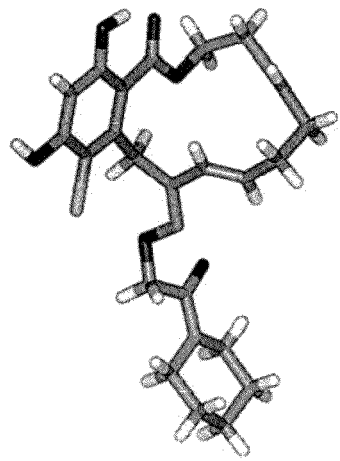

Provided are novel compounds based on the resorcylic acid lactones that are useful as inhibitors of kinases and HSP90. Also provided are compositions comprising the compounds and processes for the preparation of the compounds. Use of the compounds for the inhibition of kinases and HSP-90, and a method for the treatment of kinase-mediated or HSP90-mediated diseases comprising administering an effective kinase-inhibiting amount or an effective HSP90-inhibiting amount of a compound of formula I, I', II, II', III, III', IV or V to a patient with a kinase-mediated or HSP90-mediated disease, are provided.

Compounds

In a first embodiment of the invention, a compound of formula I, a tautomer thereof, or a pharmaceutically acceptable salt, solvate, ester or prodrug thereof, is provided:

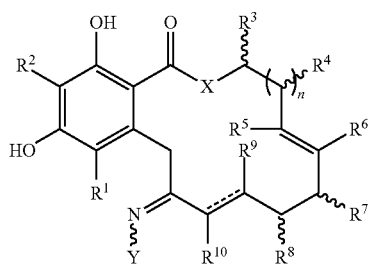

wherein:
X is O, S or NR;
Y is —OR, —O—(CH$_2$)$_m$COOR, —O—(CH$_2$)$_m$CON (R)$_2$, —N(R)$_2$, —N(R)SOR or —N(R)SO$_2$R, wherein the groups bound to the nitrogen atom may be in Z- or E-configuration;
R$^1$ and R$^2$ are independently hydrogen, halogen, OR, N(R)$_2$, SR, azido, nitro, cyano, aliphatic, aryl, alkylaryl, aralkyl, heterocyclyl, heteroaryl, —S(O)R, —S(O)$_2$R, —SO$_2$N(R)$_2$, —N(R)SO$_2$R, —N(CO)R, —N(CO)N(R)$_2$, —N(CO)OR, —O(CO)R, —(CO)R, —(CO)OR, —(CO)N (R)$_2$, —O(CO)OR, or —O(CO)N(R)$_2$;
R$^3$, R$^4$, R$^5$, R$^6$, R$^7$, R$^8$, R$^9$ and R$^{10}$ are independently hydrogen, halogen, azido, nitro, cyano, aliphatic, alkylaryl, aralkyl, aryl, heteroalkyl, alkylheteroaryl, heterocyclyl, heteroaryl, OR, N(R)$_2$, SR, —O(CH$_2$)$_m$N(R)C(O)(CH$_2$)$_p$R, —O(CH$_2$)$_m$OC(O)(CH$_2$)$_p$R, —O(CH$_2$)$_m$C(O)(CH$_2$)$_p$N(R)$_2$, —O(CH$_2$)$_m$C(O)(CH$_2$)$_p$OR, —O(CH$_2$)$_m$N(R)C(O)(CH$_2$)$_p$OR, —O(CH$_2$)$_m$N(R)C(O)(CH$_2$)$_p$N(R)$_2$, —O(CH$_2$)$_m$OC(O)(CH$_2$)$_p$OR, —O(CH$_2$)$_m$OC(O)(CH$_2$)$_p$N(R)$_2$, —NR(CH$_2$)$_m$N(R)C(O)(CH$_2$)$_p$R, —NR(CH$_2$)$_m$OC(O)(CH$_2$)$_p$R, —NR(CH$_2$)$_m$C(O)(CH$_2$)$_p$N(R)$_2$, —NR(CH$_2$)$_m$C(O)(CH$_2$)$_p$OR, —NR(CH$_2$)$_m$N(R)C(O)(CH$_2$)$_p$OR, —NR(CH$_2$)$_m$N(R)C(O)(CH$_2$)$_p$N(R)$_2$, —NR(CH$_2$)$_m$OC(O)(CH$_2$)$_p$OR, —NR(CH$_2$)$_m$OC(O)(CH$_2$)$_p$N(R)$_2$, —(CH$_2$)$_m$N(R)C(O)CH$_2$)$_p$R, —(CH$_2$)$_m$OC(O)(CH$_2$)$_p$R, —(CH$_2$)$_m$C(O)(CH$_2$)$_p$N(R)$_2$, —(CH$_2$)$_m$C(O)(CH$_2$)$_p$OR, —(CH$_2$)$_m$N(R)C(O)(CH$_2$)$_p$OR, —(CH$_2$)$_m$N(R)C(O)(CH$_2$)$_p$N(R)$_2$, —(CH$_2$)$_m$OC(O)(CH$_2$)$_p$OR, —(CH$_2$)$_m$OC(O)(CH$_2$)$_p$N(R)$_2$, —(CH$_2$)$_m$N$_3$, —O(CH$_2$)$_m$N$_3$—(CH$_2$)$_m$N(R)$_2$, —(CH$_2$)$_m$OR, —(CH$_2$)$_m$S(O)(CH$_2$)$_p$R, —(CH$_2$)$_m$S(O)$_2$(CH$_2$)$_p$R, —(CH$_2$)$_m$SO$_2$(CH$_2$)$_p$N(R)$_2$, or —(CH$_2$)$_m$N(R)SO$_2$(CH$_2$)$_p$R; and each R is independently R$^{11}$, hydrogen, aliphatic, amino, azido, cyano, nitro, alkylamino, dialkylamino, OH, alkoxy, carbonylamino, aminocarbonyl, alkoxycarbonyl, carbonyloxy, carboxy, acyl, aryl, alkaryl, arylalkyl including benzyl, heteroalkyl, heteroaryl, heterocyclyl, or a protecting group; or two R on the same nitrogen are taken together with the nitrogen to form a 5-8 membered, optionally substituted heterocyclic or heteroaryl ring; wherein R is optionally substituted, and each R can be the same or different;

R$^{11}$ is the group:

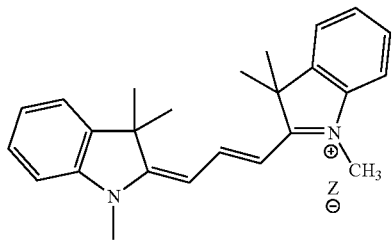

where Z is an inorganic or organic counterion;

n is 0, 1 or 2;

m and p are independently 0, 1, 2, 3, 4 or 5; and the dashed lines indicate either a single or a double bond, where the valence requirements are fulfilled by additional hydrogen atoms.

In a second embodiment, a compound of formula I', a tautomer thereof, or a pharmaceutically acceptable salt, solvate, ester or prodrug thereof, is provided,

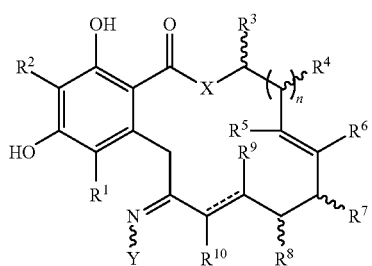

wherein X, Y, R$^1$, R$^2$, R$^3$, R$^4$, R$^5$, R$^6$, R$^7$, R$^8$, R$^9$, R$^{10}$, R, n, m and p are as defined for formula I above and the dashed lines represent a single or double bond, with the provisos that when n is 1, and X is O and a double bond is present between the carbon atoms bearing R$^9$ and R$^{10}$, then at least one of R$^5$, R$^6$, R$^7$, R$^8$, R$^9$ or R$^{10}$ is not hydrogen; and when n is 1 and X is O and the bond between the carbon atoms bearing R$^9$ and R$^{10}$ is a single bond, then at least one of R$^5$, R$^6$, R$^7$ or R$^8$ is not hydrogen.

In one embodiment of formula I or I', n is 0. In another embodiment of formula I or I', n is 1. In still another embodiment of formula I or I', n is 2.

In another embodiment of formula I or I', X is O or NR and n is 1. In another embodiment of formula I or I', X is O or NR, n is 1 and a double bond is present between the carbon atoms bearing R$^9$ and R$^{10}$.

In yet another embodiment of formula I or I', X is O or NR, n is 1 and the bond between the carbon atoms bearing R$^9$ and R$^{10}$ is a single bond.

In another embodiment of formula I or I', Y is —O—(CH$_2$)$_m$COOR or —O—(CH$_2$)$_m$CON(R)$_2$, wherein the groups bound to the nitrogen atom may be in the Z- or E-configuration.

In another embodiment of formula I or I', R$^1$ and R$^2$ are hydrogen.

In still another embodiment of formula I or I', R$^3$ and R$^4$ are independently alkyl or hydrogen.

In still another embodiment of formula I or I', X is O, and R$^9$ and R$^{10}$ are hydrogen.

In another embodiment of formula I or I', X is O, Y is —O—(CH$_2$)$_m$COOR or —O—(CH$_2$)$_m$CON(R)$_2$, wherein the groups bound to the nitrogen atom may be in the Z- or E-configuration; R$^1$ and R$^2$ are independently hydrogen or halogen; and R$^9$ and R$^{10}$ are hydrogen.

In another embodiment of formula I or I', R$^7$ or R$^8$ are not hydrogen or aliphatic.

In another embodiment of formula I or I', R$^3$ or R$^4$ are not hydrogen or aliphatic.

In one embodiment of formula I or I', the invention provides a compound wherein:

X is O or NR;

Y is —O—(CH$_2$)$_m$COOR or —O—(CH$_2$)$_m$CON(R)$_2$, wherein the groups bound to the nitrogen atom may be in the Z- or E-configuration;

R$^1$ and R$^2$ are independently hydrogen, halogen, OR, N(R)$_2$ or aliphatic;

R$^3$ and R$^4$ are independently hydrogen, aliphatic, OR, N(R)$_2$, —(CH$_2$)$_m$N(R)C(O)CH$_2$)$_p$R, —(CH$_2$)$_m$OC(O)(CH$_2$)$_p$R, —(CH$_2$)$_m$C(O)(CH$_2$)$_p$N(R)$_2$, —(CH$_2$)$_m$C(O)(CH$_2$)$_p$OR, —(CH$_2$)$_m$N(R)C(O)(CH$_2$)$_p$OR, —(CH$_2$)$_m$N(R)C(O)(CH$_2$)$_p$N(R)$_2$, —(CH$_2$)$_m$OC(O)(CH$_2$)$_p$OR, —(CH$_2$)$_m$OC(O)(CH$_2$)$_p$N(R)$_2$, —(CH$_2$)$_m$N$_3$, —O(CH$_2$)$_m$N$_3$—(CH$_2$)$_m$N(R)$_2$, —(CH$_2$)$_m$OR, —(CH$_2$)$_m$S(O)(CH$_2$)$_p$R, —(CH$_2$)$_m$S(O)$_2$(CH$_2$)$_p$R, —(CH$_2$)$_m$SO$_2$(CH$_2$)$_p$N(R)$_2$, or —(CH$_2$)$_m$N(R)SO$_2$(CH$_2$)$_p$R;

R$^5$, R$^6$, R$^9$ and R$^{10}$ are independently hydrogen, aliphatic, alkylaryl, aralkyl, aryl, heteroalkyl, alkylheteroaryl, heterocyclyl, heteroaryl, OR, SR, —O(CH$_2$)$_m$N(R)C(O)(CH$_2$)$_p$R, —O(CH$_2$)$_m$OC(O)(CH$_2$)$_p$R, —O(CH$_2$)$_m$C(O)(CH$_2$)$_p$N(R)$_2$, —O(CH$_2$)$_m$C(O)(CH$_2$)$_p$OR, —O(CH$_2$)$_m$N(R)C(O)(CH$_2$)$_p$OR, —O(CH$_2$)$_m$N(R)C(O)(CH$_2$)$_p$N(R)$_2$, —O(CH$_2$)$_m$OC(O)(CH$_2$)$_p$OR, —O(CH$_2$)$_m$OC(O)(CH$_2$)$_p$N(R)$_2$, —NR(CH$_2$)$_m$N(R)C(O)(CH$_2$)$_p$R, —NR(CH$_2$)$_m$OC(O)(CH$_2$)$_p$R, —NR(CH$_2$)$_m$C(O)(CH$_2$)$_p$N(R)$_2$, —NR(CH$_2$)$_m$C(O)(CH$_2$)$_p$OR, —NR(CH$_2$)$_m$N(R)C(O)(CH$_2$)$_p$OR, —NR(CH$_2$)$_m$N(R)C(O)(CH$_2$)$_p$N(R)$_2$, —NR(CH$_2$)$_m$OC(O)(CH$_2$)$_p$OR, —NR(CH$_2$)$_m$OC(O)(CH$_2$)$_p$N(R)$_2$, —(CH$_2$)$_m$N(R)C(O)CH$_2$)$_p$R, —(CH$_2$)$_m$OC(O)(CH$_2$)$_p$R, —(CH$_2$)$_m$C(O)(CH$_2$)$_p$N(R)$_2$, —(CH$_2$)$_m$C(O)(CH$_2$)$_p$OR, —(CH$_2$)$_m$N(R)C(O)(CH$_2$)$_p$OR, —(CH$_2$)$_m$N(R)C(O)(CH$_2$)$_p$N(R)$_2$, —(CH$_2$)$_m$OC(O)(CH$_2$)$_p$OR, —(CH$_2$)$_m$OC(O)(CH$_2$)$_p$N(R)$_2$, —(CH$_2$)$_m$N$_3$, —O(CH$_2$)$_m$N$_3$—(CH$_2$)$_m$N(R)$_2$, —(CH$_2$)$_m$OR, —(CH$_2$)$_m$S(O)(CH$_2$)$_p$R, —(CH$_2$)$_m$S(O)$_2$(CH$_2$)$_p$R, —(CH$_2$)$_m$SO$_2$(CH$_2$)$_p$N(R)$_2$, or —(CH$_2$)$_m$N(R)SO$_2$(CH$_2$)$_p$R;

R$^7$ and R$^8$ are independently hydrogen, halogen, aliphatic, alkylaryl, aralkyl, aryl, heteroalkyl, alkylheteroaryl, heterocyclyl, heteroaryl, OR, N(R)$_2$, SR, —O(CH$_2$)$_m$N(R)C(O)(CH$_2$)$_p$R, —O(CH$_2$)$_m$OC(O)(CH$_2$)$_p$R, —O(CH$_2$)$_m$C(O)(CH$_2$)$_p$N(R)$_2$, —O(CH$_2$)$_m$C(O)(CH$_2$)$_p$OR, —O(CH$_2$)$_m$N(R)C(O)(CH$_2$)$_p$OR, —O(CH$_2$)$_m$N(R)C(O)(CH$_2$)$_p$N(R)$_2$, —O(CH$_2$)$_m$OC(O)(CH$_2$)$_p$OR, —O(CH$_2$)$_m$OC(O)(CH$_2$)$_p$N(R)$_2$, —NR(CH$_2$)$_m$N(R)C(O)(CH$_2$)$_p$R, —NR(CH$_2$)$_m$OC(O)(CH$_2$)$_p$R, —NR(CH$_2$)$_m$C(O)(CH$_2$)$_p$N(R)$_2$, —NR(CH$_2$)$_m$C(O)(CH$_2$)$_p$OR, —NR(CH$_2$)$_m$N(R)C(O)(CH$_2$)$_p$OR, —NR(CH$_2$)$_m$N(R)C(O)(CH$_2$)$_p$N(R)$_2$, —NR(CH$_2$)$_m$OC(O)(CH$_2$)$_p$OR, —NR(CH$_2$)$_m$OC(O)(CH$_2$)$_p$N(R)$_2$, —(CH$_2$)$_m$N(R)C(O)CH$_2$)$_p$R, —(CH$_2$)$_m$OC(O)(CH$_2$)$_p$R, —(CH$_2$)$_m$C(O)(CH$_2$)$_p$N(R)$_2$, —(CH$_2$)$_m$C(O)(CH$_2$)$_p$OR, —(CH$_2$)$_m$N(R)C(O)(CH$_2$)$_p$OR, —(CH$_2$)$_m$N(R)C(O)(CH$_2$)$_p$N(R)$_2$, —(CH$_2$)$_m$OC(O)(CH$_2$)$_p$OR, —(CH$_2$)$_m$OC(O)(CH$_2$)$_p$N(R)$_2$, —(CH$_2$)$_m$N$_3$, —O(CH$_2$)$_m$N$_3$—(CH$_2$)$_m$N(R)$_2$, —(CH$_2$)$_m$OR, —(CH$_2$)$_m$S(O)(CH$_2$)$_p$R, —(CH$_2$)$_m$S(O)$_2$(CH$_2$)$_p$R, —(CH$_2$)$_m$SO$_2$(CH$_2$)$_p$N(R)$_2$, or —(CH$_2$)$_m$N(R)SO$_2$(CH$_2$)$_p$R.

In yet another embodiment of formula I or I', X is O or NR; Y is —O—(CH$_2$)$_m$COOR or —O—(CH$_2$)$_m$CON(R)$_2$, wherein the groups bound to the nitrogen atom may be in the Z- or E-configuration;

R$^1$ and R$^2$ are independently hydrogen, halogen;

R$^3$ and R$^4$ are independently hydrogen, aliphatic, —(CH$_2$)$_m$\N(R)C(O)CH$_2$)$_p$R, —(CH$_2$)$_m$OC(O)(CH$_2$)$_p$R, —(CH$_2$)$_m$N(R)C(O)(CH$_2$)$_p$OR, —(CH$_2$)$_m$N(R)C(O)(CH$_2$)$_p$N(R)$_2$, —(CH$_2$)$_m$OC(O)(CH$_2$)$_p$OR, —(CH$_2$)$_m$OC(O)(CH$_2$)$_p$N(R)$_2$, —(CH$_2$)$_m$N$_3$, —(CH$_2$)$_m$N(R)$_2$, or —(CH$_2$)$_m$OR;

R$^5$, R$^6$, R$^9$ and R$^{10}$ are independently hydrogen, aliphatic, aralkyl, heteroalkyl, heterocyclyl, or heteroaryl; and R$^7$ and R$^8$ are independently hydrogen, aliphatic, alkylaryl, aralkyl, aryl, heteroalkyl, alkylheteroaryl, heterocyclyl, heteroaryl, OR, N(R)$_2$, SR, —O(CH$_2$)$_m$N(R)C(O)(CH$_2$)$_p$R, —O(CH$_2$)$_m$OC(O)(CH$_2$)$_p$R, —O(CH$_2$)$_m$C(O)(CH$_2$)$_p$N(R)$_2$, —O(CH$_2$)$_m$C(O)(CH$_2$)$_p$OR, —O(CH$_2$)$_m$N(R)C(O)(CH$_2$)$_p$OR, —O(CH$_2$)$_m$N(R)C(O)(CH$_2$)$_p$N(R)$_2$, —O(CH$_2$)$_m$C(O)(CH$_2$)$_p$OR, —O(CH$_2$)$_m$OC(O)(CH$_2$)$_p$N(R)$_2$, —NR(CH$_2$)$_m$N(R)C(O)(CH$_2$)$_p$R, —NR(CH$_2$)$_m$OC(O)(CH$_2$)$_p$R, —NR(CH$_2$)$_m$C(O)(CH$_2$)$_p$N(R)$_2$, —NR(CH$_2$)$_m$C(O)(CH$_2$)$_p$OR, —NR(CH$_2$)$_m$N(R)C(O)(CH$_2$)$_p$OR, —NR(CH$_2$)$_m$N(R)C(O)(CH$_2$)$_p$N(R)$_2$, —NR(CH$_2$)$_m$OC(O)(CH$_2$)$_p$OR, or —NR(CH$_2$)$_m$OC(O)(CH$_2$)$_p$N(R)$_2$.

In still another embodiment of formula I or I', X is O or NR; Y is —O—(CH$_2$)$_m$COOR or —O—(CH$_2$)$_m$CON(R)$_2$, wherein the groups bound to the nitrogen atom may be in the Z- or E-configuration;

R$^1$ and R$^2$ are independently hydrogen, halogen;

R$^3$ and R$^4$ are independently hydrogen, aliphatic, —(CH$_2$)$_m$N(R)C(O)CH$_2$)$_p$R, —(CH$_2$)$_m$OC(O)(CH$_2$)$_p$R, —(CH$_2$)$_m$N(R)C(O)(CH$_2$)$_p$OR, —(CH$_2$)$_m$N(R)C(O)(CH$_2$)$_p$N(R)$_2$, —(CH$_2$)$_m$OC(O)(CH$_2$)$_p$OR, —(CH$_2$)$_m$OC(O)(CH$_2$)$_p$N(R)$_2$, —(CH$_2$)$_m$N$_3$, —(CH$_2$)$_m$N(R)$_2$, or —(CH$_2$)$_m$OR;

R$^5$, R$^6$, R$^9$ and R$^{10}$ are independently hydrogen, aliphatic, aralkyl, heteroalkyl, heterocyclyl, or heteroaryl;

R$^7$ and R$^8$ are independently alkylaryl, aralkyl, aryl, heteroalkyl, alkylheteroaryl, heterocyclyl, heteroaryl, OR, N(R)$_2$, SR, —O(CH$_2$)$_m$N(R)C(O)(CH$_2$)$_p$R, —O(CH$_2$)$_m$OC(O)(CH$_2$)$_p$R, —O(CH$_2$)$_m$C(O)(CH$_2$)$_p$N(R)$_2$, —O(CH$_2$)$_m$C(O)(CH$_2$)$_p$OR, —O(CH$_2$)$_m$N(R)C(O)(CH$_2$)$_p$OR, —O(CH$_2$)$_m$N(R)C(O)(CH$_2$)$_p$N(R)$_2$, —O(CH$_2$)$_m$OC(O)(CH$_2$)$_p$OR, —O(CH$_2$)$_m$OC(O)(CH$_2$)$_p$N(R)$_2$, —NR(CH$_2$)$_m$N(R)C(O)(CH$_2$)$_p$R, —NR(CH$_2$)$_m$OC(O)(CH$_2$)$_p$R, —NR(CH$_2$)$_m$C(O)(CH$_2$)$_p$N(R)$_2$, —NR(CH$_2$)$_m$C(O)(CH$_2$)$_p$OR, —NR(CH$_2$)$_m$N(R)C(O)(CH$_2$)$_p$OR, —NR(CH$_2$)$_m$N(R)C(O)(CH$_2$)$_p$N(R)$_2$, —NR(CH$_2$)$_m$OC(O)(CH$_2$)$_p$OR, or —NR(CH$_2$)$_m$OC(O)(CH$_2$)$_p$N(R)$_2$.

In one embodiment of formula I or I', R is R$^{11}$, where the counterion Z is a halogen, acetate, formate, sulfonate, sulfate or phosphate counterion.

In another embodiment, a compound of formula II, a tautomer thereof, or a pharmaceutically acceptable salt, solvate, ester or prodrug thereof, is provided:

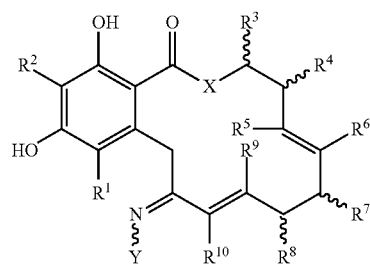

II wherein the variables X, Y, R$^1$, R$^2$, R$^3$, R$^4$, R$^5$, R$^6$, R$^7$, R$^8$, R$^9$, R$^{10}$, m and p are as defined for formula I above.

In another embodiment, a compound of formula II', a tautomer thereof, or a pharmaceutically acceptable salt, solvate, ester or prodrug thereof, is provided:

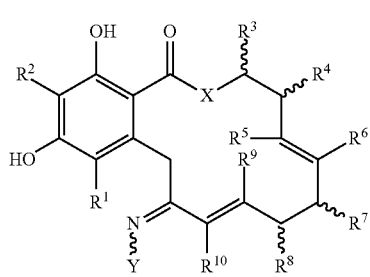

II' wherein the variables X, Y, R$^1$, R$^2$, R$^3$, R$^4$, R$^5$, R$^6$, R$^7$, R$^8$, R$^9$, R$^{10}$, R, m and p are as defined for formula I above; with the proviso that when X is O, then at least one of R$^5$, R$^6$, R$^7$, R$^8$, R$^9$ or R$^{10}$ is not hydrogen.

In one embodiment of formula II or II', X is O or NR.

In another embodiment of formula II or II', Y is —O—(CH$_2$)$_m$COOR or —O—(CH$_2$)$_m$CON(R)$_2$, wherein the groups bound to the nitrogen atom may be in the Z- or E-configuration.

In another embodiment of formula II or II', R$^1$ and R$^2$ are hydrogen.

In still another embodiment of formula II or II', R$^3$ and R$^4$ are independently alkyl or hydrogen.

In still another embodiment of formula II or II', X is O, and R$^9$ and R$^{10}$ are hydrogen.

In another embodiment of formula II or II', R$^7$ or R$^8$ are not hydrogen or aliphatic.

In another embodiment of formula II or II', R$^3$ or R$^4$ are not hydrogen or aliphatic.

In another embodiment of formula II or II', X is O, Y is —O—(CH$_2$)$_m$COOR or —O—(CH$_2$)$_m$CON(R)$_2$, wherein the groups bound to the nitrogen atom may be in the Z- or E-configuration; R$^1$ and R$^2$ are independently hydrogen or halogen; and R$^9$ and R$^{10}$ are hydrogen.

In one embodiment of formula II or II', the invention provides a compound wherein:

X is O or NR;

Y is —O—$(CH_2)_m$COOR or —O—$(CH_2)_m$CON$(R)_2$, wherein the groups bound to the nitrogen atom may be in the Z- or E-configuration;

$R^1$ and $R^2$ are independently hydrogen, halogen, OR, N$(R)_2$ or aliphatic;

$R^3$ and $R^4$ are independently hydrogen, aliphatic, OR, N$(R)_2$, —$(CH_2)_m$N(R)C(O)$CH_2)_p$R, —$(CH_2)_m$OC(O)$(CH_2)_p$R, —$(CH_2)_p$C(O)$(CH_2)_p$N$(R)_2$, —$(CH_2)_p$C(O)$(CH_2)_p$OR, —$(CH_2)_m$N(R)C(O)$(CH_2)_p$OR, —$(CH_2)_m$N(R)C(O)$(CH_2)_p$N$(R)_2$, —$(CH_2)_m$OC(O)$(CH_2)_p$OR, —$(CH_2)_m$OC(O)$(CH_2)_p$N$(R)_2$, —$(CH_2)_m$N$_3$, —O$(CH_2)_m$N$_3$—$(CH_2)_m$N$(R)_2$, —$(CH_2)_m$OR, —$(CH_2)_m$S(O)$(CH_2)_p$R, —$(CH_2)_m$S(O)$_2(CH_2)_p$R, —$(CH_2)_m$SO$_2(CH_2)_p$N$(R)_2$, or —$(CH_2)_m$N(R)SO$_2(CH_2)_p$R;

$R^5$, $R^6$, $R^9$ and $R^{10}$ are independently hydrogen, aliphatic, alkylaryl, aralkyl, aryl, heteroalkyl, alkylheteroaryl, heterocyclyl, heteroaryl, —$(CH_2)_m$N(R)C(O)$CH_2)_p$R, —$(CH_2)_m$OC(O)$(CH_2)_p$R, —$(CH_2)_m$C(O)$(CH_2)_p$N$(R)_2$, —$(CH_2)_m$C(O)$(CH_2)_p$OR, —$(CH_2)_m$N(R)C(O)$(CH_2)_p$OR, —$(CH_2)_m$N(R)C(O)$(CH_2)_p$N$(R)_2$, —$(CH_2)_m$OC(O)$(CH_2)_p$OR, —$(CH_2)_m$OC(O)$(CH_2)_p$N$(R)_2$, —$(CH_2)_m$N$_3$, —O$(CH_2)_m$N$_3$—$(CH_2)_m$N$(R)_2$, —$(CH_2)_m$OR, —$(CH_2)_m$S(O)$(CH_2)_p$R, —$(CH_2)_m$S(O)$_2(CH_2)_p$R, —$(CH_2)_m$SO$_2(CH_2)_p$N$(R)_2$, or —$(CH_2)_m$N(R)SO$_2(CH_2)_p$R; and $R^7$ and $R^8$ are independently hydrogen, halogen, aliphatic, alkylaryl, aralkyl, aryl, heteroalkyl, alkylheteroaryl, heterocyclyl, heteroaryl, OR, N$(R)_2$, SR, —O$(CH_2)_m$N(R)C(O)$(CH_2)_p$R, —O$(CH_2)_m$OC(O)$(CH_2)_p$R, —O$(CH_2)_m$C(O)$(CH_2)_p$N$(R)_2$, —O$(CH_2)_m$C(O)$(CH_2)_p$OR, —O$(CH_2)_m$N(R)C(O)$(CH_2)_p$OR, —O$(CH_2)_m$N(R)C(O)$(CH_2)_p$N$(R)_2$, —O$(CH_2)_m$OC(O)$(CH_2)_p$OR, —O$(CH_2)_m$OC(O)$(CH_2)_p$N$(R)_2$, —NR$(CH_2)_m$N(R)C(O)$(CH_2)_p$R, —NR$(CH_2)_m$OC(O)$(CH_2)_p$R, —NR$(CH_2)_m$C(O)$(CH_2)_p$N$(R)_2$, —NR$(CH_2)_m$C(O)$(CH_2)_p$OR, —NR$(CH_2)_m$N(R)C(O)$(CH_2)_p$OR, —NR$(CH_2)_m$N(R)C(O)$(CH_2)_p$N$(R)_2$, —NR$(CH_2)_m$OC(O)$(CH_2)_p$OR, —NR$(CH_2)_m$OC(O)$(CH_2)_p$N$(R)_2$, —$(CH_2)_m$N(R)C(O)$CH_2)_p$R, —$(CH_2)_m$OC(O)$(CH_2)_p$R, —$(CH_2)_m$C(O)$(CH_2)_p$N$(R)_2$, —$(CH_2)_m$C(O)$(CH_2)_p$OR, —$(CH_2)_m$N(R)C(O)$(CH_2)_p$OR, —$(CH_2)_m$N(R)C(O)$(CH_2)_p$N$(R)_2$, —$(CH_2)_m$OC(O)$(CH_2)_p$OR, —$(CH_2)_m$OC(O)$(CH_2)_p$N$(R)_2$, —$(CH_2)_m$N$_3$, —O$(CH_2)_m$N$_3$—$(CH_2)_m$N$(R)_2$, —$(CH_2)_m$OR, —$(CH_2)_m$S(O)$(CH_2)_p$R, —$(CH_2)_m$S(O)$_2(CH_2)_p$R, —$(CH_2)_m$SO$_2(CH_2)_p$N$(R)_2$, or —$(CH_2)_m$N(R)SO$_2(CH_2)_p$R.

In yet another embodiment of formula II or II', X is O or NR;

Y is —O—$(CH_2)_m$COOR or —O—$(CH_2)_m$CON$(R)_2$, wherein the groups bound to the nitrogen atom may be in the Z- or E-configuration;

$R^1$ and $R^2$ are independently hydrogen or halogen;

$R^3$ and $R^4$ are independently hydrogen, aliphatic, —$(CH_2)_m$N(R)C(O)$CH_2)_p$R, —$(CH_2)_m$OC(O)$(CH_2)_p$R, —$(CH_2)_m$N(R)C(O)$(CH_2)_p$OR, —$(CH_2)_m$N(R)C(O)$(CH_2)_p$N$(R)_2$, —$(CH_2)_m$OC(O)$(CH_2)_p$OR, —$(CH_2)_m$OC(O)$(CH_2)_p$N$(R)_2$, —$(CH_2)_m$N$_3$, —$(CH_2)_m$N$(R)_2$, or —$(CH_2)_m$OR;

$R^5$, $R^6$, $R^9$ and $R^{10}$ are independently hydrogen, aliphatic, aralkyl, heteroalkyl, heterocyclyl, or heteroaryl; and $R^7$ and $R^8$ are independently hydrogen, aliphatic, alkylaryl, aralkyl, aryl, heteroalkyl, alkylheteroaryl, heterocyclyl, heteroaryl, OR, N$(R)_2$, SR, —O$(CH_2)_m$N(R)C(O)$(CH_2)_p$R, —O$(CH_2)_m$OC(O)$(CH_2)_p$R, —O$(CH_2)_m$C(O)$(CH_2)_p$N$(R)_2$, —O$(CH_2)_m$C(O)$(CH_2)_p$OR, —O$(CH_2)_m$N(R)C(O)$(CH_2)_p$OR, —O$(CH_2)_m$N(R)C(O)$(CH_2)_p$N$(R)_2$, —O$(CH_2)_m$OC(O)$(CH_2)_p$OR, —O$(CH_2)_m$OC(O)$(CH_2)_p$N$(R)_2$, —NR$(CH_2)_m$N(R)C(O)$(CH_2)_p$R, —NR$(CH_2)_m$OC(O)$(CH_2)_p$R, —NR$(CH_2)_m$C(O)$(CH_2)_p$N$(R)_2$, —NR$(CH_2)_m$C(O)$(CH_2)_p$OR, —NR$(CH_2)_m$N(R)C(O)$(CH_2)_p$OR, —NR$(CH_2)_m$N(R)C(O)$(CH_2)_p$N$(R)_2$, —NR$(CH_2)_m$OC(O)$(CH_2)_p$OR, or —NR$(CH_2)_m$OC(O)$(CH_2)_p$N$(R)_2$.

In still another embodiment of formula II or II', X is O or NR;

Y is —O—$(CH_2)_m$COOR or —O—$(CH_2)_m$CON$(R)_2$, wherein the groups bound to the nitrogen atom may be in the Z- or E-configuration;

$R^1$ and $R^2$ are independently hydrogen or halogen;

$R^3$ and $R^4$ are independently hydrogen, aliphatic, —$(CH_2)_m$N(R)C(O)$CH_2)_p$R, —$(CH_2)_m$OC(O)$(CH_2)_p$R, —$(CH_2)_m$N(R)C(O)$(CH_2)_p$OR, —$(CH_2)_m$N(R)C(O)$(CH_2)_p$N$(R)_2$, —$(CH_2)_m$OC(O)$(CH_2)_p$OR, —$(CH_2)_m$OC(O)$(CH_2)_p$N$(R)_2$, —$(CH_2)_m$N$_3$, —$(CH_2)_m$N$(R)_2$, or —$(CH_2)_m$OR;

$R^5$, $R^6$, $R^9$ and $R^{10}$ are independently hydrogen, aliphatic, aralkyl, heteroalkyl, heterocyclyl, or heteroaryl;

$R^7$ and $R^8$ are independently alkylaryl, aralkyl, aryl, heteroalkyl, alkylheteroaryl, heterocyclyl, heteroaryl, OR, N$(R)_2$, SR, —O$(CH_2)_m$N(R)C(O)$(CH_2)_p$R, —O$(CH_2)_m$OC(O)$(CH_2)_p$R, —O$(CH_2)_m$C(O)$(CH_2)_p$N$(R)_2$, —O$(CH_2)_m$C(O)$(CH_2)_p$OR, —O$(CH_2)_m$N(R)C(O)$(CH_2)_p$OR, —O$(CH_2)_m$N(R)C(O)$(CH_2)_p$N$(R)_2$, —O$(CH_2)_m$OC(O)$(CH_2)_p$OR, —O$(CH_2)_m$OC(O)$(CH_2)_p$N$(R)_2$, —NR$(CH_2)_m$N(R)C(O)$(CH_2)_p$R, —NR$(CH_2)_m$OC(O)$(CH_2)_p$R, —NR$(CH_2)_m$C(O)$(CH_2)_p$N$(R)_2$, —NR$(CH_2)_m$C(O)$(CH_2)_p$OR, —NR$(CH_2)_m$N(R)C(O)$(CH_2)_p$OR, —NR$(CH_2)_m$N(R)C(O)$(CH_2)_p$N$(R)_2$, —NR$(CH_2)_m$OC(O)$(CH_2)_p$OR, or —NR$(CH_2)_m$OC(O)$(CH_2)_p$N$(R)_2$.

In yet another embodiment of formula II or II', X is O or NR;

Y is —O—$(CH_2)_m$COOR or —O—$(CH_2)_m$CON$(R)_2$, wherein the groups bound to the nitrogen atom may be in the Z- or E-configuration;

$R^1$ and $R^2$ are independently hydrogen or halogen;

$R^3$ and $R^4$ are independently hydrogen, aliphatic, —$(CH_2)_m$N(R)C(O)$CH_2)_p$R, —$(CH_2)_m$OC(O)$(CH_2)_p$R, —$(CH_2)_m$N(R)C(O)$(CH_2)_p$OR, —$(CH_2)_m$N(R)C(O)$(CH_2)_p$N$(R)_2$, —$(CH_2)_m$OC(O)$(CH_2)_p$OR, —$(CH_2)_m$OC(O)$(CH_2)_p$N$(R)_2$, —$(CH_2)_m$N$_3$, —$(CH_2)_m$N$(R)_2$, or —$(CH_2)_m$OR;

$R^5$, $R^6$, $R^9$ and $R^{10}$ are independently hydrogen, aliphatic, aralkyl, heteroalkyl, heterocyclyl, or heteroaryl; and $R^7$ and $R^8$ are independently —OR, —N$(R)_2$, —SR, —O$(CH_2)_m$N(R)C(O)$(CH_2)_p$R, —O$(CH_2)_m$OC(O)$(CH_2)_p$R, —O$(CH_2)_m$C(O)$(CH_2)_p$N$(R)_2$, —O$(CH_2)_m$C(O)$(CH_2)_p$OR, —O$(CH_2)_m$N(R)C(O)$(CH_2)_p$OR, —O$(CH_2)_m$N(R)C(O)$(CH_2)_p$N$(R)_2$, —O$(CH_2)_m$OC(O)$(CH_2)_p$OR, —O$(CH_2)_m$OC(O)$(CH_2)_p$N$(R)_2$, —NR$(CH_2)_m$N(R)C(O)$(CH_2)_p$R, —NR$(CH_2)_m$OC(O)$(CH_2)_p$R, —NR$(CH_2)_m$C(O)$(CH_2)_p$N$(R)_2$, —NR$(CH_2)_m$C(O)$(CH_2)_p$OR, —NR$(CH_2)_m$N(R)C(O)$(CH_2)_p$OR, —NR$(CH_2)_m$N(R)C(O)$(CH_2)_p$N$(R)_2$, —NR$(CH_2)_m$OC(O)$(CH_2)_p$OR, or —NR$(CH_2)_m$OC(O)$(CH_2)_p$N$(R)_2$.

In another embodiment, a compound of formula III, a tautomer thereof, or a pharmaceutically acceptable salt, solvate, ester or prodrug thereof, is provided:

III wherein the variables X, Y, $R^1$, $R^2$, $R^3$, $R^4$, $R^5$, $R^6$, $R^7$, $R^8$, $R^9$, $R^{10}$, R, m and p are as defined for formula I above.

In another embodiment of the invention, a compound of formula III', a tautomer thereof, or a pharmaceutically acceptable salt, solvate, ester or prodrug thereof, is provided:

III' wherein the variables X, Y, $R^1$, $R^2$, $R^3$, $R^4$, $R^5$, $R^6$, $R^7$, $R^8$, $R^9$, $R^{10}$, R, m and p are as defined for formula I above; with the proviso that at least one of $R^5$, $R^6$, $R^7$ or $R^8$ is not hydrogen.

In one embodiment of formula III or X is O or NR.

In another embodiment of formula III or III', Y is —O—$(CH_2)_m$COOR or —O—$(CH_2)_m$CON$(R)_2$, wherein the groups bound to the nitrogen atom may be in the Z- or E-configuration.

In another embodiment of formula III or $R^1$ and $R^2$ are hydrogen.

In still another embodiment of formula III or III', $R^3$ and $R^4$ are independently alkyl or hydrogen.

In still another embodiment of formula III or X is O, and $R^9$ and $R^{10}$ are hydrogen.

In another embodiment of formula III or III or $R^3$ or $R^4$ are not hydrogen or aliphatic.

In another embodiment of formula III or III', $R^7$ or $R^8$ are not hydrogen or aliphatic.

In still another embodiment of formula III or III', $R^9$ or $R^{10}$ are independently OR, SR, —O$(CH_2)_m$N(R)C(O)$(CH_2)_p$R, —O$(CH_2)_m$OC(O)$(CH_2)_p$R, —O$(CH_2)_m$C(O)$(CH_2)_p$N$(R)_2$, —O$(CH_2)_m$C(O)$(CH_2)_p$OR, —O$(CH_2)_m$N(R)C(O)$(CH_2)_p$OR, —O$(CH_2)_m$N(R)C(O)$(CH_2)_p$N$(R)_2$, —O$(CH_2)_m$OC(O)$(CH_2)_p$OR, —O$(CH_2)_m$OC(O)$(CH_2)_p$N$(R)_2$, —NR$(CH_2)_m$N(R)C(O)$(CH_2)_p$R, —NR$(CH_2)_m$OC(O)$(CH_2)_9$R, —NR$(CH_2)_m$C(O)$(CH_2)_p$N$(R)_2$, —NR$(CH_2)_m$C(O)$(CH_2)_p$OR, —NR$(CH_2)_m$N(R)C(O)$(CH_2)_p$OR, —NR$(CH_2)_m$NR)C(O)$(CH_2)_p$N$(R)_2$, or —NR$(CH_2)_m$OC(O)$(CH_2)_p$OR, —NR$(CH_2)_m$OC(O)$(CH_2)_p$N$(R)_2$.

In another embodiment of formula III or X is O, Y is —O—$(CH_2)_m$COOR or —O—$(CH_2)_m$CON$(R)_2$, wherein the groups bound to the nitrogen atom may be in the Z- or E-configuration; $R^1$ and $R^2$ are independently hydrogen or halogen; and $R^9$ and $R^{10}$ are hydrogen.

In one embodiment of formula III or the invention provides a compound wherein:

X is O or NR;

Y is —O—$(CH_2)_m$COOR or —O—$(CH_2)_m$CON$(R)_2$, wherein the groups bound to the nitrogen atom may be in the Z- or E-configuration;

$R^1$ and $R^2$ are independently hydrogen, halogen, OR, N$(R)_2$ or aliphatic;

$R^3$ and $R^4$ are independently hydrogen, aliphatic, OR, N$(R)_2$, —$(CH_2)_m$N(R)C(O)$CH_2)_p$R, —$(CH_2)_m$OC(O)$(CH_2)_p$R, —$(CH_2)_m$C(O)$(CH_2)_p$N$(R)_2$, —$(CH_2)_m$C(O)$(CH_2)_p$OR, —$(CH_2)_m$N(R)C(O)$(CH_2)_p$OR, —$(CH_2)_m$N(R)C(O)$(CH_2)_p$N$(R)_2$, —$(CH_2)_m$OC(O)$(CH_2)_p$OR, —$(CH_2)_m$OC(O)$(CH_2)_p$N$(R)_2$, —$(CH_2)_m$N$_3$, —O$(CH_2)_m$N$_3$—$(CH_2)_m$N$(R)_2$, —$(CH_2)_m$OR, —$(CH_2)_m$S(O)$(CH_2)_p$R, —$(CH_2)_m$S(O)$_2$$(CH_2)_p$R, —$(CH_2)_m$SO$_2$$(CH_2)_p$N$(R)_2$, or —$(CH_2)_m$N(R)SO$_2$$(CH_2)_p$R;

$R^5$ and $R^6$ are independently hydrogen, aliphatic, alkylaryl, aralkyl, aryl, heteroalkyl, alkylheteroaryl, heterocyclyl, heteroaryl, OR, SR, —O$(CH_2)_m$N(R)C(O)$(CH_2)_p$R, —O$(CH_2)_m$OC(O)$(CH_2)_p$R, —O$(CH_2)_m$C(O)$(CH_2)_p$N$(R)_2$, —O$(CH_2)_m$C(O)$(CH_2)_p$OR, —O$(CH_2)_m$N(R)C(O)$(CH_2)_p$OR, —O$(CH_2)_m$N(R)C(O)$(CH_2)_p$N$(R)_2$, —O$(CH_2)_m$OC(O)$(CH_2)_p$OR, —O$(CH_2)_m$OC(O)$(CH_2)_p$N$(R)_2$, —NR$(CH_2)_m$N(R)C(O)$(CH_2)_p$R, —NR$(CH_2)_m$OC(O)$(CH_2)_p$R, —NR$(CH_2)_m$C(O)$(CH_2)_p$N$(R)_2$, —NR$(CH_2)_m$C(O)$(CH_2)_p$OR, —NR$(CH_2)_m$N(R)C(O)$(CH_2)_p$OR, —NR$(CH_2)_m$N(R)C(O)$(CH_2)_p$N$(R)_2$, —NR$(CH_2)_m$OC(O)$(CH_2)_p$OR, —NR$(CH_2)_m$OC(O)$(CH_2)_p$N$(R)_2$, —$(CH_2)_m$N(R)C(O)$CH_2)_p$R, —$(CH_2)_m$OC(O)$(CH_2)_p$R, —$(CH_2)_m$C(O)$(CH_2)_p$N$(R)_2$, —$(CH_2)_m$C(O)$(CH_2)_p$OR, —$(CH_2)_m$N(R)C(O)$(CH_2)_p$OR, —$(CH_2)_m$N(R)C(O)$(CH_2)_p$N$(R)_2$, —$(CH_2)_m$OC(O)$(CH_2)_p$OR, —$(CH_2)_m$OC(O)$(CH_2)_p$N$(R)_2$, —$(CH_2)_m$N$_3$, —O$(CH_2)_m$N$_3$—$(CH_2)_m$N$(R)_2$, —$(CH_2)_m$OR, —$(CH_2)_m$S(O)$(CH_2)_p$R, —$(CH_2)_m$S(O)$_2$$(CH_2)_p$R, —$(CH_2)_m$SO$_2$$(CH_2)_p$N$(R)_2$, or —$(CH_2)_m$N(R)SO$_2$$(CH_2)_p$R;

$R^7$, $R^8$, $R^9$ and $R^{10}$ are independently hydrogen, halogen, aliphatic, alkylaryl, aralkyl, aryl, heteroalkyl, alkylheteroaryl, heterocyclyl, heteroaryl, OR, N$(R)_2$, SR, —O$(CH_2)_m$N(R)C(O)$(CH_2)_p$R, —O$(CH_2)_m$OC(O)$(CH_2)_p$R, —O$(CH_2)_m$C(O)$(CH_2)_p$N$(R)_2$, —O$(CH_2)_m$C(O)$(CH_2)_p$OR, —O$(CH_2)_m$N(R)C(O)$(CH_2)_p$OR, —O$(CH_2)_m$N(R)C(O)$(CH_2)_p$N$(R)_2$, —O$(CH_2)_m$OC(O)$(CH_2)_p$OR, —O$(CH_2)_m$OC(O)$(CH_2)_p$N$(R)_2$, —NR$(CH_2)_m$N(R)C(O)$(CH_2)_p$R, —NR$(CH_2)_m$OC(O)$(CH_2)_p$R, —NR$(CH_2)_m$C(O)$(CH_2)_p$N$(R)_2$, —NR$(CH_2)_m$C(O)$(CH_2)_p$OR, —NR$(CH_2)_m$N(R)C(O)$(CH_2)_p$OR, —NR$(CH_2)_m$N(R)C(O)$(CH_2)_p$N$(R)_2$, —NR$(CH_2)_m$OC(O)$(CH_2)_p$OR, —NR$(CH_2)_m$OC(O)$(CH_2)_p$NR)_2$, —$(CH_2)_m$N(R)C(O)$CH_2)_p$R, —$(CH_2)_m$OC(O)$(CH_2)_p$R, —$(CH_2)_m$C(O)$(CH_2)_p$N$(R)_2$, —$(CH_2)_m$C(O)$(CH_2)_p$OR, —$(CH_2)_m$N(R)C(O)$(CH_2)_p$OR, —$(CH_2)_m$N(R)C(O)$(CH_2)_p$N$(R)_2$, —$(CH_2)_m$OC(O)$(CH_2)_p$OR, —$(CH_2)_m$OC(O)$(CH_2)_p$N$(R)_2$, —$(CH_2)_m$N$_3$, —O$(CH_2)_m$N$_3$—$(CH_2)_m$N$(R)_2$, —$(CH_2)_m$OR, —$(CH_2)_m$S(O)$(CH_2)_p$R, —$(CH_2)_m$S(O)$_2$$(CH_2)_p$R, —$(CH_2)_m$SO$_2$$(CH_2)_p$N$(R)_2$, or —$(CH_2)_m$N(R)SO$_2$$(CH_2)_p$R; and R, m and p are as defined above for formula I.

In yet another embodiment of formula III or III', X is O or NR;

Y is —O—$(CH_2)_m$COOR or —O—$(CH_2)_m$CON$(R)_2$, wherein the groups bound to the nitrogen atom may be in the Z- or E-configuration;

$R^1$ and $R^2$ are independently hydrogen, halogen;

$R^3$ and $R^4$ are independently hydrogen, aliphatic, OR, N$(R)_2$, —$(CH_2)_m$N(R)C(O)$CH_2)_p$R, —$(CH_2)_m$OC(O)$(CH_2)_p$R, —$(CH_2)_m$N(R)C(O)$(CH_2)_p$OR, —$(CH_2)_m$N(R)C $(O)(CH_2)_pN(R)_2$, —$(CH_2)_mOC(O)(CH_2)_pOR$, —$(CH_2)_mOC(O)(CH_2)_pN(R)_2$, —$(CH_2)_mN_3$, —$(CH_2)_mN(R)_2$, or —$(CH_2)_mOR$;

$R^5$ and $R^6$ are independently hydrogen, aliphatic, aralkyl, heteroalkyl, heterocyclyl, or heteroaryl; and $R^7$, $R^8$, $R^9$ and $R^{10}$ are independently hydrogen, aliphatic, alkylaryl, aralkyl, aryl, heteroalkyl, alkylheteroaryl, heterocyclyl, heteroaryl, OR, $N(R)_2$, SR, —$O(CH_2)_mN(R)C(O)(CH_2)_pR$, —$O(CH_2)_mOC(O)(CH_2)_pR$, —$O(CH_2)_mC(O)(CH_2)_pN(R)_2$, —$O(CH_2)_mC(O)(CH_2)_pOR$, —$O(CH_2)_mN(R)C(O)(CH_2)_pOR$, —$O(CH_2)_mN(R)C(O)(CH_2)_pN(R)_2$, —$O(CH_2)_mOC(O)(CH_2)_pOR$, —$O(CH_2)_mOC(O)(CH_2)_pN(R)_2$, —$NR(CH_2)_mN(R)C(O)(CH_2)_pR$, —$NR(CH_2)_mOC(O)(CH_2)_pR$, —$NR(CH_2)_mC(O)(CH_2)_pN(R)_2$, —$NR(CH_2)_mC(O)(CH_2)_pOR$, —$NR(CH_2)_mN(R)C(O)(CH_2)_pOR$, —$NR(CH_2)_mN(R)C(O)(CH_2)_pN(R)_2$, —$NR(CH_2)_mOC(O)(CH_2)_pOR$, or —$NR(CH_2)_mOC(O)(CH_2)_pN(R)_2$.

In yet another embodiment of formula III or III', X is O or NR;

Y is —O—$(CH_2)_m$COOR or —O—$(CH_2)_m$CON$(R)_2$, wherein the groups bound to the nitrogen atom may be in the Z- or E-configuration;

$R^1$ and $R^2$ are independently hydrogen, halogen;

$R^3$ and $R^4$ are independently hydrogen, aliphatic, —$(CH_2)_mN(R)C(O)CH_2)_pR$, —$(CH_2)_mOC(O)(CH_2)_pR$, —$(CH_2)_mN(R)C(O)(CH_2)_pOR$, —$(CH_2)_mN(R)C(O)(CH_2)_pN(R)_2$, —$(CH_2)_mOC(O)(CH_2)_pOR$, —$(CH_2)_mOC(O)(CH_2)_pN(R)_2$, —$(CH_2)_mN_3$, —$(CH_2)_mN(R)_2$, or —$(CH_2)_mOR$;

$R^5$ and $R^6$ are independently hydrogen, aliphatic, aralkyl, heteroalkyl, heterocyclyl, or heteroaryl;

$R^7$, $R^8$ are independently alkylaryl, aralkyl, aryl, heteroalkyl, alkylheteroaryl, heterocyclyl, heteroaryl, OR, $N(R)_2$, SR, —$O(CH_2)_mN(R)C(O)(CH_2)_pR$, —$O(CH_2)_mOC(O)(CH_2)_pR$, —$O(CH_2)_mC(O)(CH_2)_pN(R)_2$, —$O(CH_2)_mC(O)(CH_2)_pOR$, —$O(CH_2)_mN(R)C(O)(CH_2)_pOR$, —$O(CH_2)_mN(R)C(O)(CH_2)_pN(R)_2$, —$O(CH_2)_mOC(O)(CH_2)_pOR$, —$O(CH_2)_mOC(O)(CH_2)_pN(R)_2$, —$NR(CH_2)_mN(R)C(O)(CH_2)_pR$, —$NR(CH_2)_mOC(O)(CH_2)_pR$, —$NR(CH_2)_mC(O)(CH_2)_pN(R)_2$, —$NR(CH_2)_mC(O)(CH_2)_pOR$, —$NR(CH_2)_mN(R)C(O)(CH_2)_pOR$, —$NR(CH_2)_mN(R)C(O)(CH_2)_pN(R)_2$, —$NR(CH_2)_mOC(O)(CH_2)_pOR$, or —$NR(CH_2)_mOC(O)(CH_2)_pN(R)_2$; and $R^9$ and $R^{10}$ independently hydrogen, aliphatic, alkylaryl, aralkyl, aryl, heteroalkyl, alkylheteroaryl, heterocyclyl, heteroaryl, OR, $N(R)_2$, SR, —$O(CH_2)_mN(R)C(O)(CH_2)_pR$, —$O(CH_2)_mOC(O)(CH_2)_pR$, —$O(CH_2)_mC(O)(CH_2)_pN(R)_2$, —$O(CH_2)_mC(O)(CH_2)_pOR$, —$O(CH_2)_mN(R)C(O)(CH_2)_pOR$, —$O(CH_2)_mN(R)C(O)(CH_2)_pN(R)_2$, —$O(CH_2)_mOC(O)(CH_2)_pOR$, —$O(CH_2)_mOC(O)(CH_2)_pN(R)_2$, —$NR(CH_2)_mN(R)C(O)(CH_2)_pR$, —$NR(CH_2)_mOC(O)(CH_2)_pR$, —$NR(CH_2)_mC(O)(CH_2)_pN(R)_2$, —$NR(CH_2)_mC(O)(CH_2)_pOR$, —$NR(CH_2)_mN(R)C(O)(CH_2)_pOR$, —$NR(CH_2)_mN(R)C(O)(CH_2)_pN(R)_2$, $NR(CH_2)_mOC(O)(CH_2)_pOR$, or —$NR(CH_2)_mOC(O)(CH_2)_pN(R)_2$.

In yet another embodiment of formula III or III', X is O or NR;

Y is —O—$(CH_2)_m$COOR or —O—$(CH_2)_m$CON$(R)_2$, wherein the groups bound to the nitrogen atom may be in the Z- or E-configuration;

$R^1$ and $R^2$ are independently hydrogen, halogen;

$R^3$ and $R^4$ are independently hydrogen, aliphatic, —$(CH_2)_mN(R)C(O)CH_2)_pR$, —$(CH_2)_mOC(O)(CH_2)_pR$, —$(CH_2)_mN(R)C(O)(CH_2)_pOR$, —$(CH_2)_mN(R)C(O)(CH_2)_pN(R)_2$, —$(CH_2)_mOC(O)(CH_2)_pOR$, —$(CH_2)_mOC(O)(CH_2)_pN(R)_2$, —$(CH_2)_mN_3$, —$(CH_2)_mN(R)_2$, or —$(CH_2)_mOR$;

$R^5$ and $R^6$ are independently hydrogen, aliphatic, aralkyl, heteroalkyl, heterocyclyl, or heteroaryl;

$R^7$, $R^8$ are independently OR, $N(R)_2$, SR, —$O(CH_2)_mN(R)C(O)(CH_2)_pR$, —$O(CH_2)_mOC(O)(CH_2)_pR$, —$O(CH_2)_mC(O)(CH_2)_pN(R)_2$, —$O(CH_2)_mC(O)(CH_2)_pOR$, —$O(CH_2)_mN(R)C(O)(CH_2)_pOR$, —$O(CH_2)_mN(R)C(O)(CH_2)_pN(R)_2$, —$O(CH_2)_mOC(O)(CH_2)_pOR$, —$O(CH_2)_mOC(O)(CH_2)_pN(R)_2$, —$NR(CH_2)_mN(R)C(O)(CH_2)_pR$, —$NR(CH_2)_mOC(O)(CH_2)_pR$, —$NR(CH_2)_mC(O)(CH_2)_pN(R)_2$, —$NR(CH_2)_mC(O)(CH_2)_pOR$, —$NR(CH_2)_mN(R)C(O)(CH_2)_pOR$, —$NR(CH_2)_mN(R)C(O)(CH_2)_pN(R)_2$, —$NR(CH_2)_mOC(O)(CH_2)_pOR$, or —$NR(CH_2)_mOC(O)(CH_2)_pN(R)_2$; and $R^9$ and $R^{10}$ independently hydrogen, aliphatic, alkylaryl, aralkyl, aryl, heteroalkyl, alkylheteroaryl, heterocyclyl, heteroaryl, OR, $N(R)_2$, SR, —$O(CH_2)_mN(R)C(O)(CH_2)_pR$, —$O(CH_2)_mOC(O)(CH_2)_pR$, —$O(CH_2)_mC(O)(CH_2)_pN(R)_2$, —$O(CH_2)_mC(O)(CH_2)_pOR$, —$O(CH_2)_mN(R)C(O)(CH_2)_pOR$, —$O(CH_2)_mN(R)C(O)(CH_2)_pN(R)_2$, —$O(CH_2)_mOC(O)(CH_2)_pOR$, —$O(CH_2)_mOC(O)(CH_2)_pN(R)_2$, —$NR(CH_2)_mN(R)C(O)(CH_2)_pR$, —$NR(CH_2)_mOC(O)(CH_2)_pR$, —$NR(CH_2)_mC(O)(CH_2)_pN(R)_2$, —$NR(CH_2)_mC(O)(CH_2)_pOR$, —$NR(CH_2)_mN(R)C(O)(CH_2)_pOR$, —$NR(CH_2)_mN(R)C(O)(CH_2)_pN(R)_2$, —$NR(CH_2)_mOC(O)(CH_2)_pOR$, or —$NR(CH_2)_mOC(O)(CH_2)_pN(R)_2$.

In another embodiment of the invention, a compound of formula IV, a tautomer thereof, or a pharmaceutically acceptable salt, solvate, ester or prodrug thereof, is provided:

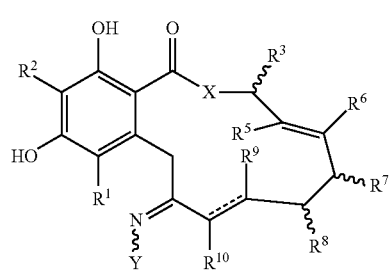

IV wherein the variables X, Y, $R^1$, $R^2$, $R^3$, $R^5$, $R^6$, $R^7$, $R^8$, $R^9$, $R^{10}$, R, m and p are as defined for formula I above; and the dashed lines represents a single or double bond.

In one embodiment of formula IV, X is O or NR.

In another embodiment of formula IV, Y is —O—$(CH_2)_m$COOR or —O—$(CH_2)_m$CON$(R)_2$, wherein the groups bound to the nitrogen atom may be in the Z- or E-configuration.

In another embodiment of formula IV, $R^1$ and $R^2$ are hydrogen.

In still another embodiment of formula IV, $R^3$ and $R^4$ are independently alkyl or hydrogen.

In still another embodiment, X is O, and $R^9$ and $R^{10}$ are hydrogen.

In another embodiment of formula IV, $R^7$ or $R^8$ are not hydrogen or aliphatic.

In another embodiment of formula IV, $R^3$ or $R^4$ are not hydrogen or aliphatic.

In another embodiment of formula IV, X is O, Y is —O—$(CH_2)_m$COOR or —O—$(CH_2)_m$CON$(R)_2$, wherein the groups bound to the nitrogen atom may be in the Z- or E-configuration; $R^1$ and $R^2$ are independently hydrogen or halogen; and $R^9$ and $R^{10}$ are hydrogen.

In another embodiment of formula IV, X is O or NR, and a double bond is present between the carbon atoms bearing $R^9$ and $R^{10}$.

In yet another embodiment of formula IV, X is O or NR, and the bond between the carbon atoms bearing $R^9$ and $R^{10}$ is a single bond.

In another embodiment of formula IV, Y is —O—$(CH_2)_m$COOR or —O—$(CH_2)_m$CON$(R)_2$, wherein the groups bound to the nitrogen atom may be in the Z- or E-configuration.

In one embodiment of formula IV, the invention provides a compound wherein:

X is O or NR;

Y is —O—$(CH_2)_m$COOR or —O—$(CH_2)_m$CON$(R)_2$, wherein the groups bound to the nitrogen atom may be in the Z- or E-configuration;

$R^1$ and $R^2$ are independently hydrogen, halogen, OR, N$(R)_2$ or aliphatic;

$R^3$ is hydrogen, aliphatic, OR, N$(R)_2$, —$(CH_2)_m$N(R)C(O)CH$_2)_p$R, —$(CH_2)_m$OC(O)$(CH_2)_p$R, —$(CH_2)_m$C(O)$(CH_2)_p$N$(R)_2$, —$(CH_2)_m$C(O)$(CH_2)_p$OR, —$(CH_2)_m$N(R)C(O)$(CH_2)_p$OR, —$(CH_2)_m$N(R)C(O)$(CH_2)_p$N$(R)_2$, —$(CH_2)_m$OC(O)$(CH_2)_p$OR, —$(CH_2)_m$OC(O)$(CH_2)_p$N$(R)_2$, —$(CH_2)_m$N$_3$, —O$(CH_2)_m$N$_3$—$(CH_2)_m$N$(R)_2$, —$(CH_2)_m$OR, —$(CH_2)_m$S(O)$(CH_2)_p$R, —$(CH_2)_m$S(O)$_2$$(CH_2)_p$R, —$(CH_2)_m$SO$_2$$(CH_2)_p$N$(R)_2$, or —$(CH_2)_m$N(R)SO$_2$$(CH_2)_p$R;

$R^5$, $R^6$, $R^9$ and $R^{10}$ are independently hydrogen, aliphatic, alkylaryl, aralkyl, aryl, heteroalkyl, alkylheteroaryl, heterocyclyl, heteroaryl, OR, SR, —O$(CH_2)_m$N(R)C(O)$(CH_2)_p$R, —O$(CH_2)_m$OC(O)$(CH_2)_p$R, —O$(CH_2)_m$C(O)$(CH_2)_p$N$(R)_2$, —O$(CH_2)_m$C(O)$(CH_2)_p$OR, —O$(CH_2)_m$N(R)C(O)$(CH_2)_p$OR, —O$(CH_2)_m$N(R)C(O)$(CH_2)_p$N$(R)_2$, —O$(CH_2)_m$OC(O)$(CH_2)_p$OR, —O$(CH_2)_m$OC(O)$(CH_2)_p$N$(R)_2$, —NR$(CH_2)_m$N(R)C(O)$(CH_2)_p$R, —NR$(CH_2)_m$OC(O)$(CH_2)_p$R, —NR$(CH_2)_m$C(O)$(CH_2)_p$N$(R)_2$, —NR$(CH_2)_m$C(O)$(CH_2)_p$OR, —NR$(CH_2)_m$N(R)C(O)$(CH_2)_p$OR, —NR$(CH_2)_m$N(R)C(O)$(CH_2)_p$N$(R)_2$, —NR$(CH_2)_m$OC(O)$(CH_2)_p$OR, —NR$(CH_2)_m$OC(O)$(CH_2)_p$N$(R)_2$, —$(CH_2)_m$N(R)C(O)$(CH_2)_p$R, —$(CH_2)_m$OC(O)$(CH_2)_p$R, —$(CH_2)_m$C(O)$(CH_2)_p$N$(R)_2$, —$(CH_2)_m$C(O)$(CH_2)_p$OR, —$(CH_2)_m$N(R)C(O)$(CH_2)_p$OR, —$(CH_2)_m$N(R)C(O)$(CH_2)_p$N$(R)_2$, —$(CH_2)_m$OC(O)$(CH_2)_p$OR, —$(CH_2)_m$OC(O)$(CH_2)_p$N$(R)_2$, —$(CH_2)_m$N$_3$, —O$(CH_2)_m$N$_3$—$(CH_2)_m$N$(R)_2$, —$(CH_2)_p$OR, —$(CH_2)_m$S(O)$(CH_2)_p$R, —$(CH_2)_m$S(O)$_2$$(CH_2)_p$R, —$(CH_2)_m$SO$_2$$(CH_2)_p$N$(R)_2$, or —$(CH_2)_m$N(R)SO$_2$$(CH_2)_p$R; and $R^7$ and $R^8$ are independently hydrogen, halogen, aliphatic, alkylaryl, aralkyl, aryl, heteroalkyl, alkylheteroaryl, heterocyclyl, heteroaryl, OR, N$(R)_2$, SR, —O$(CH_2)_m$N(R)C(O)$(CH_2)_p$R, —O$(CH_2)_m$OC(O)$(CH_2)_p$R, —O$(CH_2)_m$C(O)$(CH_2)_p$N$(R)_2$, —O$(CH_2)_m$C(O)$(CH_2)_p$OR, —O$(CH_2)_m$N(R)C(O)$(CH_2)_p$OR, —O$(CH_2)_m$N(R)C(O)$(CH_2)_p$N$(R)_2$, —O$(CH_2)_m$OC(O)$(CH_2)_p$OR, —O$(CH_2)_m$OC(O)$(CH_2)_p$N$(R)_2$, —NR$(CH_2)_m$N(R)C(O)$(CH_2)_p$R, —NR$(CH_2)_m$OC(O)$(CH_2)_p$R, —NR$(CH_2)_m$C(O)$(CH_2)_p$N$(R)_2$, —NR$(CH_2)_m$C(O)$(CH_2)_p$OR, —NR$(CH_2)_m$N(R)C(O)$(CH_2)_p$OR, —NR$(CH_2)_m$N(R)C(O)$(CH_2)_p$N$(R)_2$, —NR$(CH_2)_m$OC(O)$(CH_2)_p$OR, —NR$(CH_2)_m$OC(O)$(CH_2)_p$N$(R)_2$, —$(CH_2)_m$N(R)C(O)$(CH_2)_p$R, —$(CH_2)_m$OC(O)$(CH_2)_p$R, —$(CH_2)_m$C(O)$(CH_2)_p$N$(R)_2$, —$(CH_2)_m$C(O)$(CH_2)_p$OR, —$(CH_2)_m$N(R)C(O)$(CH_2)_p$OR, —$(CH_2)_m$N(R)C(O)$(CH_2)_p$N$(R)_2$, —$(CH_2)_m$OC(O)$(CH_2)_p$OR, —$(CH_2)_m$OC(O)$(CH_2)_p$N$(R)_2$, —$(CH_2)_m$N$_3$, —O$(CH_2)_m$N$_3$—$(CH_2)_m$N$(R)_2$, —$(CH_2)_m$OR, —$(CH_2)_m$S(O)$(CH_2)_p$R, —$(CH_2)_m$S(O)$_2$$(CH_2)_p$R, —$(CH_2)_m$SO$_2$$(CH_2)_p$N$(R)_2$, or —$(CH_2)_m$N(R)SO$_2$$(CH_2)_p$R.

In yet another embodiment of formula IV, X is O or NR;

Y is —O—$(CH_2)_m$COOR or —O—$(CH_2)_m$CON$(R)_2$, wherein the groups bound to the nitrogen atom may be in the Z- or E-configuration;

$R^1$ and $R^2$ are independently hydrogen, halogen;

$R^3$ is hydrogen, aliphatic, OR, N$(R)_2$, —$(CH_2)_m$N(R)C(O)CH$_2)_p$R, —$(CH_2)_m$OC(O)$(CH_2)_p$R, —$(CH_2)_m$N(R)C(O)$(CH_2)_p$OR, —$(CH_2)_m$N(R)C(O)$(CH_2)_p$N$(R)_2$, —$(CH_2)_m$OC(O)$(CH_2)_p$OR, —$(CH_2)_m$OC(O)$(CH_2)_p$N$(R)_2$, —$(CH_2)_m$N$_3$, —$(CH_2)_m$N$(R)_2$, or —$(CH_2)_m$OR;

$R^5$, $R^6$, $R^9$ and $R^{10}$ are independently hydrogen, aliphatic, aralkyl, heteroalkyl, heterocyclyl, or heteroaryl; and $R^7$ and $R^8$ are independently hydrogen, aliphatic, alkylaryl, aralkyl, aryl, heteroalkyl, alkylheteroaryl, heterocyclyl, heteroaryl, OR, N$(R)_2$, SR, —O$(CH_2)_m$N(R)C(O)$(CH_2)_p$R, —O$(CH_2)_m$OC(O)$(CH_2)_p$R, —O$(CH_2)_m$C(O)$(CH_2)_p$N$(R)_2$, —O$(CH_2)_m$C(O)$(CH_2)_p$OR, —O$(CH_2)_m$N(R)C(O)$(CH_2)_p$OR, —O$(CH_2)_{Dp}$N(R)C(O)$(CH_2)_p$N$(R)_2$, —O$(CH_2)_m$OC(O)$(CH_2)_p$OR, —O$(CH_2)_m$OC(O)$(CH_2)_p$N$(R)_2$, —NR$(CH_2)_m$N(R)C(O)$(CH_2)_p$R, —NR$(CH_2)_m$OC(O)$(CH_2)_p$R, —NR$(CH_2)_m$C(O)$(CH_2)_p$N$(R)_2$, —NR$(CH_2)_m$C(O)$(CH_2)_p$OR, —NR$(CH_2)_m$N(R)C(O)$(CH_2)_p$OR, —NR$(CH_2)_m$N(R)C(O)$(CH_2)_p$N$(R)_2$, —NR$(CH_2)_m$OC(O)$(CH_2)_p$OR, or —NR$(CH_2)_m$OC(O)$(CH_2)_p$N$(R)_2$.

In yet another embodiment of formula IV, X is O or NR;

Y is —O—$(CH_2)_m$COOR or —O—$(CH_2)_m$CON$(R)_2$, wherein the groups bound to the nitrogen atom may be in the Z- or E-configuration;

$R^1$ and $R^2$ are independently hydrogen, halogen;

$R^3$ is hydrogen, aliphatic, OR, N$(R)_2$, —$(CH_2)_m$N(R)C(O)CH$_2)_p$R, —$(CH_2)_m$OC(O)$(CH_2)_p$R, —$(CH_2)_m$N(R)C(O)$(CH_2)_p$OR, —$(CH_2)_m$N(R)C(O)$(CH_2)_p$N(t)$_2$, —$(CH_2)_m$OC(O)$(CH_2)_p$OR, —$(CH_2)_m$OC(O)$(CH_2)_p$N$(R)_2$, —$(CH_2)_m$N$_3$—$(CH_2)_m$N$(R)_2$, or —$(CH_2)_m$OR;

$R^5$, $R^6$, $R^9$ and $R^{10}$ are independently hydrogen, aliphatic, aralkyl, heteroalkyl, heterocyclyl, or heteroaryl;

$R^7$ and $R^8$ are independently OR, N$(R)_2$, SR, —O$(CH_2)_m$N(R)C(O)$(CH_2)_p$R, —O$(CH_2)_m$OC(O)$(CH_2)_p$R, —O$(CH_2)_m$C(O)$(CH_2)_p$N$(R)_2$, —O$(CH_2)_m$C(O)$(CH_2)_p$OR, —O$(CH_2)_m$N(R)C(O)$(CH_2)_p$OR, —O$(CH_2)_m$N(R)C(O)$(CH_2)_p$N$(R)_2$, —O$(CH_2)_m$OC(O)$(CH_2)_p$OR, —O$(CH_2)_m$OC(O)$(CH_2)_p$N$(R)_2$, —NR$(CH_2)_m$N(R)C(O)$(CH_2)_p$R, —NR$(CH_2)_m$OC(O)$(CH_2)_p$R, —NR$(CH_2)_m$C(O)$(CH_2)_p$N$(R)_2$, —NR$(CH_2)_m$C(O)$(CH_2)_p$OR, —NR$(CH_2)_m$N(R)C(O)$(CH_2)_p$OR, —NR$(CH_2)_m$N(R)C(O)$(CH_2)_p$N$(R)_2$, —NR$(CH_2)_m$OC(O)$(CH_2)_p$OR, or —NR$(CH_2)_m$OC(O)$(CH_2)_p$N$(R)_2$.

In another embodiment of the invention, a compound of formula V, a tautomer thereof, or a pharmaceutically acceptable salt, solvate, ester or prodrug thereof, is provided,

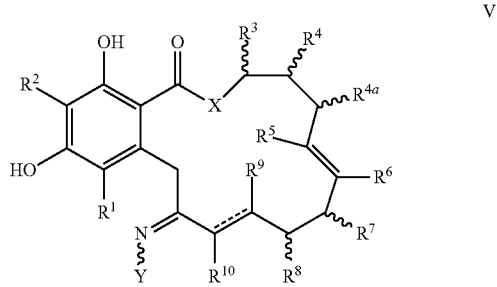

V wherein the variables X, Y, $R^1$, $R^2$, $R^3$, $R^4$, $R^5$, $R^6$, $R^7$, $R^8$, $R^9$, $R^{10}$, R, m and p are as defined for formula I above; and $R^{4a}$ is as defined for $R^4$ in formula I above; and the dashed lines represents a single or double bond.

In one embodiment of formula V, X is O or NR. In another embodiment of formula V, X is O or NR, and a double bond is present between the carbon atoms bearing $R^9$ and $R^{10}$.

In yet another embodiment of formula V, X is O or NR, and the bond between the carbon atoms bearing $R^9$ and $R^{10}$ is a single bond.

In another embodiment of formula V, Y is —O—$(CH_2)_m$COOR or —O—$(CH_2)_m$CON$(R)_2$, wherein the groups bound to the nitrogen atom may be in the Z- or E-configuration.

In another embodiment of formula V, $R^1$ and $R^2$ are hydrogen.

In still another embodiment of formula V, $R^3$ is alkyl or hydrogen.

In still another embodiment of formula V, $R^4$ and $R^{4a}$ are independently alkyl or hydrogen.

In still another embodiment of formula V, X is O, and $R^9$ and $R^{10}$ are hydrogen.

In another embodiment of formula V, X is O, Y is —O—$(CH_2)_m$COOR or —O—$(CH_2)_m$CON$(R)_2$, wherein the groups bound to the nitrogen atom may be in the Z- or E-configuration; $R^1$ and $R^2$ are independently hydrogen or halogen; and $R^9$ and $R^{10}$ are hydrogen.

In one embodiment of formula V, the invention provides a compound wherein:

X is O or NR;

Y is —O—$(CH_2)_m$COOR or —O—$(CH_2)_m$CON$(R)_2$, wherein the groups, bound to the nitrogen atom may be in the Z- or E-configuration;

$R^1$ and $R^2$ are independently hydrogen, halogen, OR, N$(R)_2$ or aliphatic;

$R^3$, $R^4$ and $R^{4a}$ are independently hydrogen, aliphatic, OR, N$(R)_2$, —$(CH_2)_m$N(R)C(O)$CH_2)_p$R, —$(CH_2)_m$OC(O)$(CH_2)_p$R, —$(CH_2)_m$C(O)$(CH_2)_p$N$(R)_2$, —$(CH_2)_m$C(O)$(CH_2)_p$OR, —$(CH_2)_m$N(R)C(O)$(CH_2)_p$OR, —$(CH_2)_m$N(R)C(O)$(CH_2)_p$N$(R)_2$, —$(CH_2)_m$OC(O)$(CH_2)_p$OR, —$(CH_2)_m$OC(O)$(CH_2)_p$N$(R)_2$, —$(CH_2)_m$N$_3$, —O$(CH_2)_m$N$_3$—$(CH_2)_m$N$(R)_2$, —$(CH_2)_m$S(O)$(CH_2)_p$R, —$(CH_2)_m$S(O)$_2$$(CH_2)_p$R, —$(CH_2)_m$SO$_2$$(CH_2)_p$N$(R)_2$, or —$(CH_2)_m$N(R)SO$_2$$(CH_2)_p$R;

$R^5$, $R^6$, $R^9$ and $R^{10}$ are independently hydrogen, aliphatic, alkylaryl, aralkyl, aryl, heteroalkyl, alkylheteroaryl, heterocyclyl, heteroaryl, OR, SR, —O$(CH_2)_m$N(R)C(O)$(CH_2)_p$R, —O$(CH_2)_m$OC(O)$(CH_2)_p$R, —O$(CH_2)_m$C(O)$(CH_2)_p$N$(R)_2$, —O$(CH_2)_m$C(O)$(CH_2)_p$OR, —O$(CH_2)_m$N(R)C(O)$(CH_2)_p$OR, —O$(CH_2)_m$N(R)C(O)$(CH_2)_p$N$(R)_2$, —O$(CH_2)_m$OC(O)$(CH_2)_p$OR, —O$(CH_2)_m$OC(O)$(CH_2)_p$N$(R)_2$, —NR$(CH_2)_m$N(R)C(O)$(CH_2)_p$, R, —NR$(CH_2)_m$OC(O)$(CH_2)_p$R, —NR$(CH_2)_m$C(O)$(CH_2)_p$N$(R)_2$, —NR$(CH_2)_m$C(O)$(CH_2)_p$OR, —NR$(CH_2)_m$N(R)C(O)$(CH_2)_p$OR, —NR$(CH_2)_m$N(R)C(O)$(CH_2)_p$N$(R)_2$, —NR$(CH_2)_m$OC(O)$(CH_2)_p$OR, —NR$(CH_2)_m$OC(O)$(CH_2)_p$N$(R)_2$, —$(CH_2)_m$N(R)C(O)$(CH_2)_p$R, —$(CH_2)_m$OC(O)$(CH_2)_p$R, —$(CH_2)_m$C(O)$(CH_2)_p$N$(R)_2$, —$(CH_2)_m$C(O)$(CH_2)_p$OR, —$(CH_2)_m$N(R)C(O)$(CH_2)_p$OR, —$(CH_2)_m$N(R)C(O)$(CH_2)_p$N$(R)_2$, —$(CH_2)_m$OC(O)$(CH_2)_p$OR, —$(CH_2)_m$OC(O)$(CH_2)_p$N$(R)_2$, —$(CH_2)_m$N$_3$, —O$(CH_2)_m$N$_3$—$(CH_2)_m$N$(R)_2$, —$(CH_2)_m$OR, —$(CH_2)_m$S(O)$(CH_2)_p$R, —$(CH_2)_m$S(O)$_2$$(CH_2)_p$R, —$(CH_2)_m$SO$_2$$(CH_2)_p$N$(R)_2$, or —$(CH_2)_m$N(R)SO$_2$$(CH_2)_p$R;

$R^7$ and $R^8$ are independently hydrogen, halogen, aliphatic, alkylaryl, aralkyl, aryl, heteroalkyl, alkylheteroaryl, heterocyclyl, heteroaryl, OR, N$(R)_2$, SR, —O$(CH_2)_m$N(R)C(O)$(CH_2)_p$R, —O$(CH_2)_m$OC(O)$(CH_2)_p$R, —O$(CH_2)_m$C(O)$(CH_2)_p$N$(R)_2$, —O$(CH_2)_m$C(O)$(CH_2)_p$OR, —O$(CH_2)_m$N(R)C(O)$(CH_2)_p$OR, —O$(CH_2)_m$N(R)C(O)$(CH_2)_p$N$(R)_2$, —O$(CH_2)_m$OC(O)$(CH_2)_p$OR, —O$(CH_2)_m$OC(O)$(CH_2)_p$N$(R)_2$, —NR$(CH_2)_m$N(R)C(O)$(CH_2)_p$R, —NR$(CH_2)_m$OC(O)$(CH_2)_p$R, —NR$(CH_2)_m$C(O)$(CH_2)_p$N$(R)_2$, —NR$(CH_2)_m$C(O)$(CH_2)_p$OR, —NR$(CH_2)_m$N(R)C(O)$(CH_2)_p$OR, —NR$(CH_2)_m$N(R)C(O)$(CH_2)_p$N$(R)_2$, —NR$(CH_2)_m$OC(O)$(CH_2)_p$OR, —NR$(CH_2)_m$OC(O)$(CH_2)_p$N$(R)_2$, —$(CH_2)_m$N(R)C(O)$(CH_2)_p$R, —$(CH_2)_m$OC(O)$(CH_2)_p$R, —$(CH_2)_m$C(O)$(CH_2)_p$N$(R)_2$, —$(CH_2)_m$C(O)$(CH_2)_p$OR, —$(CH_2)_m$N(R)C(O)$(CH_2)_p$OR, —$(CH_2)_m$N(R)C(O)$(CH_2)_p$N$(R)_2$, —$(CH_2)_m$OC(O)$(CH_2)_p$OR, —$(CH_2)_m$OC(O)$(CH_2)_p$N$(R)_2$, —$(CH_2)_m$N$_3$, —O$(CH_2)_m$N$_3$—$(CH_2)_m$N$(R)_2$, —$(CH_2)_m$OR, —$(CH_2)_m$S(O)$(CH_2)_p$R, —$(CH_2)_m$S(O)$_2$$(CH_2)_p$R, —$(CH_2)_m$SO$_2$$(CH_2)_p$N$(R)_2$, or —$(CH_2)_m$N(R)SO$_2$$(CH_2)_p$R.

In yet another embodiment of formula V, X is O or NR;

Y is —O—$(CH_2)_m$COOR or —O—$(CH_2)_m$CON$(R)_2$, wherein the groups bound to the nitrogen atom may be in the Z- or E-configuration;

$R^1$ and $R^2$ are independently hydrogen, halogen;

$R^3$, $R^4$ and $R^{4a}$ are independently hydrogen, aliphatic, OR, N$(R)_2$, —$(CH_2)_m$N(R)C(O)$CH_2)_p$R, —$(CH_2)_m$OC(O)$(CH_2)_p$R, —$(CH_2)_m$N(R)C(O)$(CH_2)_p$OR, —$(CH_2)_m$N(R)C(O)$(CH_2)_p$N$(R)_2$, —$(CH_2)_m$OC(O)$(CH_2)_p$OR, —$(CH_2)_m$OC(O)$(CH_2)_p$N$(R)_2$, —$(CH_2)_m$N$_3$, —$(CH_2)_m$N$(R)_2$, or —$(CH_2)_m$OR;

$R^5$, $R^6$, $R^9$ and $R^{10}$ are independently hydrogen, aliphatic, aralkyl, heteroalkyl, heterocyclyl, or heteroaryl; and $R^7$ and $R^8$ are independently hydrogen, aliphatic, alkylaryl, aralkyl, aryl, heteroalkyl, alkylheteroaryl, heterocyclyl, heteroaryl, OR, N$(R)_2$, SR, —O$(CH_2)_m$N(R)C(O)$(CH_2)_p$R, —O$(CH_2)_m$OC(O)$(CH_2)_p$R, —O$(CH_2)_m$C(O)$(CH_2)_p$N$(R)_2$, —O$(CH_2)_m$C(O)$(CH_2)_p$OR, —O$(CH_2)_m$N(R)C(O)$(CH_2)_p$OR, —O$(CH_2)_m$N(R)C(O)$(CH_2)_p$N$(R)_2$, —O$(CH_2)_m$OC(O)$(CH_2)_p$OR, —O$(CH_2)_m$OC(O)$(CH_2)_p$N$(R)_2$, —NR$(CH_2)_m$N(R)C(O)$(CH_2)_p$R, —NR$(CH_2)_m$OC(O)$(CH_2)_p$R, —NR$(CH_2)_m$C(O)$(CH_2)_p$N$(R)_2$, —NR$(CH_2)_m$C(O)$(CH_2)_p$OR, —NR$(CH_2)_m$N(R)C(O)$(CH_2)_p$OR, —NR$(CH_2)_m$N(R)C(O)$(CH_2)_p$N$(R)_2$, —NR$(CH_2)_m$OC(O)$(CH_2)_p$OR, or —NR$(CH_2)_m$OC(O)$(CH_2)_p$N$(R)_2$.

In yet another embodiment of formula V, X is O or NR;

Y is —O—$(CH_2)_m$COOR or —O—$(CH_2)_m$CON$(R)_2$, wherein the groups bound to the nitrogen atom may be in the Z- or E-configuration;

$R^1$ and $R^2$ are independently hydrogen, halogen;

$R^3$, $R^4$ and $R^{4a}$ are independently hydrogen, aliphatic, —$(CH_2)_m$N(R)C(O)$CH_2)_p$R, —$(CH_2)_m$OC(O)$(CH_2)_p$R, —$(CH_2)_m$N(R)C(O)$(CH_2)_p$OR, —$(CH_2)_m$N(R)C(O)$(CH_2)_p$N$(R)_2$, —$(CH_2)_m$OC(O)$(CH_2)_p$OR, —$(CH_2)_m$OC(O)$(CH_2)_p$N$(R)_2$, —$(CH_2)_m$N$_3$, —$(CH_2)_m$N$(R)_2$, or —$(CH_2)_m$OR;

$R^5$, $R^6$, $R^9$ and $R^{10}$ are independently hydrogen, aliphatic aralkyl, heteroalkyl, heterocyclyl, or heteroaryl;

$R^7$ and $R^8$ are independently OR, N$(R)_2$, SR, —O$(CH_2)_m$N(R)C(O)$(CH_2)_p$R, —O$(CH_2)_m$OC(O)$(CH_2)_p$R, —O$(CH_2)_m$C(O)$(CH_2)_p$N$(R)_2$, —O$(CH_2)_m$C(O)$(CH_2)_p$OR, —O$(CH_2)_m$N(R)C(O)$(CH_2)_p$OR, —O$(CH_2)_m$N(R)C(O)$(CH_2)_p$N$(R)_2$, —O$(CH_2)_m$OC(O)$(CH_2)_p$OR, —O$(CH_2)_m$OC(O)$(CH_2)_p$N$(R)_2$, —NR$(CH_2)_m$N(R)C(O)$(CH_2)_p$R, —NR$(CH_2)_m$OC(O)$(CH_2)_p$R, —NR$(CH_2)_m$C(O)$(CH_2)_p$N$(R)_2$, —NR$(CH_2)_m$C(O)$(CH_2)_p$OR, —NR$(CH_2)_m$N(R)C(O)$(CH_2)_p$OR, —NR$(CH_2)_m$N(R)C(O)$(CH_2)_p$N$(R)_2$, —NR$(CH_2)_m$OC(O)$(CH_2)_p$OR, or —NR$(CH_2)_m$OC(O)$(CH_2)_p$N$(R)_2$.

In specific embodiments of the present invention, the compounds presented in Table 1, tautomers thereof, or pharmaceutically acceptable salts, solvates, esters or prodrugs thereof, are provided:

TABLE 1

TABLE 1-continued
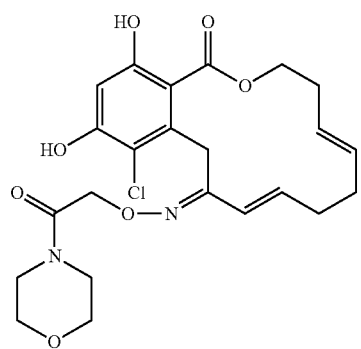 [SMILES: O=C1OCC/C=C/CC/C=C/C(=N/OCC(=O)N2CCOCC2)Cc2c(Cl)c(O)cc(O)c21]
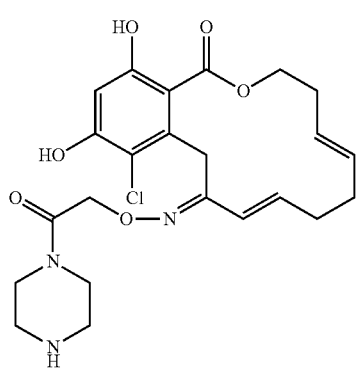
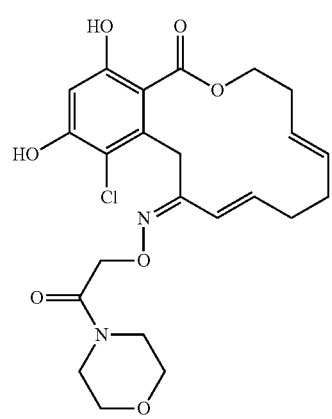
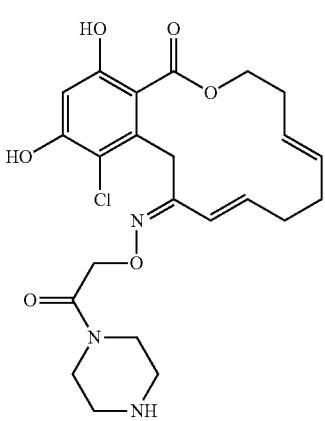
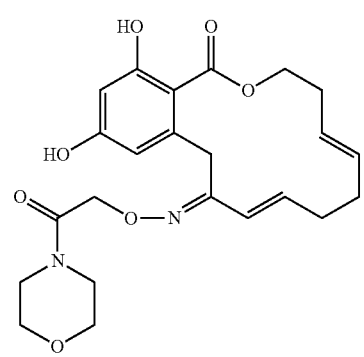 [SMILES: O=C1OCC/C=C/CC/C=C/C(=N/OCC(=O)N2CCOCC2)Cc2cc(O)cc(O)c21]
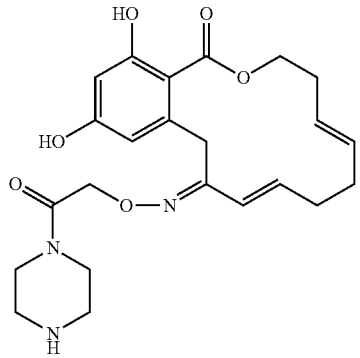
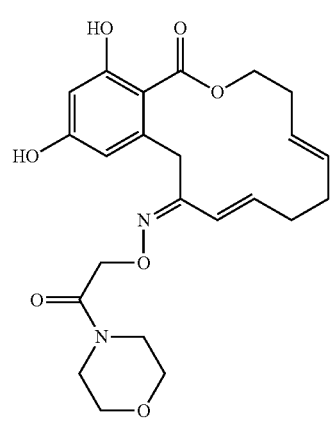 [SMILES: O=C1OCC/C=C/CC/C=C/C(=N\OCC(=O)N2CCOCC2)Cc2cc(O)cc(O)c21]
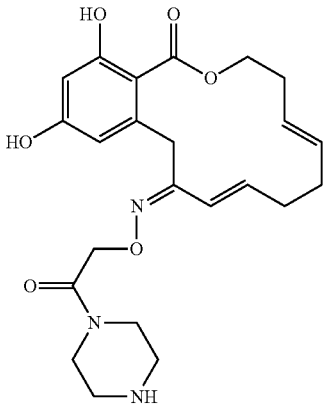 [SMILES: O=C1OCC/C=C/CC/C=C/C(=N\OCC(=O)N2CCNCC2)Cc2cc(O)cc(O)c21]

TABLE 1-continued
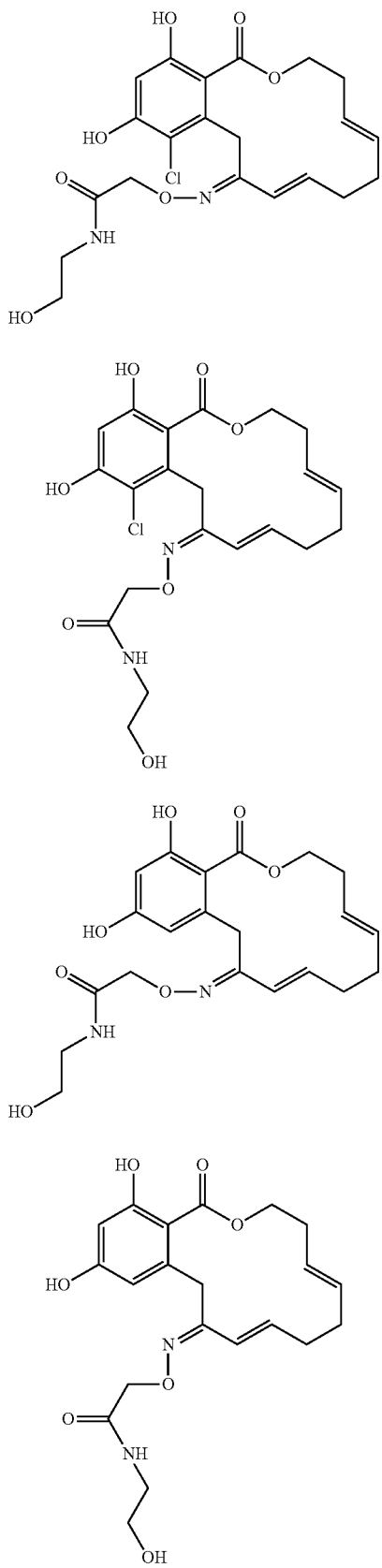
TABLE 1-continued
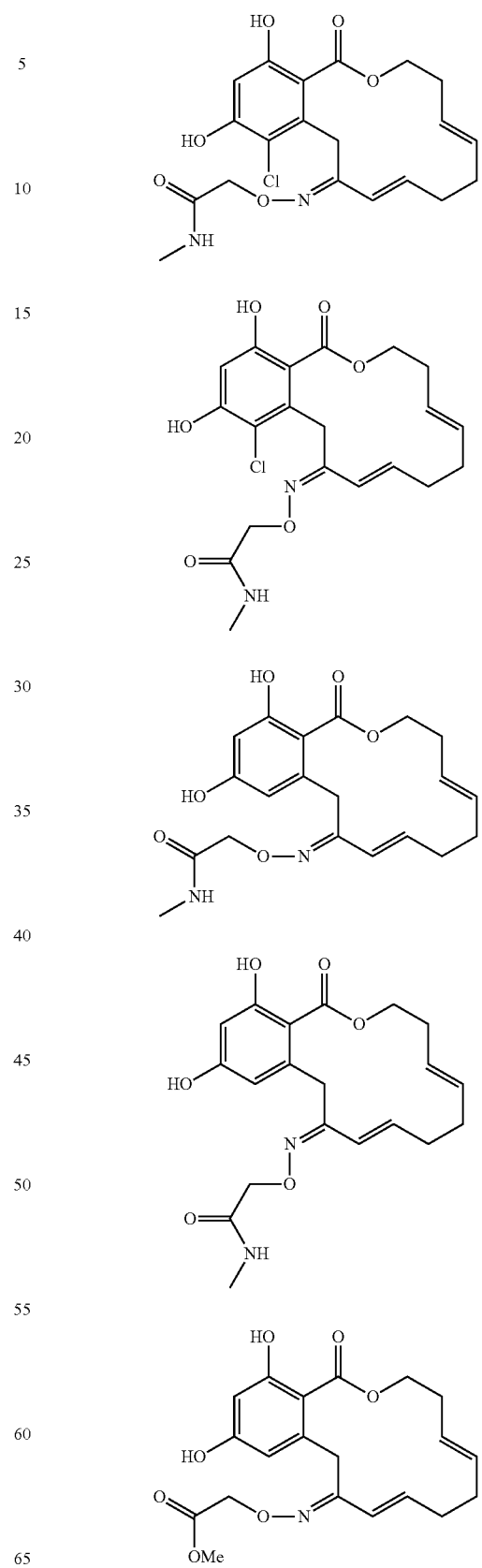

TABLE 1-continued
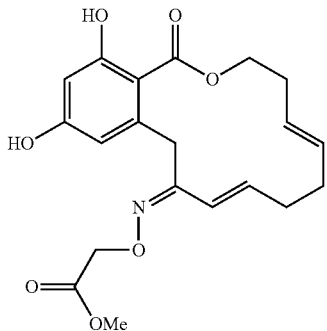
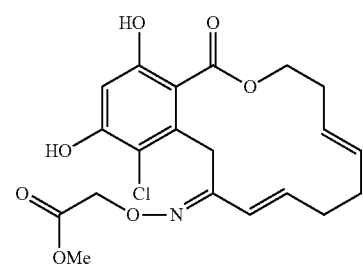 [SMILES: COC(=O)CO/N=C1/C=C/CC/C=C/CCOC(=O)c2c(O)cc(O)c(Cl)c2C1]
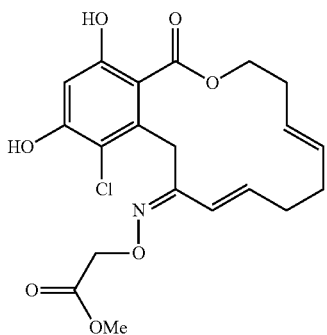 [SMILES: COC(=O)CO/N=C1\C=C\CC/C=C/CCOC(=O)c2c(O)cc(O)c(Cl)c2C1]
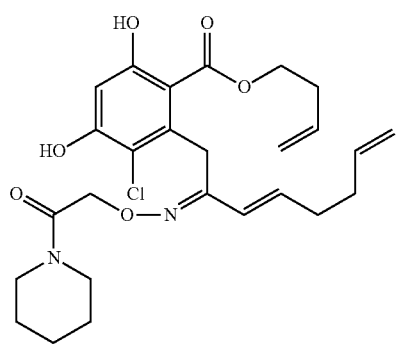 [SMILES: C=CCC/C=C/C(Cc1c(Cl)c(O)cc(O)c1C(=O)OCCC=C)=N/OCC(=O)N1CCCCC1]
TABLE 1-continued
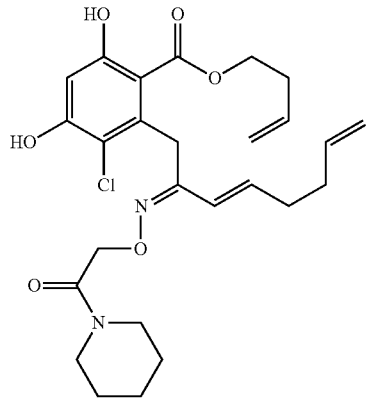 [SMILES: C=CCC/C=C/C(Cc1c(Cl)c(O)cc(O)c1C(=O)OCCC=C)=N\OCC(=O)N1CCCCC1]
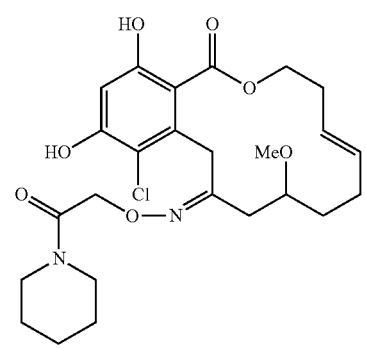 [SMILES: COC1CC/C=C/CCOC(=O)c2c(O)cc(O)c(Cl)c2C/C(=N\OCC(=O)N2CCCCC2)C1]
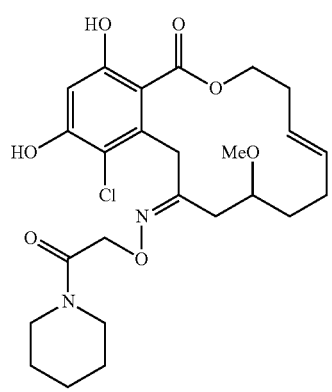 [SMILES: COC1CC/C=C/CCOC(=O)c2c(O)cc(O)c(Cl)c2C/C(=N/OCC(=O)N2CCCCC2)C1]
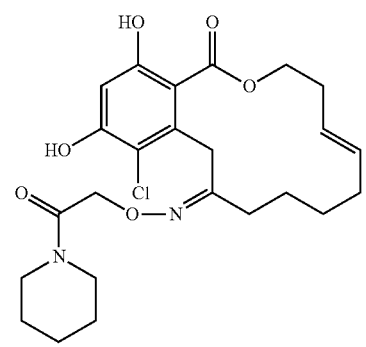 [SMILES: O=C1OCC/C=C/CCCC/C(=N/OCC(=O)N2CCCCC2)Cc2c(Cl)c(O)cc(O)c21]

TABLE 1-continued
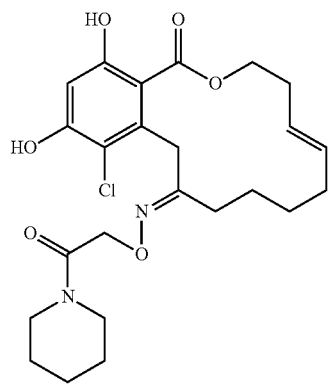 [SMILES: O=C1OCC/C=C/CCCC/C(=N\OCC(=O)N2CCCCC2)Cc2c(Cl)c(O)cc(O)c21]
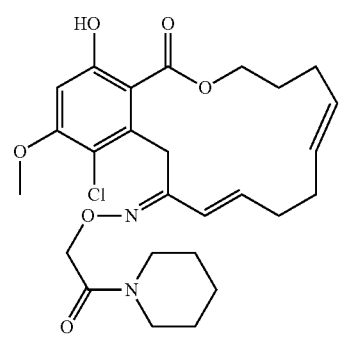 [SMILES: COc1cc(O)c2c(c1Cl)CC(=N\OCC(=O)N1CCCCC1)/C=C/CC/C=C/CCCOC2=O]
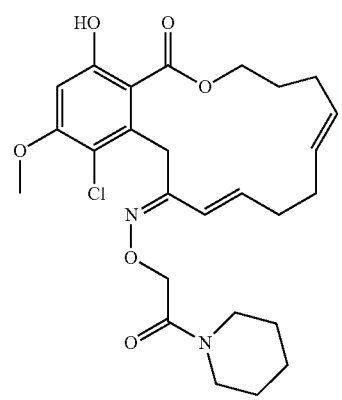 [SMILES: COc1cc(O)c2c(c1Cl)CC(=N/OCC(=O)N1CCCCC1)/C=C/CC/C=C/CCCOC2=O]
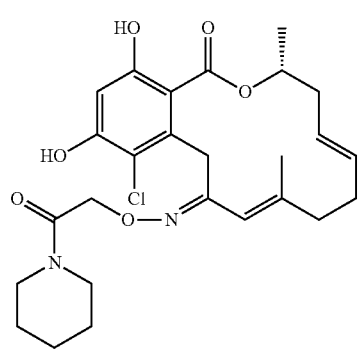 [SMILES: C/C1=C\C(=N\OCC(=O)N2CCCCC2)Cc2c(Cl)c(O)cc(O)c2C(=O)O[C@H](C)C/C=C/CC1]
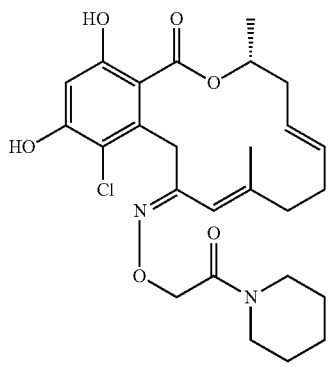
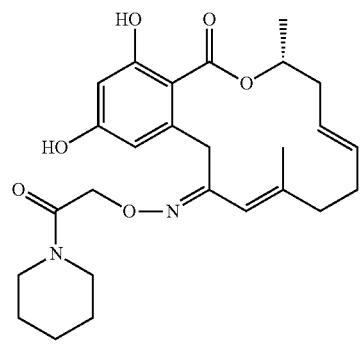 [SMILES: C/C1=C\C(=N\OCC(=O)N2CCCCC2)Cc2cc(O)cc(O)c2C(=O)O[C@H](C)C/C=C/CC1]
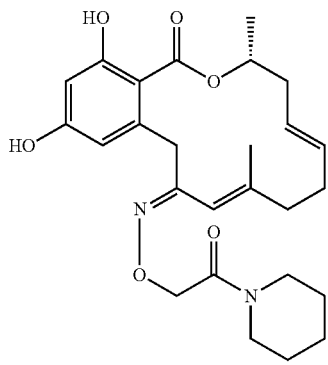 [SMILES: C/C1=C\C(=N/OCC(=O)N2CCCCC2)Cc2cc(O)cc(O)c2C(=O)O[C@H](C)C/C=C/CC1]
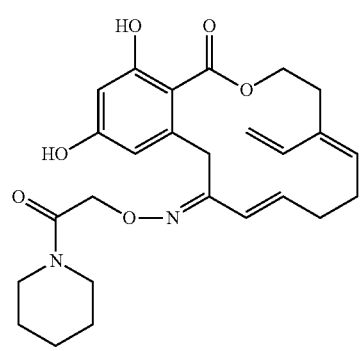 [SMILES: C=C/C1=C\CC/C=C/C(=N/OCC(=O)N2CCCCC2)Cc2cc(O)cc(O)c2C(=O)OCC1]

TABLE 1-continued
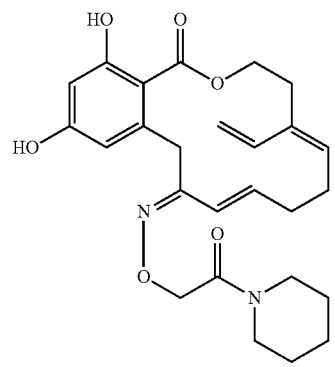
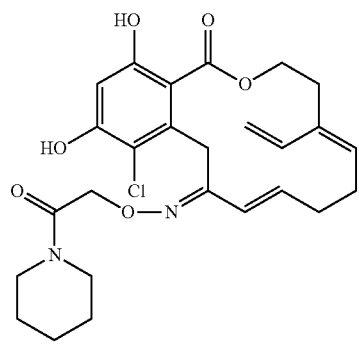 [SMILES: C=C/C1=C\CC/C=C/C(=N/OCC(=O)N2CCCCC2)Cc2c(Cl)c(O)cc(O)c2C(=O)OCC1]
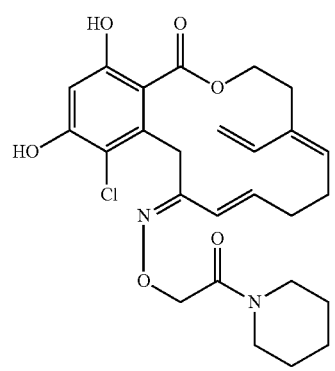 [SMILES: C=C/C1=C\CC/C=C/C(=N\OCC(=O)N2CCCCC2)Cc2c(Cl)c(O)cc(O)c2C(=O)OCC1]
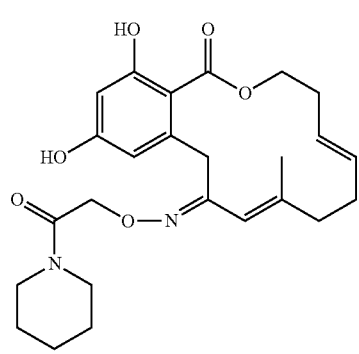
TABLE 1-continued
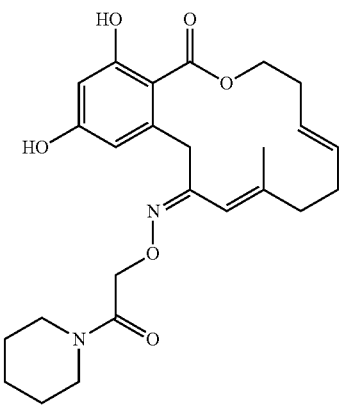 [SMILES: C/C1=C\C(=N/OCC(=O)N2CCCCC2)Cc2cc(O)cc(O)c2C(=O)OCC/C=C/CC1]
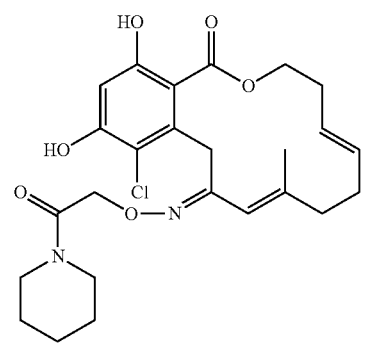 [SMILES: C/C1=C\C(=N\OCC(=O)N2CCCCC2)Cc2c(Cl)c(O)cc(O)c2C(=O)OCC/C=C/CC1]
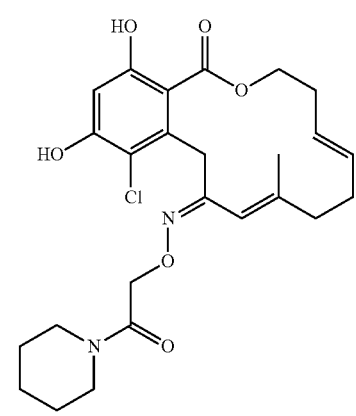 [SMILES: C/C1=C\C(=N/OCC(=O)N2CCCCC2)Cc2c(Cl)c(O)cc(O)c2C(=O)OCC/C=C/CC1]
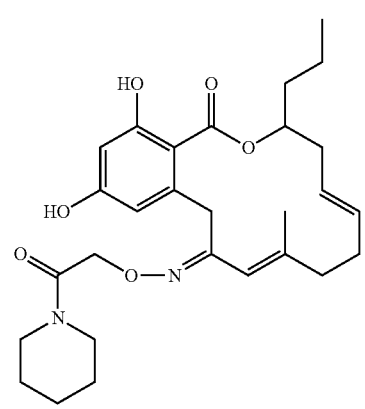 [SMILES: CCCC1C/C=C/CC/C(C)=C/C(=N/OCC(=O)N2CCCCC2)Cc2cc(O)cc(O)c2C(=O)O1]

TABLE 1-continued

TABLE 1-continued
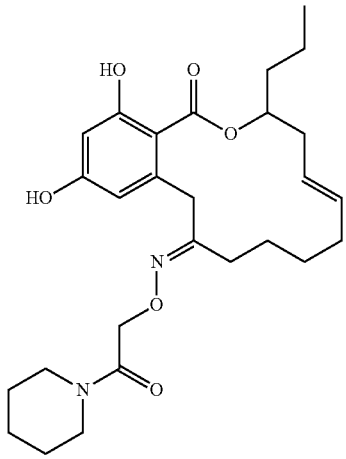 [SMILES: CCCC1C/C=C/CCCC/C(=N\OCC(=O)N2CCCCC2)Cc2cc(O)cc(O)c2C(=O)O1]
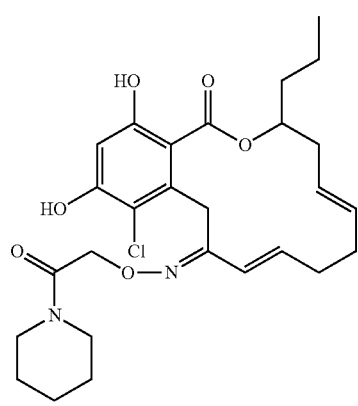 [SMILES: CCCC1C/C=C/CC/C=C/C(=N/OCC(=O)N2CCCCC2)Cc2c(Cl)c(O)cc(O)c2C(=O)O1]
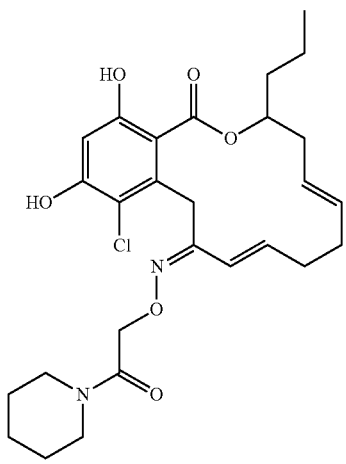 [SMILES: CCCC1C/C=C/CC/C=C/C(=N\OCC(=O)N2CCCCC2)Cc2c(Cl)c(O)cc(O)c2C(=O)O1]
TABLE 1-continued
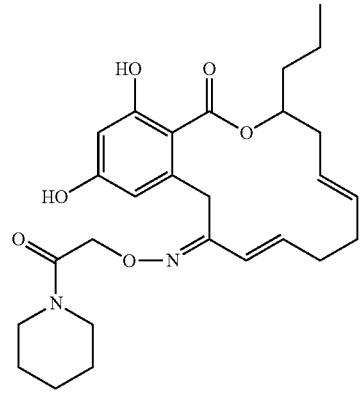 [SMILES: CCCC1C/C=C/CC/C=C/C(=N/OCC(=O)N2CCCCC2)Cc2cc(O)cc(O)c2C(=O)O1]
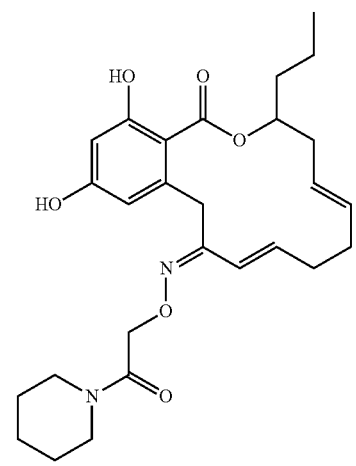 [SMILES: CCCC1C/C=C/CC/C=C/C(=N\OCC(=O)N2CCCCC2)Cc2cc(O)cc(O)c2C(=O)O1]
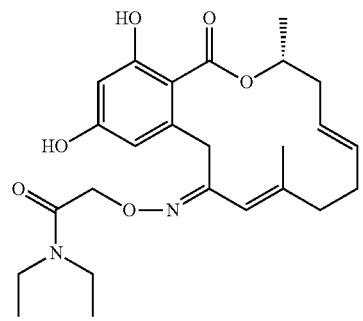 [SMILES: CCN(CC)C(=O)CO/N=C1/C=C(\C)CC/C=C/C[C@@H](C)OC(=O)c2c(O)cc(O)cc2C1]
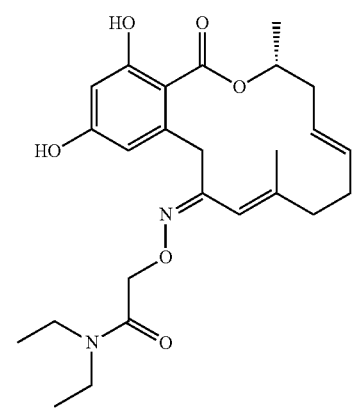 [SMILES: CCN(CC)C(=O)CO/N=C1\C=C(/C)CC/C=C/C[C@@H](C)OC(=O)c2c(O)cc(O)cc2C1]

TABLE 1-continued
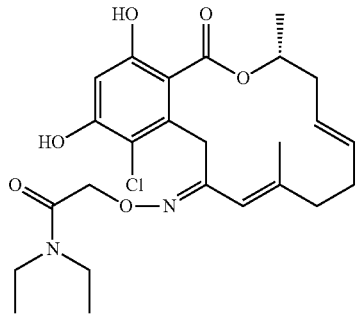 [SMILES: CCN(CC)C(=O)CO/N=C1/C=C(\C)CC/C=C/C[C@@H](C)OC(=O)c2c(O)cc(O)c(Cl)c2C1]
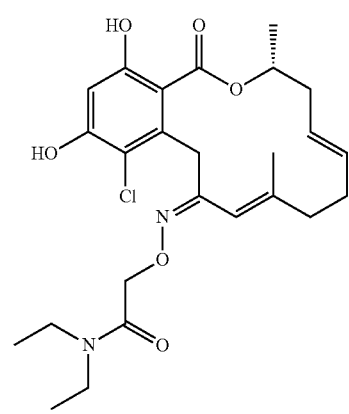 [SMILES: CCN(CC)C(=O)CO/N=C1\C=C(/C)CC/C=C/C[C@@H](C)OC(=O)c2c(O)cc(O)c(Cl)c2C1]
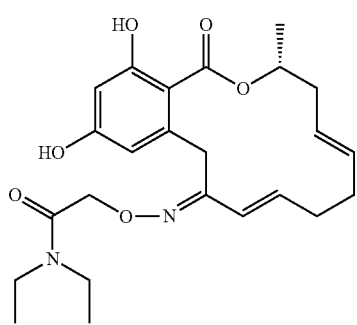 [SMILES: CCN(CC)C(=O)CO/N=C1/C=C/CC/C=C/C[C@@H](C)OC(=O)c2c(O)cc(O)cc2C1]
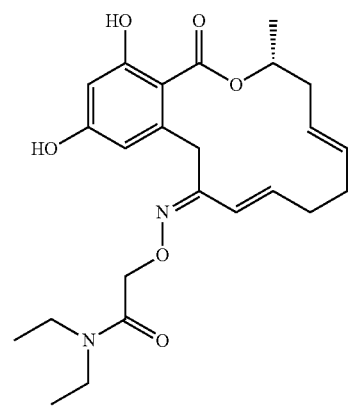 [SMILES: CCN(CC)C(=O)CO/N=C1\C=C\CC/C=C/C[C@@H](C)OC(=O)c2c(O)cc(O)cc2C1]
TABLE 1-continued
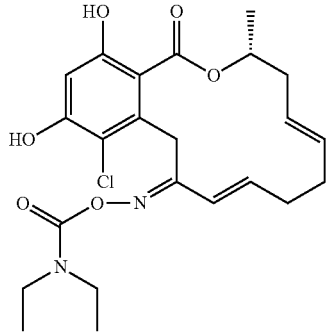 [SMILES: CCN(CC)C(=O)O/N=C1/C=C/CC/C=C/C[C@@H](C)OC(=O)c2c(O)cc(O)c(Cl)c2C1]
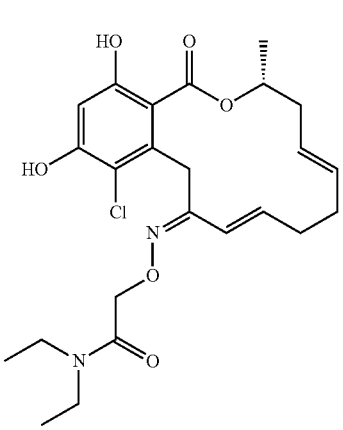
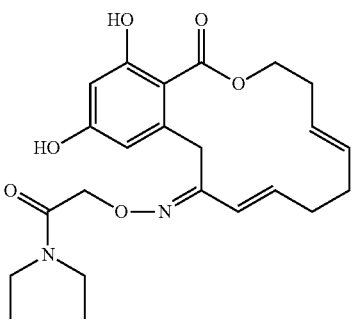 [SMILES: CCN(CC)C(=O)CO/N=C1/C=C/CC/C=C/CCOC(=O)c2c(O)cc(O)cc2C1]
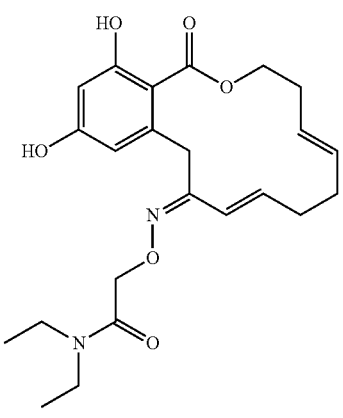 [SMILES: CCN(CC)C(=O)CO/N=C1\C=C\CC/C=C/CCOC(=O)c2c(O)cc(O)cc2C1]

TABLE 1-continued
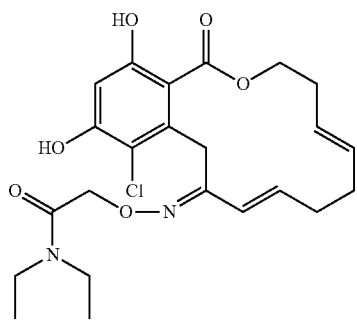 [SMILES: CCN(CC)C(=O)CO/N=C1/C=C/CC/C=C/CCOC(=O)c2c(O)cc(O)c(Cl)c2C1]
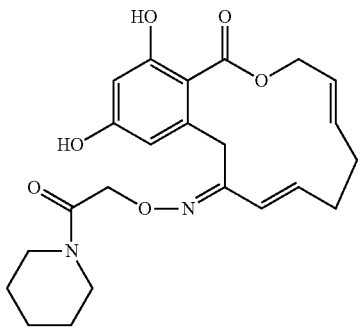
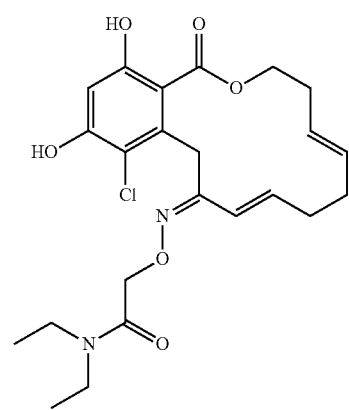 [SMILES: CCN(CC)C(=O)CO/N=C1\C=C\CC/C=C/CCOC(=O)c2c(O)cc(O)c(Cl)c2C1]
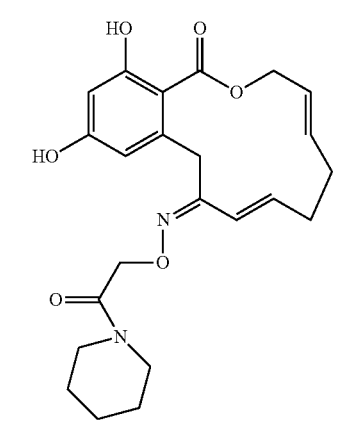
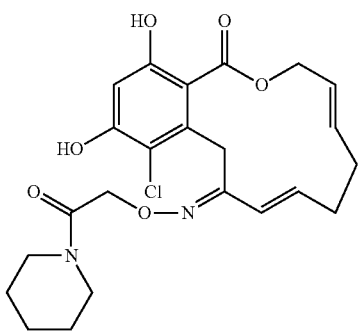 [SMILES: O=C1OC/C=C/CC/C=C/C(=N/OCC(=O)N2CCCCC2)Cc2c(Cl)c(O)cc(O)c21]
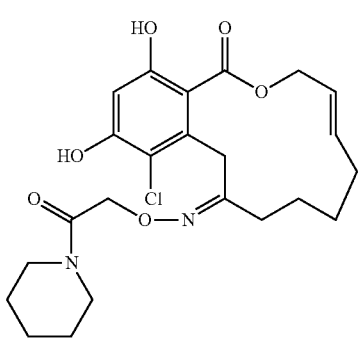
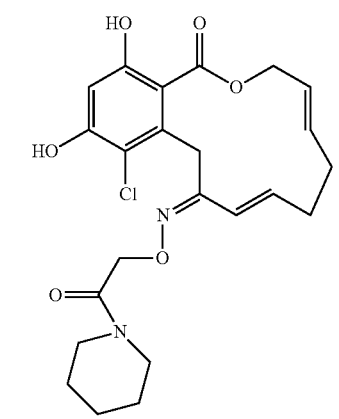 [SMILES: O=C1OC/C=C/CC/C=C/C(=N\OCC(=O)N2CCCCC2)Cc2cc(O)cc(O)c21]
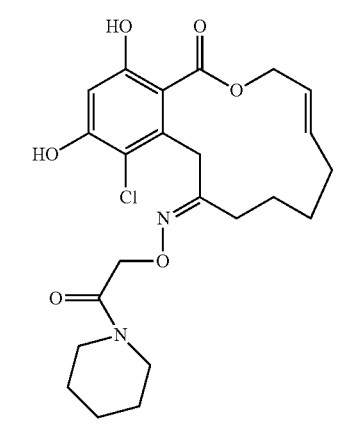

TABLE 1-continued
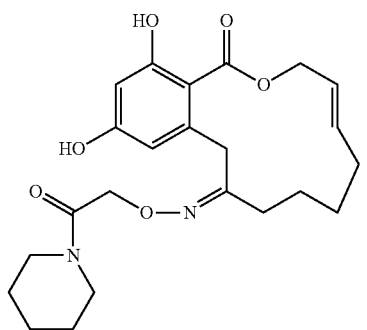 [SMILES: O=C1OC/C=C/CCCC/C(=N/OCC(=O)N2CCCCC2)Cc2cc(O)cc(O)c21]
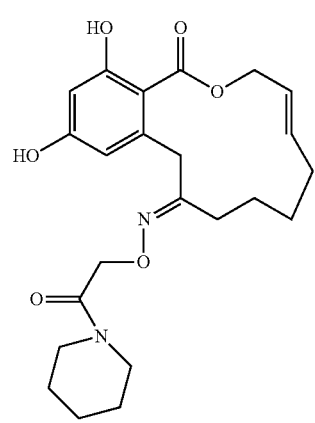 [SMILES: O=C1OC/C=C/CCCC/C(=N\OCC(=O)N2CCCCC2)Cc2cc(O)cc(O)c21]
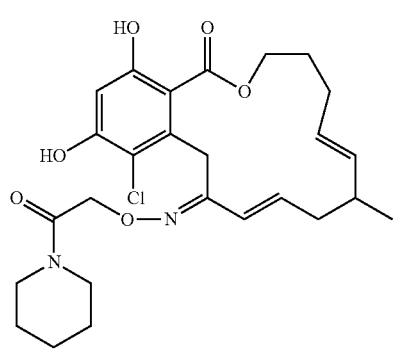 [SMILES: CC1/C=C/CCCOC(=O)c2c(O)cc(O)c(Cl)c2CC(=N\OCC(=O)N2CCCCC2)/C=C/C1]
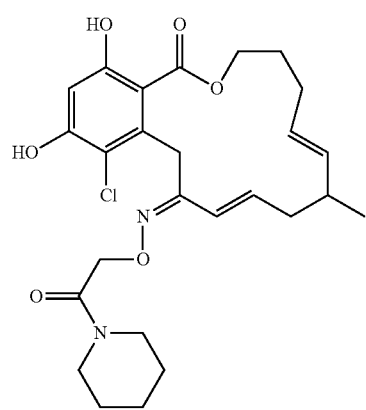 [SMILES: CC1/C=C/CCCOC(=O)c2c(O)cc(O)c(Cl)c2CC(=N/OCC(=O)N2CCCCC2)/C=C/C1]
TABLE 1-continued
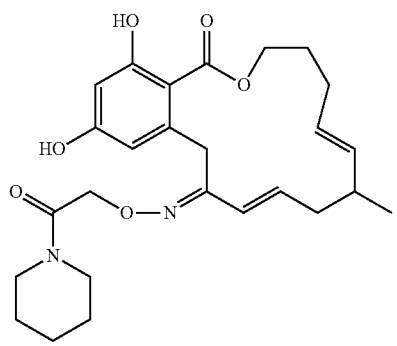 [SMILES: CC1/C=C/CCCOC(=O)c2c(O)cc(O)cc2CC(=N\OCC(=O)N2CCCCC2)/C=C/C1]
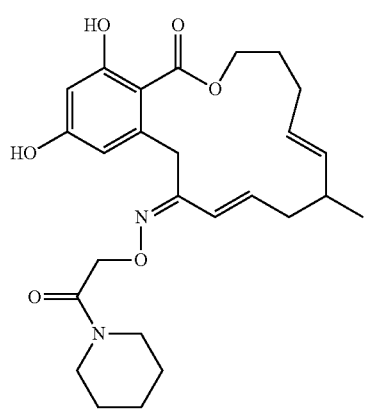 [SMILES: CC1/C=C/CCCOC(=O)c2c(O)cc(O)cc2CC(=N/OCC(=O)N2CCCCC2)/C=C/C1]
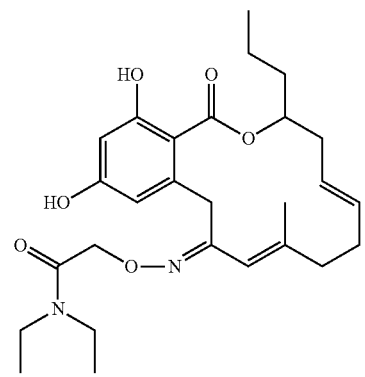 [SMILES: CCCC1C/C=C/CC/C(C)=C/C(=N/OCC(=O)N(CC)CC)Cc2cc(O)cc(O)c2C(=O)O1]
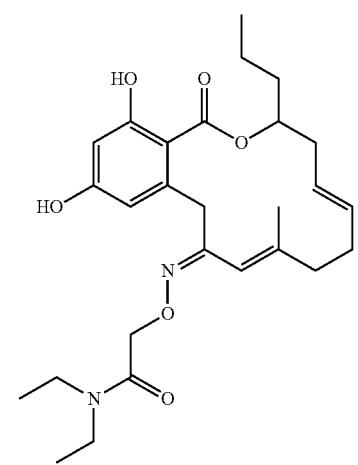 [SMILES: CCCC1C/C=C/CC/C(C)=C/C(=N\OCC(=O)N(CC)CC)Cc2cc(O)cc(O)c2C(=O)O1]

TABLE 1-continued
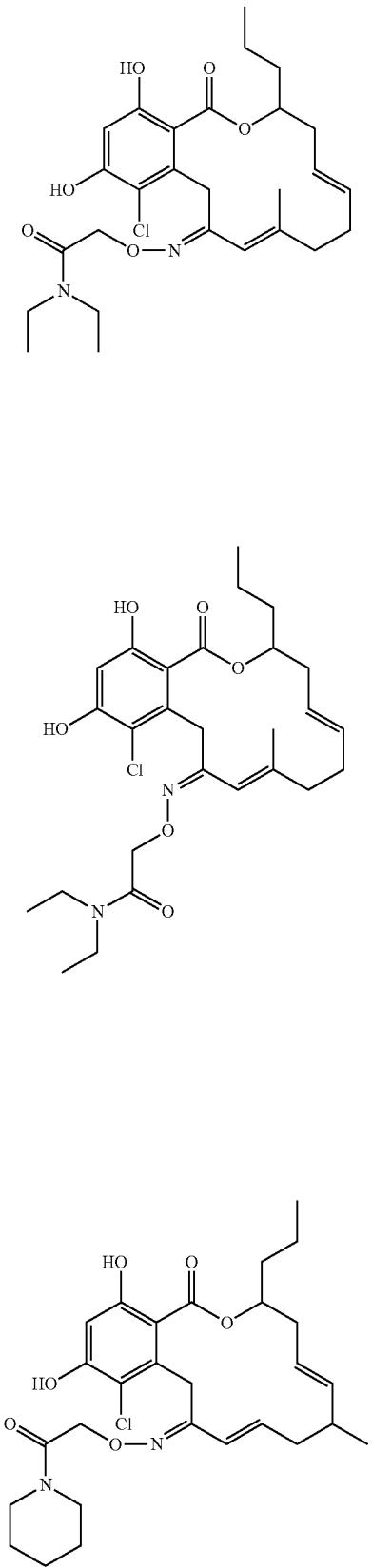
TABLE 1-continued
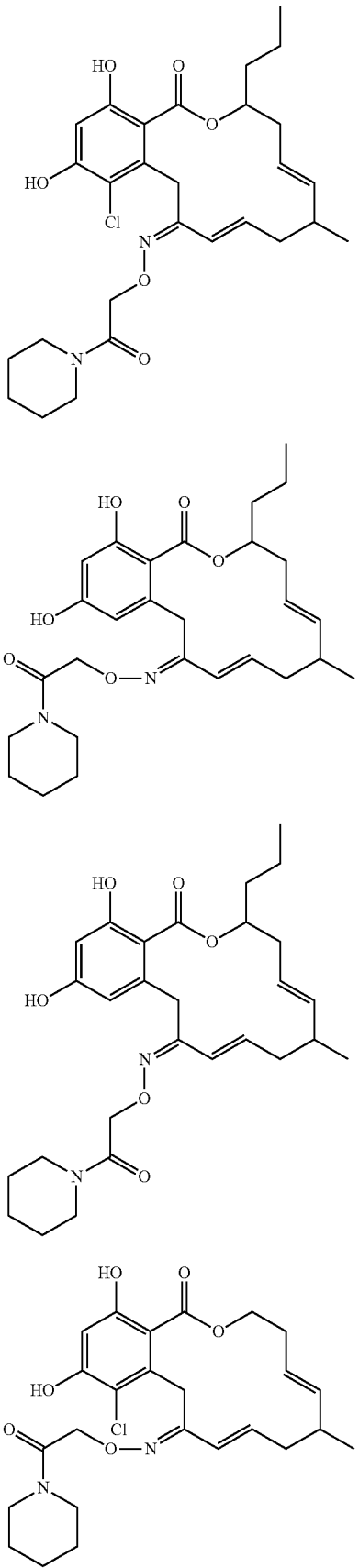

TABLE 1-continued
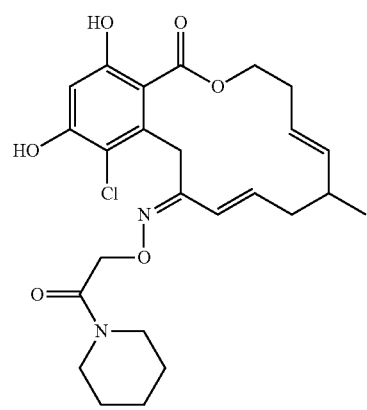 [SMILES: CC1/C=C/CCOC(=O)c2c(O)cc(O)c(Cl)c2CC(=N/OCC(=O)N2CCCCC2)/C=C/C1]
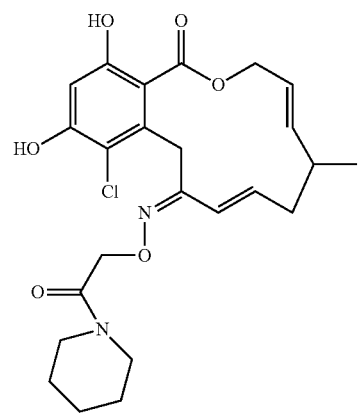
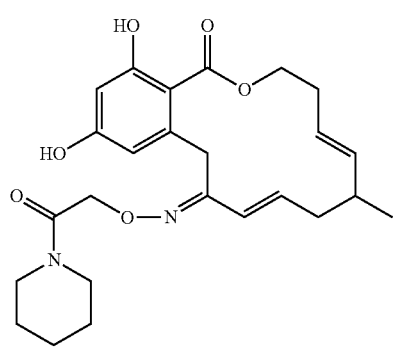 [SMILES: CC1/C=C/CCOC(=O)c2c(O)cc(O)cc2CC(=N\OCC(=O)N2CCCCC2)/C=C/C1]
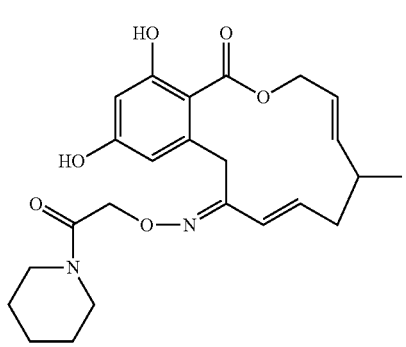
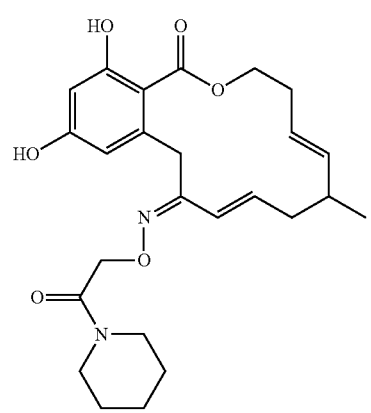 [SMILES: CC1/C=C/CCOC(=O)c2c(O)cc(O)cc2CC(=N/OCC(=O)N2CCCCC2)/C=C/C1]
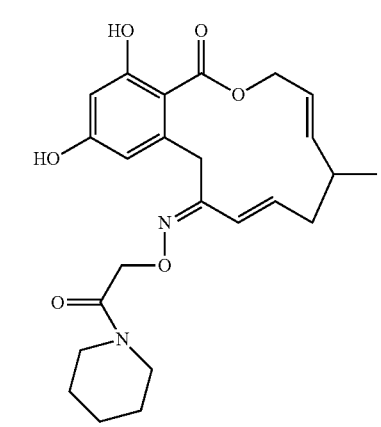
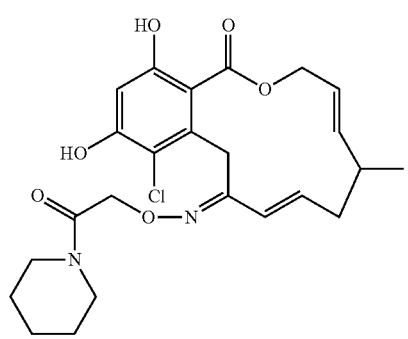 [SMILES: CC1/C=C/COC(=O)c2c(O)cc(O)c(Cl)c2CC(=N\OCC(=O)N2CCCCC2)/C=C/C1]
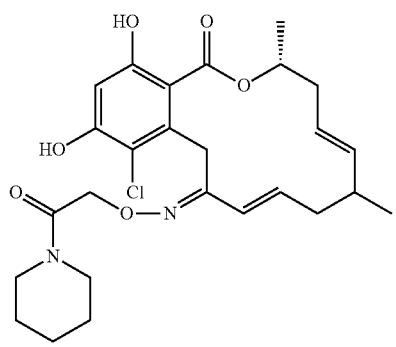 [SMILES: CC1/C=C/C[C@@H](C)OC(=O)c2c(O)cc(O)c(Cl)c2CC(=N\OCC(=O)N2CCCCC2)/C=C/C1]

TABLE 1-continued
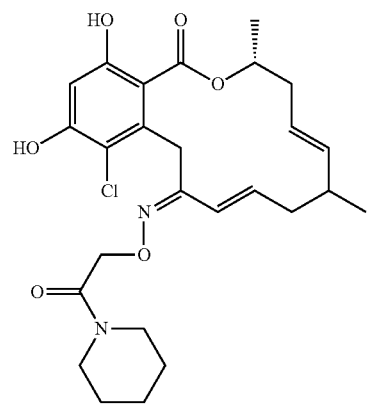 [SMILES: CC1/C=C/C[C@@H](C)OC(=O)c2c(O)cc(O)c(Cl)c2CC(=N/OCC(=O)N2CCCCC2)/C=C/C1]
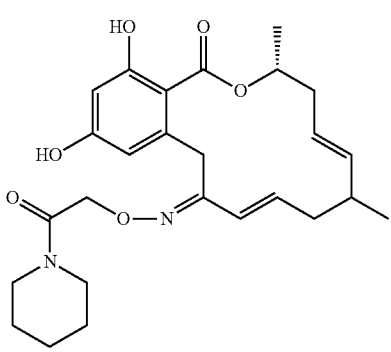 [SMILES: CC1/C=C/C[C@@H](C)OC(=O)c2c(O)cc(O)cc2CC(=N\OCC(=O)N2CCCCC2)/C=C/C1]
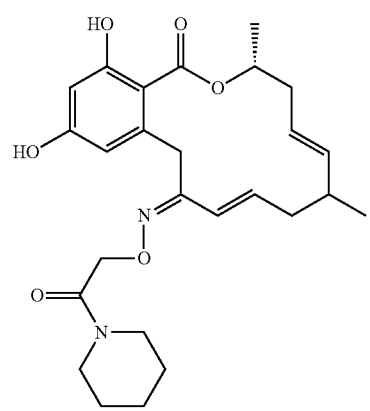 [SMILES: CC1/C=C/C[C@@H](C)OC(=O)c2c(O)cc(O)cc2CC(=N/OCC(=O)N2CCCCC2)/C=C/C1]
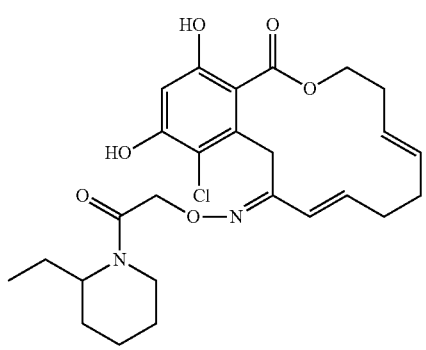 [SMILES: CCC1CCCCN1C(=O)CO/N=C1/C=C/CC/C=C/CCOC(=O)c2c(O)cc(O)c(Cl)c2C1]
TABLE 1-continued
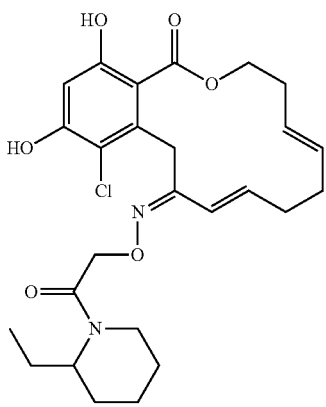 [SMILES: CCC1CCCCN1C(=O)CO/N=C1\C=C\CC/C=C/CCOC(=O)c2c(O)cc(O)c(Cl)c2C1]
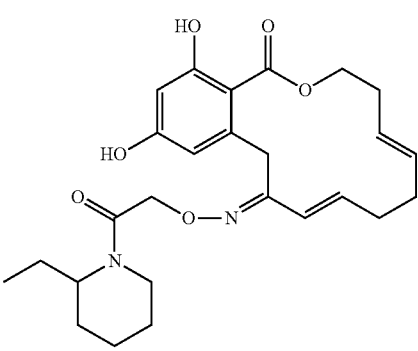 [SMILES: CCC1CCCCN1C(=O)CO/N=C1/C=C/CC/C=C/CCOC(=O)c2c(O)cc(O)cc2C1]
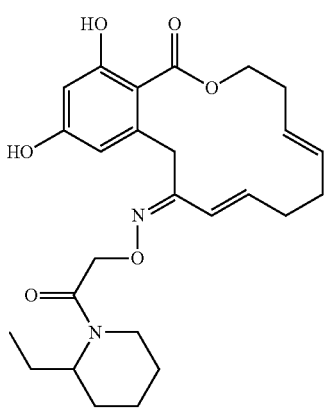 [SMILES: CCC1CCCCN1C(=O)CO/N=C1\C=C\CC/C=C/CCOC(=O)c2c(O)cc(O)cc2C1]
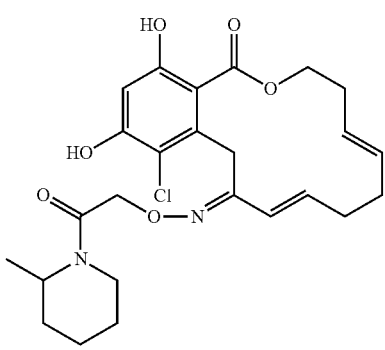 [SMILES: CC1CCCCN1C(=O)CO/N=C1/C=C/CC/C=C/CCOC(=O)c2c(O)cc(O)c(Cl)c2C1]

TABLE 1-continued
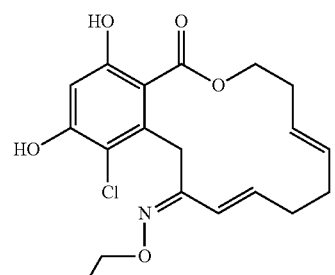
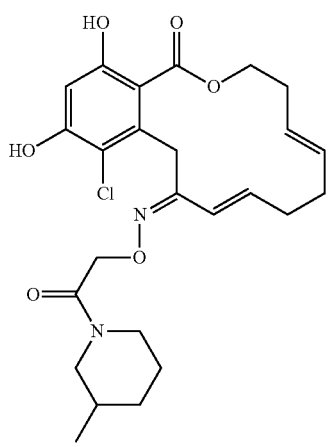
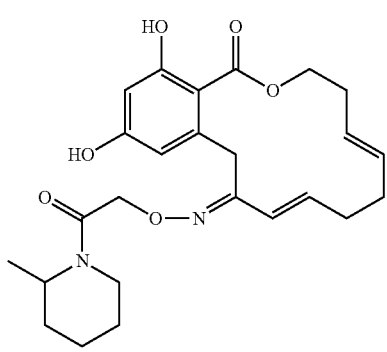 [SMILES: CC1CCCCN1C(=O)CO/N=C1/C=C/CC/C=C/CCOC(=O)c2c(O)cc(O)cc2C1]
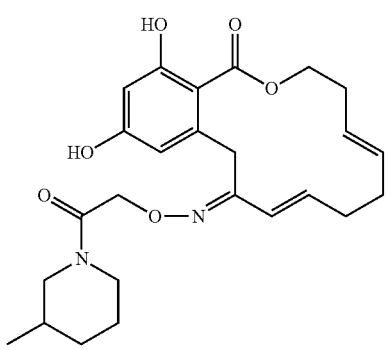
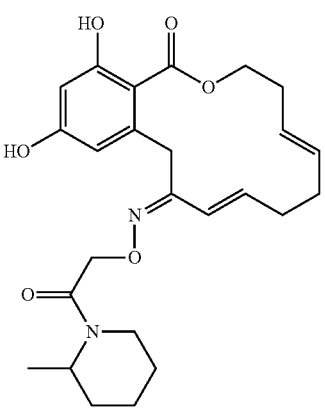 [SMILES: CC1CCCCN1C(=O)CO/N=C1\C=C\CC/C=C/CCOC(=O)c2c(O)cc(O)cc2C1]
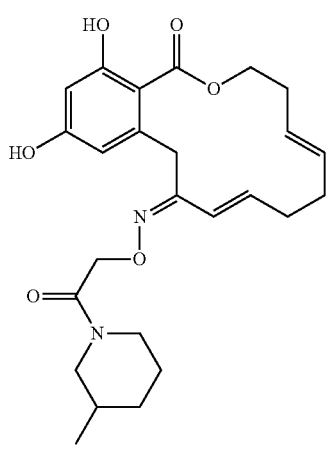
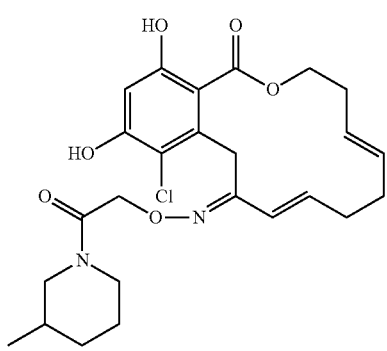 [SMILES: CC1CCCN(C(=O)CO/N=C2/C=C/CC/C=C/CCOC(=O)c3c(O)cc(O)c(Cl)c3C2)C1]
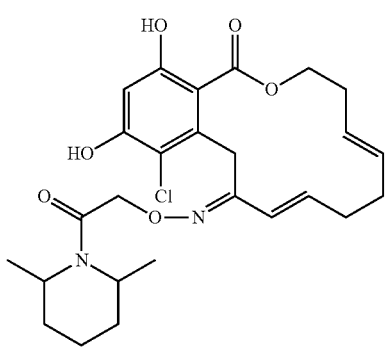 [SMILES: CC1CCCC(C)N1C(=O)CO/N=C1/C=C/CC/C=C/CCOC(=O)c2c(O)cc(O)c(Cl)c2C1]

TABLE 1-continued
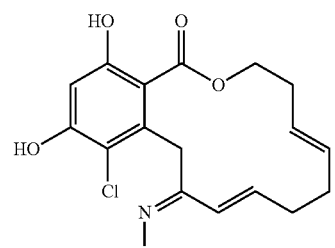
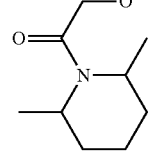
TABLE 1-continued
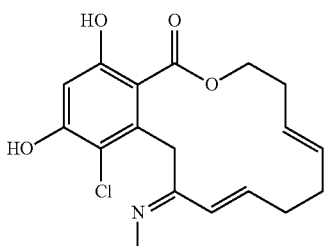
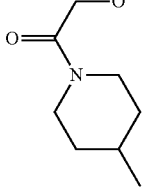

TABLE 1-continued
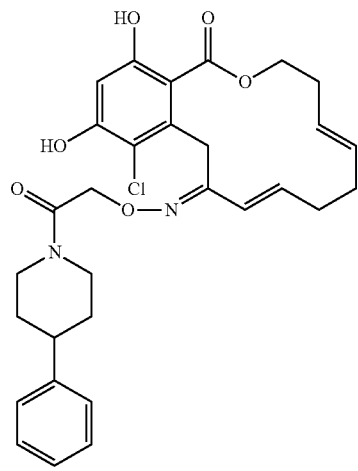 [SMILES: O=C1OCC/C=C/CC/C=C/C(=N/OCC(=O)N2CCC(c3ccccc3)CC2)Cc2c(Cl)c(O)cc(O)c21]
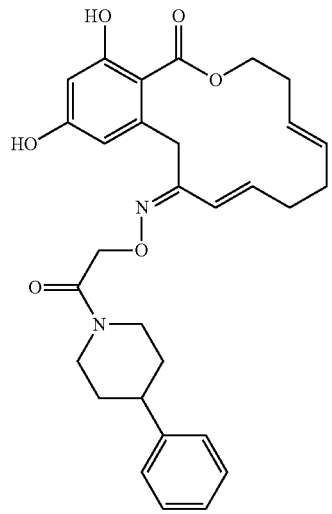
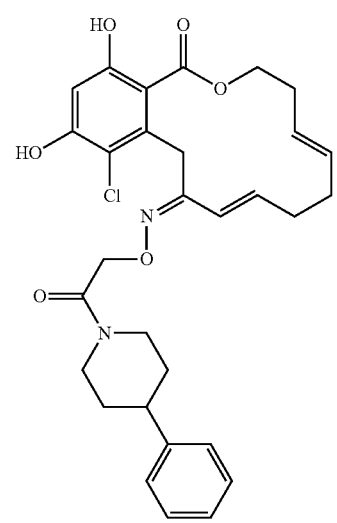 [SMILES: O=C1OCC/C=C/CC/C=C/C(=N\OCC(=O)N2CCC(c3ccccc3)CC2)Cc2c(Cl)c(O)cc(O)c21]
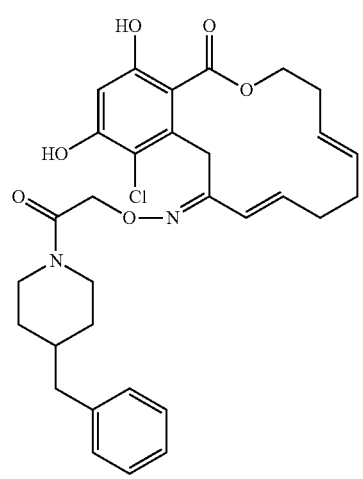
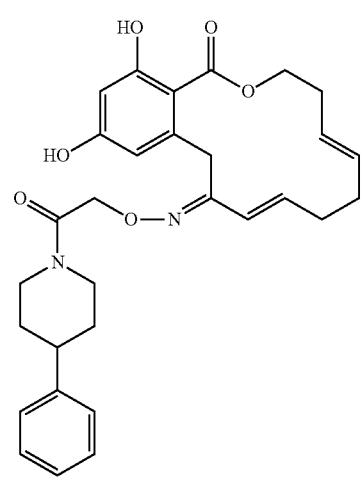 [SMILES: O=C1OCC/C=C/CC/C=C/C(=N/OCC(=O)N2CCC(c3ccccc3)CC2)Cc2cc(O)cc(O)c21]
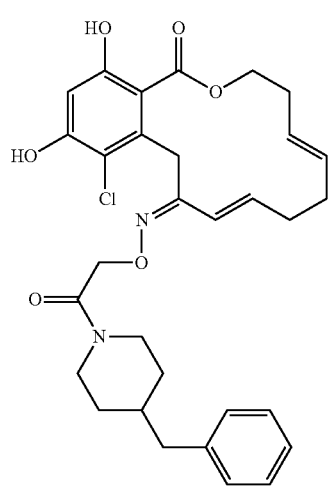 [SMILES: O=C1OCC/C=C/CC/C=C/C(=N\OCC(=O)N2CCC(Cc3ccccc3)CC2)Cc2c(Cl)c(O)cc(O)c21]

TABLE 1-continued
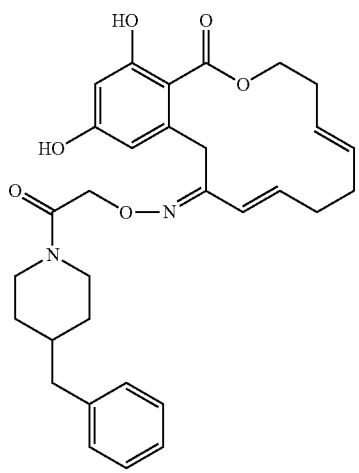 [SMILES: O=C1OCC/C=C/CC/C=C/C(=N/OCC(=O)N2CCC(Cc3ccccc3)CC2)Cc2cc(O)cc(O)c21]
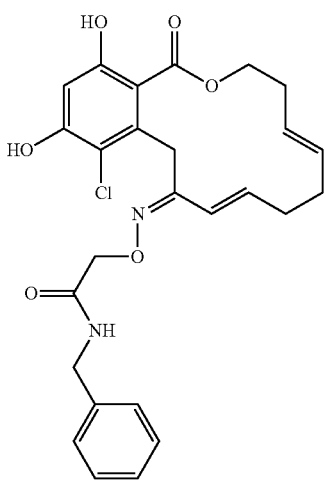
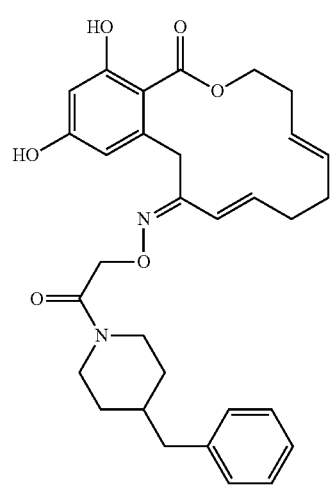 [SMILES: O=C1OCC/C=C/CC/C=C/C(=N\OCC(=O)N2CCC(Cc3ccccc3)CC2)Cc2cc(O)cc(O)c21]
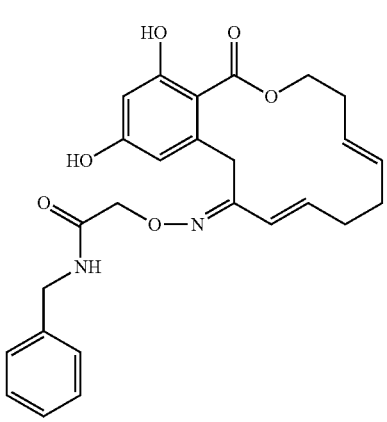
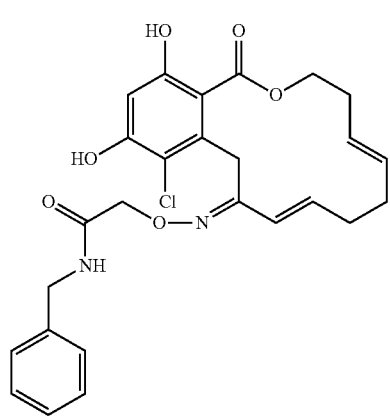 [SMILES: O=C(CO/N=C1/C=C/CC/C=C/CCOC(=O)c2c(O)cc(O)c(Cl)c2C1)NCc1ccccc1]
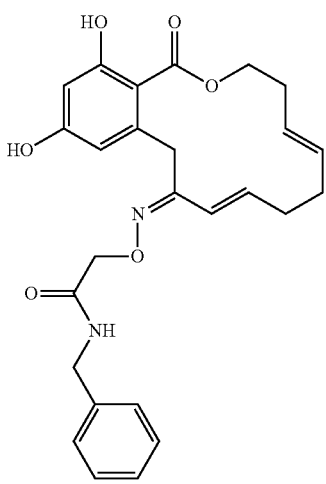 [SMILES: O=C(CO/N=C1\C=C\CC/C=C/CCOC(=O)c2c(O)cc(O)cc2C1)NCc1ccccc1]

TABLE 1-continued
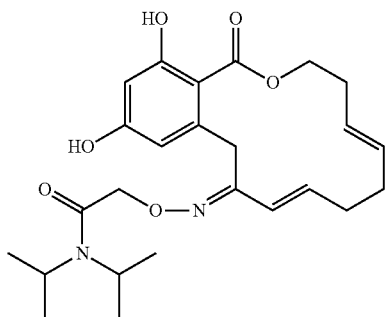 [SMILES: CC(C)N(C(=O)CO/N=C1/C=C/CC/C=C/CCOC(=O)c2c(O)cc(O)cc2C1)C(C)C]
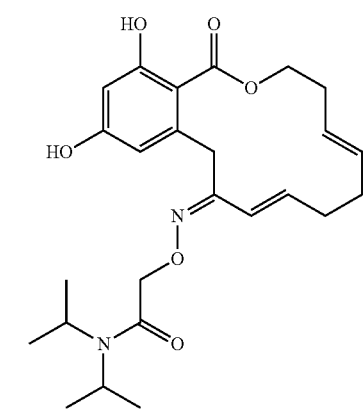 [SMILES: CC(C)N(C(=O)CO/N=C1\C=C\CC/C=C/CCOC(=O)c2c(O)cc(O)cc2C1)C(C)C]
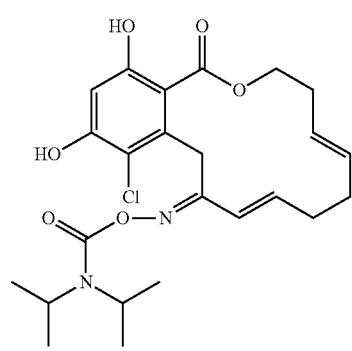 [SMILES: CC(C)N(C(=O)O/N=C1/C=C/CC/C=C/CCOC(=O)c2c(O)cc(O)c(Cl)c2C1)C(C)C]
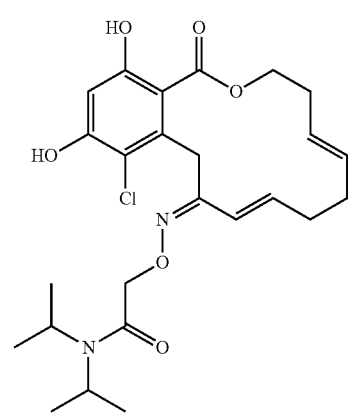 [SMILES: CC(C)N(C(=O)CO/N=C1\C=C\CC/C=C/CCOC(=O)c2c(O)cc(O)c(Cl)c2C1)C(C)C]
TABLE 1-continued
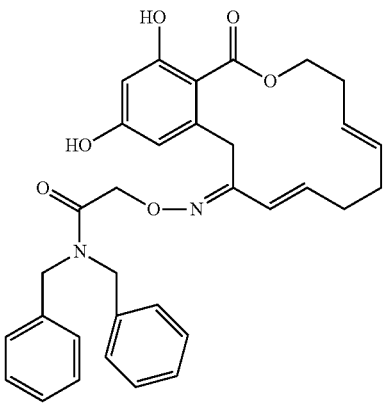 [SMILES: O=C1OCC/C=C/CC/C=C/C(=N/OCC(=O)N(Cc2ccccc2)Cc2ccccc2)Cc2cc(O)cc(O)c21]
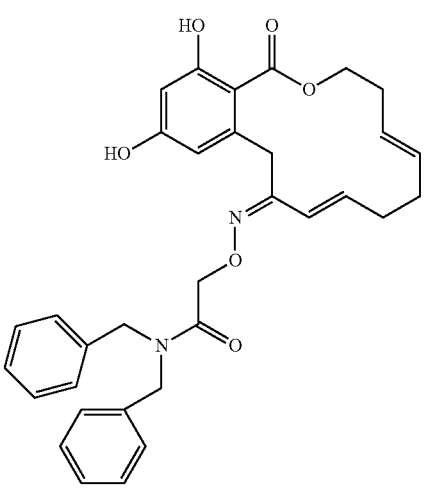 [SMILES: O=C1OCC/C=C/CC/C=C/C(=N\OCC(=O)N(Cc2ccccc2)Cc2ccccc2)Cc2cc(O)cc(O)c21]
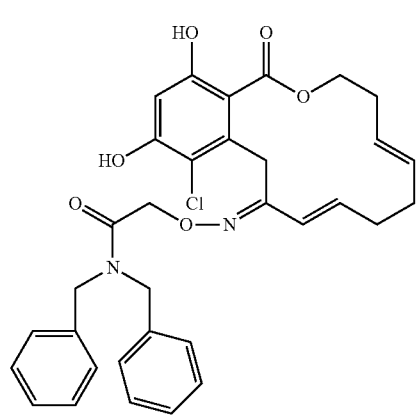 [SMILES: O=C1OCC/C=C/CC/C=C/C(=N/OCC(=O)N(Cc2ccccc2)Cc2ccccc2)Cc2c(Cl)c(O)cc(O)c21]

TABLE 1-continued
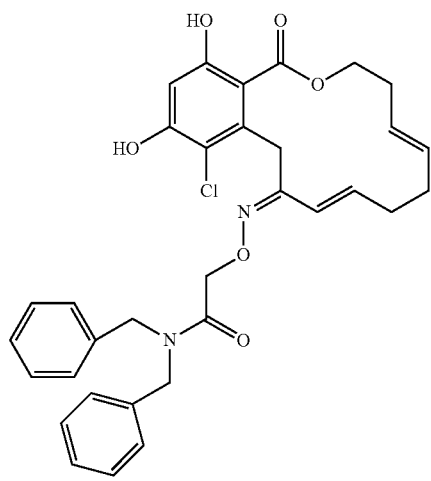 [SMILES: O=C1OCC/C=C/CC/C=C/C(=N\OCC(=O)N(Cc2ccccc2)Cc2ccccc2)Cc2c(Cl)c(O)cc(O)c21]
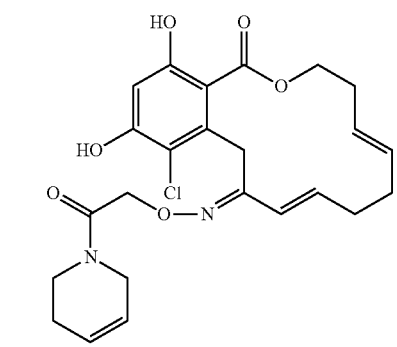 [SMILES: O=C1OCC/C=C/CC/C=C/C(=N/OCC(=O)N2CC=CCC2)Cc2c(Cl)c(O)cc(O)c21]
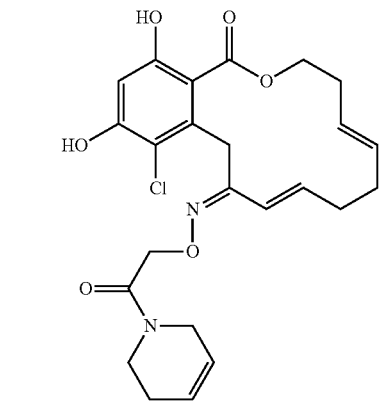 [SMILES: O=C1OCC/C=C/CC/C=C/C(=N\OCC(=O)N2CC=CCC2)Cc2c(Cl)c(O)cc(O)c21]
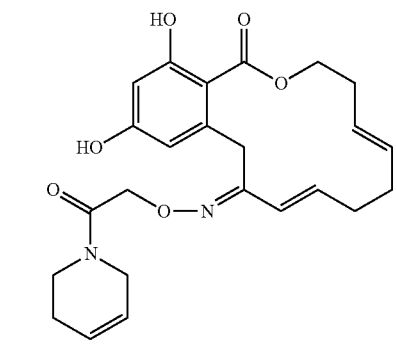 [SMILES: O=C1OCC/C=C/CC/C=C/C(=N/OCC(=O)N2CC=CCC2)Cc2cc(O)cc(O)c21]
TABLE 1-continued
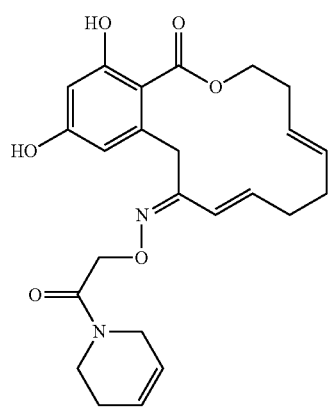 [SMILES: O=C1OCC/C=C/CC/C=C/C(=N\OCC(=O)N2CC=CCC2)Cc2cc(O)cc(O)c21]
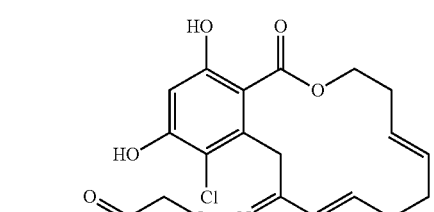
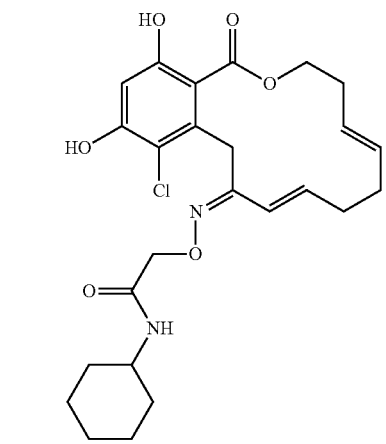 [SMILES: O=C(CO/N=C1\C=C\CC/C=C/CCOC(=O)c2c(O)cc(O)c(Cl)c2C1)NC1CCCCC1]
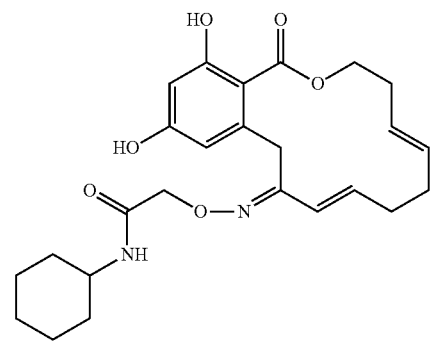 [SMILES: O=C(CO/N=C1/C=C/CC/C=C/CCOC(=O)c2c(O)cc(O)cc2C1)NC1CCCCC1]

TABLE 1-continued
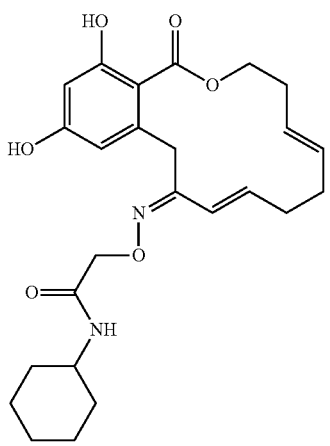 [SMILES: O=C(CO/N=C1\C=C\CC/C=C/CCOC(=O)c2c(O)cc(O)cc2C1)NC1CCCCC1]
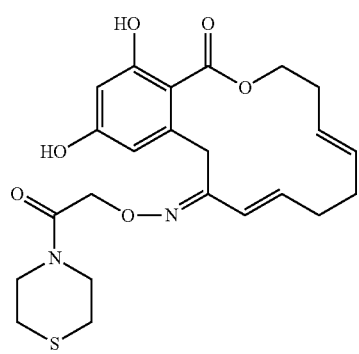
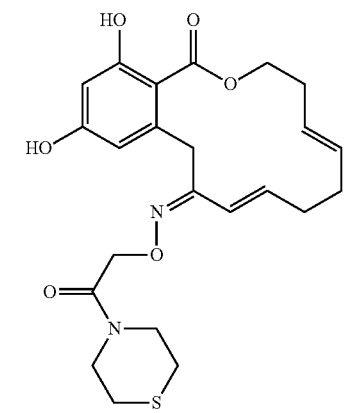
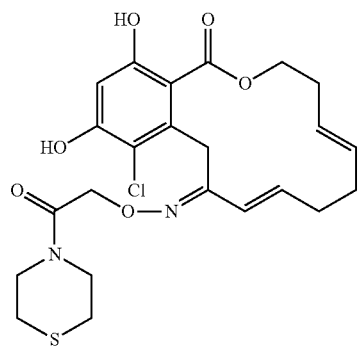 [SMILES: O=C1OCC/C=C/CC/C=C/C(=N/OCC(=O)N2CCSCC2)Cc2c(Cl)c(O)cc(O)c21]
TABLE 1-continued
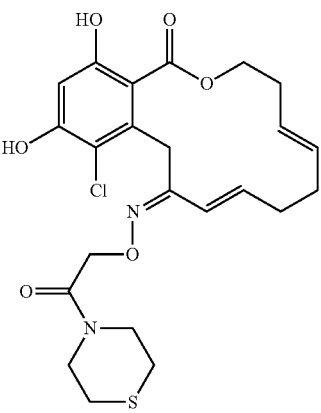 [SMILES: O=C1OCC/C=C/CC/C=C/C(=N\OCC(=O)N2CCSCC2)Cc2c(Cl)c(O)cc(O)c21]
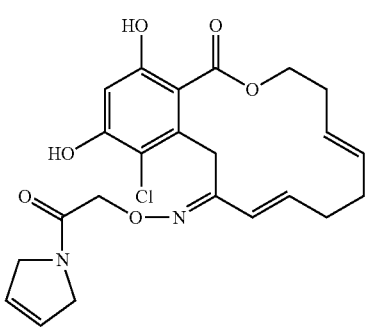 [SMILES: O=C1OCC/C=C/CC/C=C/C(=N/OCC(=O)N2CC=CC2)Cc2c(Cl)c(O)cc(O)c21]
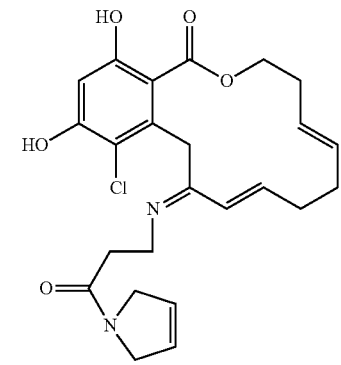 [SMILES: O=C1OCC/C=C/CC/C=C/C(=N\CCC(=O)N2CC=CC2)Cc2c(Cl)c(O)cc(O)c21]
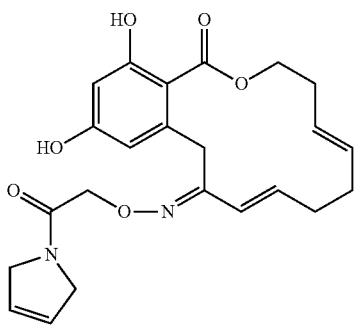 [SMILES: O=C1OCC/C=C/CC/C=C/C(=N/OCC(=O)N2CC=CC2)Cc2cc(O)cc(O)c21]

TABLE 1-continued

TABLE 1-continued
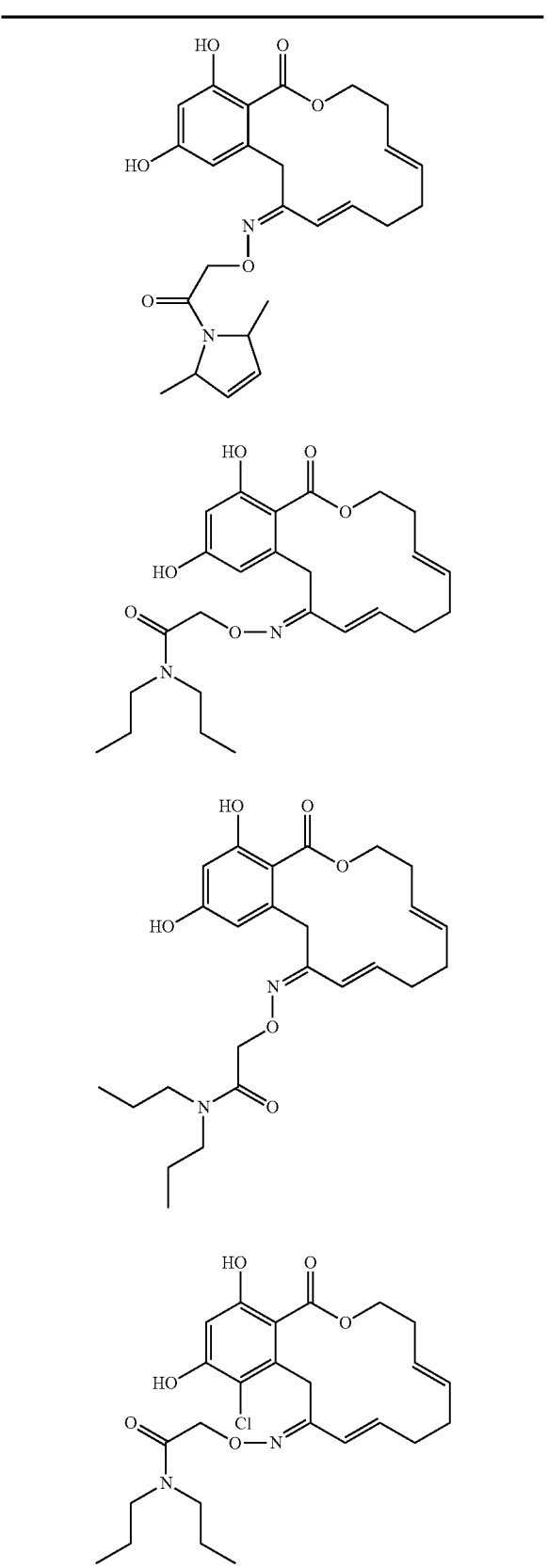
TABLE 1-continued
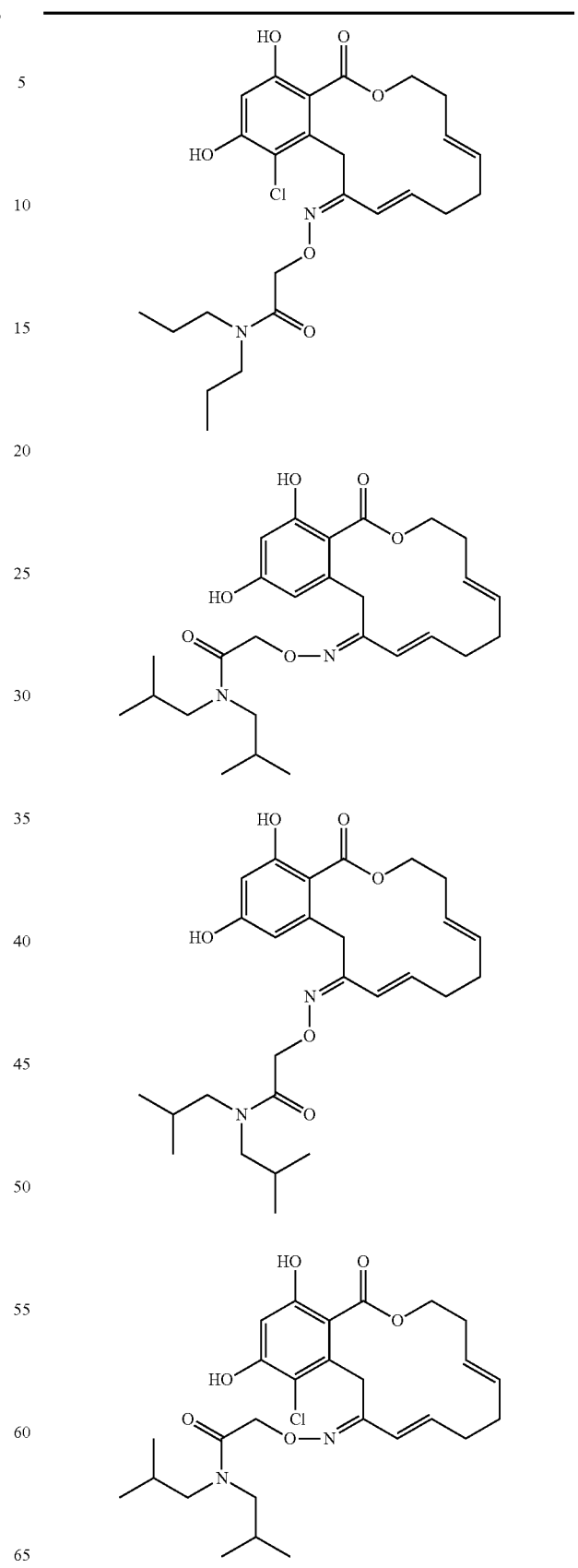

TABLE 1-continued
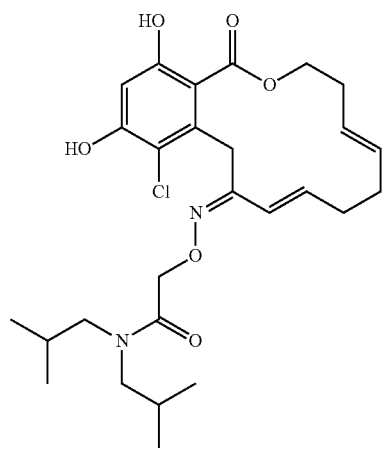 [SMILES: CC(C)CN(CC(C)C)C(=O)CO/N=C1\C=C\CC/C=C/CCOC(=O)c2c(O)cc(O)c(Cl)c2C1]
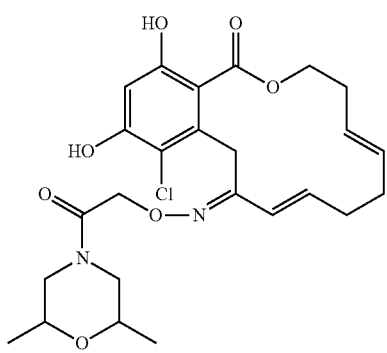 [SMILES: CC1CN(C(=O)CO/N=C2/C=C/CC/C=C/CCOC(=O)c3c(O)cc(O)c(Cl)c3C2)CC(C)O1]
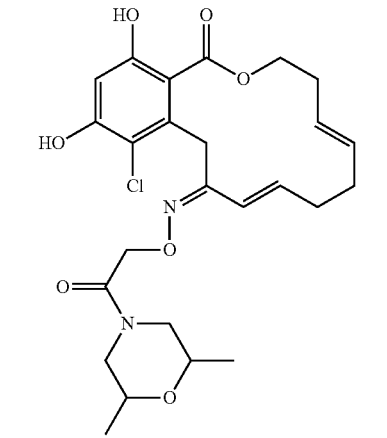 [SMILES: CC1CN(C(=O)CO/N=C2\C=C\CC/C=C/CCOC(=O)c3c(O)cc(O)c(Cl)c3C2)CC(C)O1]
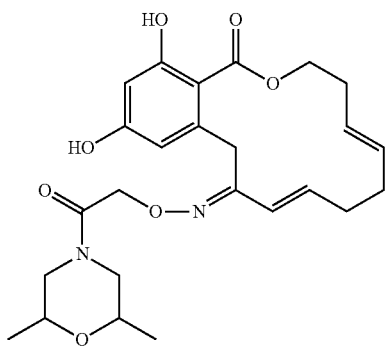 [SMILES: CC1CN(C(=O)CO/N=C2/C=C/CC/C=C/CCOC(=O)c3c(O)cc(O)cc3C2)CC(C)O1]
TABLE 1-continued
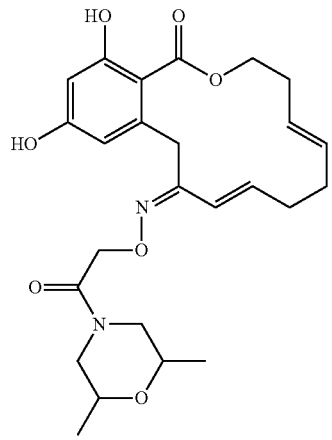 [SMILES: CC1CN(C(=O)CO/N=C2\C=C\CC/C=C/CCOC(=O)c3c(O)cc(O)cc3C2)CC(C)O1]
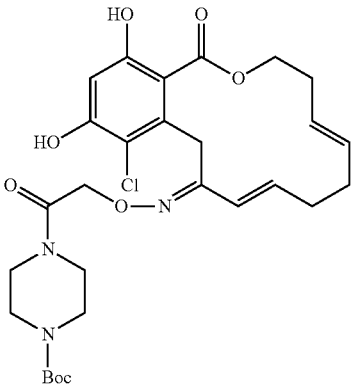 [SMILES: CC(C)(C)OC(=O)N1CCN(C(=O)CO/N=C2/C=C/CC/C=C/CCOC(=O)c3c(O)cc(O)c(Cl)c3C2)CC1]
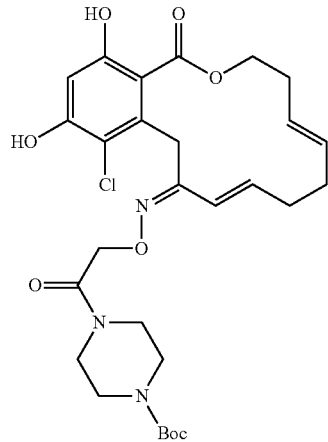 [SMILES: CC(C)(C)OC(=O)N1CCN(C(=O)CO/N=C2\C=C\CC/C=C/CCOC(=O)c3c(O)cc(O)c(Cl)c3C2)CC1]
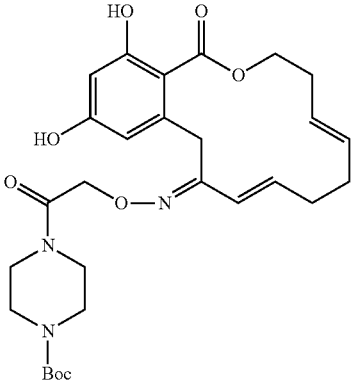 [SMILES: CC(C)(C)OC(=O)N1CCN(C(=O)CO/N=C2/C=C/CC/C=C/CCOC(=O)c3c(O)cc(O)cc3C2)CC1]

TABLE 1-continued
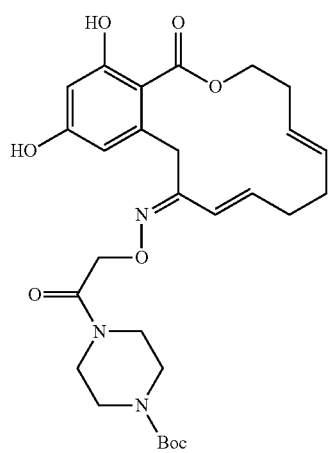 [SMILES: CC(C)(C)OC(=O)N1CCN(C(=O)CO/N=C2\C=C\CC/C=C/CCOC(=O)c3c(O)cc(O)cc3C2)CC1]
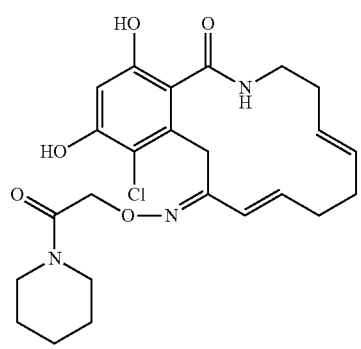 [SMILES: O=C1NCC/C=C/CC/C=C/C(=N/OCC(=O)N2CCCCC2)Cc2c(Cl)c(O)cc(O)c21]
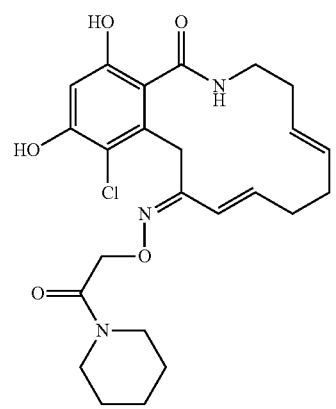 [SMILES: O=C1NCC/C=C/CC/C=C/C(=N\OCC(=O)N2CCCCC2)Cc2c(Cl)c(O)cc(O)c21]
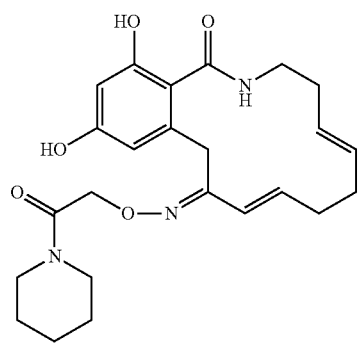
TABLE 1-continued
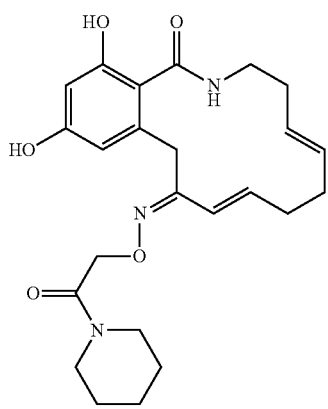 [SMILES: O=C1NCC/C=C/CC/C=C/C(=N\OCC(=O)N2CCCCC2)Cc2cc(O)cc(O)c21]
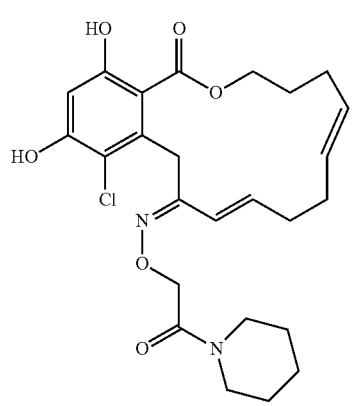 [SMILES: O=C1OCCC/C=C/CC/C=C/C(=N\OCC(=O)N2CCCCC2)Cc2c(Cl)c(O)cc(O)c21]
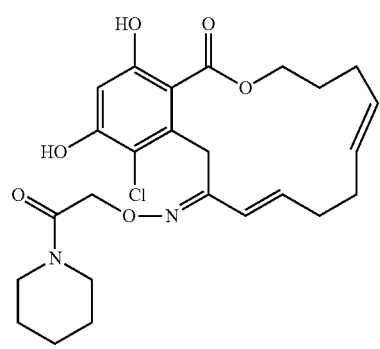 [SMILES: O=C1OCCC/C=C/CC/C=C/C(=N/OCC(=O)N2CCCCC2)Cc2c(Cl)c(O)cc(O)c21]
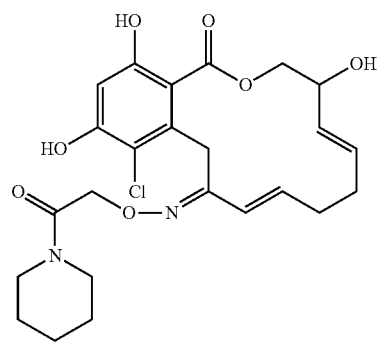 [SMILES: O=C1OCC(O)/C=C/CC/C=C/C(=N/OCC(=O)N2CCCCC2)Cc2c(Cl)c(O)cc(O)c21]

TABLE 1-continued
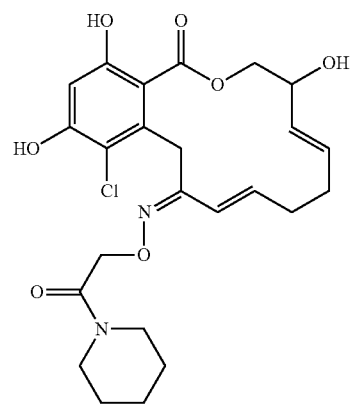 [SMILES: O=C1OCC(O)/C=C/CC/C=C/C(=N\OCC(=O)N2CCCCC2)Cc2c(Cl)c(O)cc(O)c21]
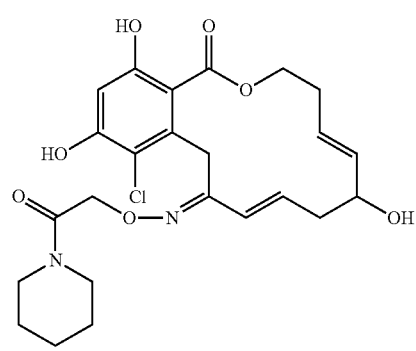 [SMILES: O=C1OCC/C=C/C(O)C/C=C/C(=N/OCC(=O)N2CCCCC2)Cc2c(Cl)c(O)cc(O)c21]
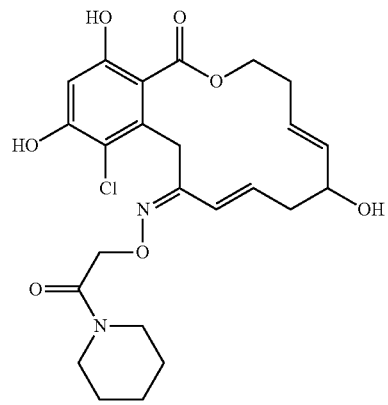 [SMILES: O=C1OCC/C=C/C(O)C/C=C/C(=N\OCC(=O)N2CCCCC2)Cc2c(Cl)c(O)cc(O)c21]
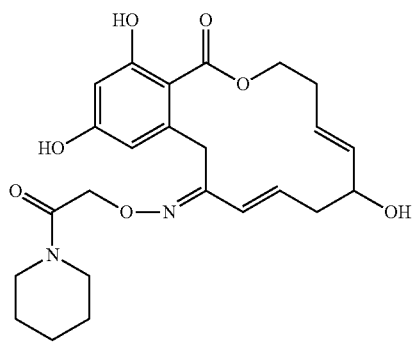 [SMILES: O=C1OCC/C=C/C(O)C/C=C/C(=N/OCC(=O)N2CCCCC2)Cc2cc(O)cc(O)c21]
TABLE 1-continued
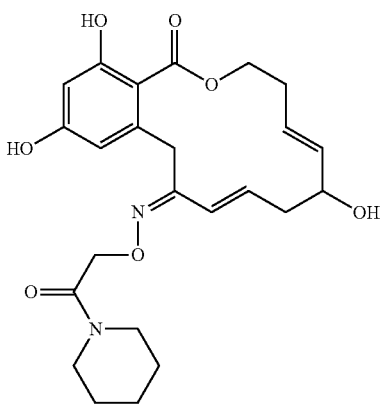 [SMILES: O=C1OCC/C=C/C(O)C/C=C/C(=N\OCC(=O)N2CCCCC2)Cc2cc(O)cc(O)c21]
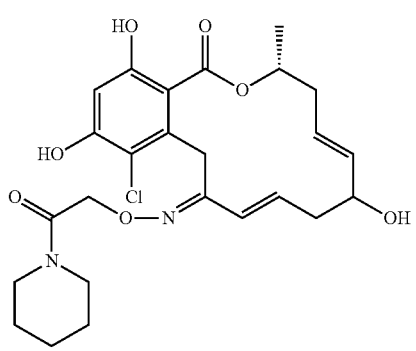 [SMILES: C[C@@H]1C/C=C/C(O)C/C=C/C(=N/OCC(=O)N2CCCCC2)Cc2c(Cl)c(O)cc(O)c2C(=O)O1]
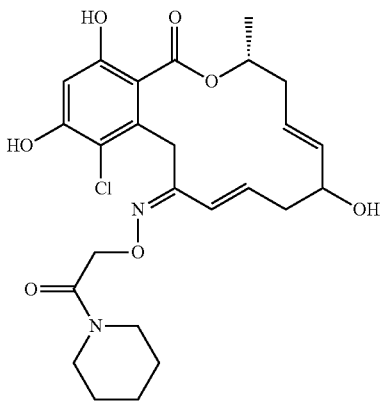 [SMILES: C[C@@H]1C/C=C/C(O)C/C=C/C(=N\OCC(=O)N2CCCCC2)Cc2c(Cl)c(O)cc(O)c2C(=O)O1]
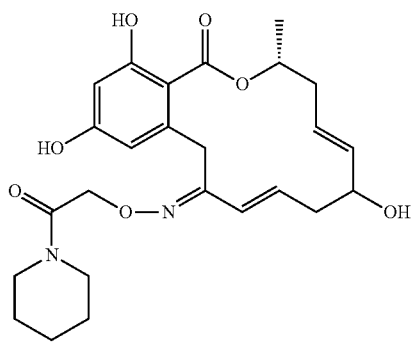 [SMILES: C[C@@H]1C/C=C/C(O)C/C=C/C(=N/OCC(=O)N2CCCCC2)Cc2cc(O)cc(O)c2C(=O)O1]

TABLE 1-continued
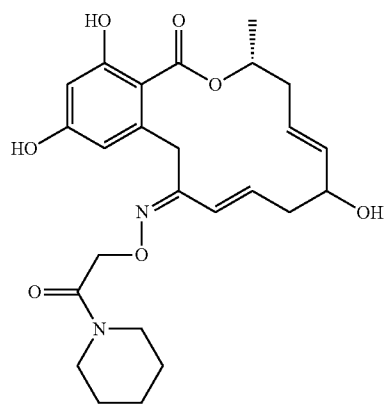 [SMILES: C[C@@H]1C/C=C/C(O)C/C=C/C(=N\OCC(=O)N2CCCCC2)Cc2cc(O)cc(O)c2C(=O)O1]
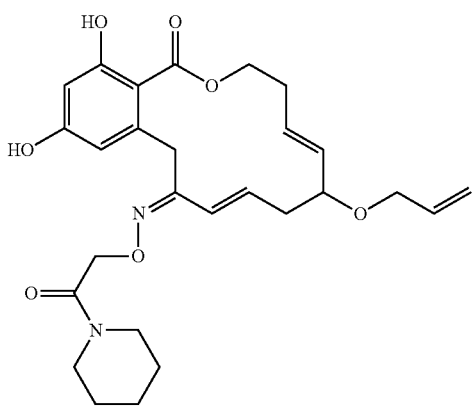
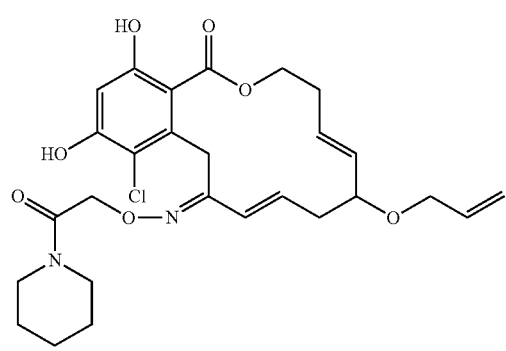
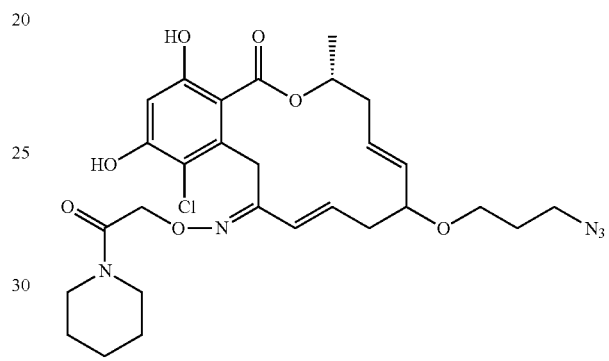
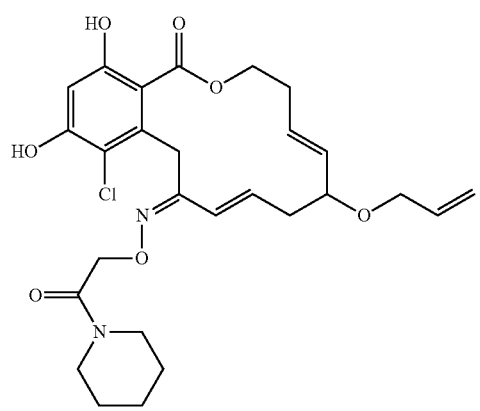 [SMILES: C=CCOC1/C=C/CCOC(=O)c2c(O)cc(O)c(Cl)c2CC(=N/OCC(=O)N2CCCCC2)/C=C/C1]
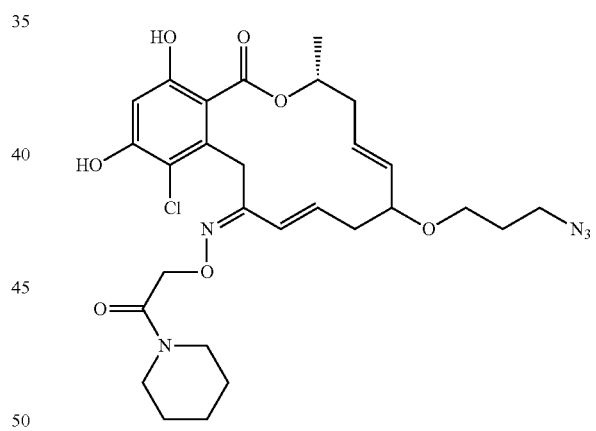
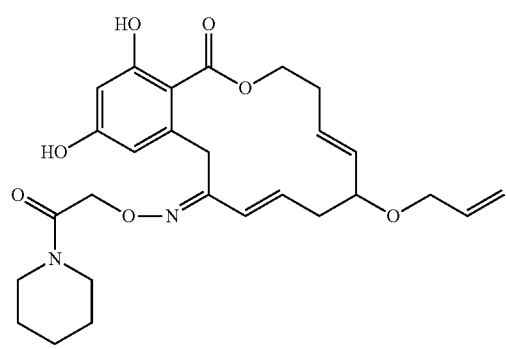 [SMILES: C=CCOC1/C=C/CCOC(=O)c2c(O)cc(O)cc2CC(=N\OCC(=O)N2CCCCC2)/C=C/C1]
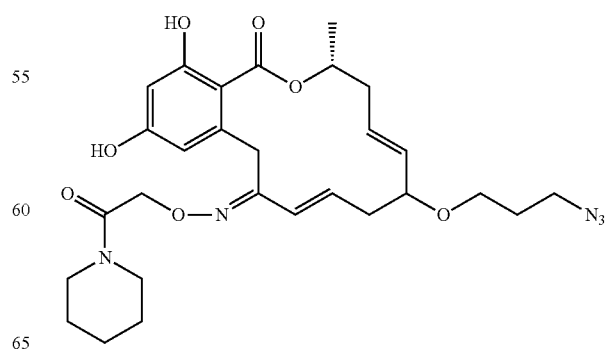

TABLE 1-continued
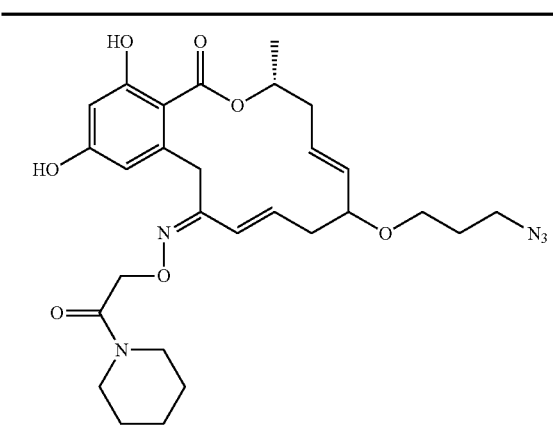
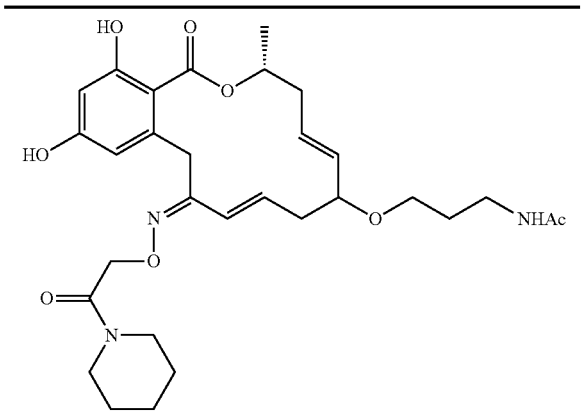
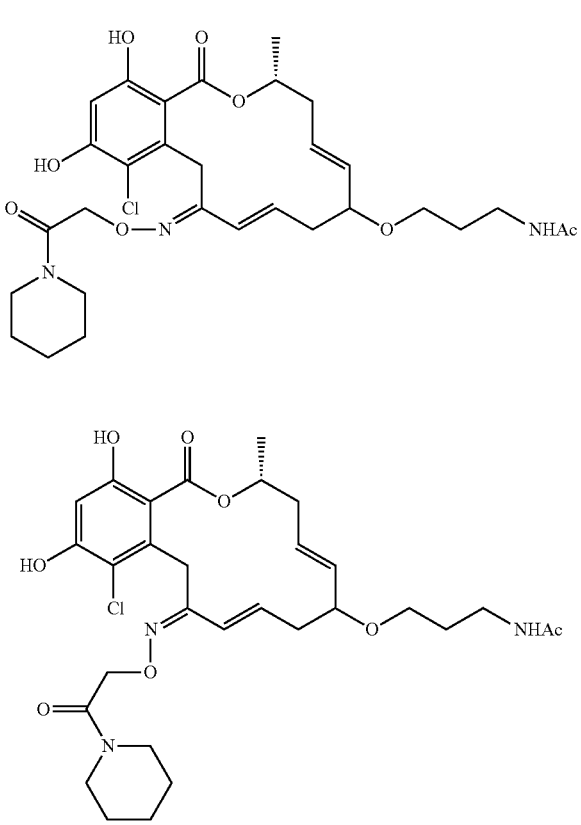
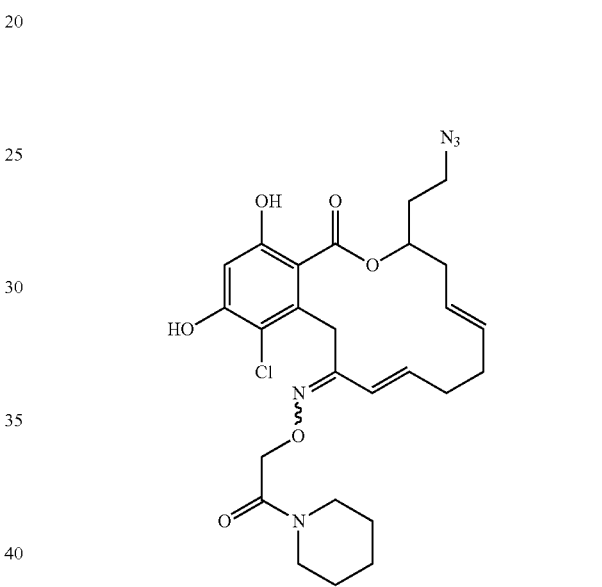
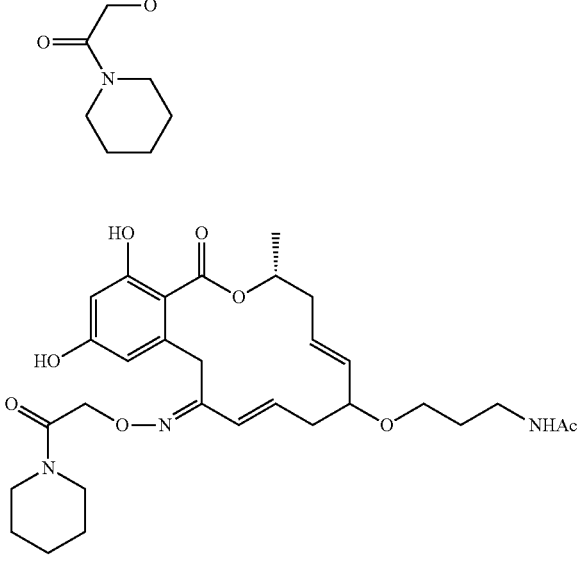
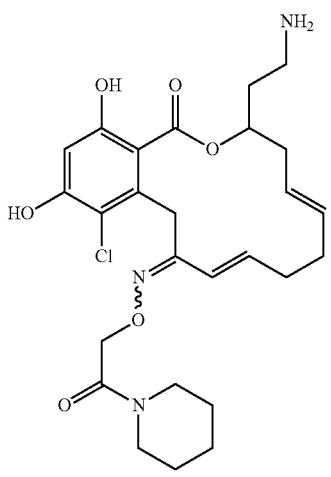 [SMILES: NCCC1C/C=C/CC/C=C/C(=NOCC(=O)N2CCCCC2)Cc2c(Cl)c(O)cc(O)c2C(=O)O1]

TABLE 1-continued
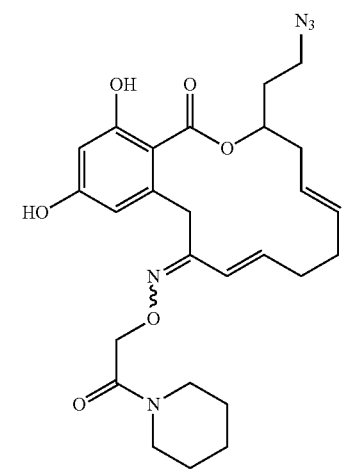 [SMILES: [N-]=[N+]=NCCC1C/C=C/CC/C=C/C(=NOCC(=O)N2CCCCC2)Cc2cc(O)cc(O)c2C(=O)O1]
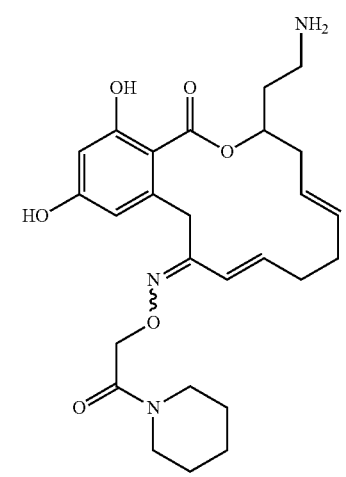 [SMILES: NCCC1C/C=C/CC/C=C/C(=NOCC(=O)N2CCCCC2)Cc2cc(O)cc(O)c2C(=O)O1]
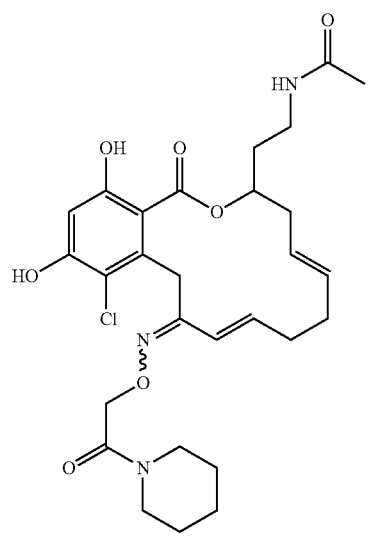 [SMILES: CC(=O)NCCC1C/C=C/CC/C=C/C(=NOCC(=O)N2CCCCC2)Cc2c(Cl)c(O)cc(O)c2C(=O)O1]
TABLE 1-continued
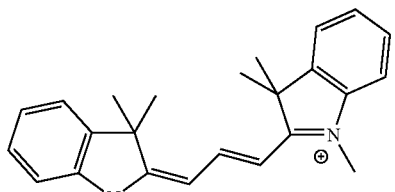
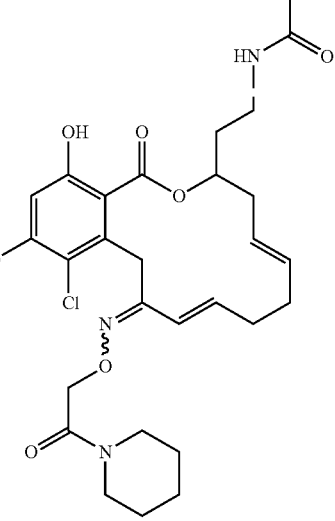
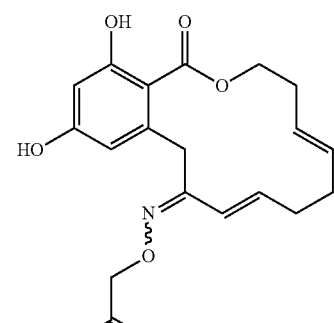
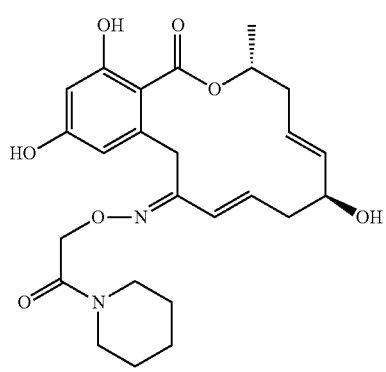 [SMILES: C[C@@H]1C/C=C/[C@@H](O)C/C=C/C(=N/OCC(=O)N2CCCCC2)Cc2cc(O)cc(O)c2C(=O)O1]

85
TABLE 1-continued
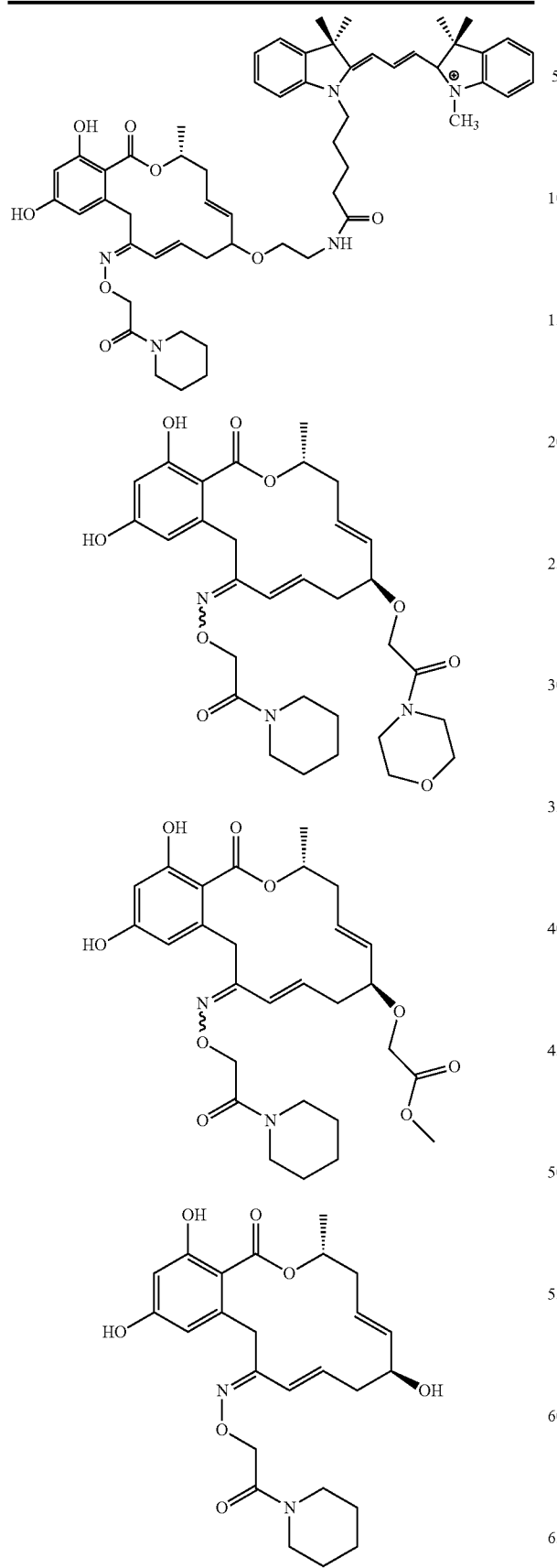
86
TABLE 1-continued
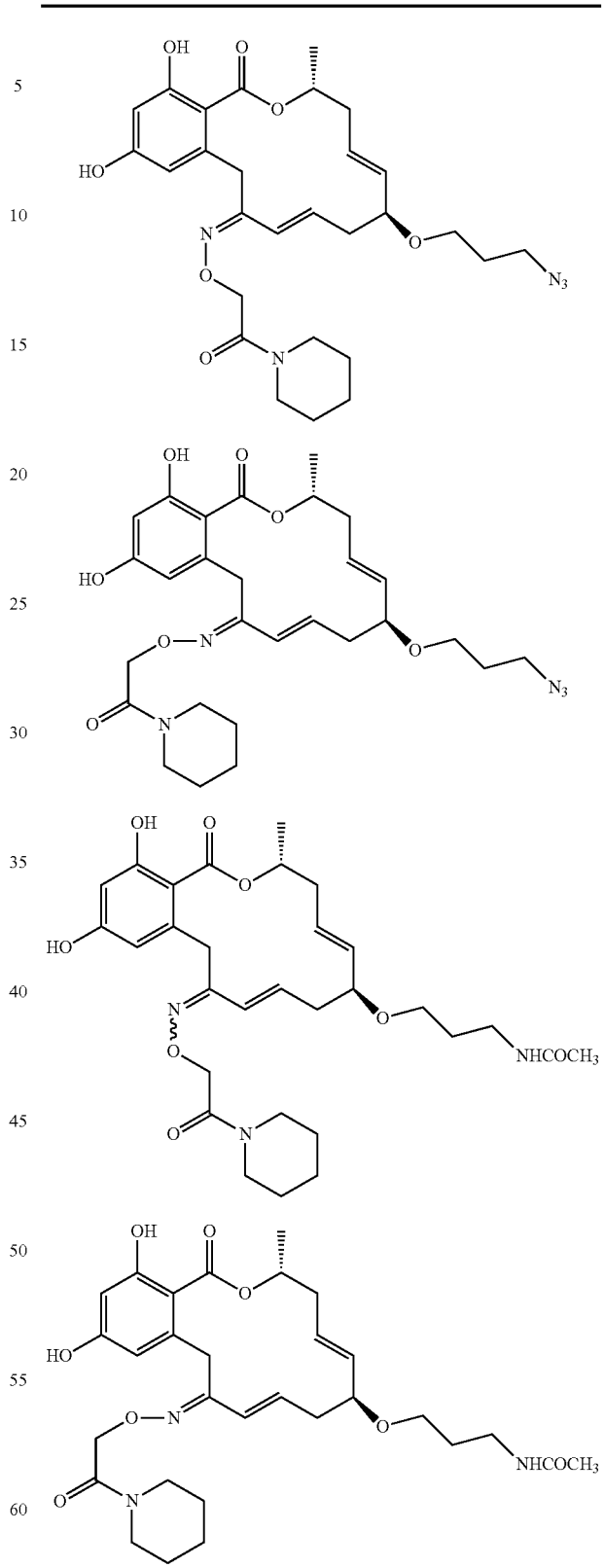
Pharmaceutically Acceptable Salts and Prodrugs
The terms "pharmaceutically acceptable salt" and "prodrug" are used throughout the specification to describe any pharmaceutically acceptable form (such as a salt, an ester, a phosphate ester, salt of an ester or a related group) of a compound which, upon administration to a patient, provides the compound described in the specification. In cases where compounds are sufficiently basic or acidic to form stable nontoxic acid or base salts, administration of the compounds as salts may be appropriate. The term pharmaceutically acceptable salts or complexes refers to salts or complexes that retain the desired biological activity of the compounds of the present invention and exhibit minimal undesired toxicological effects.

Non-limiting examples of such salts are (a) acid addition salts formed with inorganic acids such as sulfate, nitrate, hydrochloric, phosphate, and the like. For example, salts formed by the addition of hydrochloric acid, hydrobromic acid, sulfuric acid, phosphoric acid, nitric acid, and the like. In addition, salts formed with organic acids are encompassed by the invention, including tosylate, methanesulfonate, acetate, citrate, malonate, tartrate, succinate, benzoate, ascorbate, α-ketoglutarate, and α-glycerophosphate salts, such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalcturonic acid. The invention also encompasses (b) base addition salts, including formed with metal cations such as zinc, calcium, bismuth, barium, magnesium, aluminum, copper, cobalt, nickel, cadmium, sodium, potassium, lithium and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like. Also included in this definition are pharmaceutically acceptable quaternary salts known by those skilled in the art, which specifically include the quaternary ammonium salt of the formula —$NR^+A^-$, wherein R is as defined above and A is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate.

Pharmaceutically acceptable salts may be obtained using standard procedures well known in the art, for example by reacting a sufficiently basic compound such as an amine with a suitable acid affording a physiologically acceptable anion.

Pharmaceutically acceptable "prodrugs" refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. For example, a suitable prodrug may be an ester or an amide of a carboxylic acid that is hydrolyzed to form the acid. Non-limiting examples of prodrugs include but are not limited to alkyl or aralkyl esters or amides, including methyl, ethyl, propyl, benzyl and substituted benzyl esters or amides. Prodrugs also comprise phosphate esters of the compounds.

Stereoisomerism and Polymorphism

Compounds of the present invention having a chiral center may exist in and be isolated in optically active and racemic forms. The present invention encompasses any racemic, optically-active, diastereomeric, polymorphic, or stereoisomeric form, or mixtures thereof, of a compound of the invention, which possess the useful properties described herein.

In one embodiment, the compounds are prepared in optically active form by asymmetric synthesis using the processes described herein or synthetic transformations known to those skilled in the art.

Other methods to obtain optically active materials are known in the'art, and include at least the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that Converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent; or xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

Definitions

Whenever a term in the specification is identified as a range (i.e. $C_{1-4}$ alkyl), the range independently refers to each element of the range. As a non-limiting example, $C_{1-4}$ alkyl means, independently, $C_1$, $C_2$, $C_3$ or $C_4$ alkyl. Similarly, when one or more substituents are referred to as being "independently selected from" a group, this means that each substituent can be any element of that group, and any combination of these groups can be separated from the group. For example, if $R^1$ and $R^2$ can be independently selected from X, Y and Z, this separately includes the groups $R^1$ is X and $R^2$ is X; $R^1$ is X and $R^2$ is Y; $R^1$ is X and $R^2$ is Z; $R^1$ is Y and $R^2$ is X; $R^1$ is Y and $R^2$ is Y; $R^1$ is Y and $R^2$ is Z; $R^1$ is Z and $R^2$ is X; $R^1$ is Z and $R^2$ is Y; and $R^1$ is Z and $R^2$ is Z.

The term "aliphatic" as used herein means straight-chain, branched or cyclic typically of $C_1$ to $C_{18}$, and in certain embodiment of $C_1$ to $C_{10}$ or of $C_1$ to $C_6$, hydrocarbons which are completely saturated or which contain one or more units of unsaturation but which are not aromatic. For example, suitable aliphatic groups include substituted or unsubstituted linear, branched or cyclic alkyl, alkenyl, alkynyl groups and hybrids thereof such as (cycloalkyl)alkyl, (cycloalkenyl)alkyl or (cycloalkyl)alkenyl. The terms "alkyl", "alkoxy", "hydroxyalkyl", "alkoxyalkyl", and "alkoxycarbonyl", used alone or as part of a larger moiety includes both straight and branched chains containing one to twelve carbon atoms. The terms "alkenyl" and "alkynyl" used alone or as part of a larger moiety shall include both straight and branched chains containing two to twelve carbon atoms. The term "cycloalkyl" used alone or as part of a larger moiety shall include cyclic $C_3$-$C_{12}$ hydrocarbons which are completely saturated or which contain one or more units of unsaturation, but which are not aromatic, including but not limited to cyclopropyl, cyclobutyl, cyclopentyl, cyclohexyl, cycloheptyl and cyclooctyl. Aliphatic groups can be optionally substituted with one or more moieties, including but not limited to, alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, thiol, imine, sulfonic acid, sulfate, sulfonyl, sulfanyl, sulfinyl, sulfamoyl, ester, carboxylic acid, amide, phosphonyl, phosphinyl, phosphoryl, phosphine, thioester, thioether, acid halide, anhydride, oxime, hydrozine, carbamate, phosphonic acid, phosphate, phosphonate, or any other viable functional group that does not inhibit the pharmacological activity of this compound, either unprotected, or protected as necessary, as known to those skilled in the art, for example, as taught in Greene, et al., Protective Groups in Organic Synthesis, John Wiley and Sons, Second Edition, 1991, hereby incorporated by reference.

The term "alkyl" as used herein, unless otherwise specified, refers to a saturated straight, branched, or cyclic, primary, secondary, or tertiary hydrocarbon, including but not limited to groups typically of $C_1$ to $C_{18}$ and in certain embodiment of $C_1$ to $C_{10}$ or of $C_1$ to $C_6$, and specifically includes methyl, ethyl, propyl, isopropyl, butyl, isobutyl, t-butyl, pentyl, cyclopentyl, isopentyl, neopentyl, hexylisohexyl, cyclohexyl, cyclohexylmethyl, 3-methylpentyl, 2,2-dimethylbutyl and 2,3-dimethylbutyl. Alkyl groups may be substituted as noted above for the term "aliphatic."

The term "lower alkyl," as used herein, and unless otherwise specified, refers to optionally substituted $C_1$ to $C_4$ saturated straight, branched, or if appropriate, a cyclic (for example, cyclopropyl) alkyl group, including both substituted and unsubstituted forms.

Illustrative examples of alkyl groups are methyl, ethyl, propyl, isopropyl, cyclopropyl, butyl, secbutyl, isobutyl, tertbutyl, cyclobutyl, 1-methylbutyl, 1,1-dimethylpropyl, pentyl, cyclopentyl, isopentyl, neopentyl, cyclopentyl, hexyl, isohexyl, and cyclohexyl. Unless otherwise specified, the alkyl group can be unsubstituted or substituted with one or more moieties selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, thiol, imine, sulfonic acid, sulfate, sulfonyl, sulfanyl, sulfinyl, sulfamoyl, ester, carboxylic acid, amide, phosphonyl, phosphinyl, phosphoryl, phosphine, thioester, thioether, acid halide, anhydride, oxime, hydrozine, carbamate, phosphonic acid, phosphate, phosphonate, or any other viable functional group that does not inhibit the pharmacological activity of this compound, either unprotected, or protected as necessary, as known to those skilled in the art, for example, as taught in Greene et al., Protective Groups in Organic Synthesis, John Wiley & Sons, 3rd Ed., 1999.

The term "halo" or "halogen", as used herein, includes chloro, bromo, iodo, and fluoro.

The term "chiral" as used herein includes a compound that has the property that it is not superimposable on its mirror image.

The term "tautomer" as used herein refers to alternate structures which are recognized in the art to be in equilibrium with the depicted structure. For example, the enol structure below is a tautomer of the ketone structure and recognized to be in equilibrium with the ketone structure.

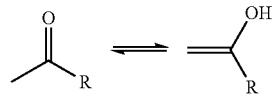

As used herein, the term "solvate" or "pharmaceutically acceptable solvate," is a solvate formed from the association of one or more solvent molecules to one or more molecules of a compound of any one of formulas I, I', II, II', III, III', IV or V or the compounds depicted in Table 1. The term solvate includes hydrates (e.g., hemi-hydrate, mono-hydrate, dihydrate, trihydrate, tetrahydrate, and the like).

The term "alkylthio" refers to a straight or branched chain alkylsulfide of the number of carbons specified, such as for example, $C_{1-4}$alkylthio, ethylthio, —S-alkyl, —S-alkenyl, —S-alkynyl, etc.

The terms "alkylamino" or "arylamino" refer to an amino group that has one or two alkyl or aryl substituents, respectively. Unless otherwise specifically stated in this application, when alkyl is a suitable moiety, then it is a lower alkyl, whether substituted or unsubstituted.

The term "alkylsulfonyl" means a straight or branched alkylsulfone of the number of carbon atoms specified, as for example, $C_{1-6}$ alkylsulfonyl or methylsulfonyl.

The term "alkoxycarbonyl" refers to a straight or branched chain ester of a carboxylic acid derivative of the number of carbon atoms specified, such as for example, a methoxycarbonyl, MeOCO—.

As used herein, the term "nitro" means —NO$_2$; the term "sulfhydryl" means —SH; and the term "sulfonyl" means —SO$_2$.

The terms "alkenyl" and "alkynyl" refer to alkyl moieties, including both substituted and unsubstituted forms wherein at least one saturated C—C bond is replaced by a double or triple bond. Thus, $C_{2-6}$ alkenyl may be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl. Similarly, $C_{2-6}$ alkynyl may be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl.

The term "alkylene" includes a saturated, straight chain, divalent alkyl radical of the formula —(CH$_2$)$_n$—, wherein "n" may be any whole integer from 1 to 12.

"Alkyl", "alkoxy", "alkenyl", "alkynyl", etc., includes both straight chain and branched groups. However, reference to an individual radical such as "propyl" embraces only that straight-chain radical, whereas a branched chain isomer such as "isopropyl" is specifically termed such.

The term "aryl" as used herein and unless otherwise specified refers to any stable monocyclic, bicyclic, or tricyclic carbon ring of up to 8 members in each ring, wherein at least one ring is aromatic as defined by the Huckel 4n+2 rule, and especially phenyl, biphenyl, or naphthyl. The term includes both substituted and unsubstituted moieties. The aryl group can be optionally substituted with one or more moieties. Examples of substituents include alkyl, halo, haloalkyl, hydroxyl, carboxyl, acyl, acyloxy, amino, amido, carboxyl derivatives, alkylamino, diallylamino, arylamino, alkoxy, aryloxy, nitro, cyano, sulfonic acid, thiol, imine, sulfate, sulfonyl, sulfanyl, sulfinyl, sulfamoyl, ester, carboxylic acid, amide, phosphate, phosphonyl, phosphinyl, phosphoryl, phosphine, thioester, thioether, acid halide, anhydride, oxime, hydrozine, carbamate, phosphonic acid, phosphonate, either unprotected, or protected as necessary, as known to those skilled in the art, for example, as taught in Greene, et al., "Protective Groups in Organic Synthesis," John Wiley and Sons, Second Edition, 1991.

The term "alkaryl" or "alkylaryl" refers to an alkyl group with an aryl substituent or an alkyl group linked to the molecule through an aryl group as defined herein. The term "aralkyl" or "arylalkyl" refers to an aryl group substituted with an alkyl substituent or linked to the molecule through an alkyl group as defined above.

The term "alkoxy" means a straight or branched chain alkyl group having an attached oxygen radical, the alkyl group having the number of carbons specified or any number within this range. For example, a "—O-alkyl", $C_{1-4}$ alkoxy, methoxy, etc.

The term "acyl" includes a group of the formula C(O)R', wherein R' is an straight, branched, or cyclic alkyl (including lower alkyl), carboxylate residue of an amino acid, aryl including phenyl, heteroaryl, alkaryl, aralkyl including benzyl, alkoxyalkyl including methoxymethyl, aryloxyalkyl such as phenoxymethyl; or substituted alkyl (including lower alkyl), aryl including phenyl optionally substituted with chloro, bromo, fluoro, iodo, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxy-trityl, substituted benzyl, alkaryl, aralkyl including benzyl, alkoxyalkyl including methoxymethyl, aryloxyalkyl such as phenoxymethyl. Aryl groups optimally comprise a phenyl group. In non-limiting embodiments, acyl groups include acetyl, trifluoroacetyl, methylacetyl, cyclopropylacetyl, cyclopropyl-carboxy, propionyl, butyryl, isobutyryl, hexanoyl, heptanoyloctanoyl, neo-heptanoyl, phenylacetyl, 2-acetoxy-2-phenylacetyl, diphenylacetyl, α-methoxy-α-trifluoromethyl-phenylacetyl, bromoacetyl, 2-nitro-benzeneacetyl, 4-chloro-benzeneacetyl, 2-chloro-2, 2-diphenylacetyl, 2-chloro-2-phenylacetyl, trimethylacetyl, chlorodifluoroacetyl, perfluoroacetyl, fluoroacetyl, bromodifluoroacetyl, methoxyacetyl, 2-thiopheneacetyl, chlorosulfonylacetyl, 3-methoxyphenylacetyl, phenoxyacetyl, tert-butylacetyl, trichloroacetyl, monochloro-acetyl, dichloroacetyl, 7H-dodecafluoro-heptanoyl, perfluoro-heptanoyl, 7H-dodeca-fluoroheptanoyl, 7-chlorododecafluoro-heptanoyl, 7-chloro-dodecafluoro-heptanoyl, 7H-dodecafluoro-heptanoyl, 7H-dodeca-fluoroheptanoyl, nona-fluoro-3,6-di-oxa-heptanoyl, nonafluoro-3,6-dioxaheptanoyl, perfluoroheptanoyl, methoxybenzoyl, methyl 3-amino-5-phenyl thiophene-2-carboxyl, 3,6-di chloro-2-methoxy-benzoyl, 4-(1,1,2,2-tetrafluoro-ethoxy)-benzoyl, 2-bromo-propionyl, omega-aminocapryl, decanoyl, n-pentadecanoyl, stearyl, 3-cyclopentyl-propionyl, 1-benzene-carboxyl, O-acetylmandelyl, pivaloyl acetyl, 1-adamantane-carboxyl, cyclohexane-carboxyl, 2,6-pyridinedicarboxyl, cyclopropane-carboxyl, cyclobutane-carboxyl, perfluorocyclohexyl carboxyl, 4-methylbenzoyl, chloromethyl isoxazolyl carbonyl, perfluorocyclohexyl carboxyl, crotonyl, 1-methyl-1H-indazole-3-carbonyl, 2-propenyl, isovaleryl, 1-pyrrolidinecarbonyl, 4-phenylbenzoyl.

The term "acylamino" includes a group having a structure of "—N(R')—C(=O)—R''', wherein each R' is independently as defined above.

The term "ester" includes a group of the structure "—C(=O)—O—R'" or "—O—C(=O)—R'", wherein R' is an straight, branched, or cyclic alkyl (including lower alkyl), carboxylate residue of an amino acid, aryl including phenyl, heteroaryl, alkaryl, aralkyl including benzyl, alkoxyalkyl including methoxymethyl, aryloxyalkyl such as phenoxymethyl; or substituted alkyl (including lower alkyl), aryl including phenyl optionally substituted with chloro, bromo, fluoro, iodo, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxy-trityl, substituted benzyl, alkaryl, aralkyl including benzyl, alkoxyalkyl including methoxymethyl, aryloxyalkyl such as phenoxymethyl. Aryl groups optimally comprise a phenyl group.

The term "heteroatom" includes an atom other than carbon or hydrogen in the structure of a heterocyclic compound, nonlimiting examples of which are nitrogen, oxygen, sulfur, phosphorus or boron.

The term "carbonyl" or "includes a group of the structure "—C(=O)—X—R'" or "X—C(=O)—R'", where X is O, S, or a bond, and each R is independently as defined above for "ester".

The term "heterocycle", "heterocyclyl", or "heterocyclic" as used herein includes non-aromatic ring systems having four to fourteen members, preferably five to ten, in which one or more ring carbons, preferably one to four, are each replaced by a heteroatom. Examples of heterocyclic rings include 3-1H-benzimidazol-2-one, (1-substituted)-2-oxo-benzimidazol-3-yl, 2-tetrahydro-furanyl, 3-tetrahydrofuranyl, 2-tetrahydropyranyl, 3-tetrahydropyranyl, 4-tetra-hydropyranyl,

[1,3]-dioxalanyl, [1,3]-dithiolanyl, [1,3]-dioxanyl, 2-tetrahydro-thiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclyl" or "heterocyclic", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. The term "heterocycle", "heterocyclyl", or "heterocyclic" whether saturated or partially unsaturated, also refers to rings that are optionally substituted.

The term "heteroaryl", used alone or as part of a larger moiety as in "heteroaralkyl" or "heteroarylalkoxy", refers to heteroaromatic ring groups having five to fourteen members. Examples of heteroaryl rings include 2-furanyl, 3-furanyl, 3-furazanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 2-pyrazolyl, 3-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, and benzoisoxazolyl. Also included within the scope of the term "heteroaryl", as it is used herein, is a group in which a heteroatomic ring is fused to one or more aromatic or nonaromatic rings where the radical or point of attachment is on the heteroaromatic ring. Examples include tetrahydroquinolinyl, tetrahydroisoquinolinyl, and pyrido[3,4-d]pyrimidinyl. The term "heteroaryl" also refers to rings that are optionally substituted. The term "heteroaryl" may be used interchangeably with the term "heteroaryl ring" or the term "heteroaromatic".

The term "amino" as used herein unless otherwise specified, includes a moiety represented by the structure "—N(R)₂", and includes primary; secondary and tertiary airlines optionally substituted by alkyl, aryl, heterocyclyl, and/or sulfonyl groups. Thus (R)₂ may represent two hydrogen atoms, two alkyl moieties, or one hydrogen and one alkyl moiety.

The term "amido" as used herein includes an amino-substituted carbonyl, while the term "amidino" means a group having the structure "—C(=NH)—NH₂".

The term "counterion" refers to a negatively or positively charged ionic species that accompanies an oppositely charged ionic species in order to maintain electric neutrality. Negatively charged counterions include inorganic counterions and organic counterions, including but not limited to, chloro, bromo, iodo, fluoro, phosphate, acetate, formate, sulfonate, trifluoroacetate acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Positively charged counterions include, but are not limited to, alkali metal (e.g., sodium and potassium), alkaline earth metal (e.g., magnesium), ammonium and N⁺(C₁₋₄ alkyl)₄ counterions.

The term "quaternary amine" as used herein includes quaternary ammonium salts that have a positively charged nitrogen. They are formed by the reaction between a basic nitrogen in the compound of interest and an appropriate quaternizing agent such as, for example, methyliodide or benzyliodide. Appropriate counterions accompanying a quaternary amine include acetate, trifluoroacetate, chloro, bromo and iodo ions.

The term "substituted" includes multiple degrees of substitution by one or more named substituents such as, for example, halo, hydroxyl, thio, alkyl, alkenyl, alkynyl, nitro, cyano, azido, amino, carboxamido, etc. Where multiple substituent possibilities exist, the compound can be substituted by one or more of the disclosed or claimed substituent groups, independently from one another, and taken singly or in plural.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

The term "protecting group" as used herein refers to a group that may be attached to a reactive group; including heteroatoms such as oxygen or nitrogen, to prevent the reactive group from participating in a reaction. Any protecting groups taught in for example, in Greene et al., *Protective Groups in Organic Synthesis*, John Wiley & Sons, 3$^{rd}$ Ed., 1999, may be used. Examples of suitable protecting groups include but are not limited to alkoxyalkyl groups such as ethoxymethyl and methoxymethyl; silyl protecting groups, such tert-butyldimethyl silyl (TBS), phenyldimethylsilyl, trimethylsilyl (TMS), 2-trimethylsilylethoxymethyl (SEM) and 2-trimethylsilylethyl; and benzyl and substituted benzyl.

It should be understood that the various possible stereoisomers of the groups mentioned above and herein are within the meaning of the individual terms and examples, unless otherwise specified. As an illustrative example, "1-methylbutyl" exists in both (R) and the (S) form, thus, both (R)-1-methyl-butyl and (S)-1-methyl-butyl is covered by the term "1-methyl-butyl", unless otherwise specified.

The term "patient" includes human and veterinary subjects.

An "effective amount" is the quantity of compound in which a beneficial outcome is achieved when the compound is administered to a patient or alternatively, the quantity of compound that possesses a desired activity in vivo or in vitro. In the case of proliferative disorders, a beneficial clinical outcome includes reduction in the extent or severity of the symptoms associated with the disease or disorder and/or an increase in the longevity and/or quality of life of the patient compared with the absence of the treatment. For example, for a subject with cancer, a "beneficial clinical outcome" includes a reduction in tumor mass, a reduction in the rate of tumor growth, a reduction in metastasis, a reduction in the severity of the symptoms associated with the cancer and/or an increase in the longevity of the subject compared with the absence of the treatment. The precise amount of compound administered to a subject will depend on the type and severity of the disease or condition and on the characteristics of the patient, such as general health, age, sex, body weight and tolerance to drugs. It will also depend on the degree, severity and type of proliferative disorder. The skilled artisan will be able to determine appropriate dosages depending on these and other factors.

The term "kinase-inhibiting amount" as used herein, refers to an amount of the compound that inhibits a kinase enzyme compared to a control as tested by the methods described herein.

The term "HSP 90-inhibiting amount" as used herein, refers to an amount of the compound that inhibits HSP90 compared to a control as tested by the methods described herein.

The term "biological sample", as used herein, includes, without limitation, cell cultures or extracts thereof; preparations of an enzyme suitable for in vitro assay; biopsied material obtained from a mammal or extracts thereof; and blood, saliva, urine, feces, semen, tears, or other body fluids or extracts thereof.

The term "cancer" includes, but is not limited to, solid tumors and blood borne tumors and include, but is not limited to, the following cancers: breast, ovary, cervix, prostate, testis, genitourinary tract, esophagus, larynx, glioblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia. The term "cancer" includes primary cancer, cancers secondary to treatment, and metastatic cancers.

The term "pharmaceutically acceptable carrier" refers to a non-toxic carrier, adjuvant, or vehicle that may be administered to a patient, together with a compound of this invention, and which does not destroy the pharmacological activity thereof.

The terms "GSK-3-mediated disease, or "GSK-3-mediated condition", as used herein, mean any disease or other deleterious condition or state in which GSK-3 is known to play a role. Such diseases or conditions include, without limitation, diabetes, Alzheimer's disease, Huntington's Disease, Parkinson's Disease, AIDS-associated dementia, amyotrophic lateral sclerosis (AML), multiple sclerosis (MS), schizophrenia, cardiomycete hypertrophy, reperfusion/ischemia, and baldness.

The terms "CDK-2-mediated disease" or CDK-2-mediated condition", as used herein, mean any disease or other deleterious condition in which CDK-2 is known to play a role. The terms "CDK-2-mediated disease" or "CDK-2-mediated condition" also mean those diseases or conditions that are alleviated by treatment with a CDK-2 inhibitor. Such conditions include, without limitation, cancer, Alzheimer's disease, restenosis, angiogenesis, glomerulonephritis, cytomegalovirus, HIV, herpes, psoriasis, atherosclerosis, alopecia, and autoimmune diseases such as rheumatoid arthritis, such as are described for example in Fischer, P. M. and Lane, D. P., Current Medicinal Chemistry, 7, 1213-1245 (2000); Mani, S., Wang, C., Wu, K., Francis, R. and Pestell, R., Exp. Opin. Invest. Drugs, 9, 1849 (2000); Fry, D. W. and Garrett, M. D., Current Opinion in Oncologic, Endocrine & Metabolic Investigational Drugs, 2, 40-59 (2000).

The terms "ERK-mediated disease" or "ERK-mediated condition", as used herein mean any disease or other deleterious condition in which ERK may play a role. The terms "ERK-2-mediated disease" or "ERK-2-mediated condition" also mean those diseases or conditions that are alleviated by treatment with a ERK-2 inhibitor. Such conditions include, without limitation, cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases. ERK-2 protein kinase and its implication in various diseases has been described for example in Bokemeyer et al. 1996, Kidney Int. 49, 1187; Anderson et al., 1990, Nature 343, 651; Crews et al., 1992, Science 258, 478; Bjorbaek et al., 1995, J. Biol. Chem. 270, 18848; Rouse et al., 1994, Cell 78, 1027; Raingeaud et al., 1996, Mol. Cell. Biol. 16, 1247; Raingeaud et al. 1996; Chen et al., 1993 Proc. Natl. Acad. Sci. USA 90, 10952; Oliver et al., 1995, Proc. Soc. Exp. Biol. Med. 210, 162; Moodie et al., 1993, Science 260, 1658; Frey and Mulder, 1997, Cancer Res. 57, 628; Sivaraman et al., 1997, J. Clin. Invest. 99, 1478; Whelchel et al., 1997, Am. J. Respir. Cell Mol. Biol. 16, 589.

The terms "AKT-mediated disease" or "AKT-mediated condition", as used herein, mean any disease or other deleterious condition in which AKT is known to play a role. The terms "AKT-mediated disease" or "AKT-mediated condition" also mean those diseases or conditions that are alleviated by treatment with a AKT inhibitor. AKT-mediated diseases or conditions include, but are not limited to, proliferative disorders, cancer, and neurodegenerative disorders. The association of AKT, also known as protein kinase B, with various diseases has been described for example in Khwaja, A., Nature, pp. 33-34, 1990; Zang, Q. Y., et al, Oncogene, 19 2000; Kazuhiko, N., et: al, The Journal of Neuroscience, 20 2000.

The terms "Src-mediated disease" or "Src-mediated condition", as used herein mean any disease or other deleterious condition in which Src is known to play a role. The terms "Src-mediated disease" or "Src-mediated condition" also mean those diseases or conditions that are alleviated by treatment with a Src inhibitor. Such conditions include, without limitation, hypercalcemia, osteoporosis, osteoarthritis, cancer, symptomatic treatment of bone metastasis, and Paget's disease. Src protein kinase and its implication in various diseases has been described for example in Soriano, Cell, 69, 551 (1992); Soriano et al., Cell, 64, 693 (1991); Takayanagi, J. Clin. Invest., 104, 137 (1999); Boschelli, Drugs of the Future 2000, 25(7), 717, (2000); Talamonti, J. Clin. Invest., 91, 53 (1993); Lutz, Biochem. Biophys. Res. 243, 503 (1998); Rosen, J. Biol. Chem., 261, 13754 (1986); Bolen, Proc. Natl. Acad. Sci. USA, 84, 2251 (1987); Masaki, Hepatology, 27, 1257 (1998); Biscardi, Adv. Cancer Res., 76, 61 (1999); Lynch, Leukemia, 7, 1416 (1993); Wiener, Clin. Cancer Res., 5, 2164 (1999); Staley, Cell Growth Diff., 8, 269 (1997).

The terms "Lck-mediated disease" or "Lck-mediated condition", as used herein, mean any disease state or other deleterious condition in which Lck is known to play a role. The terms "Lck-mediated disease" or "Lck-mediated condition" also mean those diseases or conditions that are alleviated by treatment with an Lck inhibitor. Lck-mediated diseases or conditions include, but are not limited to, autoimmune diseases such as transplant rejection, allergies, rheumatoid arthritis, and leukemia. The association of Lck with various diseases has been described for example in Molina et al., Nature, 357, 161 (1992).

The terms "Abl-mediated disease" or "Abl-mediated condition", as used herein, mean any disease state or other deleterious condition in which Abl is known to play a role. The terms "Abl-mediated disease" or "Abl-mediated condition"

also mean those diseases or conditions that are alleviated by treatment with an Abl inhibitor. Abl-mediated diseases or conditions include, but are not limited to, leukemias, particularly chronic myeloid leukemia. The association of Abl with various diseases has been described for example in Druker, et al., *N. Engl. J. Med.* 2001, 344, 1038-1042.

The terms "cKit-mediated disease" or "cKit-mediated condition", as used herein, mean any disease state or other deleterious condition in which cKit is known to play a role. The terms "cKit-mediated disease" or "cKit-mediated condition" also mean those diseases or conditions that are alleviated by treatment with an cKit inhibitor. cKit-mediated diseases or conditions include, but are not limited to, mastocytosis/mast cell leukemia, gastrointestinal stromal tumor, sinonasal natural killer/T-cell lymphoma, seminoma/dysgerminoma, throid carcinoma, small-cell lung carcinoma, malignant melanoma, adenoid cystic carcinoma, ovarian carcinoma, acute myelogenious leukemia, anaplastic large-cell lymphoma, angiosarcoma, endometrial carcinom, pediatric T-cell ALL/lymphoma, breast carcinoma and prostate carcinoma. The association of cKit with various diseases has been described for example in Heinrich, et al., *J. Clinical Oncology* 2002, 20, 1692-1703.

The terms "Flt3-mediated disease" or "Flt3-mediated condition", as used herein, mean any disease state or other deleterious condition in which Flt3 is known to play a role. The terms "Flt3-mediated disease" or "Flt3-mediated condition" also mean those diseases or conditions that are alleviated by treatment with an Flt3 inhibitor. Flt3-mediated diseases or conditions include, but are not limited to, acute myelogenous leukemia, mixed lineage leukemia and acute lymphocytic leukemia. The association of Flt3 with various diseases has been described for example in Sternberg and Licht, *Curr. Opin Hematol.* 2004, 12, 7-13.

The terms "KDR-mediated disease" or "KDR-mediated condition", as used herein, mean any disease state or other deleterious condition in which KDR is known to play a role. The terms "KDR-mediated disease" or "KDR-mediated condition" also mean those diseases or conditions that are alleviated by treatment with an KDR inhibitor. KDR-mediated diseases or conditions include, but are not limited to, carcinoma of the lung, breast, gastrointestinal tract, kidney, bladder, ovary and endometrium, intracranial tumors including glioblatoma multiforme, sporadic capillary hemangioblastoma, hematological malignancies, including T cell lymphoma, acute lymphoblastic leukemia, Burkitt's lymphoma and promyelocytic leukemia, age-related macular degeneration, herpetic ocular disease, rheumatoid arthritis, cerebral ischemia and endometriosis. The association of KDR with various diseases has been described for example in Ferrara, *Endocrine Reviews* 2004, 25, 581-611.

The term "HSP90-mediated disease" or "HSP90-mediated condition" refers to a condition in which HSP90 is known to pay a role. The conditions include but are not limited to inflammatory disorders, abnormal cellular proliferation, autoimmune disorders, ischemia, fibrogenetic disorders including but not limited to scleroderma, polymyositis, systemic lupus, rheumatoid arthritis, liver cirrhosis, keloid formation, interstitial nephritis, and pulmonary fibrosis. (Strehlow, WO 02/02123; PCT/US01/20578).

Method of Treatment

The compounds described herein, are particularly useful for the treatment or prevention of a disorder mediated by kinases or mediated by HSP90. In one embodiment, the compounds described herein, are useful for the treatment or prevention of a proliferative disorder, including cancer metastasis. In another embodiment, the compounds described herein, are useful for the treatment or prevention of an inflammatory or autoimmune disorder associated by kinases or HSP90.

An aspect of the invention relates to compounds and compositions that are useful for treating cancer.

Another aspect of the invention relates to the treatment of the following cancers: breast, ovary, cervix, prostate, testis, genitourinary tract, esophagus, larynx, glioblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia.

Another aspect of the invention is a method for treating cancer comprising administering an effective amount of a compound of formula I, I', II, II', III, III', IV or V described herein to a patient with cancer.

Angiogenesis is characterized by the proliferation of endothelial cells to form new blood vessels (often called neovascularization). Inhibition of mitosis of endothelial cells results in inhibition of angiogenesis. Another aspect of this invention therefore relates to inhibition of undesirable mitosis, including undesirable angiogenesis. A mammalian disease characterized by undesirable cell mitosis, as defined herein, includes, but is not limited to, excessive or abnormal stimulation of endothelial cells (e.g., atherosclerosis), solid tumors and tumor metastasis, benign tumors, for example, hemangiomas, trachomas, and pyogenic granulomas, vascular malfunctions, abnormal wound healing, inflammatory and immune disorders, Bechet's disease, gout or gouty arthritis, abnormal angiogenesis accompanying rheumatoid arthritis, skin diseases, such as psoriasis, diabetic retinopathy and other ocular angiogenic diseases such as retinopathy of prematurity (retrolental fibroplasic), macular degeneration, corneal graft rejection, neovascular glaucoma and Osler Weber syndrome (Osler-Weber-Rendu disease).

Other undesired angiogenesis involves normal processes including ovulation and implantation of a blastula. The compositions described above can be used as a birth control agent by reducing or preventing uterine vascularization required for embryo implantation. Accordingly, the compositions described above can be used to block ovulation and implantation of a blastula or to block menstruation (induce amenorrhea).

Diseases associated with undesirable mitosis including neovascularization can be treated according to the present invention. Such diseases include, but are not limited to, ocular neovascular disease, diabetic retinopathy, retinopathy of prematurity, corneal graft rejection, neovascular glaucoma and retrolental fibroplasias, epidemic keratoconjunctivitis, Vitamin A deficiency, contact lens overwear, atopic keratitis, superior limbic keratitis, pterygium keratitis sicca, Sjögren's syndrome, acne rosacea, phylectenulosis, syphilis, *Mycobacteria* infections, lipid degeneration, chemical burns, bacterial ulcers, fungal ulcers, Herpes simplex infections, Herpes zoster infections, protozoan infections, Kaposi's sarcoma, Mooren's ulcer, Terrien's marginal degeneration, marginal keratolysis, trauma, rheumatoid arthritis, systemic lupus, polyarteritis, Wegener's sarcoidosis, Scleritis, Steven-Johnson disease, pemphigoid, radial keratotomy, and corneal graph rejection.

Other diseases associated with undesirable mitosis including neovascularization can be treated according to the present invention. Such diseases include, but are not limited to, sickle cell anemia, sarcoid, pseudoxanthoma elasticum, Paget's disease, vein occlusion, artery occlusion, carotid obstructive disease, chronic uveitis/vitritis, Lyme's disease, systemic lupus erythematosis, Eales' disease, Bechet's disease, infections causing a retinitis or choroiditis, presumed ocular histoplasmosis, Best's disease, myopia, optic pits, Stargart's disease, pars planitis, chronic retinal detachment, hyperviscosity syndromes, toxoplasmosis, and post-laser complications. Other diseases include, but are not limited to, diseases associated with rubeosis (neovascularization of the iris and the angle) and diseases caused by the abnormal proliferation of fibrovascular or fibrous tissue including all forms of proliferative vitreoretinopathy, whether or not associated with diabetes.

Another aspect of the invention relates to the treatment of inflammatory diseases including, but no limited to, excessive or abnormal stimulation of endothelial cells (e.g., atherosclerosis), solid tumors and tumor metastasis, benign tumors, for example, hemangiomas, acoustic neuromas, trachomas, and pyogenic granulomas, vascular malfunctions, abnormal wound healing, inflammatory and immune disorders, Bechet's disease, gout or gouty arthritis, abnormal angiogenesis accompanying rheumatoid arthritis, skin diseases, such as psoriasis, diabetic retinopathy and other ocular angiogenic diseases such as retinopathy of prematurity (retrolental fibroplasic), macular degeneration, corneal graft rejection, neovascular glaucoma and Osler Weber syndrome (Osler-Weber-Rendu disease). Other undesired angiogenesis involves normal processes including ovulation and implantation of a blastula. Accordingly, the compositions described above can be used to block ovulation and implantation of a blastula or to block menstruation (induce amenorrhea).

Another aspect of this invention relates to a method of inhibiting HSP90 activity in a patient, comprising administering to a patient an effective amount of a compound of formula I, I', II, II', III, III', IV or V or a pharmaceutically acceptable salt or prodrug thereof. The invention also provides a method for treating a disease that is mediated by HSP90.

Another aspect of this invention relates to a method of inhibiting Aurora A activity in a patient, comprising administering to a patient an effective amount of a compound of formula I, I', II, II', III, III', IV or V or a pharmaceutically acceptable salt or prodrug thereof. Another aspect of this invention relates to a method of treating or preventing a GSK-3-mediated disease with a GSK-3 inhibitor, comprising administering to a patient an effective amount of a compound Of formula I, I', II, II', III, III', IV or V or a pharmaceutically acceptable salt or prodrug thereof.

One aspect of this invention relates to a method of enhancing glycogen synthesis and/or lowering blood levels of glucose in a patient in need thereof, Which method comprises administering to the patient a therapeutically effective amount of a compound of formula I, I', II, II', III, III', IV or V or a pharmaceutical composition thereof. This method is especially useful for diabetic patients. Another method relates to inhibiting the production of hyperphosphorylated Tau protein, which is useful in halting or slowing the progression of Alzheimer's disease. Another method relates to inhibiting the phosphorylation of β-catenin, which is useful for treating schizophrenia.

Another aspect of the invention relates to inhibiting GSK-3 activity in a biological sample, which method comprises contacting the biological sample with a GSK-3 inhibitor of formula I, I', II, II', III, III', IV or V.

Another aspect of this invention relates to a method of inhibiting GSK-3 activity in a patient comprising administering to the patient a compound of formula I, I', II, II', III, III', IV or V or a composition comprising said compound.

Another aspect of this invention relates to a method of treating or preventing a CDK-2-mediated disease comprising administering to a patient in need of such a treatment a therapeutically effective amount of a compound of formula I, I', II, II', III, III', IV or V or a pharmaceutical composition thereof.

Another aspect of the invention relates to inhibiting CDK-2 activity in a biological sample or a patient, which method comprises administering to the patient a compound of formula I, I', II, II', III, III', IV or V, or a composition comprising said compound.

Another aspect of this invention relates to a method of treating or preventing an ERK-2-mediated diseases comprising administering to a patient in need of such a treatment a therapeutically effective amount of a compound of formula I, I', II, II', III, III', IV or V or a pharmaceutical composition thereof.

Another aspect of the invention relates to inhibiting ERK-2 activity in a biological sample or a patient, which method comprises administering to the patient a compound of formula I, I', II, II', III, III', IV or V, or a composition comprising said compound.

Another aspect of this invention relates to a method of treating or preventing an AKT-mediated diseases comprising administering to a patient in need of such a treatment a therapeutically effective amount of a compound of formula I, I', II, II', III, III', IV or V or a pharmaceutical composition thereof.

Another aspect of the invention relates to inhibiting AKT activity in a biological sample or a patient, which method comprises administering to the patient a compound of formula I, I', H, II', III, III', IV or V, or a composition comprising said compound.

Another aspect of this invention relates to a method of treating or preventing a Src-mediated disease comprising administering to a patient in need of such a treatment a therapeutically effective amount of a compound of formula I, I', II, II', III, III', IV or V or a pharmaceutical composition thereof.

Another aspect of the invention relates to inhibiting Src activity in a biological sample or a patient, which method comprises administering to the patient a compound of formula I, I', II, II', III, III', IV or V, or a composition comprising said compound.

Another aspect of this invention relates to a method of treating or preventing an Lck-mediated disease with an Lck inhibitor, which method comprises administering to a patient in need of such a treatment a therapeutically effective amount of a compound of formula I, I', II, II', III, III', IV or V, or a pharmaceutical composition thereof.

Another aspect of the invention relates to inhibiting Lck activity in a biological sample or a patient, which method comprises administering to the patient a compound of formula I, I', II, II', III, III', IV or V, or a composition comprising said compound.

Another aspect of this invention relates to a method of treating or preventing an Abl-mediated disease with an Abl inhibitor, which method comprises administering to a patient in need of such a treatment a therapeutically effective amount of a compound of formula I, I', II, II', III, III', IV or V, or a pharmaceutical composition thereof.

Another aspect of the invention relates to inhibiting Abl activity in a biological sample or a patient, which method comprises administering to the patient a compound of formula I, I', II, II', III, III', IV or V, or a composition comprising said compound.

Another aspect of this invention relates to a method of treating or preventing a cKit-mediated disease comprising administering to a patient in need of such a treatment a therapeutically effective amount of a compound of formula I, I', II, II', III, III', IV or V, or a pharmaceutical composition thereof.

Another aspect of the invention relates to inhibiting cKit activity in a biological sample or a patient, which method comprises administering to the patient a compound of formula I, I', II, II', III, III', IV or V, or a composition comprising said compound.

Another aspect of this invention relates to a method of treating or preventing a Flt3-mediated disease comprising administering to a patient in need of such a treatment a therapeutically effective amount of a compound of formula I, I', II, II', III, III', IV or V, or a pharmaceutical composition thereof.

Another aspect of the invention relates to inhibiting Flt3 activity in a biological sample or a patient, which method comprises administering to the patient a compound of formula I, I', II, II', III, III', IV or V, or a composition comprising said compound.

Another aspect of this invention relates to a method of treating or preventing a KDR-mediated disease comprising administering to a patient in need of such a treatment a therapeutically effective amount of a compound of formula I, I', II, II', III, III', IV or V, or a pharmaceutical composition thereof.

Another aspect of the invention relates to inhibiting. KDR activity in a biological sample or a patient, which method comprises administering to the patient a compound of formula I, I', II, II', III, IV or V, or a composition comprising said compound.

An amount effective to inhibit protein kinase, is an amount that causes measurable inhibition of the kinase activity when compared to the activity of the enzyme in the absence of an inhibitor. Any method may be used to determine inhibition, such as, for example, the Biological Testing Examples described below.

Pharmaceutical Compositions

Mammals, and specifically humans, suffering from a respiratory disorder can be treated by the inhalation, systemic, oral, topical, or transdermal administration of a composition comprising an effective amount of the compounds described herein or a pharmaceutically acceptable salt, ester or prodrug thereof, optionally in a pharmaceutically acceptable carrier or diluent.

The compounds or compositions are typically administered by oral or inhalation administration. Alternatively, compounds can be administered subcutaneously, intravenously, intraperitoneally, intramuscularly, parenterally, orally, submucosally, by inhalation, transdermally via a slow release patch, or topically, in an effective dosage range to treat the target condition.

An effective dose can be readily determined by the use of conventional techniques and by observing results obtained under analogous circumstances. In determining the effective dose, a number of factors are considered including, but not limited to: the species of patient; its size, age, and general health; the specific disease involved; the degree of involvement or the severity of the disease; the response of the individual patient; the particular compound administered; the mode of administration; the bioavailability characteristics of the preparation administered; the dose regimen selected; and the use of concomitant medication.

In a separate embodiment, the compounds of the invention are in the form of an inhaled dosage. In this embodiment, the compounds may be in the form of an aerosol suspension, a dry powder or liquid particle form. The compounds may be prepared for delivery as a nasal spray or in an inhaler, such as a metered dose inhaler. Pressurized metered-dose inhalers ("MDI") generally deliver aerosolized particles suspended in chlorofluorocarbon propellants such as CFC-11, CFC-12, or the non-chlorofluorocarbons or alternate propellants such as the fluorocarbons, HFC-134A or HFC-227 with or without surfactants and suitable bridging agents. Dry-powder inhalers can also be used, either breath activated or delivered by air or gas pressure such as the dry-powder inhaler disclosed in the Schering Corporation International Patent Application No. PCT/US92/05225, published 7 Jan. 1993 as well as the Turbuhaler™ (available from Astra Pharmaceutical Products, Inc.) or the Rotahaler™ (available from Allen & Hanburys) which may be used to deliver the aerosolized particles as a finely milled powder in large aggregates either alone or in combination with some pharmaceutically acceptable carrier e.g. lactose; and nebulizers.

The compounds of the invention may be also administered in specific, measured amounts in the form of an aqueous suspension by use of a pump spray bottle. The aqueous suspension compositions of the present invention may be prepared by admixing the compounds with water and other pharmaceutically acceptable excipients. The aqueous suspension compositions according to the present invention may contain, inter alia, water, auxiliaries and/or one or more of the excipients, such as: suspending agents, e.g., microcrystalline cellulose, sodium carboxymethylcellulose, hydroxypropyl-methyl cellulose; humectants, e.g. glycerin and propylene glycol; acids, bases or buffer substances for adjusting the pH, e.g., citric acid, sodium citrate, phosphoric acid, sodium phosphate as well as mixtures of citrate and phosphate buffers; surfactants, e.g. Polysorbate 80; and antimicrobial preservatives, e.g., benzalkonium chloride, phenylethyl alcohol and potassium sorbate.

Typical systemic dosages for all of the herein described conditions are those ranging from 0.01 mg/kg to 1500 mg/kg of body weight per day as a single daily dose or divided daily doses. Preferred dosages for the described conditions range from 0.5-1500 mg per day. A more particularly preferred dosage for the desired conditions ranges from 5-750 mg per day. Typical dosages can also range from 0.01 to 1500, 0.02 to 1000, 0.2 to 500, 0.02 to 200, 0.05 to 100, 0.05 to 50, 0.075 to 50, 0.1 to 50, 0.5 to 50, 1 to 50, 2 to 50, 5 to 50, 10 to 50, 25 to 50, 25 to 75, 25 to 100, 100 to 150, or 150 or more mg/kg/day, as a single daily dose or divided daily doses. In one embodiment, the compounds are given in doses of between about 1 to about 5, about 5 to about 10, about 10 to about 25 or about 25 to about 50 mg/kg. Typical dosages for topical application are those ranging from 0.001 to 100% by weight of the active compound.

The compounds are conveniently administered in units of any suitable dosage form, including but not limited to one containing from about 7 to 3000 mg, from about 70 to 1400 mg, or from about 25 to 1000 mg of active ingredient per unit dosage form. For example, an oral dosage of from about 50 to 1000 mg is usually convenient, including in one or multiple dosage forms of 50, 100, 200, 250, 300, 400, 500, 600, 700, 800, 900 or 1000 mgs. Lower dosages may be preferable, for example, from about 10-100 or 1-50 mgs. Also contemplated are doses of 0.1-50 mg, 0.1-20 mgs., or 0.1-10 mgs. Furthermore, lower doses may be utilized in the case of administration by a non-oral route, as for example, by injection or inhalation.

The compound is administered for a sufficient time period to alleviate the undesired symptoms and the clinical signs associated with the condition being treated.

The active compound is included in the pharmaceutically acceptable carrier or diluent in an amount sufficient to deliver to a patient a therapeutic amount of compound in vivo in the absence of serious toxic effects. Pharmaceutically acceptable carriers that may be used in these pharmaceutical compositions are generally known in the art. They include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, solvents, salts or electrolytes, such as protamine sulfate, disodium hydrogen phosphate, potassium hydrogen phosphate, sodium chloride, zinc salts, silicates, colloidal silica, magnesium trisilicate, polyvinyl pyrrolidone, cellulose-based substances, polyethylene glycol, sodium carboxymethylcellulose, polyacrylates, waxes, oils, polyethylene-polyoxypropylene-block polymers, polyethylene glycol and wool fat. Pharmaceutically accepted vehicles can contain mixtures of more than one excipient in which the components and the ratios can be selected to optimize desired characteristics of the formulation including but not limited to shelf-life, stability, drug load, site of delivery, dissolution rate, self-emulsification, control of release rate and site of release, and metabolism.

Formulations can be prepared by a variety of techniques known in the art. Examples of formulation techniques can be found in literature publications and in texts such as "Water-insoluble drug formulation", edited by Rong Liu, 2000, Interpharm Press.

If administered intravenously, carriers can be physiological saline, bacteriostatic water, Cremophor EL™ (BASF, Parsippany, N.J.) or phosphate buffered saline (PBS). Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other surface-active emulsifying agents or bioavailability enhancers which are commonly used in the manufacture of pharmaceutically acceptable solid, liquid, or other dosage forms may also be used for the purposes of formulation.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. The active ingredient may be administered at once, or may be divided into a number of smaller doses to be administered at varying intervals of time.

One mode of administration of the active compound for systemic delivery is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound or its salts can be administered as a component of an elixir, suspension, syrup, wafer, chewing gum or the like. A syrup may contain, in addition to the active compounds, sucrose as a sweetening agent and certain preservatives, dyes and colorings and flavors.

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the compound is then introduced into the container. The container is then swirled by hand to free lipid material from the sides of the container and to disperse lipid aggregates, thereby forming the liposomal suspension.

Suitable vehicles or carriers for topical application can be prepared by conventional techniques, such as lotions, suspensions, ointments, creams, gels, tinctures, sprays, powders, pastes, slow-release transdermal patches, suppositories for application to rectal, vaginal, nasal or oral mucosa. In addition to the other materials listed above for systemic administration, thickening agents, emollients, and stabilizers can be used to prepare topical compositions. Examples of thickening agents include petrolatum, beeswax, xanthan gum, or polyethylene, humectants such as sorbitol, emollients such as mineral oil, lanolin and its derivatives, or squalene.

Combination Treatment

The compound can also be mixed with other active materials which do not impair the desired action, or with materials that supplement the desired action. The active compounds can be administered in conjunction, i.e. combination or alternation, with other medications used in the treatment of disorders that are mediated by kinases or HSP90.

The compounds can be administered in combination or alternation with drugs typically useful for treatment or prevention of asthma, such as certain anti-inflammatory drugs and bronchodilators. Corticosteroids (inhaled and oral), mast cell stabilizers, and the leukotriene modifier drugs are typically a useful anti-inflammatory medication for people suffering from asthma. These drugs reduce swelling and mucus production in the airways. Bronchodilators typically relieve the symptoms of asthma by relaxing the muscle bands that tighten around the airways. This action rapidly opens the airways, letting more air come in and out of the lungs. Bronchodilators also help clear mucus from the lungs.

Typically used compounds include Inhaled corticosteroids, which prevent rather than relieve symptoms. Inhaled corticosteroids include: Advair (a combination medication that includes a corticosteroid (fluticasone) plus a long acting bronchodilator drug (in this case a β-2 adrenergic receptor agonist, salmeterol)), aerobid (flunisolide), azmacort (triamcinolone), flovent (fluticasone), methylprednisolone, prednisone, pulmicort or serevent diskus (salmeterol powder), theophylline, qvar, and xopenex (levalbuterol), Inhaled corticosteroids come in three forms: the metered dose inhaler (MDI), dry powder inhaler (DPI) and nebulizer solutions. Systemic steroids include: methylprednisolone (Medrol, Methylpred, Solu-Medrol), prednisone (Deltasone) and prednisolone (Prelone, Pediapred, Orapred). Mast Cell Stabilizers include Intal and Tilade, which work by preventing the release of irritating and inflammatory substances from mast cells. Leukotriene modifiers include accolate and singular and accolate (zafirlukast), singulair (montelukast) and zyflo (zileuton).

Other non-limiting examples of corticosteriods that can be used in alternation or combination therapy include but are not limited to glucocorticoids (GC), Aerobid (Aerobid-M, flunisolide), Azmacort (triamcinolone acetonide), Beclovet (Vanceril, beclomethasone dipropionate), Flovent (fluticasone), Pulmicort (budesonide), prednisolone, hydrocortisone, adrenaline, Alclometasone Dipropionate, Aldosterone, Amcinonide, Beclomethasone Dipropionate, Bendacort, Betamethasone (Betamethasone Acetate, Betamethasone Benzoate, Betamethasone Dipropionate, Betamethasone Sodium Phosphate, Betamethasone Valerate), Budesonide, Ciclomethasone, Ciprocinonide, Clobetasol Propionate, Clobetasone Butyrate, Clocortolone Pivalate, Cloprednol, Cortisone Acetate, Cortivazol, Deflazacort, Deoxycortone Acetate (Deoxycortone Pivalate), Deprodone, Desonide, Desoxymethasone, Dexamethasone (Dexamethasone Acetate, Dexamethasone Isonicotinate, Dexamethasone Phosphate, Dexamnethasone Sodium Metasulphobenzoate, Dexamethasone Sodium Phosphate), Dichlorisone Acetate, Diflorasone Diacetate, Diflucortolone Valerate, Difluprednate, Domoprednate, Endryson, Fluazacort, Fluclorolone Acetonide, Fludrocortisone Acetate, Flumethasone (Flumethasone Pivalate), Flunisolide, Fluocinolone Acetonide, Fluocinonide, Fluocortin Butyl, Fluocortolone (Fluocortolone Hexanoate, Fluocortolone Pivalate), Fluorometholone (Fluorometholone Acetate), Fluprednidene Acetate, Fluprednisolone, Flurandrenolone, Fluticasone Propionate, Formocortal, Halcinonide, Halobetasol Propionate, Halometasone, Hydrocortamate Hydrochloride, Hydrocortisone (Hydrocortisone Acetate, Hydrocortisone Butyrate, Hydrocortisone Cypionate, Hydrocortisone Hemisuccinate, Hydrocortisone Sodium Phosphate, Hydrocortisone Sodium Succinate, Hydrocortisone Valerate), Medrysone, Meprednisone, Methylprednisolone (Methylprednisolone Acetate, Methylprednisolone, Hemisuccinate, Methylprednisolone Sodium Succinate), Mometasone Furoate, Paramethasone Acetate, Prednicarbate, Prednisolamate Hydrochloride, Prednisolone (Prednisolone Acetate, Prednisolone Hemisuccinate, Prednisolone Hexanoate, Prednisolone Pivalate, Prednisolone Sodium Metasulphobenzoate, Prednisolone Sodium Phosphate, Prednisolone Sodium Succinate, Prednisolone Steaglate, Prednisolone Tebutate), Prednisone (Prednisone Acetate), Prednylidene, Procinonide, Rimexolone, Suprarenal Cortex, Tixocortol Pivalate, Triamcinolone (Triamcinolone Acetonide, Triamcinolone Diacetate and Triamcinolone Hexacetonide).

When used to treat rheumatoid arthritis, the compounds of the present invention can be used in alternation or combination with any agent or drug known for the treatment of rheumatoid arthritic, including but not limited to: Remicade® (infliximab); methotrexate; Nonsteroidal anti-inflammatory drugs (NSAIDs) such as aspirin and ibuprofen; corticosteroid medications, such as Prednisone; Leflunomide; biologic agents such as etanercept, infliximab, adalimumab, and anakinra; celecoxib; tetracyclines; tumour necrosis factor (TNF) antagonists; nonsteroidal anti-inflammatories; cyclooxygenase-2 inhibitors; interleukin-1-receptor antagonist Drugs in clinical investigation are contemplated, including but not limited to: 681323 (p38 alpha kinase inhibitor) (GlaxoSmithKline); 683699 (T-0047) (dual alpha 4 integrin antaginist) (GlaxoSmithKline); ABT-963 (Abbott Laboratories); AGIX-4207 (Atherogenics); alpha-L-iduronidase (Genzyme General), AMG719 (Amgen); AnergiX.RA (Corixa); anti-CD11 humanized MAb (Genentech); Arava (Aventis Pharmaceuticals); CDP 870 (Pfizer); CDP-870 (Pfizer); Celebrex (Pfizer); COX 189 (Novartis); eculizumab (Alexion Pharmaceuticals); HuMax-IL15 (Amgen); IDEC 151 (IDEC Pharmaceuticals); IDEC-151/clenoliximab (IDEC Pharmaceuticals; IL-1 trap (Rengeneron Pharmaceuticals); interleukin-1 (Regeneron Pharmaceuticals); interleukin-18 (Regeneron Pharmaceuticals); J695 (Abbott Laboratories); Oraprine (DORBioPharma); pegsunercept (soluble tumor necrosis factor-a receptor type 1)(Amgen); pralnacasan (Aventis); Prograf (Fujisawa Healthcare); r-IL-18 by (Serono); R1487 (kinase inhibitor)(Roche); Rituxan (Genentech); SB281832 (GlaxoSmithKline); SCIO-323 (Scio); SCIO-469 (Scio) and Vitaxin (MedImmune).

In one embodiment, the compound of the present invention can also be administered in combination or alternation with apazone, amitriptyline, chymopapain, collegenase, cyclobenzaprine, diazepam, fluoxetine, pyridoxine, ademetionine, diacerein, glucosamine, hylan (hyaluronate), misoprostol, paracetamol, superoxide dismutase mimics, TNFα receptor antagonists, TNFα antibodies, P38 Kinase inhibitors, tricyclic antidepressants, cJun kinase inhibitors or immunosuppressive agents, IV gamma globulin, troleandomycin, cyclosporin (Neoral), methotrexate, FK-506, gold compounds such as Myochrysine (gold sodium thiomalate), platelet activating factor (PAF) antagonists such as thromboxane inhibitors, leukotriene-$D_4$-receptor antagonists such as Accolate (zafirlukast), Ziflo (zileuton), leukotriene $C_1$, $C_2$ antagonists and inhibitors of leukotriene synthesis such as zileuton for the treatment of arthritic disorders, inducible nitric oxide sythase inhibitors.

In another embodiment, the active compound is administered in combination or alternation with one or more other non-steroidal anti-inflammatory drug(s) (NSAIDS). Examples of NSAIDS that can be used in alternation or combination therapy are carboxylic acids, propionic acids, fenamates, acetic acids, pyrazolones, oxicans, alkanones, gold compounds and others that inhibit prostaglandin synthesis, preferably by selectively inhibiting cylcooxygenase-2 (COX-2). Some nonlimiting examples of COX-2 inhibitors are Celebrex (celecoxib) and Vioxx (rofacoxib). Some nonlimiting examples of NSAIDS are aspirin (acetylsalicylic acid), Dolobid (diflunisal), Disalcid (salsalate, salicylsalicylate), Trisilate (choline magnesium trisalicylate), sodium salicylate, Cuprimine (penicillamine), Tolectin (tolmetin), ibuprofen (Motrin, Advil, Nuprin Rufen), Naprosyn (naproxen, Anaprox, naproxen sodium), Nalfon (fenoprofen), Orudis (ketoprofen), Ansaid (flurbiprofen), Daypro (oxaprozin), meclofenamate (meclofanamic acid, Meclomen), mefenamic acid, Indocin (indomethacin), Clinoril (sulindac), tolmetin, Voltaren (diclofenac), Lodine (etodolac), ketorolac, Butazolidin (phenylbutazone), Tandearil (oxyphenbutazone), piroxicam (Feldene), Relafen (nabumetone), Myochrysine (gold sodium thiomalate), Ridaura (auranofin), Solganal (aurothioglucose), acetaminophen, colchicine, Zyloprim (allopurinol), Benemid (probenecid), Anturane (sufinpyrizone), Plaquenil (hydroxychloroquine), Aceclofenac, Acemetacin, Acetanilide, Actarit, Alclofenac, Alminoprofen, Aloxiprin, Aluminium Aspirin, Amfenac Sodium, Amidopyrine, Aminopropylone, Ammonium Salicylate, Ampiroxicam, Amyl Salicylate, Anirolac, Aspirin, Auranofin, Aurothioglucose, Aurotioprol, Azapropazone, Bendazac (Bendazac Lysine), Benorylate, Benoxaprofen, Benzpiperylone, Benzydamine hydrochloride, Bornyl Salicylate, Bromfenac Sodium, Bufexamac, Bumadizone Calcium, Butibufen Sodium, Capsaicin, Carbaspirin Calcium, Carprofen, Chlorthenoxazin, Choline Magnesium Trisalicylate, Choline Salicylate, Cinmetacin, Clofexamide, Clofezone, Clometacin, Clonixin, Cloracetadol, Cymene, Diacerein, Diclofenac (Diclofenac Diethylammonium Salt, Diclofenac Potassium, Diclofenac Sodium), Diethylamine Salicylate, Diethylsalicylamide, Difenpiramide, Diflunisal, Dipyrone, Droxicam, Epirizole, Etenzamide, Etersalate, Ethyl Salicylate, Etodolac, Etofenamate, Felbinac, Fenbufen, Fenclofenac, Fenoprofen Calcium, Fentiazac, Fepradinol, Feprazone, Floctafenine, Flufenamic, Flunoxaprofen, Flurbiprofen (Flurbiprofen Sodium), Fosfosal, Furprofen, Glafenine, Glucametacin, Glycol Salicylate, Gold Keratinate, Harpagophytum Procumbens, Ibufenac, Ibuprofen, Ibuproxam, Imidazole Salicylate, Indomethacin (Indomethacin Sodium), Indoprofen, Isamifazone, Isonixin, Isoxicam, Kebuzone, Ketoprofen, Ketorolac Trometamol, Lithium Salicylate, Lonazolac Calcium, Lomoxicam, Loxoprofen Sodium, Lysine Aspirin, Magnesium Salicylate, Meclofenamae Sodium, Mefenamic Acid, Flufenamic Acid, Meloxicam, Methyl Butetisalicylate, Methyl Gentisate, Methyl Salicylate, Metiazinic Acid, Metifenazone, Mofebutazone, Mofezolac, Morazone Hydrochloride, Morniflumate, Morpholine Salicylate, Nabumetone, Naproxen (Naproxen Sodium), Nifenazone, Niflumic Acid, Nimesulide, Oxametacin, Oxaprozin, Oxindanac, Oxyphenbutazone, Parsalmide, Phenybutazone, Phenyramidol Hydrochloride, Picenadol Hydrochloride, Picolamine Salicylate, Piketoprofen, Pirazolac, Piroxicam, Pirprofen, Pranoprofen, Pranosal, Proglumetacin Maleate, Proquazone, Protizinic Acid, Ramifenazone, Salacetamide, Salamidacetic Acid, Salicylamide, Salix, Salol, Salsalate, Sodium Aurothiomalate, Sodium Gentisate, Sodium Salicylate, Sodium Thiosalicylate, Sulindac, Superoxide Dismutase (Orgotein, Pegorgotein, Sudismase), Suprofen, Suxibuzone, Tenidap Sodium, Tenoxicam, Tetrydamine, Thurfyl Salicylate, Tiaprofenic, Tiaramide Hydrochloride, Tinoridine Hydrochloride, Tolfenamic Acid, Tometin Sodium, Triethanolamine Salicylate, Ufenamate, Zaltoprofen, Zidometacin and Zomepirac Sodium.

In one embodiment, the compound(s) of the present invention can be administered in combination or alternation one or more anti-proliferative agents. Any of the antiproliferative agents listed below, or any other such agent known or discovered to exhibit an antiproliferative effect can be used in combination or alternation with the present invention to achieve a combination therapeutic effect.

Representative adjuncts include levamisole, gallium nitrate, granisetron, sargramostim strontium-89 chloride, filgrastim, pilocarpine, dexrazoxane, and ondansetron. *Physicians' Desk Reference,* 50th Edition, 1996.

Representative androgen inhibitors include flutamide and leuprolide acetate. *Physicians' Desk Reference,* 50th Edition, 1996.

Representative antibiotic derivatives include doxorubicin, bleomycin sulfate, daunorubicin, dactinomycin, and idarubicin.

Representative antiestrogens include tamoxifen citrate and analogs thereof. *Physicians' Desk Reference,* 50th Edition, 1996. Additional antiestrogens include nonsteroidal antiestrogens such as toremifene, droloxifene and roloxifene. Magarian et al., *Current Medicinal Chemistry,* 1994, Vol. 1, No. 1.

Representative antimetabolites include fluorouracil, fludarabine phosphate, floxuridine, interferon alfa-2b recombinant, methotrexate sodium, plicamycin, mercaptopurine, and thioguanine. *Physicians' Desk Reference,* 50th Edition, 1996.

Representative cytotoxic agents include doxorubicin, carmustine (BCNU), lomustine (CCNU), cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa-2a recombinant, paclitaxel, teniposide, and streptozoci. *Physicians' Desk Reference,* 50th Edition, 1996.

Representative hormones include medroxyprogesterone acetate, estradiol, megestrol acetate, octreotide acetate, diethylstilbestrol diphosphate, testolactone, and goserelin acetate. *Physicians' Desk Reference,* 50th Edition, 1996.

Representative immunodilators include aldesleukin. *Physicians' Desk Reference,* 50th Edition, 1996.

Representative nitrogen mustard derivatives include melphalan, chlorambucil, mechlorethamine, and thiotepa. *Physicians' Desk Reference,* 50th Edition, 1996.

Representative steroids include betamethasone sodium phosphate and betamethasone acetate. *Physicians' Desk Reference,* 50th Edition, 1996.

Representative antineoplastic agents include paclitaxel or doxorubicin.

Additional suitable chemotherapeutic agents include alkylating agents, antimitotic agents, plant alkaloids, biologicals, topoisomerase I inhibitors, topoisomerase II inhibitors, and synthetics. *Anti Cancer Agents by Mechanism*, tttp://www.dtp.nci.nih.gov/docs/cancer/searches/standard_mechanism_list.html, Apr. 12, 1999; *Approved Anti-Cancer Agents*, http://www.ctep.info.nih.gov/handbook/HandBookText/fda_agen.htm, pages 1-7, Jun. 18, 1999; *MCMP 611 Chemotherapeutic Drugs to Know*, http//www.vet.purdue.edu/depts/bms/courses/mcmp611/chrx/drg2no61.html, Jun. 24, 1999; and *Chemotherapy*, http://www.vetmed.lsu.edu/oncology/Chemotherapy.htm, Apr. 12, 1999.

Representative alkylating agents include asaley, AZQ, BCNU, busulfan, bisulphan, carboxyphthalatoplatinum, CBDCA, CCNU, CHIP, chlorambucil, chlorozotocin, cisplatinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolamide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864. *AntiCancer Agents by Mechanism*, http://dtp.nci.nih.gov/docs/cancer/searches/standard_mechanism_list.html, Apr. 12, 1999.

Representative antimitotic agents include allocolchicine, Halichondrin M, colchicine, colchicine derivatives, dolastatin 10, maytansine, rhizoxin, paclitaxel derivatives, paclitaxel, thiocolchicine, trityl cysteine, vinblastine sulfate, and vincristine sulfate. *AntiCancer Agents by Mechanism*, http://dtp.nci.nih.gov/docs/cancer/searches/standard_mechanism_list.html, Apr. 12, 1999.

Representative plant alkaloids include actinomycin D, bleomycin, L-asparaginase, idarubicin, vinblastine sulfate, vincristine sulfate, mitramycin, mitomycin, daunorubicin, VP-16-213, VM-26, navelbine and taxotere. *Approved Anti-Cancer Agents*, http://ctep.info.nih.gov/handbook/HandBook Text/fda_agent.htm, Jun. 18, 1999.

Representative biologicals include alpha interferon, BCG, G-CSF, GM-CSF, and interleukin-2. *Approved Anti-Cancer Agents*, http://ctep.info.nih.gov/handbook/HandBookText/fda_agent.htm, Jun. 18, 1999.

Representative topoisomerase I inhibitors include camptothecin, camptothecin derivatives, and morpholinodoxorubicin. *AntiCancer Agents by Mechanism*, http://dtp.nci.nih.gov/docs/cancer/searches/standard_mechanism_list.html, Apr. 12, 1999.

Representative topoisomerase II inhibitors include mitoxantron, amonafide, m-AMSA, anthrapyrazole derivatives, pyrazoloacridine, bisantrene HCL, daunorubicin, deoxydoxorubicin, menogaril, N,N-dibenzyl daunomycin, oxanthrazole, rubidazone, VM-26 and VP-16. *AntiCancer Agents by Mechanism*, http://dtp.nci.nih.gov/docs/cancer/searches/standard_mechanism_list.html, Apr. 12, 1999.

Representative synthetics include hydroxyurea, procarbazine, o,p'-DDD, dacarbazine, CCNU, BCNU, cis-diamminedichloroplatimun, mitoxantrone, CBDCA, levamisole, hexamethylmelamine, all-trans retinoic acid, gliadel and porfimer sodium. *Approved Anti-Cancer Agents*, http://ctep.info.nih.gov/handbook/HandBookText/fda_agen.htm, Jun. 18, 1999.

Representative antibodies include Monoclonal antibodies directed to proliferating cells such as Rituximab (anti-CD20) for B-cell tumors and herceptin.

Drugs in clinical trials for cancer are specifically contemplated including, but not limited to: 715992 (kinesin inhibitor)(GlaxoSmithKline); Advexin (Introgen Therapeutics); AG-002037 (Pfizer); APC8024 (Dendreon); atrasentan (ABT-627); BIBH 1 (Boerhinger-Ingelheim) CCI 779 (Wyeth Pharmaceuticals); CEA Vac (Titan Pharmaceuticals); CEA-CIDE (Immunomedics) CEA-Scan (Immunomedics); Celebrex (Pharmacia); CP-547, 632 (anti-VEGF tyrosine kinase)(OSI Pharmaceuticals); CP-724-714 (anti-ErbB2 [HER-2 neu] tyrosine kinase)(OSI Pharmaceuticals); CpG 7909 (Aventis Pharmaceuticals); dendritic/cancer cell fusion (Genzyme Molecular Oncology); ERA 923 (tissue-selective estrogen receptor modulator-SERM) (Ligand Pharmaceuticals); Ethyol (MedImmune Oncology); fowlpox-(6D)-TRICOM/vaccinia-(6D)-TRICOM vaccine (National Cancer Institute); G-3139 (Genta); Gemzar (Eli Lilly); Genasense (Genta); GeneVax (Centocor); GPI-0100 immune enhancer (adjuvant)(Galencia Pharmaceuticals); GTI 2040 (Lorus Therapeutics); GTI 2501 (Lorus Therapeutics); H11 (Viventia Biotech); interleukin-4 (IL-4) (National Cancer Institute); irofulven (National Cancer Institute); liquid IL-2 (Chiron); MAb antibody 3A1 (National Cancer Institute); multitargeted antifolate I (Eli Lily); Myocet (Liposome Company); oral paclitaxel (IVAX Pharmaceuticals); P53 and RAS vaccine (National Cancer Institute); PD-183805 (Pfizer); Proleukin (Chiron); ProMune (Chiron); R1550 (Antisoma); RAS peptides (National Cancer Institute); rebeccamycin analog (National Cancer Institute); recombinant human chorionic gonadotropin (r-hCG) (Serono); RSR-13 (Altos Therapeutics); RSR-13 (Eli Lilly); Targretin (Ligand Pharmaceuticals); tariquidar (QLT); Taxotere (Aventis Pharmaceuticals); TLK286 (Telik); vaccina-MUC-1 vaccine (Therion Biologics); vaccinia-MUC-1 vaccine (National Cancer Institute); Xtotax (Cell Therapeutics); Xyotax (Cell Therapeutics); Yondelis (ET-743)(Johnson & Johnson); Zarnestra (Johnson & Johnson); ZD6126 and ZD6474 (AstraZeneca); and Zoladex (AstraZeneca)

Processes for the Preparation of the Compounds

Modular synthetic processes directed to the synthesis of the resorcylic acid lactones of the invention are presented below. The syntheses developed may utilize resin-assisted or solid phase synthesis to minimize and facilitate the isolation of intermediate and final products.

The following abbreviations are used herein.

Ac Acetyl ($CH_3C=O$)

BBN Borabicyclononane

Bn Benzyl

Bz Benzoyl $Cy_3$ Cyanine dye labeling reagent

δ Chemical shift (NMR)

DCC Dicyclohexylcarbodiimide

DEAD Diethyl azodicarboxylate

DIAD Diisopropyl azodicarboxylate d.e. Diastereoisomeric excess

DIBAL or Dibal-H Diisobutylaluminum hydride

DIC N,N'-diisopropylcarbodiimide

DMAP 4-Dimethylaminopyridine

DMF Dimethylformamide

DMSO Dimethylsulfoxide $EC_{50}$ Plasma concentration required for obtaining 50% of maximum effect in vivo e.e. Enantiomeric excess EOM Ethoxymethyl ($CH_3CH_2OCH_2—$)

FDA Food and Drug Administration

Grubbs' II Grubbs' second generation catalyst: (ruthenium [1,3-bis(2,4,6-trimethylphenyl)-2-imidazolinylidene) dichloro(phenylmethylene) (tricyclohexylphosphane)

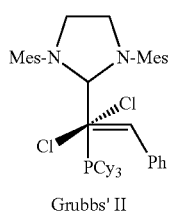

Grubbs' II

HFIP Hexafluoroisopropanol
HPLC High performance chromatography
HRMS High resolution mass spectrometry
HSP90 Heat shock protein 90
Hunig's Base Diisopropylethylamine
$IC_{50}$ Concentration of a drug that is required for 50% inhibition in vitro
$Ipc_2$ Bis-isopinocamphoryl
J Coupling constant
LDA Lithium diisopropylamide.
μM Micromolar concentration (μmol.l$^{-1}$)
M.S. Mass spectrum
NMR Nuclear magnetic resonance
PG Protecting Group
PS- Polymer supported
PS-DCC Polymer supported dicyclohexylcarbodiimide
PS-TBD (1,5,7)-Triaza-bicyclo[4.4.0]dodeca-5-ene-7-methyl polystyrene
Pyr or Py Pyridine
rac Racemic
RAL Resorcylic acid lactone
RCM Ring-closing metathesis
$R_f$ Retention factor
RT Room temperature
SEM 2-Trimethylsilylethoxymethoxy
TBAF Tetra-n-butylammonium fluoride
TBAI Tetra-n-butylammonium iodide
TBDPS t-Butyldiphenylsilyl
TBS t-Butyldimethylsilyl
TFA Trifluoroacetic acid
TFAA Trifluoroacetic acetic anhydride
THF Tetrahydrofuran
THP Tetrahydropyran
TLC Thin layer chromatography
TMS Trimethylsilyl
TMSCl Trimethylsilylchloride
TNTU 2-(endo-5-norbornene-2,3-dicarboxylimide)-,1,3,3-tetramethyluronium tetrafluoroborate
Ts Tosyl (p-$CH_3C_6H_4SO_2$)
p-TSOH para-Toluenesulfonic acid A general retrosynthetic disconnection of the synthetic strategy for preparation of the compounds of the invention is shown below (see Barluenga et al., *Angew. Chem. Int. Ed.,* 2008, 47, 4432-4435). A Mitsunobu esterification, an acylation and a ring-closing metathesis are shown as the main disconnections using three building blocks. Using these building blocks and synthetic strategy, a divergent synthesis of the compounds was developed. A similar strategy has been used to prepare a library of pochonin analogues with HSP90 activity (see Moulin et al., *Chem. Eur. J.* 2006, 12, 8819).

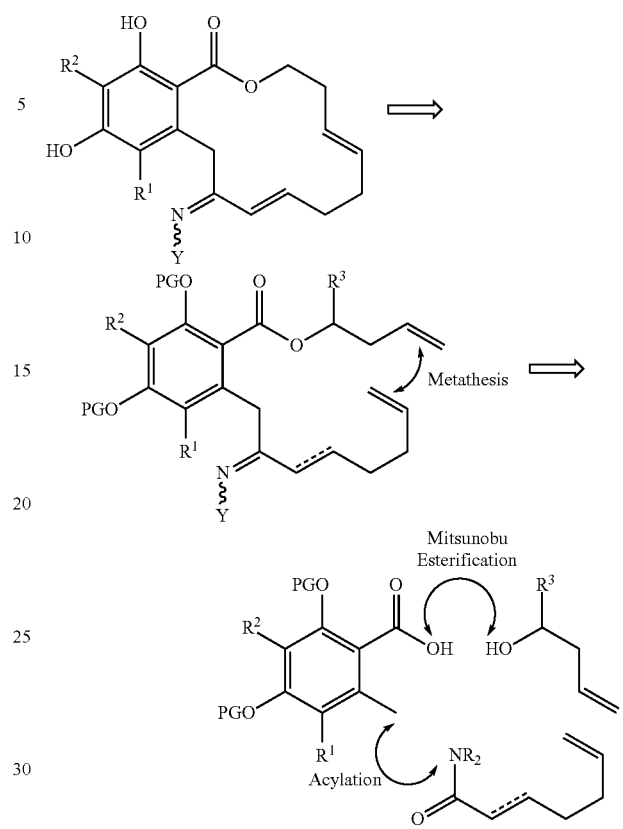

Retrosynthetic Analysis for Compounds of the Invention

The schemes illustrated below are non-limiting examples of the synthesis of the compounds of the invention and intermediates used to prepare the compounds. It will be apparent to one of skill in the art that the reactions depicted in the schemes may use alternate reagents and conditions to achieve the desired transformation. For example, various protecting groups may be used in the synthesis of the compounds, and the specific groups depicted in the schemes are non-limiting examples. For example, any suitable protecting groups for hydroxy and carboxyl groups taught in Greene et al., *Protective Groups in Organic Synthesis*, John Wiley & Sons, 3$^{rd}$ Ed., 1999 may be used instead of the protecting groups shown. Furthermore, alternate reagents known in the art for the transformations shown, including, for example, the esterification of the aromatic carboxylic acid or the ring closure reaction may be used.

Scheme 1 below shows the general synthetic protocol for one of the compounds of the invention where X=O and n=1, starting from intermediate 1-1, which is formed from readily available protected aromatic precursors by acylation of the benzylic position with a suitably substituted carboxylic acid derivative followed by formation of the substituted oxime by reaction of the acylated aromatic group with a suitable hydroxylamine reagent, such as aminooxyacetic acid. Scheme 2 below provides a non-limiting example of the preparation of an aromatic compound of structure 1-1.

To facilitate the isolation and purification of the intermediates and final compounds, intermediates such as compound 1-1 may be anchored onto a suitably functionalized resin, such as a 2-chlorotrityl resin, by reaction of the carboxylic acid group with the resin. The resin-anchored intermediate 1-2 is deprotected to provide intermediate 1-3 with the free carboxylic acid group.

The carboxylic acid 1-3 is reacted with a suitable alcohol $R^2OH$, which comprises a double bond that may be utilized for a ring-closing metathesis reaction with a suitable catalyst. Various conditions for the formation of an aromatic ester derivative may be used, including, but not limited to a Mitsunobu esterification with, for example, a homoallylic alcohol, to form the corresponding ester (not shown). The resin bound ester is then treated with a catalyst, such as Grubb's second generation catalyst, to effect ring closure to intermediate 1-4. Use of microwave irradiation during the ring closure has been found to improve the efficiency of the metathesis reaction.

It is important to note that the reaction sequence is not possible in the absence of the oxime functionality, since reaction of the corresponding benzylic ketone results in coumarin byproducts (see Barluenga et al., Chem. Eur. J. 2005, 11, 4935).

The macrocycles are removed from the resin using, for example, hexafluoropropanol (HFIP) to provide the oxime acid product 1-5. Use of the mild HFIP for the removal of the compounds from the resin left the EOM protecting groups intact, thus enabling further elaboration of other functionality on the macrocycles. The resulting product may be derivatized by reaction of the free carboxylic acid with a suitable group. Carboxylic acids are very useful for the formation of various derivatives, as known in the art. The free carboxylic acid may be derivatized by reacting with a variety of compounds to form desired products. For example, reaction with $R^4XH$ (X=O or NH), in the presence of an activating reagent, such as dicyclohexylcarbodiimide (DCC) or an alternate activating reagent, to form the corresponding ester or amide 1-6.

In non-limiting examples, the free carboxylic acid in compound 1-5 may be eracted with an amine or alcohol to form an amide or ester. In some embodiments, the amines shown below are used to form compounds of the invention. It will be apparent that alternate groups may be used to form the corresponding amide or ester.

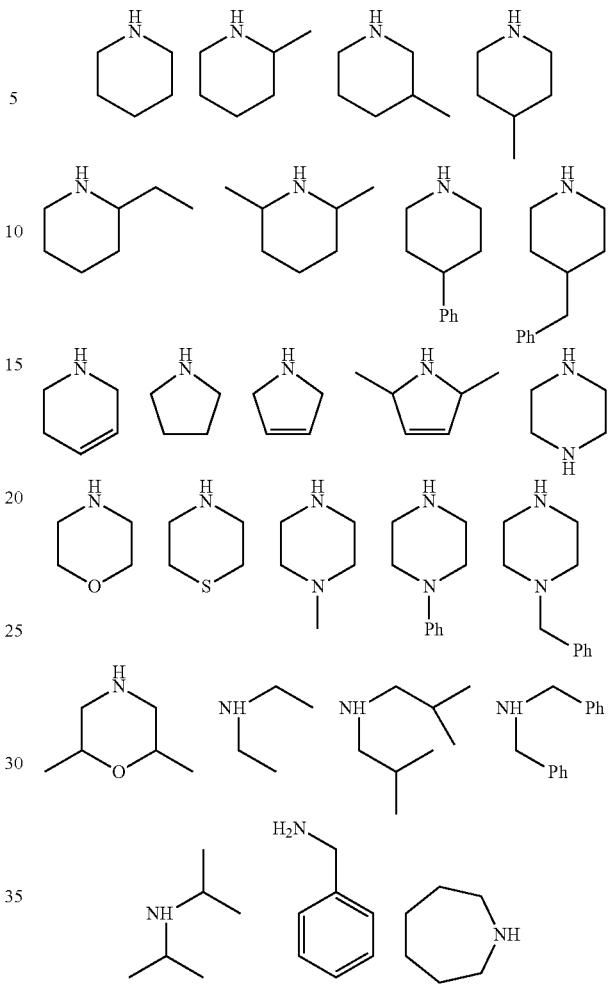

The use of resin-immobilized carbodiimide and sulfonic acid was advantageously used to form various amides and esters from the carboxylic acid moiety liberated upon removal of the macrocycles (compounds 1-5) from the resin.

Scheme 1

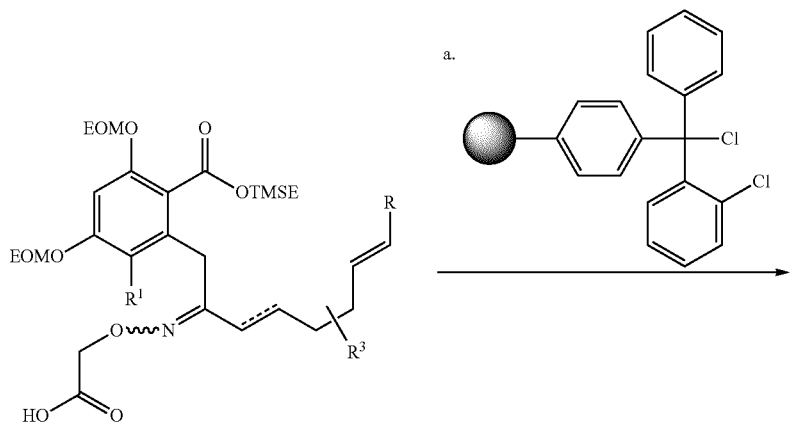

1-1

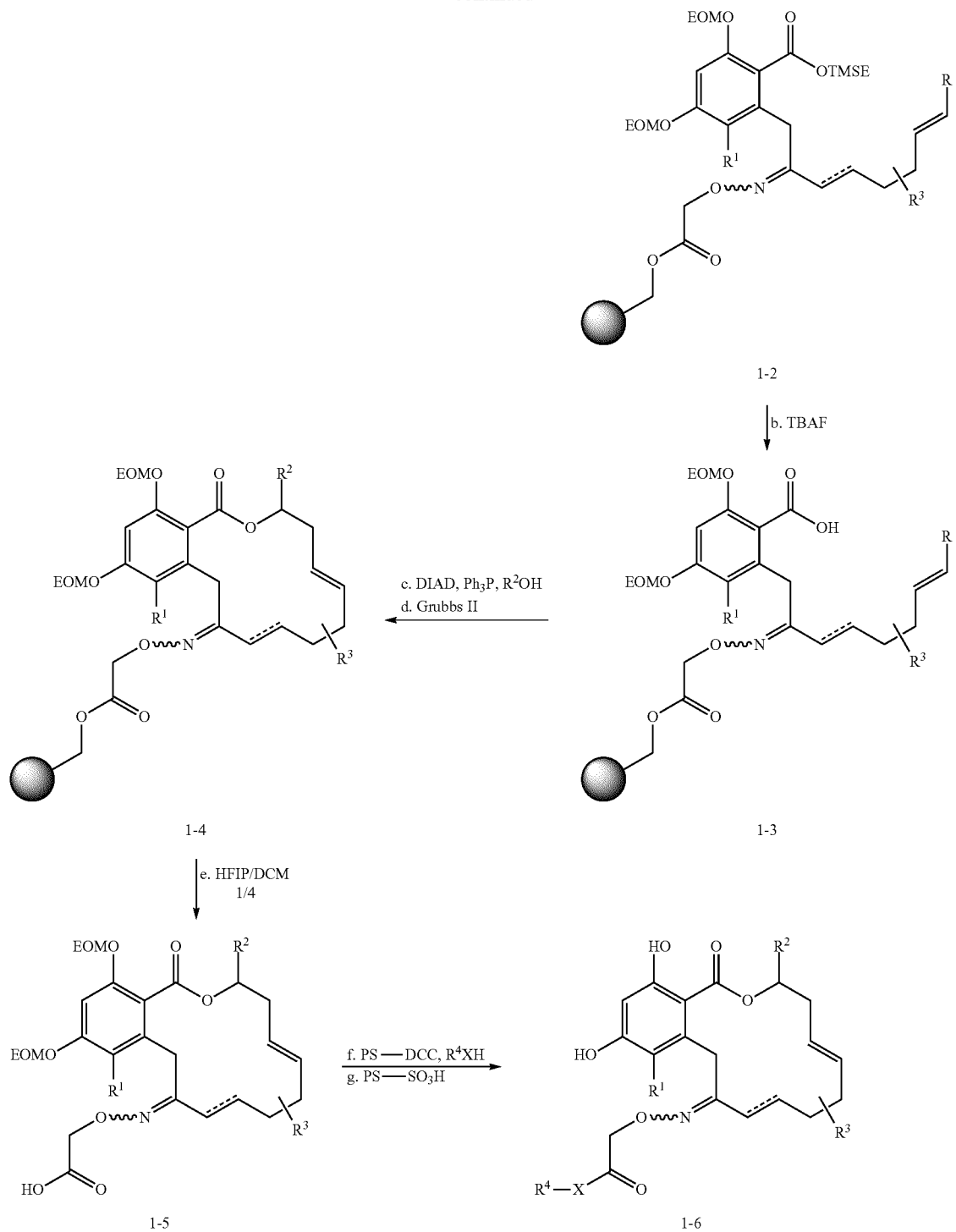

Reagents and conditions: a) PS—ClTr—Cl (3.0 equiv), DIPEA (6.0 equiv), CH$_2$Cl$_2$, 23° C., 24 h; then AcOH (20 equiv), 23° C., 24 h; b) TBAF (4.0 equiv), 23° C., 4 h; c) R$^2$OH (5.0 equiv), Ph$_3$P (2.0 equiv), DIAD (2.0 equiv), toluene, 23° C., 12 h, d) Grubb's II (0.06 equiv), CH$_2$Cl$_2$, 120° C., MW, 3 x 45 min, e) HFIP/CH$_2$Cl$_2$ 1/4, 23° C., 3 h, 20-30% over 5 steps; f) PS—DCC (3.0 equiv), DMAP (cat), R$^4$XH (2.0 equiv), 23° C., 72 h, ~75%; g) PS—SO$_3$H (10 equiv), MeOH, 23° C., 4 h, ~85%.

Scheme 2 shows an example synthesis of intermediate 1-1 from a suitably protected aromatic carboxylic acid derivative 2-1. Deprotonation of 2-1 with lithium diisopropylamide (LDA) and reaction with Weinreb amide 2-2 followed by quenching with benzoic acid resin affords intermediate 2-3. Reaction of 2-3 with excess hydroxylamine reagent results in formation of the oxime intermediate 2-4, which is utilized further, as described in scheme 1.

Scheme 2:

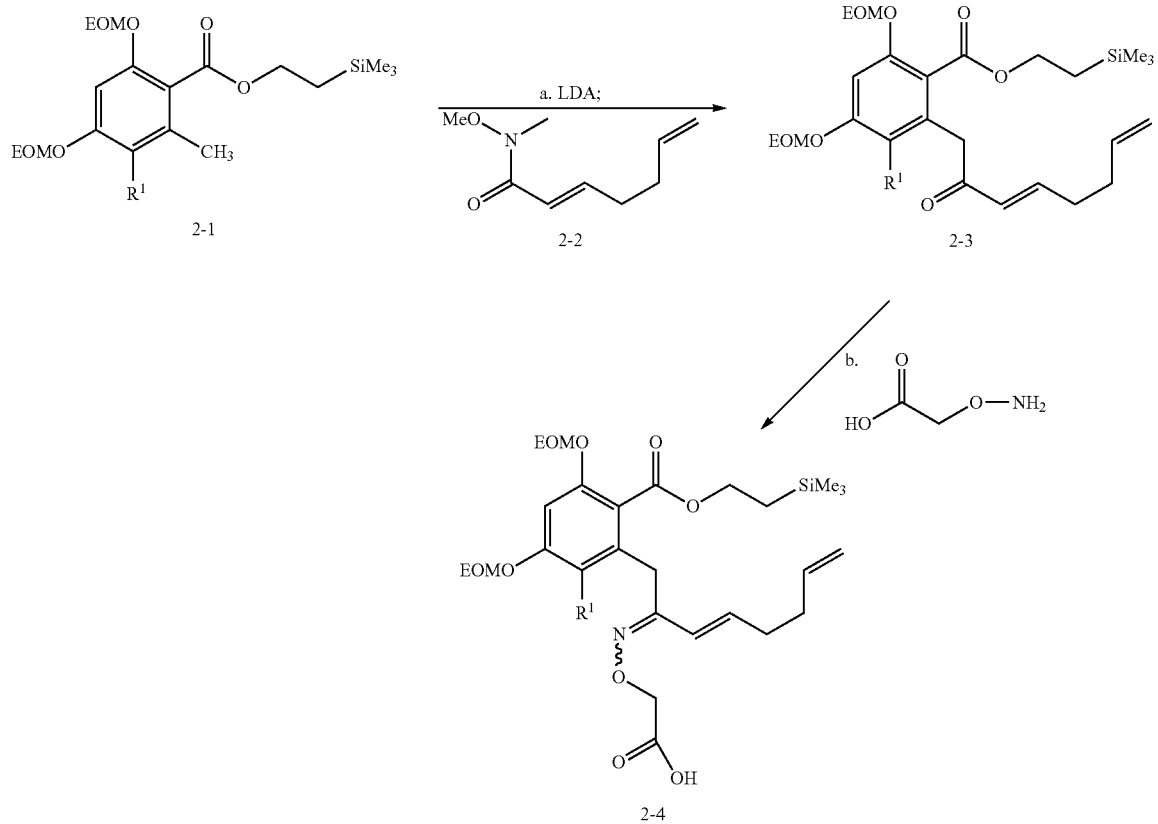

Reagents and conditions: a) LDA (2.0 eq.), THF, -78 C.; 1 eq. of Weinreb amide 2-2 then acidic resin;
b) 5.0 eq. of carboxylic acid 2-4, Py/AcOH, 40 C.

In some embodiments non-limiting embodiments, the starting aromatic starting material may be the compound shown below, where $R^1$ is H or halogen, particularly hydrogen and chlolo. As discussed, other protecting groups known in the art may be used for the phenol and carboxyl functional groups.

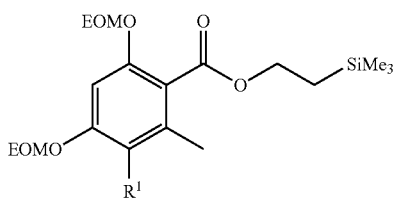

Homoallylic Alcohols

A variety of homoallylic alcohols are commercially available and may be used in the synthesis. Other homoallylic alcohols bearing various substituents may prepared by methods known in the art. Scheme 3 below illustrates a synthesis of various homoallylic alcohols that are not commercially available. In one embodiment, the homoallylic alcohols 3-3 were obtained in their highest enantiomeric form either by enzymatic resolution of the racemic alcohol (H. E. Master et al., Tet. Lett., 37:9253 (1996); S. Singh et al., Tet. Asymm., 13:2679 (2002) or via Brown allylation of the corresponding aldehyde (H. C. Brown and P. K. Jadhav J. Am. Chem. Soc., 105:2092 (1983). The phenyl (3-3a), the pyridinyl (3-3b) and the furyl (3-3c) alcohols were prepared by enzymatic resolution (Scheme 3). Racemic alcohols 3-2a-c were obtained after Grignard addition of commercially available allylmagnesium bromide on their corresponding aldehyde 3-1a-c.

Scheme 3: Synthesis of chiral alcohols 3a-c using enzymatic resolution

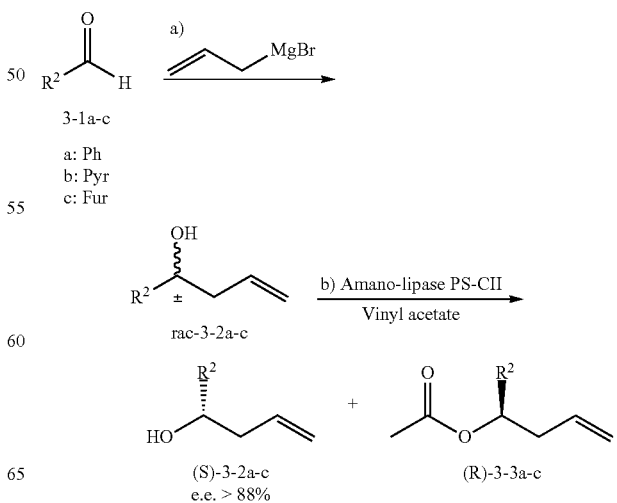

-continued

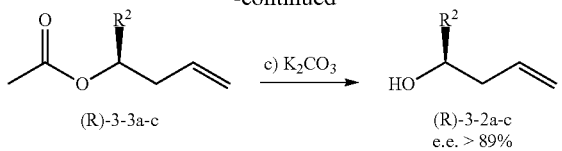

(R)-3-3a-c → (R)-3-2a-c
e.e. > 89% a) AllylMgBr (1.5 equiv.), THF, 0.5 h, 0° C., 71% (3-2a), 41% (3-2b), 74% (3-2c);
b) R² = Ph: vinyl acetate (32.5 equiv.), Amano Lipase PS-C II (50 mg/mmol of 3-2), 23° C., 30 h (monitored by ¹H NMR), R² = Pyr, Fur: vinyl acetate (10.0 equiv.), Amano Lipase PS-C II (50 mg/mmol of 3-2), THF, 23° C., 5-30 h (monitored by ¹H NMR);
c) K₂CO₃ (0.8 equiv.), MeOH, 23° C., 98% ((R)-3-2a), 92% ((R)-3-2b), 84% ((R)-3-2c).

Kinetic enzymatic resolution of racemic alcohols 3-2a-c was realized using the highly efficient Amano lipase (an immobilized version of *Pseudomonas cepacia*). This enzyme catalyzed a selective transesterification of alcohols (R)-3-2a-c with vinyl acetate as an acyl donor, the (S) alcohols 3-2a-c being isolated in excellent yields and good enantiomeric excesses (Table 2).

TABLE 2

Enantioselective acylation of alcohols rac-3-2a-c by transesterification with lipase

| Entry | Substrate | Time (h) | Conv. Ratio (%) (OH/OAc) | Yield (%) (S)-3-2 | e.e. (%) (S)-3-2 | Yield (%) (R)-3-2 | e.e. (%) (R)-3-2 |
|---|---|---|---|---|---|---|---|
| 1 | rac-3-2a | 30 | 50:50 | 45 | 98 | 49 | 93 |
| 2 | rac-3-2b | 30 | 52:48 | 50 | 89 | 39 | 94 |
| 3 | rac-3-2c | 5 | 49:51 | 44 | 88 | 49 | 89 |

Enantiomeric excess obtained with this methodology are all above 88%. Acetylated alcohols (R)-3-3 were then hydrolysed to the corresponding alcohols (R)-3-2a-c in excellent yields. Scheme 4 below illustrates an alternate process based on Brown allylation for the synthesis of the isopropyl (4-4-d), the propyl (4-4-e) and the benzyl (4-4f) alcohols (Scheme 4).

Scheme 4: Synthesis of chiral alcohols 4-3d-f using Brown allylation

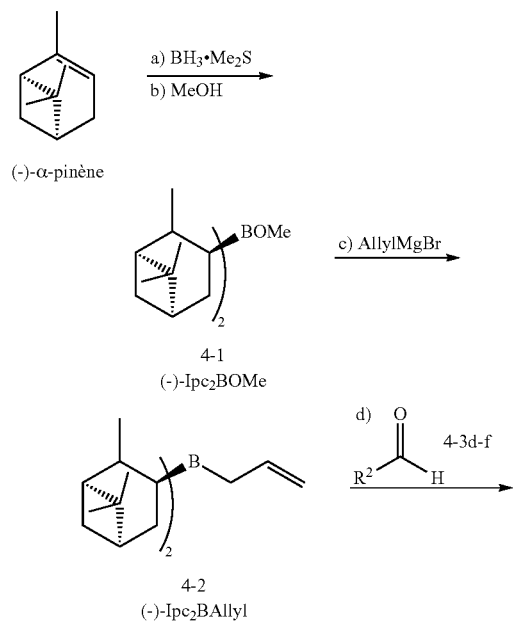

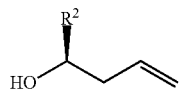

4-4d: e.e. = 80% (iPr)
4-4e: e.e. = 91% (Pr)
4-4f: e.e. = 95% (Bz)

a) (-)-α-pinene (2.4 equiv.), BH₃•Me₂S (1.0 equiv.), THF, 23° C. for 1 h and then 4° C. for 12 h, 76%;
b) MeOH (1.2 equiv.), Et₂O, 0° C., 2 h, 94%;
c) AllylMgBr (0.95 equiv.), Et₂O, 0 → 23° C., 1 h, 92%;
d) 4-3d-f (1.05 equiv.), Et₂O, -100° C., 0.5 h; 3N NaOH, H₂O₂ 35%, reflux, 3 h, 77-93%. Enantiomeric excesses of alcohols were determined by chiral HPLC analysis after acylation with 3,5-dinitrobenzoyl chloride.

(-)-B-Allyldiisopinocampheylborane (4-2, (-)-Ipc₂BAllyl) was synthesized in a three steps sequence from (-)-α-pinene involving a hydroboration, the formation of the corresponding MeO-borinic ester 4-1 and its treatment with a Grignard reagent. Further condensation on aldehydes 4-3d-f followed by oxidation of the resulting borinates with alkaline hydrogen peroxide allowed the formation of the chiral homoallylic alcohols 4-4-d-f in good enantiomeric excess.

In some embodiments of the invention, homoallylic amines may be used rather than the alcohols. The corresponding amines may be readily prepared from the alcohol by methods known in the art. In some embodiments of the invention, the homoallylic alcohols and amines shown below may be used in the preparation of the compounds of the invention.

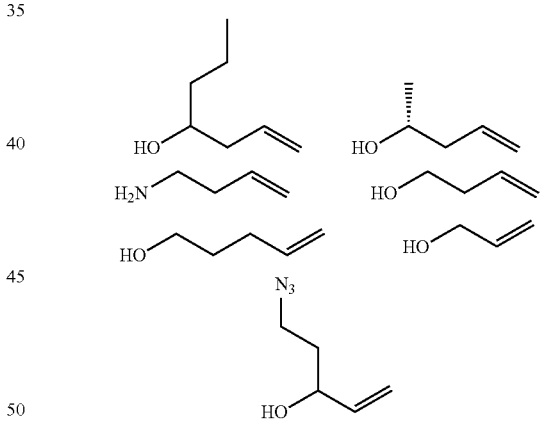

Weinreb Amides

A wide variety of Weinreb amides may be used to prepare the compounds of the invention. Weinreb amides are well known in the art, and many Weinreb amides or reagents for the preparation of Weinreb amides are commercially available. Further, methods for the preparation of Weinreb amides are know. For example, a variety of Weinreb amides may be prepared by reacting an aldehyde with the desired functionality with a Weinreb amide ylide (compound 5-4, Scheme 5) or a Weinreb amide phosphonate (compound 6-6, Scheme 6) to form the desired α,β-unsaturated Weinreb amide. In one embodiment, a Weinreb amide comprising a protected hydroxy group is prepared according to Scheme 5 below.

Scheme 5: Preparation of Weinreb amides

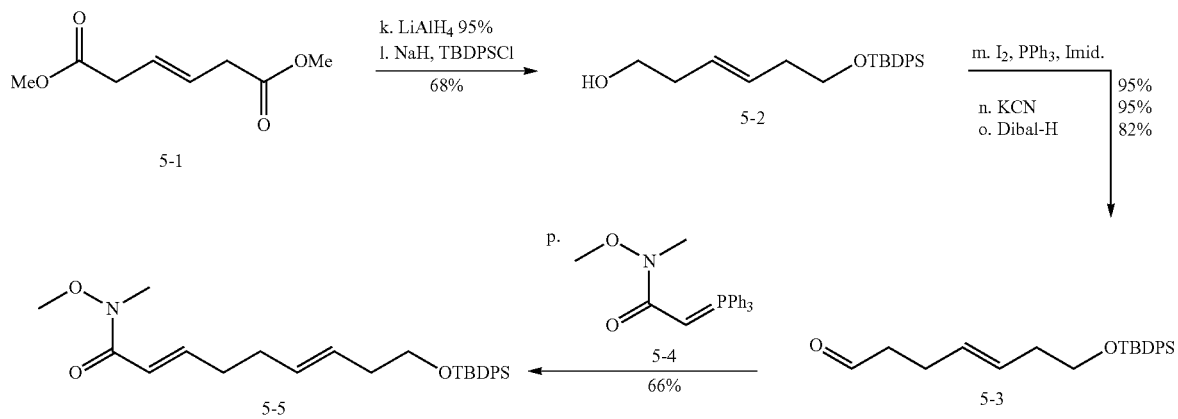

Trans-3-hexenedioic acid dimethyl ester 5-1 was reduced to the corresponding diol with lithium aluminum hydride. The diol was mono-protected as the tert-butyldiphenylsilyl ether 5-2, and the free alcohol was converted to aldehyde 5-3 in three steps via the nitrile. Aldehyde 5-3 was then treated with Weinreb amide ylide 5-4 to produce the diene Weinreb amide 5-5. Various other Weinreb amides may be prepared using compound 5-4 and an aldehyde with the desired functionality.

In another embodiment, Weinreb amides containing a hydroxy substituent may be produced using the synthetic process shown in Scheme 6.

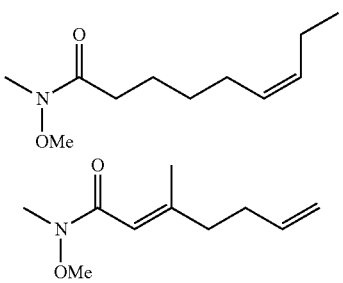

Scheme 6: Synthesis of hydroxy-substituted Weinreb amides

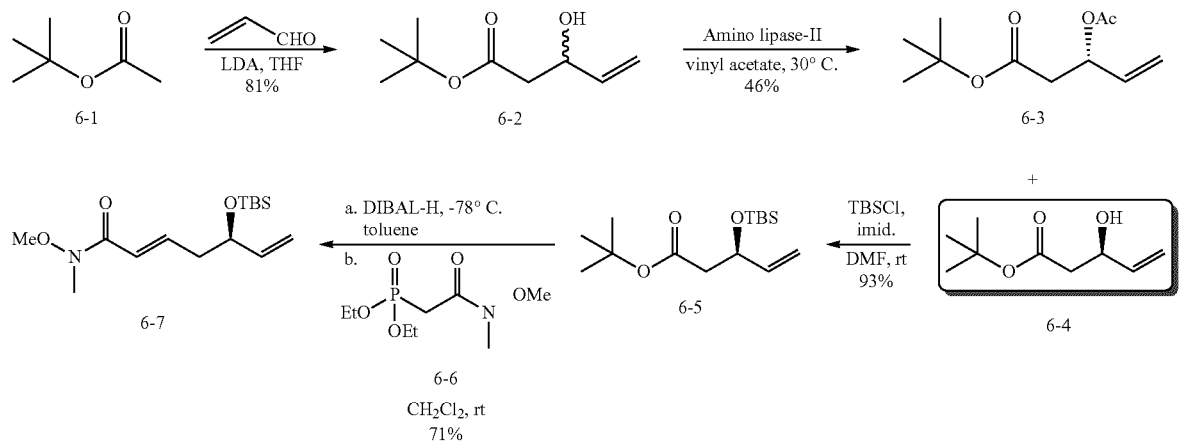

Treatment of t-butylacetate 6-1 with a bulky base, such as LDA, and reaction of the resulting enolate with a vinyl aldehyde provides alcohol 6-2. The racemic alcohol is resolved by treatment with amino lipase PS-C II to produce the chiral acetate 6-3 and the chiral alcohol 6-4. The hydroxy group is suitably protected, for example as the t-butyldimethylsilyl ether 6-5, and the corresponding aldehyde is produced by reaction with DIBAL-H. Reaction with the Weinreb phosphonate 6-6 provides the desired Weinreb amide 6-7.

In non-limiting embodiments, the Weinreb amides shown below may be used to prepare certain compounds of the invention.

-continued

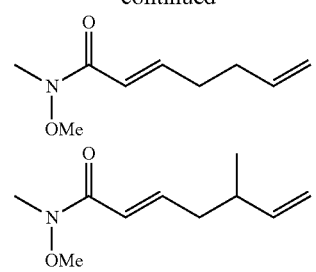

-continued

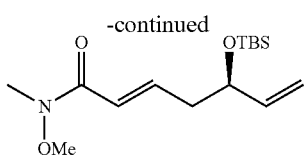

Alkylation of aromatic components such as 2-1 (Scheme 1) with Weinreb amides substituted with a protected hydroxy group or other protected functional group, allow the preparation of compounds comprising a protected hydroxy group on the macrocyclic ring, after deprotection. The hydroxy group may be derivatized to produce a variety of compounds of the invention.

Scheme 7 below illustrates, various compounds of the invention prepared from a hydroxy-substituted macrocycle, which is obtained from a corresponding Weinreb amide comprising a protected hydroxy group, such as 6-7. The silyl-protected hydroxy group in compound 7-1 is selectively deprotected to provide compound 7-2 with a free hydroxy group. The nucleophilic hydroxy group in compound 7-2 may be reacted with various reagents to provide derivatized compounds, such as amide 457/458 and azido-substituted compound 459/460. It will be apparent that various other derivatized compounds may be prepared by reacting the free hydroxyl group with a variety of reagents to produce the corresponding derivatized macrocycles of the invention.

Scheme 7: Derivatives of hydroxy-substituted macrocycles

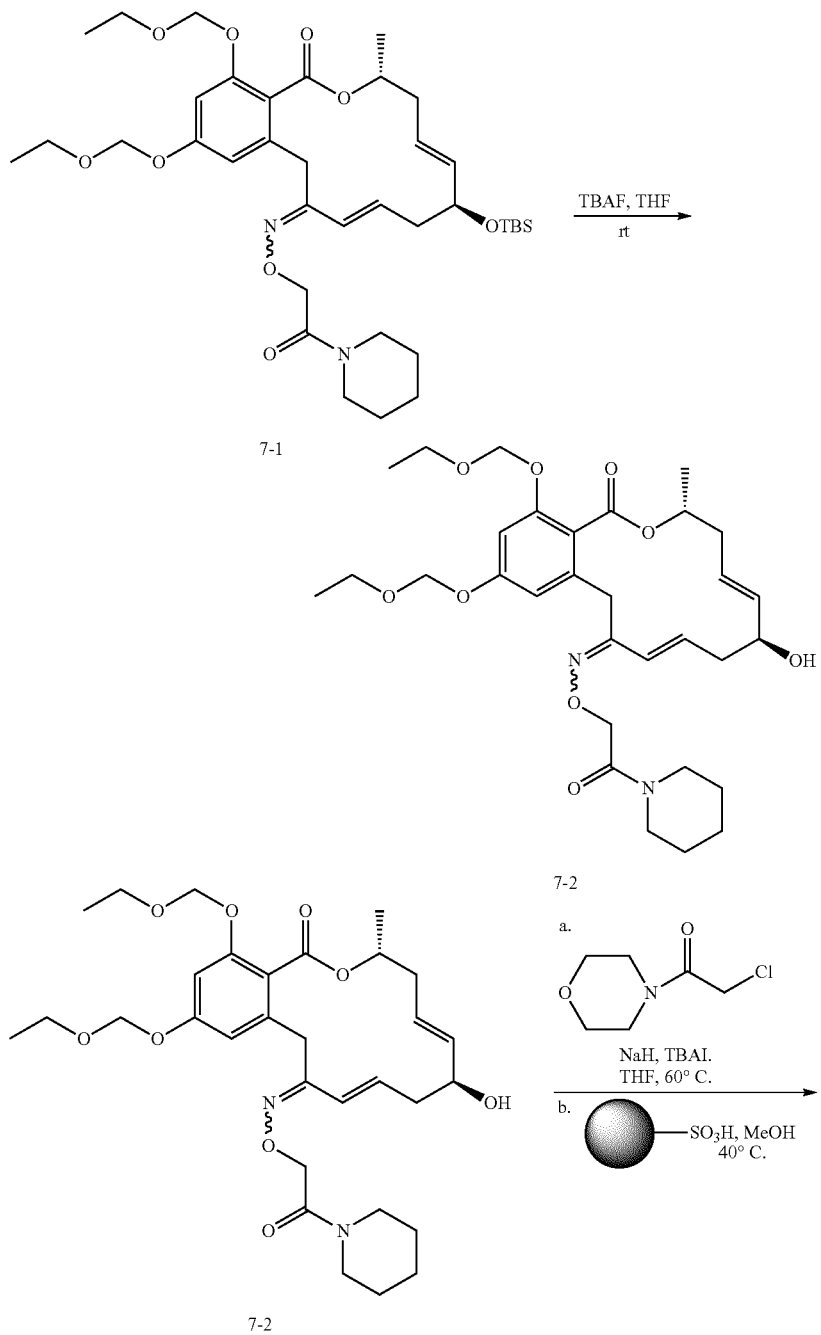

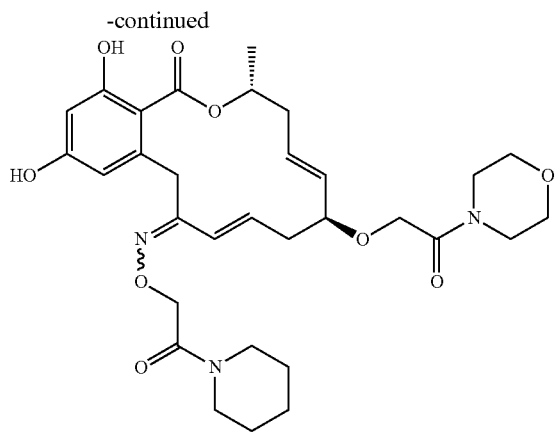

457/458

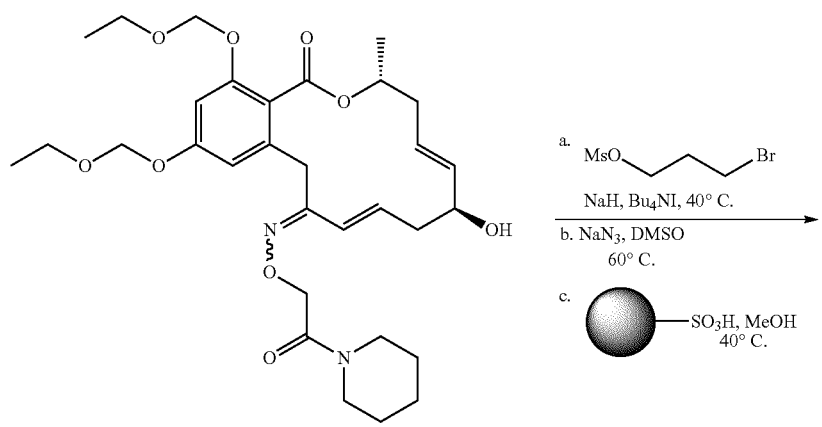

7-2

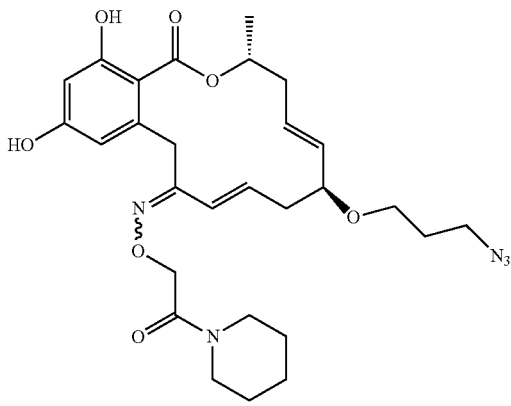 [SMILES: C[C@@H]1C/C=C/[C@@H](OCCCN=[N+]=[N-])C/C=C/C(=N\OCC(=O)N2CCCCC2)Cc2cc(O)cc(O)c2C(=O)O1]

459/460

In another embodiment of the invention, compounds of the invention substituted with an azido group, such as compounds 459/460, may be further elaborated to provide amino-substituted macrocycles by reduction of the azido group. Scheme 8 illustrates the preparation of an amino-substituted compound and the use of the compound for the synthesis of certain amide-containing derivatives. It will be apparent to one of skill in the art that the preparation of amino-substituted macrocycles provides a handle for substitution of the macrocycles with a variety of functional groups by reaction with the nucleophilic amino group.

Reduction of the azido group may be accomplished by various methods, including by treatment with triphenylphosphine, to provide the aminoalkyl-substituted compound 8-1. Use of Weinreb amide intermediates containing an azido group result in compounds with an azido functionality at another position of the macrocycle. The other azide substituted compounds may also be elaborated analogously to produce amino groups. Reaction of the free amino group of 8-1 provides access to a variety of compounds. For example, reaction of the amino group with acetic anhydride yields compound 461, and reaction with an cyanine labeling reagent provides compound 462, containing a fluorophore (see Ernst et al., *Cytometry*, 1989, 10(1), 3-10).

Scheme 8: Derivitization of amino-substituted macrocycles
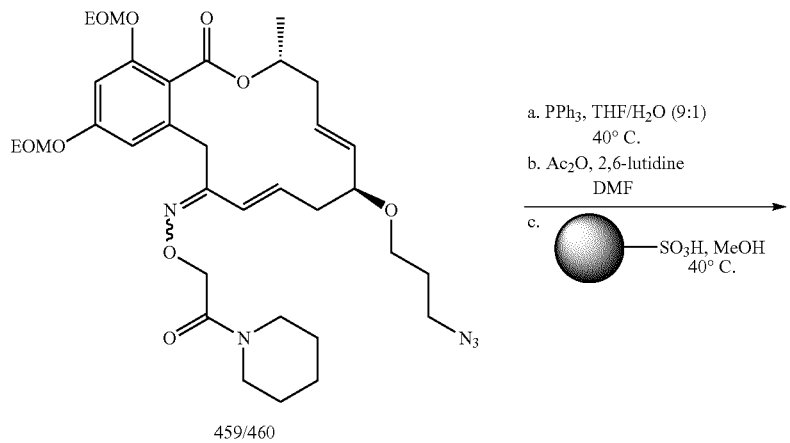
459/460
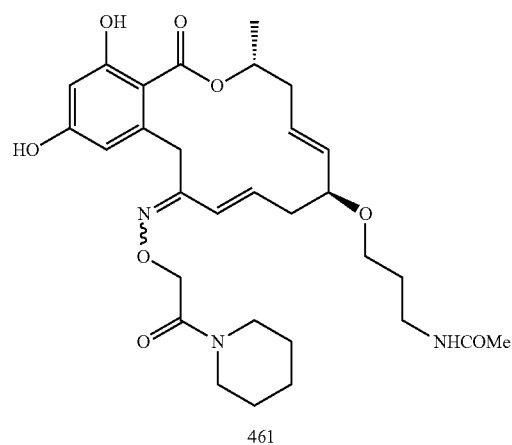
461
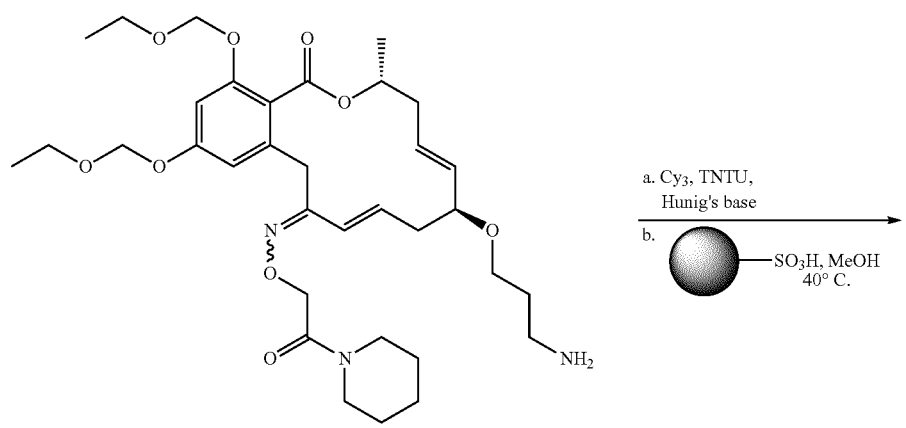
8-1

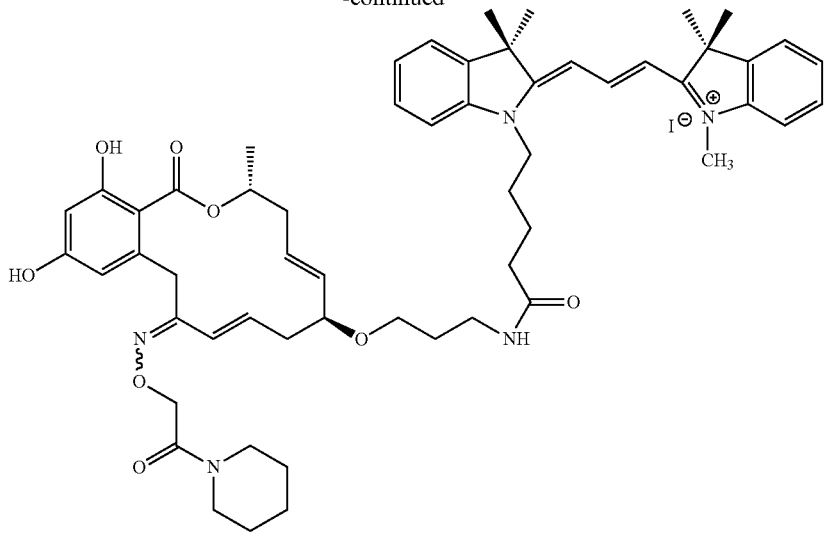

462

Alternatively, hydroxy-substituted macrocycles may be prepared by allylic oxidation of the macrocycle, as illustrated in Scheme 9. Treatment of a protected macrocycle, such as compound 9-1 with selenium dioxide in ethanol provides the hydroxy-substituted product as a mixture of isomers. The resulting alcohols may be further derivatized, as discussed above, to provide a variety of compounds of the invention. Scheme 9 illustrates the formation of allyl ethers 449 by reaction of the alcohol products with allyl chloride in the presence of a base, such as sodium hydride and subsequent removal of the phenol protecting groups.

Scheme 9: Allylic oxidation of macrocycles

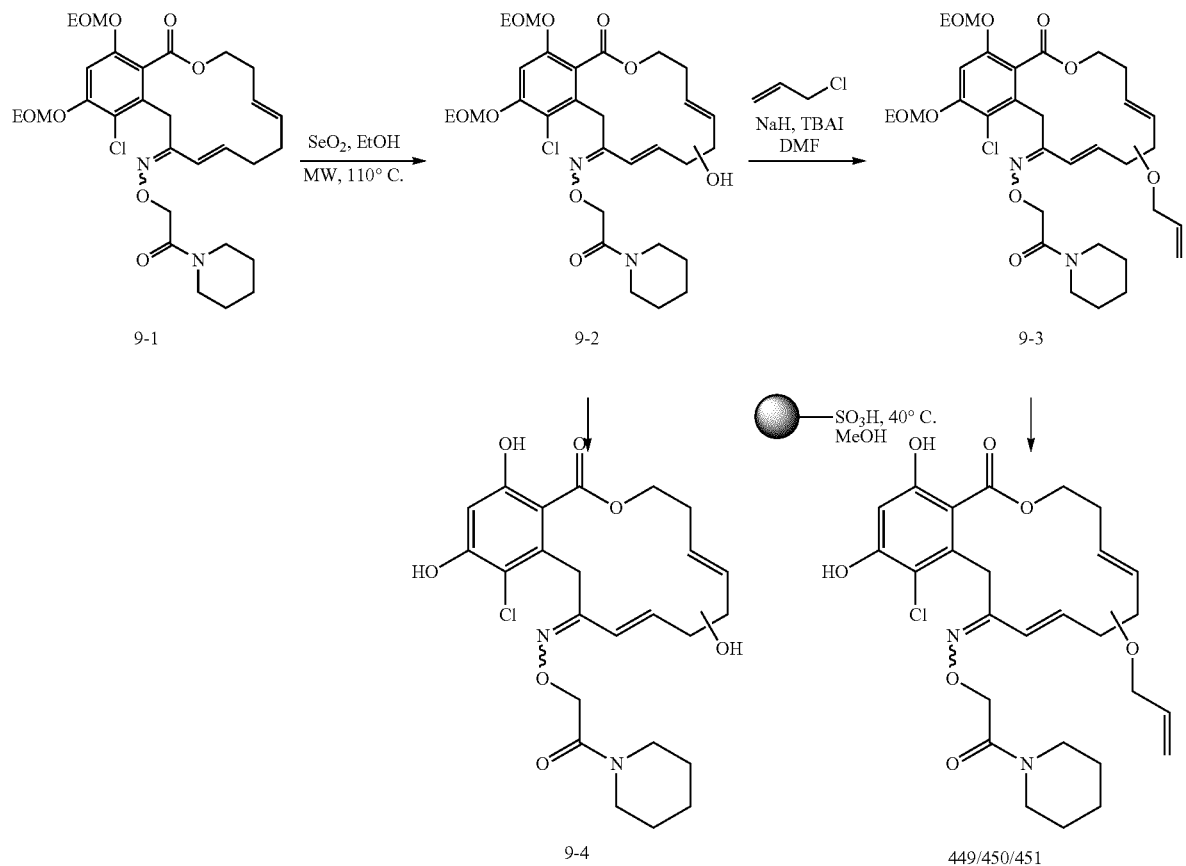

Biological Activity

The library of macrocycles was assayed for its cytotoxicity in HCC1954 and SK-BR-3 tumor cells. Compounds showing significant cytotoxicity were further examined for their ability to induce degradation of known HSP90 client proteins such as ErbB2 in SK-BR3. Thus, after 18 hrs treatment with the compounds, the whole cell protein lysates were obtained, protein concentrations were normalized and the concentration of ErbB2 was quantified by Western blotting (C. Chavany et al *J. Biol. Chem.* 271:4974-4977 (1996)). Several compounds from the library were more effective than radicicol and 17-AAG in reducing ErbB2 concentration. For example compounds 13a, 13b and 13c in the form of the E-oxime isomer was significantly more effective than both radicicol and 17-AAG.

Based on the in vitro data (see Table 3, Example 9), compound 13a was further evaluated in vivo with CB17/SCID mice with a xenograft bearing BT-474 (breast tumor cell line) was used, as this cell line has been shown to respond to HSP90 inhibitors in an animal model (Basso et al., *Oncogene* 2002, 21, 1159). Two schedules of 100 mg every other day (q2d) or every four days (q4d) during 28 days were investigated. The treatment with compound 13a resulted in a dose-dependent inhibition of the tumor growth with an 18% regression in tumor volume using the q2d schedule. The results are shown in FIG. 1. Neither the q2d nor the q4d schedules resulted in significant weight loss (FIG. 1). Histologic examination of tumors removed from animals receiving either the vehicle (DMSO) or drug for 28 days following the q2d schedule revealed a dramatic loss of cellularity in tumors obtained from drug-treated animals. Nuclei of remaining cells were uniformly condensed, suggesting the occurrence of massive apoptosis (see FIG. 2, top panels). This was confirmed by the high degree of nuclear TUNEL staining seen in tumors excised from drug treated animals, which is shown in FIG. 2, bottom panels. These data suggest that tumor regression in animals treated for 28 days according to the q2d schedule may be more dramatic than estimated with tumor volume measurements, since few to no viable cells could be identified at the end of the treatment period.

EXAMPLES

General Techniques. All reactions were carried out under a nitrogen atmosphere with dry (anhydrous) solvents under anhydrous conditions, unless otherwise noted. Anhydrous solvents were obtained by passing them through commercially available alumina column (Innovative Technology, Inc.,® VA). All substituted polystyrene resins (100-200 mesh, 1% DVB) were purchased from Novabiochem® or Aldrich®. The Grubbs' II catalyst was purchased from Materia Inc® Solid phase reactions were carried on a Quest® 210 or round bottom flasks and filtered in fritted funnels. Reactions were monitored by thin layer chromatography (TLC) carried out on 0.25 mm E. Merck® silica gel plates (60E-254) using UV light as visualizing agent and 10% ethanolic phosphomolybdic acid or vanillin solution and heat as developing agents. E. Merck® silica gel (60, particle size 0.040-0.063 mm) was used for flash column chromatography. PTLC (preparative thin layer chromatography) were carried out on 0.25 mm E. Merck® silica gel plates. NMR spectra were recorded on a Bruker Advance-400® instrument and calibrated by using residual undeuterated solvent as an internal reference. The following abbreviations were used to explain the multiplicities: s=singlet, d=doublet, t=triplet, q=quartet, m=multiplet, b=broad. IR spectra were recorded on a Perkin-Elmer 1600 series FT-IR spectrometer. LC-MS were recorded using an Agilent 1100® HPLC with a Bruker® micro-TOF instrument (ESI). Unless otherwise stated, a Supelco® C8 (5 cm×4.6 mm, 5 μm particles) column was used with a linear elution gradient from 100% $H_2O$ (0.5% $HCO_2H$) to 100% MeCN in 13 min at a flow rate of 0.5 ml/min. Unless otherwise stated, LDA was prepared at a concentration of 0.566 M by treating a solution of diisopropylamine (1.0 equiv.) in THF at −78° C. with n-butyllithium (1.0 equiv.) and stirred for 30 min at this temperature before use.

Example 1

Preparation of Weinreb Amides

As discussed above, many Weinreb amides used to prepare the compounds of the invention are prepared by methods known in the art. Characterization data is shown below for selected Weinreb amides used to prepare the compounds of the invention.

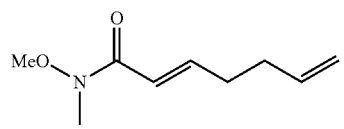

a-1

$^1$H NMR (400 MHz, CDCl$_3$, 25° C.): δ=7.33 (dd, J=15.3, 11.0 Hz, 1H), 6.52 (m, 2H), 5.61 (d, J=16.6 Hz, 1H), 5.48 (d, J=10.2 Hz, 1H), 3.73 (s, 3H), 3.27 (s, 3H); $^{13}$C NMR (100 MHz, CDCl$_3$, 25° C.): δ=166.8, 143.4, 135.1, 124.7, 119.7, 61.7, 32.3; IR (film): $v_{max}$=2936, 1658, 1598, 1427, 1382, 1181, 1095, 1005 cm$^{-1}$.

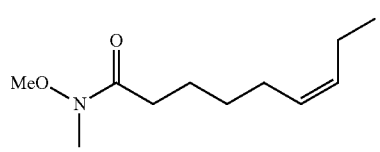

a-2

$^1$H NMR (CDCl$_3$, 400 MHz, 25° C.) δ 5.40-5.26 (m, 2H), 3.67 (s, 3H), 3.17 (s, 3H), 2.41 (t, J=7.4 Hz, 2H), 2.11-1.97 (m, 4H), 1.64 (tt, J=8.7 Hz, J=6.3 Hz, 2H), 1.39 (tt, J=8.6 Hz, J=6.7 Hz, 2H), 0.95 (t, J=7.8 Hz, 3H); $^{13}$C NMR (CDCl$_3$, 100 MHz, 25° C.) δ 131.9, 128.7, 61.2, 31.8 (×2), 29.5, 26.9, 24.3, 20.5, 14.3, one quaternary carbon is missing.

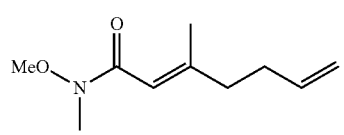

a-3

$^1$H NMR (CDCl$_3$, 400 MHz) δ 5.90 (s, 1H), 5.54-5.60 (m, 1H), 4.82 (d, J=17.0 Hz, 1H), 4.75 (d, J=10.1 Hz, 1H), 3.43 (s, 3H), 2.96 (s, 3H), 2.02 (m, 4H), 1.90 (s, 3H). $^{13}$C NMR (CDCl$_3$, 100 MHz) δ 137.55, 115.09, 114.22, 61.36, 40.26, 31.67, 18.64.

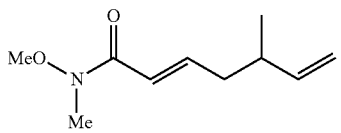

a-4

¹H NMR (CDCl₃, 400 MHz, 25° C.) δ 6.93 (dt, J=15.5, 7.6 Hz, 1H); 6.39 (d, J=15.5 Hz, 1H); 5.70-5.79 (m, 1H), 4.94-5.02 (m, 2H); 3.69 (s, 3H); 3.23 (s, 3H); 2.18-2.36 (m, 3H); 1.02 (d, J=9.9 Hz, 3H).

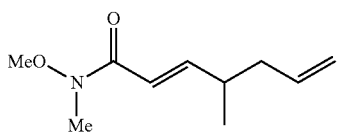

a-4

¹H NMR (CDCl₃, 400 MHz; 25° C.) δ 6.93 (dt, −15.5, 7.6 Hz, 1H); 6.39 (d, J=15.5 Hz, 1H); 5.70-5.79 (m, 1H), 4.94-5.02 (m, 2H); 3.69 (s, 3H); 3.23 (s, 3H); 2.18-2.36 (m, 3H); 1.02 (d, J=9.9 Hz, 3H).

Example 2

Preparation of Hydroxy-substituted Weinreb Amides

Weinreb amides containing a protected hydroxy group are prepared according to the procedure depicted in Scheme 6 and described below, starting with the preparation of racemic alcohols 6-2.

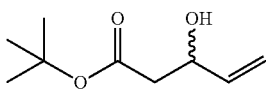

6-2

To the solution of freshly prepared LDA (0.56 M, 60 mmol) at −78° C. under nitrogen was added solution of t-butyl acetate (8.1 mL, 60 mmol; 1.0 equiv.) in THF (10 mL) dropwise. After a further one hour at −78° C., acrolein (4.5 mL, 60 mmol, 1.0 equiv.) in THF (5 mL) was added and the reaction was kept stirring at the same temperature for 5 min. The reaction was quenched with saturated NH₄Cl solution and extracted with ethyl acetate (150 mL×3), the combined organic phase was washed by brine (120 mL), dried over anhydrous Na₂SO₄, and evaporated. The residue underwent flash chromatography column (PE/EA, 8/1) to give the desired compound (8.35 g, 81%). ¹H (CDCl₃, 400 MHz, 25° C.) δ 5.82-5.91 (dt, 1H); 5.30 (dd, J=17.2 Hz, J=0.8 Hz, 1H); 5.14 (dd, J=10.4 Hz, J=0.8 Hz, 1H); 4.48 (m, 1H); 3.13 (d, 1H); 2.46 (m, 2H); 1.46 (s, 9H). ¹³H NMR of wh3-27 (CDCl₃, 400 MHz, 25° C.) δ 171.5, 138.9, 114.9, 81.2, 68.9, 42.1, 28.0

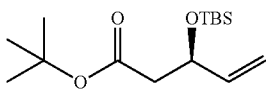

6-5

To the solution of the previously prepared racemic alcohol (8.35 g, 48.5 mmol) in vinyl acetate (120 mL) was added Amino lipase PS-C II (750 mg, 15 mg/mmol) at 30° C. The reaction was stirred for 60 hrs. After filtration, the solution was concentrated and underwent flash chromatography column (PE/EA, 15/1 to 5/1) to give the desired compound (3.86 g) in the yield of 46%. To a solution of this chiral alcohol (3.75 g, 21.7 mmol) in DMF (60 mL) at 0° C. under nitrogen atmosphere, was added imidazole (2.96 g, 43.5 mmol, 2.0 equiv.) and TBSCl (3.93 g, 26.0 mmol, 1.2 equiv.), then the reaction was allowed to warm to 23° C. and stirred for 5 hrs. The reaction was extracted from saturated NH₄Cl solution with ethyl acetate (100 mL×3), washed by brine (100 mL), dried over anhydrous Na₂SO₄. After removal of the solvent, the residue underwent flash column (PE/EA, 50/1) to obtain the TBS protected alcohol (5.85 g, 93%). (CDCl₃, 400 MHz, 25° C.) δ 5.79-5.88 (dt, 1H); 5.20 (dd, J=16.0 Hz, J=2.8 Hz, 1H); 5.05 (dd, J=10.4 Hz, J=2.8 Hz, 1H); 4.51-4.56 (m, 1H); 2.46 (dd, 1H); 2.34 (dd, 1H); 1.44 (s, 9H); 0.88 (s, 9H); 0.05 (d, 6H). ¹³C NMR (CDCl₃, 400 MHz, 25° C.) δ 170.3, 140.5, 114.4, 80.4, 70.9, 44.8, 28.1, 25.8, 18.1, −4.4, −5.0.

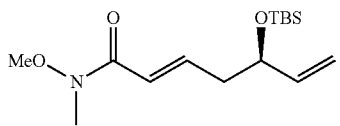

6-7

To the solution of the ester prepared in the precedent procedure (5.85 g, 20.4 mmol) in CH₂Cl₂ (100 mL) under nitrogen atmosphere, DIBAL (24.5 mL, 1M in toluene, 1.2 equiv.) was added at −78° C. and the reaction was kept stirring at the same temperature for half an hour. Then saturated tartrate salt solution (100 mL) was added to the reaction and stirred for 2 hrs until the system turned clear. The two phases were separated and extracted by CH₂Cl₂ (100 mL×2), washed by brine, dried over Na₂SO₄. After removal of the solvent, the residue (4.33 g) obtained was used for the next step without further purification. To the solution of the aldehyde (4.33 g) in CH₂Cl₂ (100 mL) was added Wittig reagent (7.33 g, 20.2 mmol, 1.0 equiv.) at 23° C. The reaction was stirred overnight. After removal of the solvent under reduced vacuum, the residue underwent flash chromatography (PE/EA=20:1, then 10/1, 3/1) afforded the desired compound (4.25 g) in the yield of 71% for the two steps. ¹H (CDCl₃, 400 MHz, 25° C.) δ 6.89-6.96 (dt, 1H); 6.41 (d, 1H); 5.77-5.85 (m, 1H); 5.18 (dd, 1H); 5.05 (dd, 1H); 4.23 (dd, 1H); 3.67 (s, 3H); 3.22 (s, 3H); 2.42 (dd, 2H); 0.88 (s, 9H); 0.03 (d, 6H). ¹³C (CDCl₃, 400 MHz, 25° C.) δ 166.6, 143.5, 140.6, 120.9, 114.3, 72.7, 61.6, 41.4, 32.3, 25.8, 18.2, −4.5, −4.9.

Example 3

Aromatic Components

Various suitably protected aromatic groups are used in the invention. Methods for the preparation of suitable resorcylic acid lactones for the preparation of the macrocycles are known in the art. For example, International Publication No. WO 2008/021213, which is incorporated by reference in its entirety, describes synthetic methods for a variety of derivatives of resorcylic acid, which can be used to prepare the compounds of the invention. Selected characterization data for aromatic compounds used in the invention are provided below.

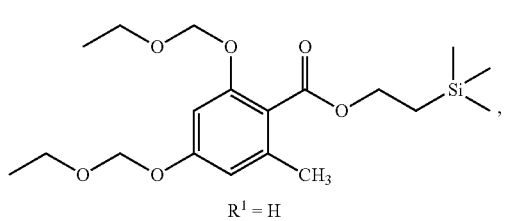

2-1

R¹ = H

¹H NMR of ester (CDCl₃, 400 MHz, 25° C.) δ 6.69 (s, 1H); 6.52 (s, 1H); 5.19 (s, 2H); 5.17 (s, 2H); 4.37 (t, 2H); 3.66-3.74 (m, 4H); 2.28 (s, 3H); 1.18-1.25 (m, 6H); 1.09 (t, 2H); 0.05 (s, 9H).

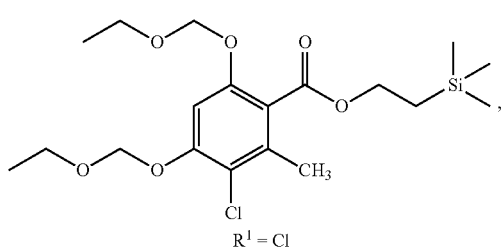

2-1

R¹ = Cl

¹H NMR of ester (CDCl₃, 400 MHz, 25° C.) δ 6.98 (s, 1H); 5.28 (s, 2H); 5.19 (s, 2H); 4.39 (t, 2H); 3.76 (q, 2H); 3.70 (q, 2H); 2.32 (s, 3H); 1.19-1.23 (m, 6H); 1.10 (t, 2H); 0.05 (s, 9H)

Example 4

Alkylation Intermediates

The preparation of alkylation intermediates derived from resorcylic acid aromatic derivatives and Weinreb amides is illustrated in Scheme 2. Various different alkylation intermediates, with varying substitution on the aromatic ring and the macrocycle, may be used to prepare the compounds of the invention. These compounds may be prepared from the desired aromatic component and Weinreb amide according to the process depicted in the scheme. Characterization data of selected alkylation intermediates used in the preparation of the compounds of the invention is provided below.

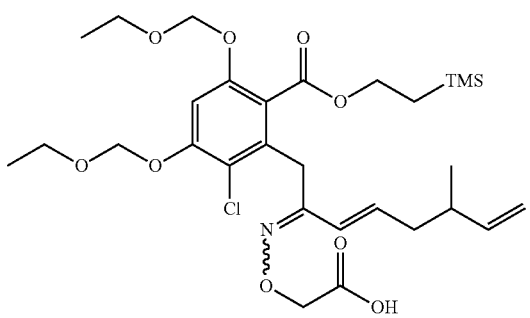

2-5

¹H NMR two isomers (1:1)(CDCl₃, 400 MHz, 25° C.) δ 9.52 (w×2, 2H); 7.04 (s×2, 2H); 6.69 (d, J=16.1 Hz, 1H); 6.26 (dt, J=16.1, 7.0 Hz, 1H); 5.97 (dt, J=16.1, 7.0 Hz, 1H); 5.76 (d, J=16.1 Hz, 1H); 5.53-5.71 (m, 2H); 5.28 (s×2, 4H); 5.18 (s, 2H); 5.17 (s, 2H); 4.91-4.96 (m, 2H); 4.81-4.84 (m, 2H); 4.65 (s, 2H); 4.49 (s, 2H); 4.27-4.33 (m, 4H); 4.02 (s, 2H); 3.87 (s, 2H); 3.67-3.77 (m, 8H); 1.98-2.26 (m, 6H); 1.17-1.22 (m, 12H); 0.99-1.06 (m, 4H); 0.96 (d, J=6.4 Hz, 3H); 0.82 (d, J=6.4 Hz, 3H); 0.05 (s, 9H); 0.03 (s, 9H).

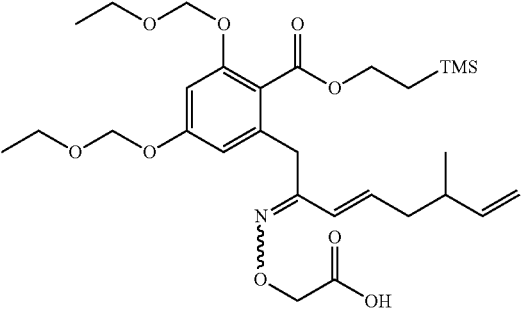

2-6

¹H NMR of two isomers (2:1) (CDCl₃, 400 MHz, 25° C.) δ 9.47 (w×2, 2H); 6.75 (d, J=2.0 Hz, 1H); 6.71 (d, J=2.1 Hz, 1H); 6.67 (d, J=16.1 Hz, 1H); 6.57 (d, J=2.1 Hz, 1H); 6.48 (d, J=2.0 Hz, 1H); 6.21 (dt, J=16.1, 7.0 Hz, 1H); 6.03-6.11 (m, 2H); 5.54-5.68 (m, 2H); 5.19 (s×2, 4H); 5.17 (s, 2H); 5.15 (s, 2H); 4.82-4.88 (m, 4H); 4.67 (s, 2H); 4.66 (s, 2H); 4.36-4.40 (m, 4H); 3.88 (s, 2H); 3.65-3.74 (m, 10H); 2.06-2.21 (m, 6H); 1.17-1.23 (m, 12H); 1.07-1.12 (m, 4H); 0.91 (d, J=6.4 Hz, 3H); 0.86 (d, J=6.4 Hz, 3H); 0.07 (s, 9H); 0.06 (s, 9H)

Example 5

Preparation of Macrocyclic Compounds of the Invention

General Procedure for the Synthesis of Compounds of the Invention.

The general synthesis of the macrocycles described below is depicted in Scheme 1, starting from carboxylic acid 1-1. To a suspension of 3.0 equiv of polystyrene based chlorotrityl resin (1.1 mmol/g) in CH₂Cl₂ at room temperature were added 6.0 equiv of Hunig's base and 1.0 equiv of the corresponding acid 1-1 (Scheme 1). After shaking the mixture for 24 hours, the different resins were capped with acetic acid for another 24 hours. After this time the resins were washed with CH₂Cl₂, DMF, CH₂Cl₂ and Et₂O, then dry and re-suspended in THF. To these suspensions, 4.0 equiv. of TBAF (1M) were added and the mixtures were shaken for 4 hours. The resins were then filtered and washed thoroughly using THF, CH₂Cl₂, 1% AcOH in CH₂Cl₂, CH₂Cl₂, Et₂O several times. The completion of the deprotection and total elimination of the tetrabutyl ammonium salts was assessed by LC-MS after cleavage of a very small portion of each resin using a solution of HFIP in CH₂Cl₂ ¼ for 30 min (LC-MS were recorded using an Agilent 1100 HPLC with a Supelco C8 (5 cm×4.6 mm, 5 μm particles) column using a linear elution gradient from 95% H₂O (0.5% HCO₂H) to 100% MeCN in 8 min at a flow rate of 0.5 mL/min). The resins were split for further diversification with the different alcohols. The Mitsunobu reactions were carried in dry toluene using 5.0 equiv of the corresponding alcohol R²OH, 2.0 equiv of Ph₃P and 2.0 equiv of DIAD and the suspensions were agitated overnight. The productivity of the esterification reactions were assessed by LC-MS after cleavage of a small portion as describe before and the pools which had not proceeded to completion were re-subjected to the same conditions. After washing and drying the resins they were suspended in toluene and submitted to the metathesis reaction. Grubbs' second generation catalyst was added to each suspension (3×0.06 equiv) and the reactions were heated at 120° C. in a CEM microwave reactor for 3×45 min (fresh catalyst was added in each cycle). The resins were then washed with $CH_2Cl_2$, DMF, $CH_2Cl_2$ and $Et_2O$ several times. Then the compounds were cleaved from the resin using a solution of HFIP in $CH_2Cl_2$ ¼ for 3 h (re-subjection of the resin to the cleavage conditions afforded minimal quantities of compound suggesting the original cleavage had proceeded to completion) and the corresponding products were purified by PTLC and isolated with yields in between 20 to 30% after 5 steps.

Each compound was dissolved $CH_2Cl_2$ and then aliquoted for further amidation. To each vial were added 2.0 equiv of the corresponding amine, 3.0 equiv of PS-DCC (DCC polystyrene resin) and cat DMAP, and the suspensions were stirred for over 72 h. The completion of each reaction was monitored by LC-MS. The corresponding amides were filtered, evaporated and re-dissolved in methanol. To each solution were added 10 equiv of sulfonic acid polystyrene resin and the suspensions were stirred for 4 h at room temperature. The final compounds were filtered and isolated with yields of 75 to 95%.

Characterization data for selected compounds of the invention are provided below.

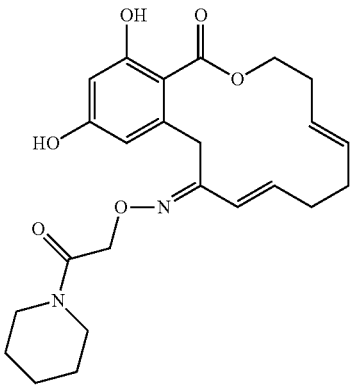

13b $^1$H NMR ($CDCl_3$, 400 MHz) δ 11.60 (s, 1H), 6.88 (d, J=1.9 Hz, 1H), 6.33 (d, J=1.9 Hz, 1H), 6.14 (dt, J=16.1, 7.5 Hz, 1H), 5.83 (d, J=16.1 Hz, 1H), 5.33 (m, 2H), 4.86 (s, 2H), 4.54-4.53 (m, 2H), 4.34 (s, 2H), 3.58-3.55 (m, 2H), 3.40-3.38 (m, 2H), 2.51-2.48 (m, 2H), 2.11-2.07 (m, 4H), 1.61-1.57 (m, 6H), 1 OH signal is not visible. $^{13}$C NMR ($CD_3OD$, 100 MHz) δ 178.0, 175.8, 168.8, 166.6, 165.7, 147.1, 145.5, 141.0, 139.0, 134.4, 122.6, 115.4, 110.4, 81.4, 73.2, 54.7, 51.6, 41.8, 41.3, 40.0, 37.6, 35.5, 34.8, 33.5; HRMS (MALDI-TOF) m/z [M+Na]$^+$ calcd for $C_{24}H_{30}N_2O_6Na$: 465.2002; found 465.2015.

Figure 4:
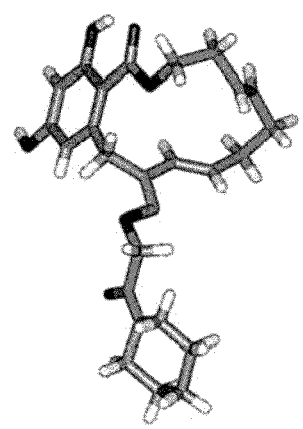
FIG. 4 shows a Wire-frame representation of the crystal structure of compound 13b.

The geometry of the oxime was determined by x-ray diffraction. FIG. 4 shows the Wire-frame representation of the crystal structure of 13b.

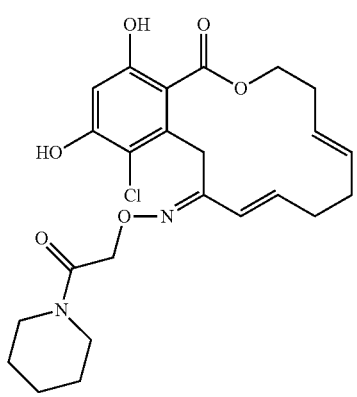

13a $^1$H NMR ($CDCl_3$, 400 MHz, 25° C.) δ 11.64 (s, 1H), 6.64 (s, 1H), 6.01 (dt, J=15.5, 7.5 Hz, 1H), 5.11 (d, J=15.5 Hz, 1H), 5.10-5.03 (m, 2H), 4.85 (s, 2H), 4.37 (t, J=4.8 Hz, 2H), 4.17 (s, 2H), 3.60 (t, J=5.0 Hz, 2H), 3.46 (t, J=5.0 Hz, 2H), 2.34 (q, J=5.4 Hz, 2H), 210-2.02 (m, 2H), 1.99-1.92 (m, 2H), 1.70-1.54 (m, 6H), 1 OH signal is not visible; $^{13}$C NMR ($CDCl_3$, 100 MHz, 25° C.) δ 170.27, 167.42, 163.21, 157.38, 155.18, 138.21, 135.62, 131.82, 129.13, 124.76, 115.55, 107.60, 103.47, 72.63, 65.03, 46.38, 43.31, 33.21, 32.76, 31.94, 31.84, 26.65, 25.64, 24.57; HRMS (MALDI-TOF) m/z [M+Na]$^+$ calcd for $C_{24}H_{29}ClN_2O_6Na$: 499.1612; found: 499.1638.

The geometry of the oxime was determined by x-ray diffraction. FIG. 3 shows the Wire-frame representation of the crystal structure of 13a.

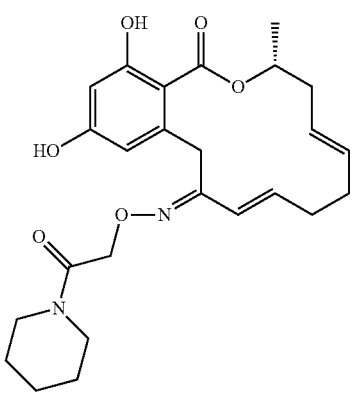

13c $^1$H NMR ($CDCl_3$, 400 MHz) δ 11.27 (brs, 1H), 9.03 (brs, 1H), 6.54 (d, J=2.1 Hz, 1H), 6.34 (d, J=2.1 Hz, 1H), 6.05 (m, 1H), 5.68 (d, J=15.5 Hz, 1H), 5.43 (m, 2H), 5.28 (m, 1H), 4.87 (d, J=14.5 Hz, 1H), 4.82 (d, J=14.5 Hz, 1H), 4.30 (d, J=15.5 Hz, 1H), 4.17 (d, J=15.5 Hz, 1H), 3.58 (m, 2H), 3.41 (m, 2H), 2.68 (m, 1H), 2.24 (m, 2H), 2.04 (m, 3H), 1.61 (m, 6H), 1.42 (d, J=6.4 Hz, 3H). $^{13}$C NMR ($CDCl_3$, 100 MHz) δ 167.42, 164.0, 161.85, 159.06, 141.91, 137.79, 132.77, 126.02, 124.63, 111.20, 104.88, 102.10, 71.42, 71.27, 71.21, 45.92, 43.10, 37.82, 32.31, 30.49, 30.24, 26.22, 25.32, 24.24, 18.92; HRMS (MALDI-TOF) m/z [M+Na]$^+$ calcd for $C_{25}H_{32}N_2O_6Na$: 479.2158; found 479.2351.

Figure 5:
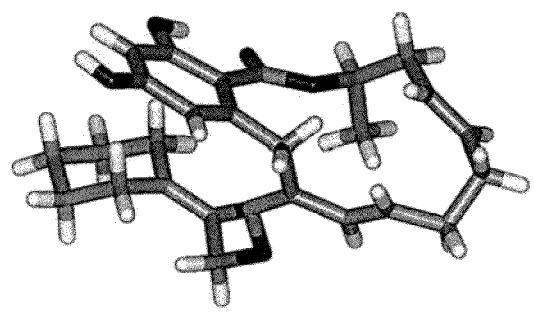
FIG. 5 shows a Wire-frame representation of the crystal structure of the Z-isomer of compound 13c.

The geometry of the oxime was deduced based on the x-ray diffraction of the Z isomer of 13c. FIG. 5 shows the Wire-frame representation of the Z isomer of 13c.

139

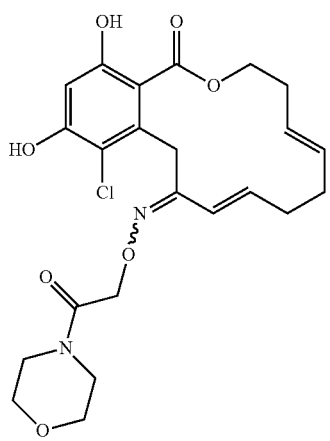

13d

¹H NMR (CD₃OD, 400 MHz) δ 6.84 (d, J=16.1 Hz, 1H), 6.63 (d, J=16.1 Hz, 1H), 6.51 (s, 1H), 6.46 (d, J=2.7 Hz, 1H), 6.21 (dt, J=16.1, 6.9 Hz, 1H), 6.09 (dt, J=16.1, 7.5 Hz, 1H), 5.31-5.23 (m, 4H), 4.91 (d, J=13.3 Hz, 2H), 4.60 (d, J=13.3 Hz, 2H), 4.45-4.39 (m, 4H), 4.18 (s, 4H), 3.76 (m, 4H), 3.69-3.67 (m, 4H), 3.62-3.46 (m, 8H), 2.59-2.55 (m, 1H), 2.45-2.43 (m, 5H), 2.37-2.33 (m, 4H), 2.15-2.14 (m, 2H), 4 OH signals are not visible; HRMS (MALDI-TOF) m/z [M+Na]⁺ calcd for $C_{23}H_{27}ClN_2O_7Na$: 501.1405; found 501.1424.

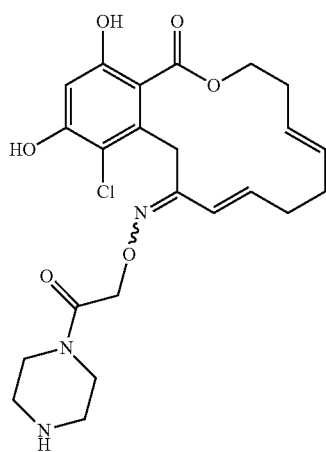

13e

¹H NMR (CD₃OD, 400 MHz) δ 6.64 (d, J=16.1 Hz, 1H), 6.53 (s, 1H), 6.48 (s, 1H), 6.25 (dt, J=16.1, 7.5 Hz, 1H), 6.09 (dt, J=15.6, 7.5 Hz, 1H), 5.52-5.48 (m, 2H), 5.33 (d, J=15.6 Hz, 1H), 5.26-5.24 (m, 2H), 4.94 (s, 2H), 4.68 (s, 2H), 4.44-4.38 (m, 4H), 4.27 (s, 2H), 4.19 (s, 2H), 3.97-3.93 (m, 4H), 3.86-3.76 (m, 4H), 3.34-3.33 (m, 4H), 3.39-3.20 (m, 4H), 2.59-2.55 (m, 1H), 2.48-2.40 (m, 3H), 2.37-2.34 (m, 4H), 2.19-2.15 (m, 2H), 2.10-2.06 (m, 2H), 4 OH and 2 NH are not visible; HRMS (MALDI-TOF) m/z [M+Na]⁺ calcd for $C_{23}H_{28}ClN_3O_6Na$: 500.1564; found 500.1590.

140

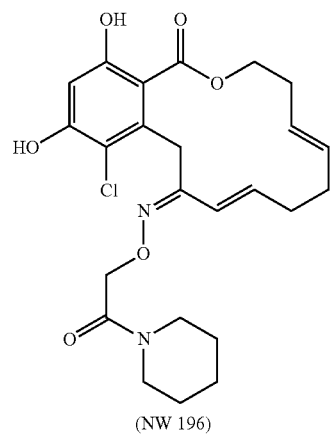

13f
(NW 196)

¹H NMR (DMSO-d6, 400 MHz, 25° C.) δ 10.2 (s, 1H), 6.45 (s, 1H), 6.44 (d, J=16.1 Hz, 1H), 6.12 (dt, J=16.1 6.4 Hz, 1H), 5.31-5.29 (m, 2H), 4.57 (s, 2H), 4.16 (t, J=4.8 Hz, 2H), 3.70 (s, 2H), 3.35-3.30 (m, 4H), 2.31 (m, 2H), 2.08-2.05 (m, 4H), 1.56-1.51 (m, 2H), 1.45-1.35 (m, 4H), 1 OH is not visible; ¹³C NMR (DMSO-d6, 100 MHz, 25° C.) δ 167.9, 166.3, 155.4, 155.2, 153.4, 140.6, 134.3, 131.4, 119.4, 113.9, 112.4, 102.1, 71.9, 65.2, 45.4, 42.1, 34.7, 31.8, 31.7, 30.9, 26.0, 25.9, 25.2, 24.0; HRMS (MALDI-TOF) m/z [M+Na]⁺ calcd for $C_{24}H_{29}ClN_2O_6H$, 499.1612; found 499.1624.

The geometry of the oxime was deduced from structure 13a.

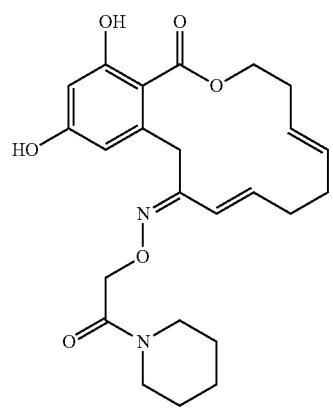

13g

¹H NMR (CDCl₃, 400 MHz) δ 11.64 (s, 1H), 6.62 (d, J=16.1 Hz, 1H), 6.62 (d, J=2.7 Hz, 1H), 6.33 (d, J=1.9 Hz, 1H), 6.25 (dt, J=16.1, 7.5 Hz, 1H), 5.35 (m, 2H), 4.79 (s, 2H), 4.54-4.53 (m, 2H), 4.08 (s, 2H), 3.56-3.54 (m, 2H), 3.38-3.37 (m, 2H), 2.50-2.48 (m, 2H), 2.12-2.08 (m, 4H), 1.66-1.57 (m, 6H), 1 OH signal is not visible. ¹³C NMR (CDCl₃, 100 MHz) δ 170.8, 167.9, 165.7, 162.0, 157.1, 143.1, 141.9, 132.2, 129.2, 118.4, 110.4, 104.4, 102.5, 71.5, 64.5, 46.0, 43.3, 35.1, 32.9, 32.7, 30.9, 26.4, 25.5, 24.5; HRMS (MALDI-TOF) m/z [M+Na]⁺ calcd for $C_{24}H_{30}N_2O_6Na$: 465.2002; found 465.2027.

The geometry of the oxime was deduced from structure 13b.

141

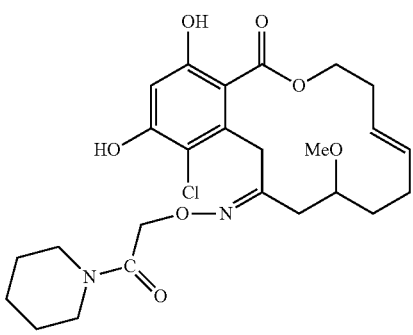

14a

¹H NMR (CDCl₃, 400 MHz) δ 11.41 (s, 1H), 11.43 (s, 1H), 6.58 (s×2, 2H), 5.56-5.43 (m, 4H), 4.53 (2×bs, 4H), 4.45-4.42 (m, 4H), 4.40 (2×d, J=16.6 Hz, 2H), 3.86 (2×d, J=16.6 Hz, 2H), 3.52-3.50 (m, 4H), 3.46-3.41 (m, 2H), 3.30 (s, 3H), 3.31 (s, 3H), 2.91 (dd, J=14.0, 8.3 Hz, 1H), 2.89-2.85 (m, 1H), 2.52-2.51 (m, 4H), 2.41 (dd, J=14.0, 4.0 Hz, 1H), 2.39-2.35 (m, 1H), 2.16-2.14 (m, 4H), 1.87-1.77 (m, 4H), 1.61-1.59 (m, 4H), 1.49-1.43 (m, 12H), 2 OH signals are not visible; HRMS (MALDI-TOF) m/z [M+Na]⁺ calcd for $C_{25}H_{33}ClN_2O_7Na$: 531.1874; found 531.1894.

The oxime geometry was assigned by comparison to 14a.

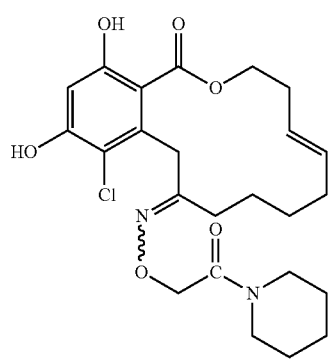

14b

¹H NMR (CDCl₃, 400 MHz, 25° C.) δ 11.44 (s, 1H), 11.32 (s, 1H), 6.61 (s, 1H), 6.57 (s, 1H), 5.55-5.42 (m, 2H), 5.38-5.35 (m, 2H), 4.77 (s, 2H), 4.52 (s, 2H), 4.48-4.44 (m, 4H), 4.22 (s, 2H), 4.17 (s, 2H), 3.58-3.49 (m, 4H), 3.31-3.28 (m, 4H), 2.50-2.46 (m, 2H), 2.42-2.36 (m, 4H), 2.06-1.99 (m, 6H), 1.96-1.92 (m, 4H), 1.66-1.36 (m, 16H), 2 OH signals are not visible; HRMS (MALDI-TOF) m/z [M+Na]⁺ calcd for HRMS (MALDI-TOF) m/z [M+Na]⁺ calcd for $C_{24}H_{31}ClN_2O_6Na$: 501.1768; found: 501.1798.

142

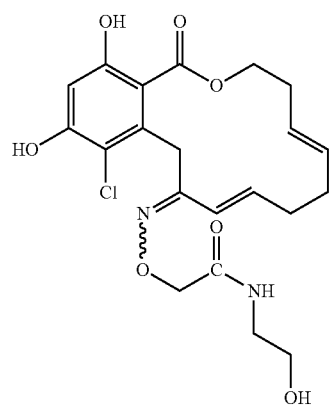

13h

¹H NMR (CDCl₃, 400 MHz, 25° C.) δ 11.35 (s, 1H), 11.14 (s, 1H), 6.63 (s, 1H), 6.56 (s, 1H), 6.48 (d, J=16.4 Hz, 1H), 6.00-5.99 (m, 2H), 5.85 (d, J=16.4 Hz, 1H), 5.37 (s, 2H), 5.15 (s, 2H), 5.14-5.09 (m, 8H), 4.68 (s, 2H), 4.63 (s, 2H), 3.76 (t, J=5.0 Hz, 2H), 3.66 (t, J=4.7 Hz, 2H), 3.52-3.48 (m, 2H), 3.39-3.36 (m, 2H), 2.52-2.48 (m, 2H), 2.41-2.32 (m, 4H), 2.30-2.27 (m, 2H), 2.15-2.10 (m, 4H), 4 OH signals and 2 NH signals are not visible; HRMS (MALDI-TOF) m/z [M+Na]⁺ calcd for HRMS (MALDI-TOF) m/z [M+Na]⁺ calcd for $C_{21}H_{25}ClN_2O_7Na$: 475.1248; found: 475.1275.

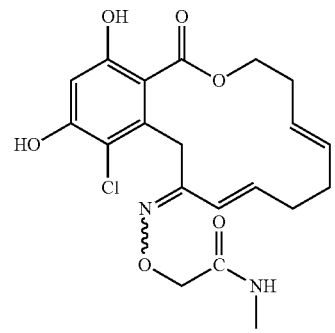

13i

¹H NMR (CDCl₃, 400 MHz, 25° C.) δ 11.46 (s, 1H), 11.02 (s, 1H), 6.65 (s, 1H), 6.65 (d, J=16.6 Hz, 1H), 6.60 (s, 1H), 6.48 (d, J=15.6 Hz, 1H), 6.08-6.00 (m, 2H), 5.34-5.25 (m, 4H), 5.16-5.12 (m, 4H), 5.14 (s, 2H), 5.10 (s, 2H), 4.72 (d, J=16.1 Hz, 1H), 4.65 (d, J=16.1 Hz, 1H), 4.41 (d, J=17.7 Hz, 1H), 4.15 (d, J=17.7 Hz, 1H), 2.91 (d, J=4.8 Hz, 3H), 2.78 (d, J=4.8 Hz, 3H), 2.59-2.52 (m, 1H), 2.51-2.38 (m, 1H), 2.24-2.12 (m, 4H), 2.07-2.00 (m, 4H), 1.95-1.87 (m, 2H), 2 OH signals and 2 NH signals are not visible; HRMS (MALDI-TOF) m/z [M+Na]⁺ calcd for HRMS (MALDI-TOF) m/z [M+Na]⁺ calcd for $C_{20}H_{23}ClN_2O_6Na$: 445.1143; found: 445.1178.

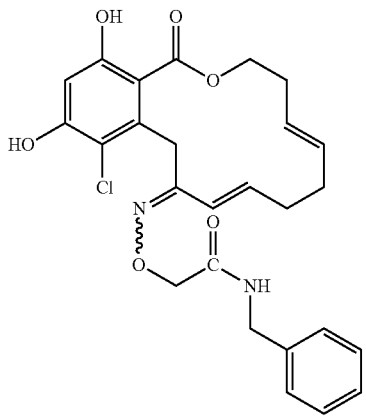

13j

¹H NMR (CDCl₃, 400 MHz, 25° C.) δ 11.32 (s, 1H), 11.04 (s, 1H), 7.32-7.29 (m, 10H), 6.61 (s, 1H), 6.57 (s, 1H), 6.42 (d, J=16.4 Hz, 1H), 6.07 (dt, J=15.8, 6.7 Hz, 1H), 5.99 (dt, J=16.4, 7.3 Hz, 1H), 5.67 (d, J=15.8 Hz, 1H), 5.37-4.95 (m, 8H), 4.73 (s, 2H), 4.69 (s, 2H), 4.64 (s, 2H), 4.56 (s, 2H), 4.54 (s, 2H), 4.52 (s, 2H), 2.34-2.25 (m, 6H), 2.12-2.05 (m, 4H), 2.00-1.99 (m, 2H), 2 OH signals and 2 NH signals are not visible; HRMS (MALDI-TOF) m/z [M+Na]⁺ calcd for HRMS (MALDI-TOF) m/z [M+Na]⁺ calcd for C₂₆H₂₇ClN₂O₆Na: 521.1456; found: 521.1498.

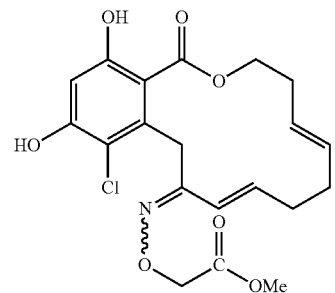

13l

¹H NMR (CDCl₃, 400 MHz, 25° C.) δ 11.20 (s, 1H), 11.00 (s, 1H), 6.62 (s, 1H), 6.56 (s, 1H), 6.55 (d, J=15.7 Hz, 1H), 6.20-6.14 (m, 1H), 6.02 (dt, J=15.7, 7.32 Hz, 1H), 5.84 (d, J=16.4 Hz, 1H), 5.18-5.06 (m, 4H), 4.74 (s, 2H), 4.58-4.55 (m, 4H), 4.44 (s, 2H), 4.26 (s, 2H), 4.22 (s, 2H), 3.78 (s, 3H), 3.66 (s, 3H), 2.51-2.48 (m, 1H), 2.39-2.36 (m, 3H), 2.32-2.29 (m, 1H), 2.26-2.24 (m, 1H), 2.14-2.06 (m, 4H), 2.00-1.99 (m, 2H), 2 OH signals are not visible; HRMS (MALDI-TOF) m/z [M+Na]⁺ calcd for HRMS (MALDI-TOF) m/z [M+Na]⁺ calcd for C₂₀H₂₂ClNO₇Na: 446.0983; found: 446.0975.

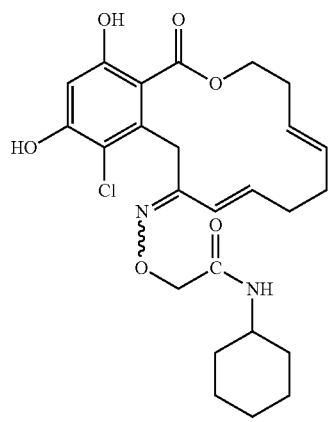

13k

¹H NMR (acetone-d6, 400 MHz, 25° C.) δ 6.62 (d, J=15.8 Hz, 1H), 6.56 (s, 1H), 6.27 (s, 1H), 6.14 (dt, J=15.8, 8.5 Hz, 1H), 6.02 (dt, J=15.5, 7.6 Hz, 1H), 5.37-5.34 (m, 5H), 5.26 (s, 1H), 5.22 (s, 1H), 4.55-4.52 (m, 2H), 4.51 (s, 2H), 4.49 (s, 2H), 4.43-4.41 (m, 2H), 4.26 (s, 2H), 4.19 (s, 2H), 3.76-3.70 (m, 1H), 3.61-3.54 (m, 1H), 2.49-2.47 (m, 2H), 2.40-2.36 (m, 2H), 2.16-1.99 (m, 8H), 1.88-1.84 (m, 4H), 1.73-1.66 (m, 4H), 1.62-1.58 (m, 4H), 1.37-1.16 (m, 8H), 2 OH signals and 2 NH signals are not visible; HRMS (MALDI-TOF) m/z [M+Na]⁺ calcd for HRMS (MALDI-TOF) m/z [M+Na]⁺ calcd for C₂₅H₃₁ClN₂O₆Na: 513.1769; found: 513.1788.

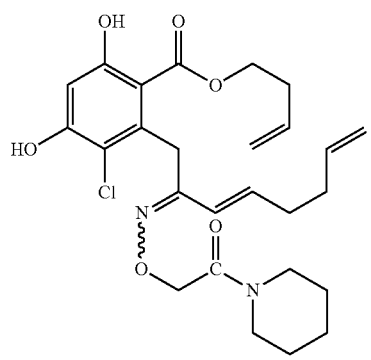

13m

¹H NMR (CDCl₃, 400 MHz, 25° C.) δ 11.57 (s, 1H), 11.44 (s, 1H), 6.91 (d, J=16.1 Hz, 1H), 6.61 (s, 1H), 6.57 (s, 1H), 6.27 (dt, J=16.1, 6.96 Hz, 1H), 6.02 (dt, J=15.6, 6.44 Hz, 1H), 5.71-5.88 (m, 3H), 5.58-5.67 (m, 1H), 5.50 (d, J=15.6 Hz, 1H), 4.99-5.15 (m, 6H), 4.84-4.91 (m, 2H), 4.80 (s, 2H), 4.50 (s, 2H), 4.30-4.36 (dt×2, J=12.3, 6.48 Hz, 4H), 4.23 (s, 2H), 4.19 (s, 2H), 3.23-3.58 (m, 8H), 2.38-2.48 (m, 4H), 2.31-2.37 (m, 2H), 2.21-2.26 (m, 2H), 2.00-2.04 (m, 4H), 1.44-1.66 (m, 12H); HRMS (MALDI-TOF) m/z [M+Na]⁺ calcd for HRMS (MALDI-TOF) m/z [M+Na]⁺ calcd for C₂₆H₃₃ClN₂O₆Na: 527.1925; found: 527.1906.

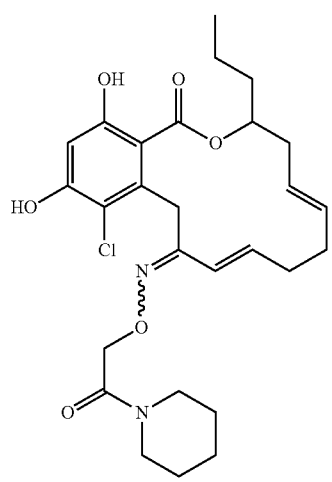

394

Mixture of isomers 3:1 in the oxime. Major isomer E: $^1$H NMR (CDCl$_3$, 400 MHz, 25° C.) δ 11.46 (bs, 1H), 6.63 (s, 1H), 6.03 (m, 1H), 5.30-5.05 (m, 2H), 5.13 (d, J=16.1 Hz, 1H), 4.84 (s, 1H), 4.82 (s, 1H), 4.27 (s, 1H), 4.15 (s, 1H), 3.65-3.40 (m, 4H), 3.34-3.21 (m, 1H), 2.65-1.92 (m, 6H), 1.35-1.20 (m, 6H), 0.97 (t, J=7.3 Hz, 3H), 0.91 (q, J=7.3 Hz, 2H), 0.90 (q, J=7.3 Hz, 2H).

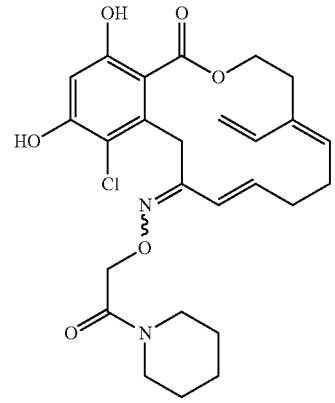

397

Mixture of isomers 3:1 in the oxime. Major isomer E $^1$H NMR (CDCl$_3$, 400 MHz, 25° C.) δ 12.07 (s, 1H), 6.56 (s, 1H), 6.20-5.88 (m, 1H), 6.03 (d, J=16 Hz, 1H), 5.60-5.46 (m, 1H), 4.92 (d, J=23.1 Hz, 2H), 4.53-4.44 (m, 1H), 4.48 (s, 2H), 4.08 (s, 2H), 3.60-3.32 (m, 4H), 3.20 (m, 2H), 2.75 (t, J=6.3 Hz, 2H), 2.50-2.39 (m, 2H), 2.28-2.15 (m, 2H), 1.37-1.23 (m, 4H), 0.93-0.78 (m, 2H).

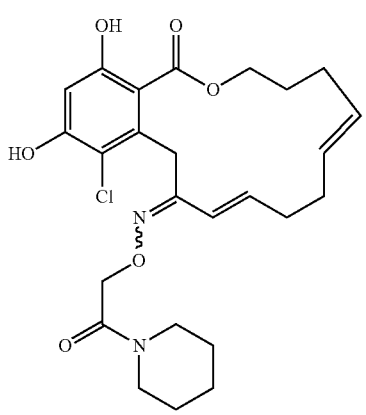

396

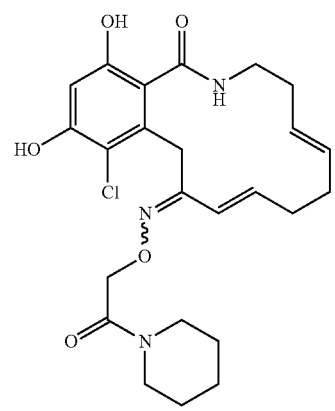

395

Mixture of isomers 4:1 in the oxime. Major isomer E $^1$H NMR (CDCl$_3$, 400 MHz, 25° C.) δ 11.31 (s, 1H), 6.41 (s, 1H), 6.22 (m, 1H), 5.50 (d, J=15.8 Hz, 1H), 5.44-5.26 (m, 2H), 4.79 (s, 2H), 4.49 (t, J=5.6 Hz, 2H), 4.21 (s, 2H), 3.62-3.37 (m, 4H), 2.33-1.93 (m, 8H), 1.34-1.21 (m, 4H), 0.93-0.79 (m, 2H).

Mixture of isomers 3:1 in the oxime. Major isomer E $^1$H NMR (CDCl$_3$, 400 MHz, 25° C.) δ 10.58 (s, 1H), 6.64 (s, 1H), 6.22-6.15 (m, 1H), 5.41 (d, J=13.3 Hz, 1H), 5.31 (s, 2H), 5.27-5.13 (m, 2H), 4.61 (s, 2H), 4.03 (t, J=7 Hz, 2H), 3.63-3.37 (m, 4H), 2.56-2.02 (m, 6H), 1.38-1.22 (m, 4H), 0.93-0.78 (m, 2H).

147

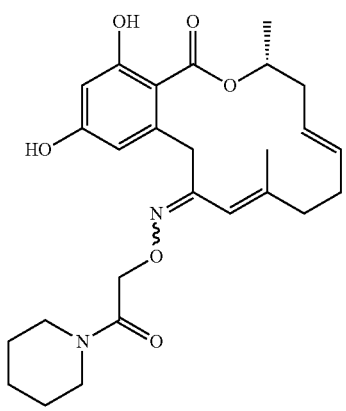

336

Mixture of isomers 1:1 in the oxime. $^1$H NMR (CDCl$_3$, 400 MHz) δ 11.92 (brs, 1H), 11.77 (brs, 1H), 6.56 (d, J=2.4 Hz, 1H), 6.53 (d, J=2.4 Hz, 1H), 6.36 (d, J=2.4 Hz, 1H), 6.35 (d, J=2.8 Hz, 1H), 5.43-5.17 (m, 6H), 5.11 (s, 1H), 5.02 (s, 1H), 4.88 (d, J=14.4 Hz, 1H), 4.81-4.74 (m, 2H), 4.70 (d, J=14.4 Hz, 1H), 4.46 (d, J=13.6 Hz, 1H), 4.16-4.09 (m, 2H), 3.96 (d, J=15.6 Hz, 1H), 3.64-3.37 (m, 8H), 2.78-2.60 (m, 4H), 2.23-2.12 (m, 8H), 1.79 (s, 3H), 1.65-1.56 (m, 12H), 1.53 (s, 3H), 1.35 (d, J=6.4 Hz, 3H), 1.29 (d, J=6.4 Hz, 3H).

148

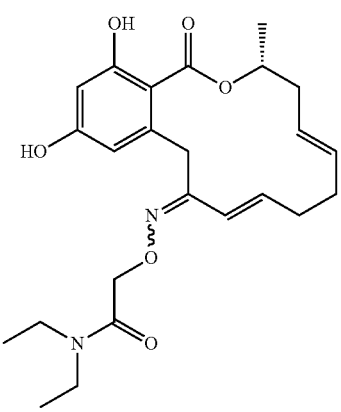

335

Mixture of isomers 1:1 in the oxime. $^1$H NMR (CDCl$_3$, 400 MHz) δ 11.21 (brs, 1H), 6.67 (d, J=2.4 Hz, 1H), 6.62 (d, J=16.4 Hz, 1H), 6.30 (d, J=2.8 Hz, 1H), 6.23-6.15 (m, 1H), 5.52-5.44 (m, 1H), 5.40-5.31 (m, 1H), 4.82 (d, J=14.8 Hz, 1H), 4.75 (d, J=14.8 Hz, 1H), 4.51 (d, J=14.8 Hz, 1H), 4.21 (t, J=6.2 Hz, 1H), 3.66 (d, J=15.2 Hz, 1H), 3.44-3.35 (m, 2H), 3.34-3.28 (m, 2H), 2.33-2.20 (m, 2H), 2.14-1.98 (m, 4H), 1.45 (d, J=6.8 Hz, 3H), 1.14 (t, J=7.2 Hz, 3H), 0.92 (t, J=7.6 Hz, 3H). HRMS (MALDI-TOF) m/z [M+Na]$^+$ calcd for C$_{24}$H$_{32}$NaN$_2$O$_6$: 467.2158; found: 467.2176

341

Mixture of isomers 1:1 in the oxime. $^1$H NMR (CDCl$_3$, 400 MHz) δ 10.95 (brs, 2H), 7.11 (d, J=2.4 Hz, 2H), 6.32 (d, J=2.4 Hz, 2H), 6.09-6.01 (m, 2H), 5.95 (d, J=16.8 Hz, 2H), 5.91 (d, J=16.4 Hz, 2H), 5.76-5.68 (m, 2H), 5.11 (s, 2H), 4.94 (s, 2H), 4.84 (s, 4H), 4.57 (t, J=5.2 Hz, 4H), 4.26 (s, 4H), 3.59-3.53 (m, 4H), 3.39-3.33 (m, 4H), 2.67 (t, J=5.2 Hz, 4H), 2.23-2.17 (m, 8H), 1.60-1.52 (m, 8H), 1.36-1.28 (m, 4H).

351

Mixture of isomers 1:1 in the oxime. $^1$H NMR (CDCl$_3$, 400 MHz) δ 11.92 (brs, 1H), 11.83 (brs, 1H), 6.98 (d, J=2.4 Hz, 2H), 6.34-6.33 (m, 2H), 5.38-5.15 (m, 6H), 4.93 (d, J=14.4 Hz, 2H), 4.79-4.68 (m, 2H), 4.75 (d, J=14.4 Hz, 2H), 4.27 (d, J=14.4 Hz, 2H), 4.04 (d, J=14.4 Hz, 2H), 3.44-3.26 (m, 8H), 2.24-2.19 (m, 4H), 1.74-1.72 (m, 14H), 1.36 (d, J=6.8 Hz, 6H), 1.34 (d, J=6.8 Hz, 6H), 1.27-1.21 (m, 6H), 1.14 (t, J=7.4 Hz, 6H). HRMS (MALDI-TOF) m/z [M+H]$^+$ calcd for C$_{25}$H$_{35}$N$_2$O$_6$: 459.2495; found: 459.2499

149

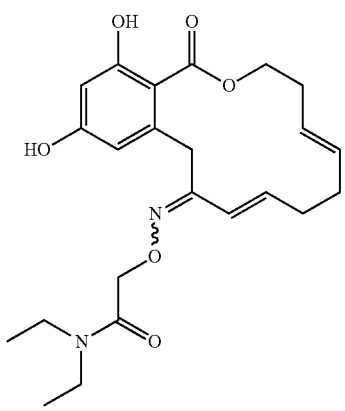

357

Mixture of isomers 1:1 in the oxime. $^1$H NMR (CDCl$_3$, 400 MHz) δ 11.70 (brs, 1H), 11.69 (brs, 1H), 6.99 (brs, 1H), 6.72 (d, J=2.8 Hz, 1H), 6.64 (d, J=16.4 Hz, 1H), 6.32 (d, J=2.4 Hz, 1H), 6.31 (d, J=2.4 Hz, 1H), 6.28-6.17 (m, 2H), 5.91 (d, J=16 Hz, 1H), 5.38-5.33 (m, 4H), 4.87 (s, 2H), 4.79 (s, 2H), 4.57-4.53 (m, 4H), 4.34 (s, 2H), 4.07 (s, 2H), 3.43-3.37 (m, 4H), 3.34-3.28 (q, J=7.2 Hz, 4H), 2.53-2.48 (m, 4H), 2.16-1.97 (m, 8H), 1.29-1.24 (m, 12H). HRMS (MALDI-TOF) m/z [M+H]$^+$ calcd for C$_{23}$H$_{37}$N$_2$O$_6$: 431.2182; found: 431.2186

150

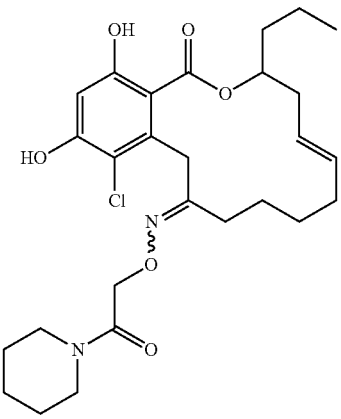

352

Mixture of isomers 1:1 in the oxime. $^1$H NMR (CDCl$_3$, 400 MHz) δ 11.79 (brs, 1H), 11.03 (brs, 1H), 6.61 (s, 1H), 6.08 (s, 1H), 5.42-5.28 (m, 6H), 4.79 (d, J=13.2 Hz, 2H), 4.74 (d, J=13.6 Hz, 2H), 4.39 (m, 2H), 4.27-4.23 (m, 3H), 3.61-3.54 (m, 4H), 3.51-3.45 (m, 4H), 2.53-2.47 (m, 2H), 2.33-2.20 (m, 4H), 2.06-1.91 (m, 8H), 1.70-1.58 (m, 12H), 1.44-129 (m, 13H), 0.95 (t, J=7.2 Hz, 6H). FIRMS (MALDI-TOF) m/z [M+Na]$^+$ calcd for C$_{27}$H$_{37}$ClNaN$_2$O$_6$: 543.2237; found: 543.2263

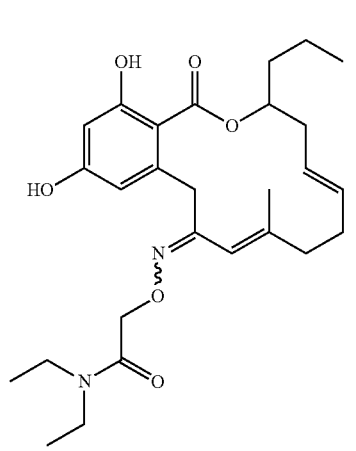

362

Mixture of isomers 7:1 in the oxime. Major isomer E $^1$H NMR (CDCl$_3$, 400 MHz) δ 11.82 (brs, 1H), 7.75 (brs, 1H), 7.02 (d, J=2.4 Hz, 1H), 6.34 (d, J=2.4 Hz, 1H), 5.35-5.28 (m, 1H), 5.20 (s, 1H), 5.14-5.10 (m, 1H), 4.94 (d, J=14.4 Hz, 1H), 4.74 (d, J=14.4 Hz, 1H), 4.31 (d, J=14.4 Hz, 1H), 4.07 (d, J=14.4 Hz, 1H), 3.44-3.28 (m, 4H), 2.70-2.63 (m, 1H), 2.25-2.18 (m, 2H), 2.14-2.07 (m, 2H), 1.73-1.72 (m, 6H), 1.25-1.21 (m, 6H), 1.14 (t, J=7.2 Hz, 3H), 0.95 (t, J=7.2 Hz, 3H). HRMS (MALDI-TOF) m/z [M+Na]$^+$ calcd for C$_{27}$H$_{38}$NaN$_2$O$_6$: 509.2627; found: 509.2652

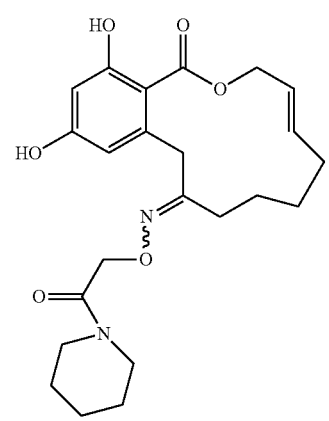

353

HRMS (MALDI-TOF) m/z [M+Na]$^+$ calcd for C$_{23}$H$_{30}$NaN$_2$O$_6$: 453.2001; found: 453.2010

151

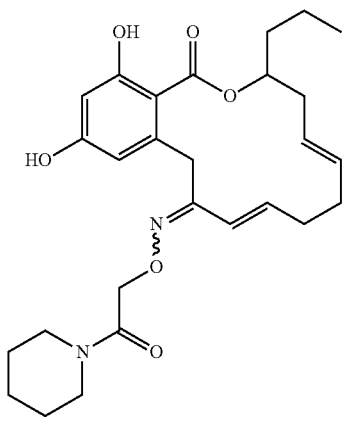

Mixture of isomers 1:1 in the oxime. $^1$H NMR (CDCl$_3$, 400 MHz) δ 6.99 (brs, 1H), 6.68 (d, J=2.4 Hz, 1H), 6.61 (d, J=16.8 Hz, 1H), 6.32 (d, J=2.4 Hz, 1H), 6.30 (d, J=2.4 Hz, 1H), 6.25-6.10 (m, 2H), 5.89 (d, J=16.4 Hz, 1H), 5.50-5.31 (m, 4H), 4.94 (d, J=14.4 Hz, 2H), 4.84-4.76 (m, 4H), 4.50 (d, J=15.2 Hz, 1H), 4.44 (d, J=14.4 Hz, 1H), 4.29 (d, J=14.4 Hz, 1H), 4.21 (t, J=6.0 Hz, 1H), 2.72-2.61 (m, 4H), 2.35-2.19 (m, 6H), 2.15-1.96 (m, 8H), 1.93-1.82 (m, 3H), 1.38-1.28 (m, 11H), 0.96 (t, J=7.6 Hz, 3H), 0.92 (t, J=7.6 Hz, 3H). HRMS (MALDI-TOF) m/z [M+H]$^+$ calcd for C$_{27}$H$_{37}$N$_2$O$_6$: 485.2651; found: 485.2611

152

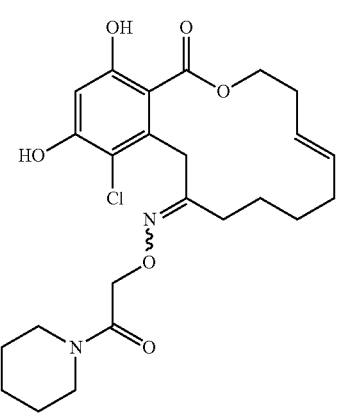

Mixture of isomers 1:1 in the oxime. $^1$H NMR (CDCl$_3$, 400 MHz) δ 6.61 (s, 1H), 6.05 (s, 1H), 5.41-5.26 (m, 6H), 4.80-4.75 (m, 3H), 4.58-4.47 (m, 4H), 4.30-4.17 (m, 3H), 4.21 (t, 2H, J=5.6 Hz), 4.05-4.01 (m, 2H), 3.61-3.54 (m, 4H), 3.49-3.42 (m, 4H), 2.46-2.40 (m, 2H), 2.24-2.20 (m, 3H), 2.07-1.90 (m, 8H), 1.34-1.28 (m, 15H). HRMS (MALDI-TOF) m/z [M+Na]$^+$ calcd for C$_{27}$H$_{31}$NaN$_2$O$_6$: 501.1768; found: 501.1718

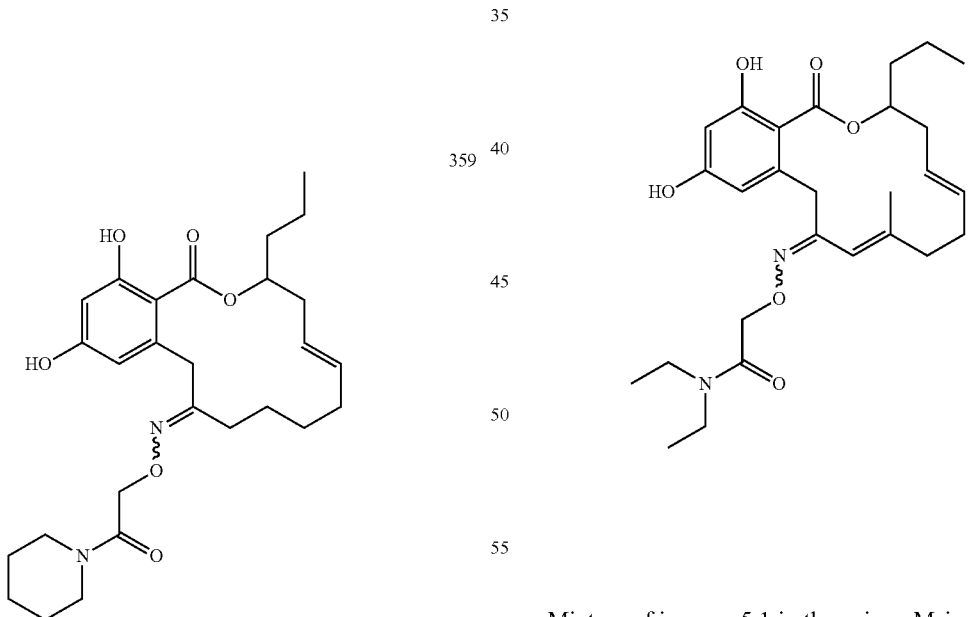

HRMS (MALDI-TOF) m/z [M+Na]$^+$ calcd for C$_{27}$H$_{38}$NaN$_2$O$_6$: 509.2628; found: 509.2639

Mixture of isomers 5:1 in the oxime. Major isomer E $^1$H NMR (CDCl$_3$, 400 MHz) δ 11.85 (brs, 1H), 7.12 (d, J=2.4 Hz, 1H), 6.34 (d, J=2.4 Hz, 1H), 5.38-5.31 (m, 2H), 5.25 (s, 1H), 5.23-5.11 (m, 2H), 4.96 (d, J=14.4 Hz, 1H), 4.74 (d, J=14.4 Hz, 1H), 4.34 (d, J=14 Hz, 1H), 4.21 (t, J=6 Hz, 1H), 4.10 (d, J=14 Hz, 1H), 3.43-3.27 (m, 4H), 1.70 (s, 3H), 1.61-1.59 (m, 4H), 1.37-1.29 (m, 7H), 1.13 (t, J=7.2 Hz, 3H), 0.95 (t, J=7.2 Hz, 3H). HRMS (MALDI-TOF) m/z [M+Na]$^+$ calcd for C$_{27}$H$_{38}$NaN$_2$O$_6$: 509.2627; found: 509.2680

153
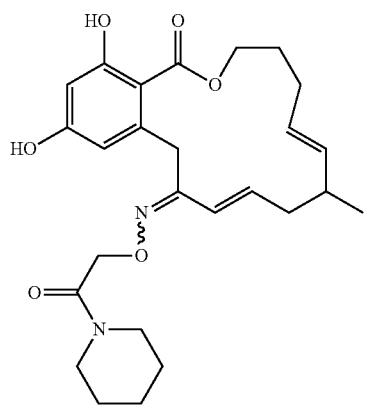
HRMS (MALDI-TOF) m/z [M+Na]+ calcd for $C_{26}H_{34}NaN_2O_6$: 493.2314; found: 493.2331
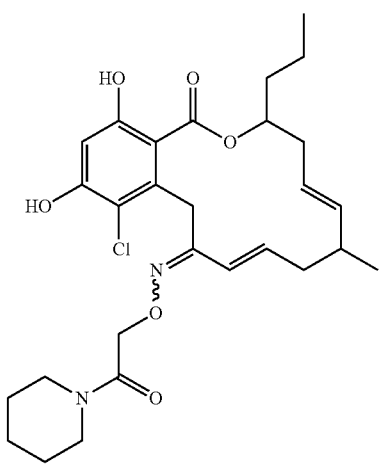
HRMS (MALDI-TOF) m/z [M+Na]+ calcd for $C_{28}H_{37}ClNaN_2O_6$: 555.2238; found: 555.2242
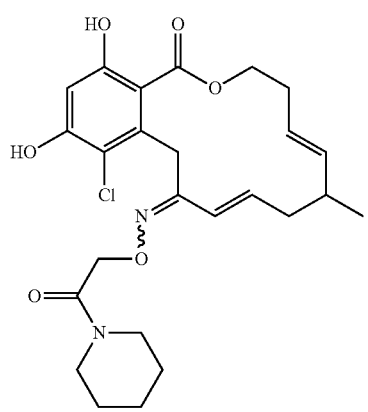
HRMS (MALDI-TOF) m/z [M+Na]+ calcd for $C_{25}H_{31}ClNaN_2O_6$: 513.1768; found: 513.1780
154
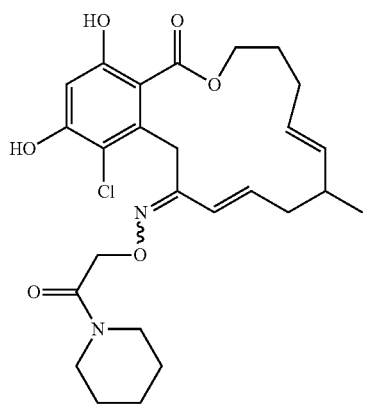
HRMS (MALDI-TOF) m/z [M+Na]+ calcd for $C_{26}H_{33}ClNaN_2O_6$: 527.1925; found: 527.1939
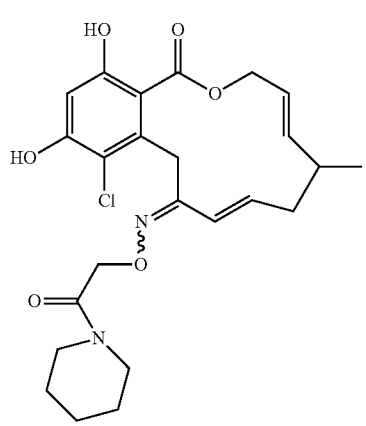
HRMS (MALDI-TOF) m/z [M+Na]+ calcd for $C_{24}H_{29}ClNaN_2O_6$: 499.1612; found: 499.1626
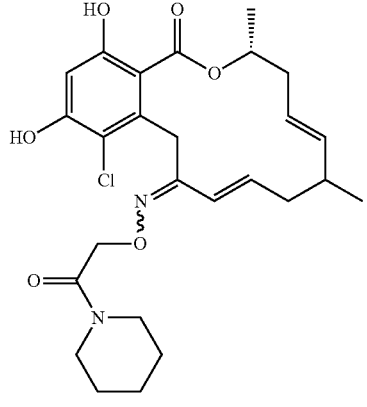
HRMS (MALDI-TOF) m/z [M+Na]+ calcd for $C_{26}H_{33}ClNaN_2O_6$: 527.1925; found: 527.1932

370

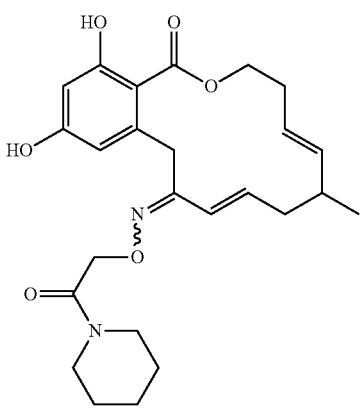

HRMS (MALDI-TOF) m/z [M+Na]⁺ calcd for C$_{25}$H$_{32}$NaN$_2$O$_6$: 479.2158; found: 479.2174

371

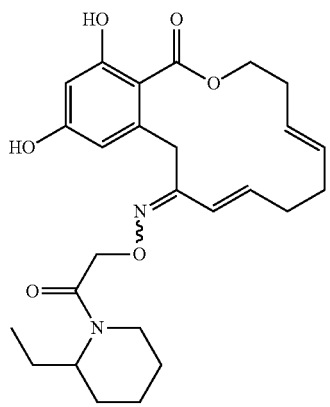

HRMS (MALDI-TOF) m/z [M+Na]⁺ calcd for C$_{26}$H$_{34}$NaN$_2$O$_6$: 493.2315; found: 493.2319

354

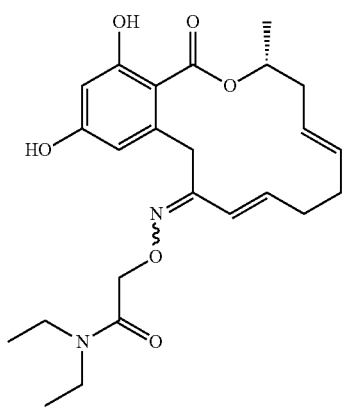

Mixture of isomers 4:1 in the oxime. Major isomer E ¹H NMR (CDCl$_3$, 400 MHz) δ 7.40 (d, J=2.4 Hz, 1H), 6.31 (d, J=2.4 Hz, 1H), 6.19-6.11 (m, 1H), 5.89 (d, J=16 Hz, 1H), 5.53-5.46 (m, 1H), 5.41-5.32 (m, 1H), 4.93 (d, J=14.8 Hz, 1H), 4.81 (d, J=14.8 Hz, 1H), 4.44 (d, J=14.8 Hz, 1H), 4.28 (d, J=14.8 Hz, 1H), 4.21 (t, J=5.6 Hz, 1H), 3.44-3.29 (m, 2H), 2.35-2.20 (m, 2H), 2.13-2.01 (m, 2H), 1.45 (d, J=6.8 Hz, 3H), 1.37-1.28 (m, 4H), 1.14 (t, J=7.2 Hz, 3H), 0.92 (t, J=7.6H, 3 Hz). HRMS (MALDI-TOF) m/z [M+Na]⁺ calcd for C$_{24}$H$_{32}$NaN$_2$O$_6$: 467.2158; found: 467.2147

378

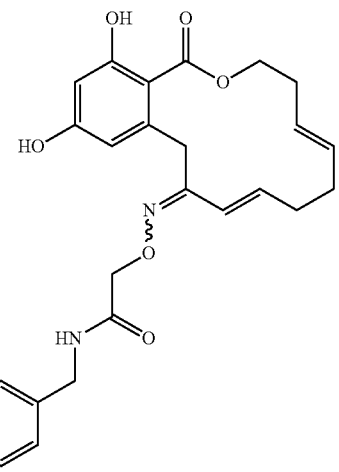

Mixture of isomers 1:1 in the oxime. ¹H NMR (CDCl$_3$, 400 MHz) δ 11.60 (brs, 1H), 11.42 (brs, 1H), 7.35-7.28 (m, 9H), 6.69-6.62 (m, 2H), 6.49 (d, J=16 Hz, 1H), 6.36 (d, J=2.4 Hz, 1H), 6.33 (d, J=2.4 Hz, 1H), 6.32 (d, J=2.4 Hz, 1H), 6.28-6.24 (m, 1H), 6.23 (d, J=2.8 H, 1H), 6.10 (dt, J=16, 7.2 Hz, 1H), 5.73 J=16 Hz, 1H), 5.36-5.31 (m, 2H), 5.27-5.18 (m, 2H), 4.70 (s, 2H), 4.65 (s, 2H), 4.55-4.51 (m, 5H), 4.45 (t, J=5.3 Hz, 2H), 4.27 (s, 2H), 4.08 (s, 2H), 2.50-2.42 (m, 4H), 2.17-2.07 (m, 8H). FIRMS (MALDI-TOF) [M+H]⁺ calcd for C$_{26}$H$_{29}$N$_2$O$_6$: 465.2025; found: 465.1981

372

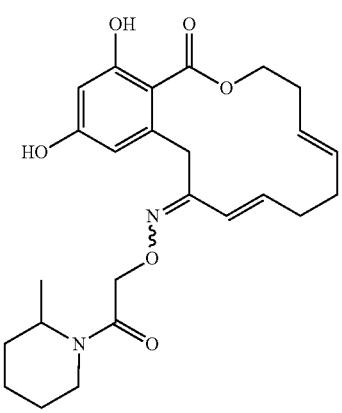

Mixture of isomers 1:1 in the oxime. ¹H NMR (CDCl$_3$, 400 MHz) δ 11.67 (brs, 1H), 11.65 (brs, 1H), 8.00 (brs, 1H), 7.77 (brs, 1H), 7.13 (brs, 1H), 6.63-6.59 (m, 2H), 6.32 (2d, J=2.8 Hz, 2H), 6.27-6.12 (m, 2H), 5.86 (d, J=16.4 Hz, 1H), 5.37-5.33 (m, 4H), 4.95-4.72 (m, 4H), 4.57-4.51 (m, 4H), 4.34 (s, 2H), 4.10 (d, J=15.2 Hz, 1H), 4.03 (d, J=15.2 Hz, 1H), 3.58-3.48 (m, 2H), 3.20-3.09 (m, 2H), 2.77-2.69 (m, 2H), 2.53-2.45 (m, 4H), 2.17-2.05 (m, 8H), 1.71-1.32 (m, 12H), 1.30-1.12 (m, 6H). HRMS (MALDI-TOF) m/z [M+H]⁺ calcd for C$_{25}$H$_{33}$N$_2$O$_6$: 457.2338; found: 457.2332

380

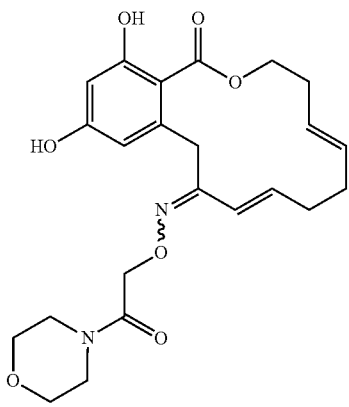

Mixture of isomers 1:1 in the oxime. $^1$H NMR (CDCl$_3$, 400 MHz) δ 11.66 (brs, 1H), 11.64 (brs, 1H), 7.56 (brs, 1H), 7.36 (brs, 1H), 6.95 (d, J=2.8 Hz, 1H), 6.59-6.54 (m, 2H), 6.33 (d, J=2.8 Hz, 1H), 6.32 (d, J=2.8 Hz, 1H), 6.28-6.13 (m, 2H), 5.84 (d, J=16.1 Hz, 1H), 5.38-5.32 (m, 4H), 4.85 (s, 2H), 4.78 (s, 2H), 4.54 (t, J=5.2 Hz, 4H), 4.33 (s, 2H), 4.07 (s, 2H), 3.71-3.64 (m, 12H), 3.52-3.48 (m, 4H), 2.50 (brt, J=4.8 Hz, 4H), 2.17-2.07 (m, 8H). HRMS (MALDI-TOF) m/z [M+Na]$^+$ calcd for C$_{23}$H$_{28}$NaN$_2$O$_7$: 467.1794; found: 467.1765

376

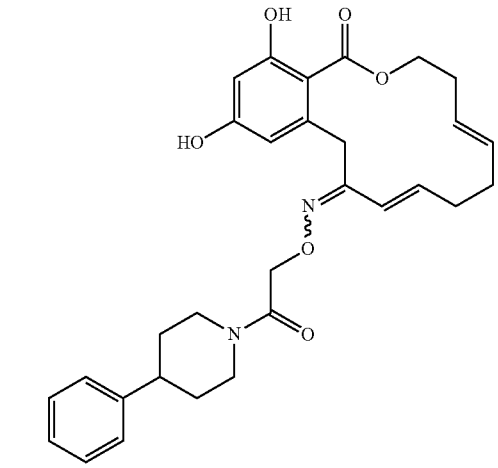

Mixture of isomers 1:1 in the oxime. $^1$H NMR (CDCl$_3$, 400 MHz) δ 11.65 (brs, 2H), 7.32-7.27 (m, 4H), 7.24-7.10 (m, 6H), 7.01 (d, J=2.4 Hz, 1H), 6.64-6.59 (m, 2H), 6.34-6.33 (m, 2H), 6.28-6.18 (m, 2H), 5.85 (d, J=16 Hz, 1H), 5.37-5.32 (m, 4H), 4.85 (s, 2H), 4.72-4.69 (m, 2H), 4.56-4.51 (m, 4H), 4.15 (d, J=15.2 Hz, 2H), 4.02 (d, J=15.2 Hz, 2H), 3.96-3.92 (m, 2H), 3.21-3.11 (m, 2H), 2.76-2.67 (m, 4H), 2.54-2.45 (m, 4H), 2.12-2.02 (m, 10H), 1.90-1.87 (m, 4H), 1.67-1.58 (m, 4H). HRMS (MALDI-TOF) m/z [M+Na]$^+$ calcd for C$_{30}$H$_{34}$NaN$_2$O$_6$: 541.2314; found: 541.2314

371

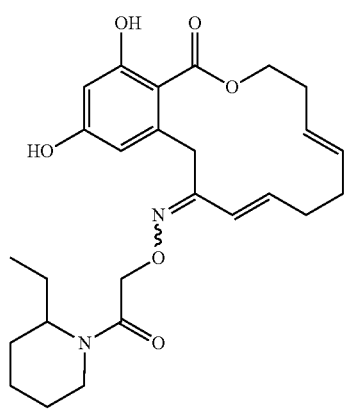

388

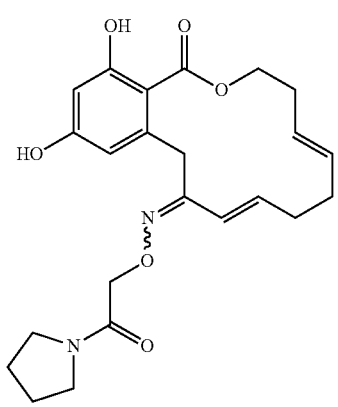

Mixture of isomers 1:1 in the oxime. $^1$H NMR (CDCl$_3$, 400 MHz) 11.62 (brs, 2H), 6.96 (d, J=2 Hz, 1H), 6.58 (d, J=2.8 Hz, 1H), 6.60 (d, J=2.8 Hz, 1H), 6.32 (brd, J=2.4 Hz, 2H), 6.24-6.10 (m, 2H), 5.81 (d, J=16 Hz, 1H), 5.35-5.32 (m, 3H), 4.92-4.72 (m, 4H), 4.56-4.45 (m, 4H), 4.31 (brs, 2H), 4.04 (brs, 2H), 3.75-3.67 (m, 1H), 3.59-3.51 (m, 1H), 3.12-3.03 (m, 1H), 2.64 (t, J=12.8 Hz, 1H), 2.52-2.46 (m, 4H), 2.14-2.04 (m, 8H), 1.70-1.58 (m, 10H). HRMS (MALDI-TOF) m/z [M+Na]$^+$ calcd for C$_{26}$H$_{34}$NaN$_2$O$_6$: 493.2314; found: 493.2332

Mixture of isomers 1:1 in the oxime. $^1$H NMR (CDCl$_3$, 400 MHz) δ 11.65 (brs, 1H), 11.64 (brs, 1H), 8.70 (brs, 1H), 8.27 (brs, 1H), 7.04 (d, J=2.4 Hz, 1H), 6.64-6.60 (m, 2H), 6.26-6.11 (m, 2H), 6.32 (2d, J=2.6 Hz, 2H), 5.82 (d, J=16 Hz, 1H), 5.36-5.32 (m, 4H), 4.76 (s, 2H), 4.70 (s, 2H), 4.53 (bit, J=5.2 Hz, 4H), 4.33 (s, 2H), 4.05 (s, 2H), 3.51 (bit, J=6.8 Hz, 4H), 3.44 (q, J=7.2 Hz, 4H), 2.52-2.46 (m, 4H), 2.16-2.05 (m, 8H), 2.02-1.93 (m, 4H), 1.90-1.84 (m, 4H). HRMS (MALDI-TOF) m/z [M+H]$^+$ calcd for C$_{23}$H$_{29}$N$_2$O$_6$: 429.2025; found: 429.2003

377

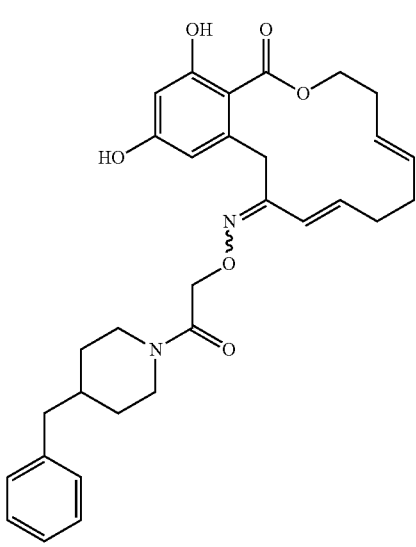

Mixture of isomers 1:1 in the oxime. $^1$H NMR (CDCl$_3$, 400 MHz) δ 11.66 (brs, 1H), 11.64 (brs, 1H), 8.15 (brs, 1H), 7.86 (brs, 1H), 7.31-7.27 (m, 4H), 7.21-7.18 (m, 2H), 7.15-7.10 (m, 4H), 7.00 (brs, 1H), 6.60 (d, J=15.6 Hz, 1H), 6.59 (d, J=2.4 Hz, 1H), 6.32 (2d, J=2.4 Hz, 2H), 6.27-6.11 (m, 2H), 5.85 (d, J=16 Hz, 1H), 5.36-5.32 (m, 4H), 4.84 (s, 2H), 4.77 (s, 2H), 4.59-4.48 (m, 4H), 4.33 (s, 2H), 4.11 (d, J=15.2 Hz, 1H), 4.02 (d, J=15.6 Hz, 1H), 3.78-3.71 (m, 2H), 3.01-2.92 (m, 2H), 2.59-2.47 (m, 8H), 2.12-2.07 (m, 8H), 1.82-1.68 (m, 6H), 1.36-1.30 (m, 8H). HRMS (MALDI-TOF) m/z [M+H]$^+$ calcd for C$_{31}$H$_{37}$N$_2$O$_6$: 533.2651; found: 533.2625

373

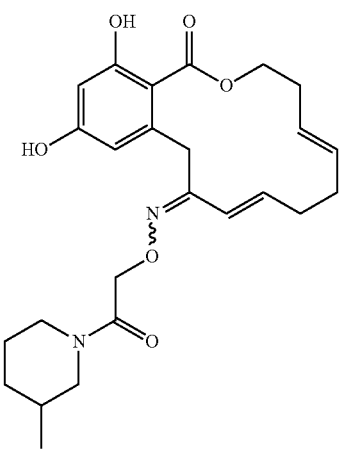

Mixture of isomers 1:1 in the oxime. $^1$H NMR (CDCl$_3$, 400 MHz) δ 11.65 (brs, 1H), 11.64 (brs, 1H), 7.00 (d, J=2.4 Hz, 1H), 6.61-6.57 (m, 2H), 6.33-6.32 (m, 2H), 6.25-6.10 (m, 2H), 5.82 (d, J=16 Hz, 1H), 5.36-5.31 (m, 4H), 4.85 (s, 2H), 4.78 (s, 2H), 4.58-4.48 (m, 4H), 4.41-4.32 (m, 4H), 4.12-3.98 (m, 2H), 3.72-3.58 (m, 2H), 3.02-2.93 (m, 1H), 2.72-2.62 (m, 2H), 2.53-2.45 (m, 4H), 2.35-2.28 (m, 1H), 2.16-2.04 (m, 8H), 1.86-1.39 (m, 8H), 1.17-1.07 (m, 2H), 0.93-0.88 (m, 6H). HRMS (MALDI-TOF) m/z [M+H]$^+$ calcd for C$_{25}$H$_{33}$N$_2$O$_6$: 457.2338; found: 457.2380

379

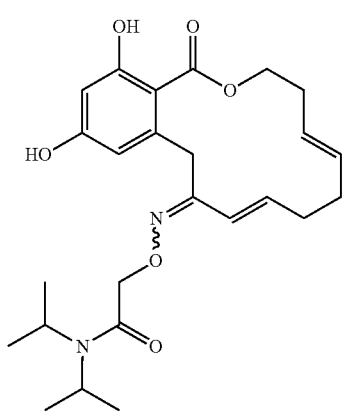

374

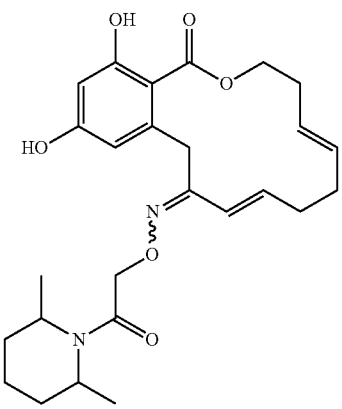

Mixture of isomers 1:1 in the oxime. $^1$H NMR (CDCl$_3$, 400 MHz) δ 11.72 (brs, 1H), 11.71 (brs, 1H), 6.71 (d, 1H, J=2.4 Hz), 6.67 (d, 1H, J=16.4 Hz), 6.35 (2d, 2H, J 3 Hz), 6.31-6.18 (m, 2H), 5.93 (d, 1H, J=16.4 Hz), 5.41-5.36 (m, 4H), 4.86 (s, 2H), 4.77 (s, 2H), 4.60-4.54 (m, 4H), 4.37 (s, 2H), 4.10 (s, 2H), 3.94-3.86 (m, 2H), 3.62-3.49 (m, 2H), 2.55-2.49 (m, 4H), 2.20-2.10 (m, 8H), 1.44-1.25 (m, 24H). HRMS (MALDI-TOF) m/z [M+H]$^+$ calcd for C$_{25}$H$_{35}$N$_2$O$_6$: 459.2495; found: 459.2514

Mixture of isomers 1:1 in the oxime. $^1$H NMR (CDCl$_3$, 400 MHz) δ 11.67 (brs, 2H), 6.99 (s, 1H), 6.68-6.63 (m, 2H), 6.32 (d, J=2.4 Hz, 1H), 6.31 (d, J=2.8 Hz, 1H), 6.27-6.14 (m, 2H), 5.90 (d, J=16 Hz, 1H), 5.37-5.34 (m, 4H), 4.77 (s, 2H), 4.63-4.46 (m, 4H), 4.36 (brs, 2H), 4.21 (t, J=6 Hz, 4H), 4.05-3.92 (m, 4H), 2.55-2.46 (m, 4H), 2.17-2.06 (m, 8H), 1.37-1.28 (m, 12H), 0.93-0.86 (m, 12H). HRMS (MALDI-TOF) m/z [M+Na]$^+$ calcd for C$_{26}$H$_{34}$NaN$_2$O$_6$: 493.2314; found: 493.2314

161

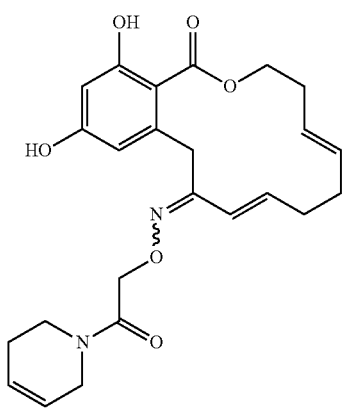

382

Mixture of isomers 2:1 in the oxime. Major isomer E $^1$H NMR (CDCl$_3$, 400 MHz) δ 11.62 (brs, 1H), 6.98 (m, 1H), 6.57 (m, 2H), 6.32 (m, 2H), 6.18 (m, 2H), 5.82 (d, J=15.6 Hz, 1H), 5.67 (m, 2H), 5.33 (m, 4H), 4.87 (d, J=13.6 Hz, 2H), 4.80 (d, J=10.8 Hz, 2H), 4.53 (m, 3H), 4.33 (s, 2H), 4.05 (brs, 4H), 3.73 (m, 2H), 3.69 (q, J=6 Hz, 2H), 3.52 (q, J=5.2 Hz, 2H), 2.48 (m, 5H), 2.13 (m, 13H). HRMS (MALDI-TOF) m/z [M+Na]$^+$ calcd for C$_{24}$H$_{28}$NaN$_2$O$_6$: 463.1845; found: 463.1870

162

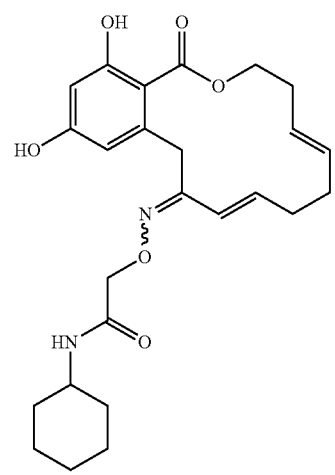

383

Mixture of isomers 1:1 in the oxime. $^1$H NMR (CDCl$_3$, 400 MHz) δ 11.60 (brs, 1H), 11.47 (brs, 1H), 8.58 (brs, 2H), 6.53 (d, J=16.4 Hz, 1H), 6.50 (d, J=2.4 Hz, 1H), 6.35 (d, J=2.4 Hz, 1H), 6.34 (d, J=2.4 Hz, 1H), 6.30 (d, J=2.4 Hz, 1H), 6.31-6.27 (m, 2H), 6.14 (m, 1H), 5.39-5.31 (m, 4H), 4.61 (s, 2H), 4.56-4.53 (m, 6H), 4.33 (s, 2H), 4.09 (s, 2H), 3.86-3.75 (m, 2H), 2.53-2.48 (m, 4H), 2.17-2.09 (m, 8H), 1.93-1.86 (m, 4H), 1.70-1.55 (m, 8H), 1.39-1.11 (m, 8H). HRMS (MALDI-TOF) m/z [M+Na]$^+$ calcd for C$_{25}$H$_{32}$NaN$_2$O$_6$: 479.2158; found: 479.2157

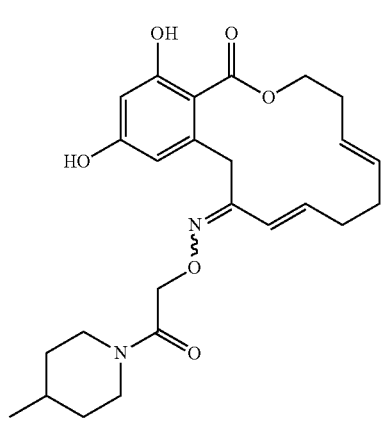

375

Mixture of isomers 1:1 in the oxime. $^1$H NMR (CDCl$_3$, 400 MHz) δ 11.66 (brs, 1H), 11.64 (brs, 1H), 8.29 (brs, 2H), 6.89 (d, J=2.8 Hz, 1H), 6.59 (d, J=16 H, 1 Hz), 6.57 (d, J=2.4 Hz, 1H), 6.33-6.32 (m, 2H), 6.24-6.09 (m, 2H), 5.79 (d, J=16 Hz, 1H), 5.34-5.30 (m, 4H), 4.85 (s, 2H), 4.78 (s, 2H), 4.56-4.48 (m, 4H), 4.31 (s, 2H), 4.10 (d, J=15.6 Hz, 1H), 4.05 (d, J=15.6 Hz, 1H), 3.80-3.71 (m, 2H), 3.06-2.96 (m, 2H), 2.61 (dt, J=12.8, 2.6 Hz, 2H), 2.52-2.46 (m, 4H), 2.16-2.05 (m, 8H), 1.71-1.58 (m, 6H), 1.17-1.05 (m, 4H), 0.94 (d, J=5.6 Hz, 3H), 0.93 0.94 (d, J=5.6 Hz, 3H). HRMS (MALDI-TOF) m/z [M+Na]$^+$ calcd for C$_{25}$H$_{32}$NaN$_2$O$_6$: 479.2158; found: 479.2182

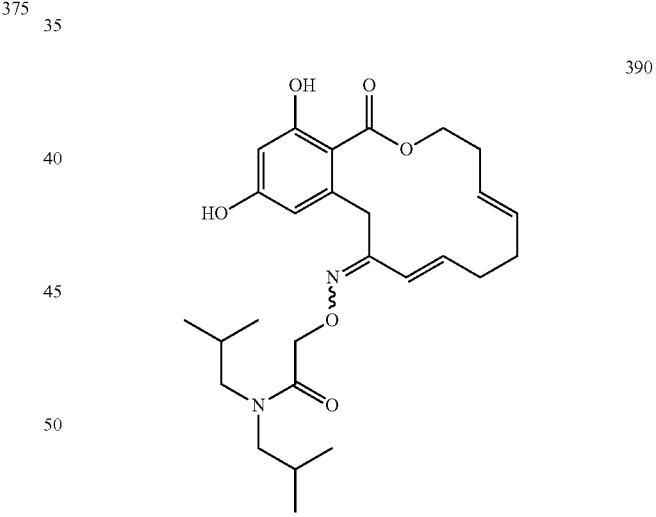

390

Mixture of isomers 1:1 in the oxime. $^1$H NMR (CDCl$_3$, 400 MHz) δ 11.65 (brs, 2H), 7.06 (d, J=2.4 Hz, 1H), 6.62-6.57 (m, 2H), 6.33 (d, J=2.4 Hz, 2H), 6.21-6.11 (m, 2H), 5.81 (d, J=16.4 Hz, 1H), 5.37-5.29 (m, 4H), 4.86 (s, 2H), 4.79 (s, 2H), 4.52 (brt, J=5.2 Hz, 4H), 4.31 (s, 2H), 4.02 (s, 2H), 3.21 (m, 4H), 3.09 (dd, J=10.8, 8.0 Hz, 4H), 2.52-2.44 (m, 4H), 2.11-1.91 (m, 12H), 0.95 (d, J=6.8 Hz, 6H), 0.93 (d, J=6.8 Hz, 6H), 0.88 (d, J=6.8 Hz, 6H), 0.86 (d, J=6.8 Hz, 6H). FIRMS (MALDI-TOF) m/z [M+Na]$^+$ calcd for C$_{27}$H$_{38}$NaN$_2$O$_6$: 509.2627; found: 509.2626

163

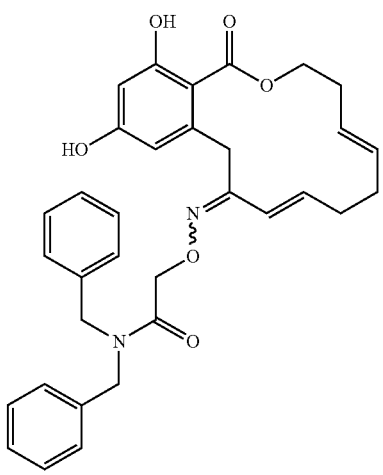

381

Mixture of isomers 1:1 in the oxime. $^1$H NMR (CDCl$_3$, 400 MHz) δ 11.67 (brs, 1H), 11.66 (brs, 1H), 7.38-7.28 (m, 12H), 7.22-7.14 (m, 8H), 6.94 (d, J=2.4 Hz, 1H), 6.57-6.53 (m, 2H), 6.33 (brd, J=2.4 Hz, 2H), 6.22-6.12 (m, 2H), 5.85 (d, J=16 Hz, 1H), 5.35-5.32 (m, 4H), 4.93 (s, 2H), 4.86 (s, 2H), 4.62 (s, 2H), 4.60 (s, 2H), 4.53 (brt, J=5.2 Hz, 4H), 4.46 (s, 2H), 4.43 (s, 2H), 4.30 (s, 2H), 4.07 (s, 2H), 3.52-3.46 (m, 4H), 2.16-2.07 (m, 8H). HRMS (MALDI-TOF) m/z [M+Na]$^+$ calcd for C$_{33}$H$_{34}$NaN$_2$O$_6$: 577.2314; found: 577.2278

164

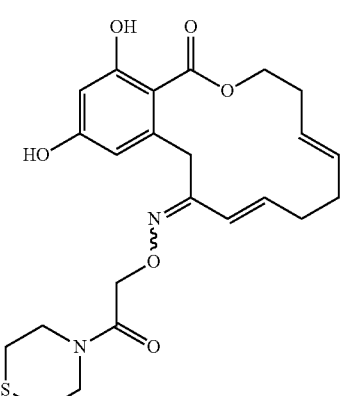

384

Mixture of isomers 1:1 in the oxime. $^1$H NMR (CDCl$_3$, 400 MHz) δ11.63 (brs, 2H), 6.88 (d, J=2.0 Hz, 1H), 6.55 (d, J=16.4 Hz, 1H), 6.43 (d, J=2.4 Hz, 1H), 6.32 (d, J=2.4 Hz 1H), 6.30 (d, J=2 Hz, 1H), 6.28-6.13 (m, 2H), 5.84 (d, J=16.1 Hz, 1H), 5.36-5.33 (m, 4H), 4.82 (s, 2H), 4.73 (s, 2H), 4.54 (t, J=5.5 Hz, 4H), 4.32 (s, 2H), 4.09 (s, 2H), 3.91-3.85 (m, 4H), 3.79-3.70 (m, 4H), 2.65-2.60 (m, 8H), 2.49 (bit, J=5.1 Hz, 4H), 2.17-2.04 (m, 8H). HRMS (MALDI-TOF) m/z [M+H]$^+$ calcd for C$_{23}$H$_{28}$N$_2$O$_6$: 461.1746; found: 461.1765

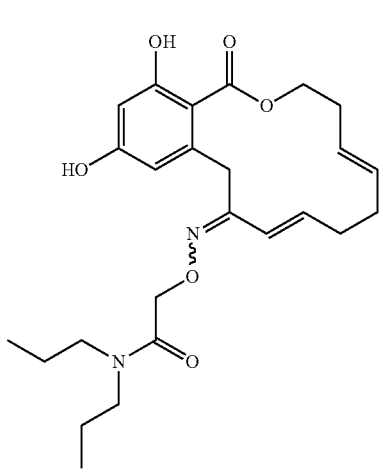

389

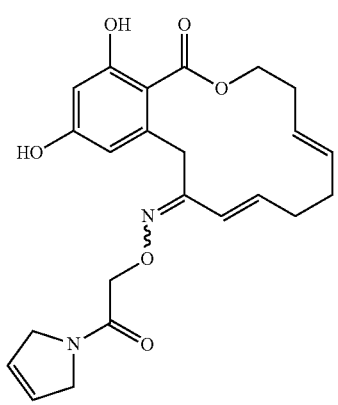

386

Mixture of isomers 1:1 in the oxime. $^1$H NMR (CDCl$_3$, 400 MHz) δ 11.66 (brs, 1H), 11.65 (brs, 1H), 7.05 (d, J=2.4 Hz, 1H), 6.62-6.55 (m, 2H), 6.32-6.29 (m, 2H), 6.23-6.11 (m, 2H), 5.82 (d, J=16 Hz, 1H), 5.34-5.29 (m, 4H), 4.85 (s, 2H), 4.77 (s, 2H), 4.54 (brt, J=5.2 Hz, 4H), 4.32 (s, 2H), 4.04 (s, 2H), 3.32-3.27 (m, 4H), 3.21-3.15 (m, 4H), 2.52-2.42 (m, 4H), 2.10-2.04 (m, 8H), 1.67-1.51 (m, 8H), 0.96-0.86 (m, 12H). HRMS (MALDI-TOF) m/z [M+Na]$^+$ calcd for C$_{25}$H$_{34}$NaN$_2$O$_6$: 481.2314; found: 481.2307

Mixture of isomers 1:1 in the oxime. $^1$H NMR (CDCl$_3$, 400 MHz) δ 11.64 (brs, 2H), 6.98 (d, J=2.3 Hz, 1H), 6.61 (d, J=16.3 Hz, 1H), 6.58 (d, J=2.4 Hz, 1H), 6.31 (2d, J=2.2 Hz, 2H), 6.27-6.12 (m, 2H), 5.87-5.78 (m, 5H), 5.45-5.33 (m, 4H), 4.74 (s, 2H), 4.69 (s, 2H), 4.53 (t, J=5.3 Hz, 4H), 4.33 (s, 2H), 4.28-4.25 (m, 8H), 4.05 (s, 2H), 2.52-2.46 (m, 4H), 2.17-2.05 (m, 8H). HRMS (MALDI-TOF) m/z [M+H]$^+$ calcd for C$_{23}$H$_{27}$N$_2$O$_6$: 427.1869; found: 427.1902

165

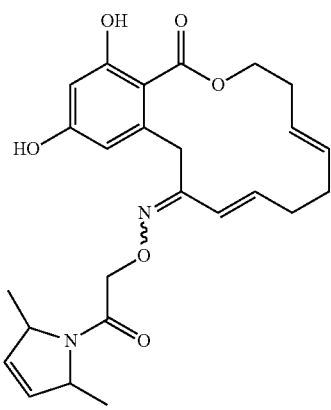

387

Mixture of isomers 1:1 in the oxime. $^1$H NMR (CDCl$_3$, 400 MHz) δ 11.68 (brs, 2H), 7.16 (d, J=2.8 Hz, 1H), 6.63 (d, J=16.3 Hz, 1H), 6.60 (d, J=2.0 Hz, 1H), 6.31 (brs, 2H), 6.26-6.13 (m, 2H), 5.85 (d, J=16.0 Hz, 1H), 5.77-5.76 (m, 4H), 5.44-5.34 (m, 4H), 4.87-4.59 (m, 10H), 4.48-4.43 (m, 2H), 4.33 (brs, 2H), 4.19 (d, J=15.3 Hz, 1H), 3.91 (d, J=15.3 Hz, 1H), 2.54-2.44 (m, 4H), 2.19-2.05 (m, 8H), 1.36-1.30 (m, 12H). HRMS (MALDI-TOF) [M+H]$^+$ calcd for C$_{25}$H$_{31}$N$_2$O$_6$: 455.2182; found: 455.2195

391

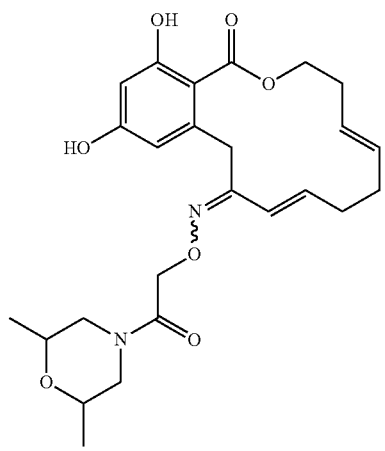

Mixture of isomers 1:1 in the oxime. $^1$H NMR (CDCl$_3$, 400 MHz) δ 11.66 (brs, 1H), 11.63 (brs, 1H), 6.93 (d, J=2.4 Hz, 1H), 6.57 (d, J=16.0 Hz, 1H), 6.52 (d, J=2.4 Hz, 1H), 6.32 (d, J=2.4 Hz, 1H), 6.31 (d, J=2.4 Hz, 1H), 6.29-6.12 (m, 2H), 5.84 (d, J=16.0 Hz, 1H), 5.38-5.32 (m, 4H), 4.91-4.71 (m, 4H), 4.59-4.49 (m, 4H), 4.37-4.26 (m, 4H), 4.13-3.97 (m, 4H), 3.78-3.68 (m, 2H), 3.62-3.52 (m, 2H), 3.35-3.15 (m, 4H), 2.50 (brt, J=5.2 Hz, 4H), 2.18-2.08 (m, 8H), 1.24-1.18 (m, 12H). HRMS (MALDI-TOF) m/z [M+Na]$^+$ calcd for C$_{25}$H$_{32}$NaN$_2$O$_7$: 495.2107; found: 495.2067

166

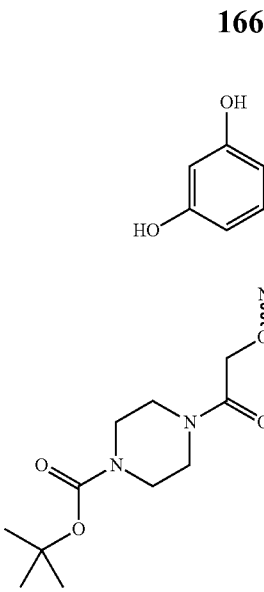

392

Mixture of isomers 1:1 in the oxime. $^1$H NMR (CDCl$_3$, 400 MHz) δ 11.65 (brs, 1H), 11.64 (brs, 1H), 6.92 (d, J=2.0 Hz, 1H), 6.57 (d, J=16.4 Hz, 1H), 6.52 (d, J=2.4 Hz, 1H), 6.32 (d, J=2.4 Hz, 1H), 6.31 (d, J=2.4 Hz, 1H), 6.28-6.13 (m, 2H), 5.84 (d, J=16 Hz, 1H), 5.38-5.31 (m, 4H), 4.86 (s, 2H), 4.77 (s, 2H), 4.56-4.52 (m, 4H), 4.34 (s, 2H), 4.07 (s, 2H), 3.61-3.45 (m, 16H), 2.54-2.46 (m, 4H), 2.16-2.05 (m, 8H), 1.47 (s, 18H). HRMS (MALDI-TOF) m/z [M+Na]$^+$ calcd for C$_{28}$H$_{37}$NaN$_3$O$_8$: 566.2478; found: 566.2459

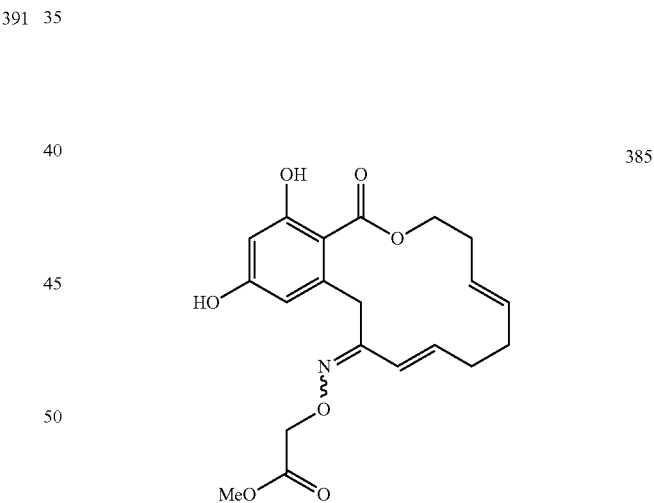

385

Mixture of isomers 1:1 in the oxime. $^1$H NMR (CDCl$_3$, 400 MHz) δ 11.70 (brs, 1H), 11.68 (brs, 1H), 6.84 (d, J=2.4 Hz, 1H), 6.61 (d, J=16.4 Hz, 1H), 6.53 (d, J=2.4 Hz, 1H), 6.34 (d, J=2.4 Hz, 1H), 6.32 (d, J=2.4 Hz, 1H), 6.28-6.13 (m, 2H), 5.86 (d, J=16.4 Hz, 1H), 5.38-5.33 (m, 4H), 4.75 (s, 2H), 4.68 (s, 2H), 4.57-4.54 (m, 4H), 4.36 (s, 2H), 4.08 (s, 2H), 3.79 (2s, 6H), 2.54-2.48 (m, 4H), 2.17-2.04 (m, 8H).

167

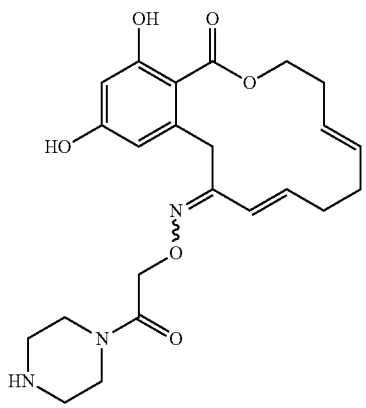

393

Mixture of isomers 1:1 in the oxime. ¹H NMR (CDCl₃, 400 MHz) δ 6.94 (d, J=2.4 Hz, 1H), 6.52 (d, J=16.0 Hz, 1H), 6.34 (d, J=2.8 Hz, 1H), 6.32 (d, J=2.0 Hz, 1H), 6.29 (d, J=2.4 Hz, 1H), 6.25-6.12 (m, 2H), 5.86 (d, J=16.0 Hz, 1H), 5.38-5.32 (m, 4H), 4.85 (s, 2H), 4.71 (s, 2H), 4.57-4.52 (m, 4H), 4.35 (s, 2H), 4.14 (s, 2H), 3.73-3.58 (m, 8H), 3.02-2.87 (m, 8H), 2.54-2.48 (m, 4H), 2.14-2.09 (m, 8H). HRMS (MALDI-TOF) m/z [M+Na]⁺ calcd for $C_{23}H_{29}NaN_3O_6$: 466.1954; found: 466.1938

168

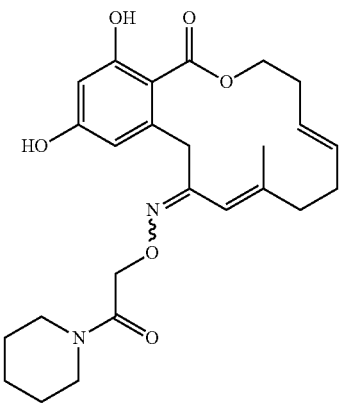

349

Mixture of isomers 1:1 in the oxime. ¹H NMR (CDCl₃, 400 MHz) 11.92 (brs, 1H), 11.84 (brs, 1H), 7.08-7.05 (m, 2H), 6.35-6.33 (m, 2H), 5.50-5.20 (m, 6H), 4.87 (s, 2H), 4.73 (s, 2H), 4.44-4.35 (m, 4H), 3.92 (s, 2H), 3.60-3.49 (m, 4H), 3.44-3.33 (m, 4H), 2.47-2.38 (m, 4H), 2.21-1.99 (m, 8H), 1.81-1.76 (m, 6H), 1.70-1.62 (m, 14H). HRMS (MALDI-TOF) m/z [M+H]⁺ calcd for $C_{25}H_{33}N_2O_6$: 457.2338; found: 457.2339

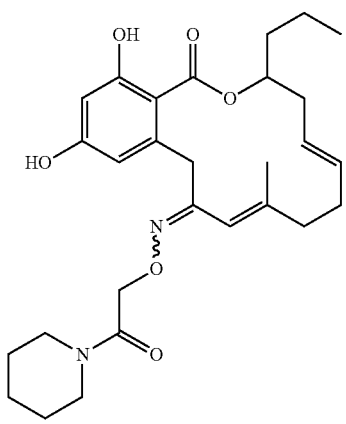

350

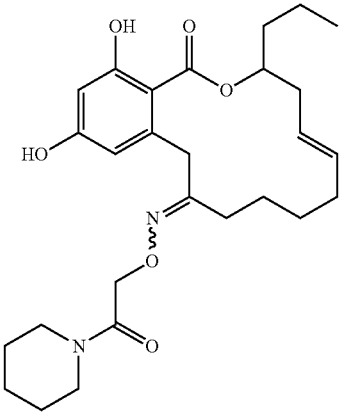

352

Mixture of isomers 1:1 in the oxime. ¹H NMR (CDCl₃, 400 MHz) δ 11.94 (brs, 1H), 11.80 (brs, 1H), 6.80 (d, J=2.4 Hz, 2H), 6.35 (d, J=2.4 Hz, 2H), 5.45-5.09 (m, 6H), 4.93 (d, J=14.4 Hz, 2H), 4.82-4.68 (m, 2H), 4.76 (d, J=14.4 Hz, 2H), 4.28 (d, J=14.8 Hz, 2H), 4.06 (d, J=14.4 Hz, 2H), 3.63-3.33 (m, 8H), 2.34-1.96 (m, 10H), 1.70-1.55 (m, 12H), 1.45-1.29 (m, 10H), 1.75 (s, 3H), 1.25 (s, 3H), 0.94 (t, J=7.2 Hz, 6H). HRMS (MALDI-TOF) m/z [M+Na]⁺ calcd for $C_{28}H_{38}NaN_2O_6$: 521.2627; found: 521.2630

Mixture of isomers 1:1 in the oxime. ¹H NMR (CDCl₃, 400. MHz) δ 11.61 (brs; 1H), 11.57 (brs, 1H), 7.86 (brs, 1H), 7.64 (brs, 1H), 7.00 (d, J=2.4 Hz, 1H), 6.51 (d, J=2.4 Hz, 1H), 6.34 (brd, J=2.0 Hz, 2H), 5.46-5.32 (m, 4H), 5.28-5.22 (m, 2H), 4.90 (d, J=14.8 Hz, 1H), 4.83 (d, J=14.4 Hz, 1H), 4.72 (d, J=14.4 Hz, 1H), 4.71 (d, J=14.8 Hz, 1H), 4.35 (d, J=16.0 Hz, 1H), 4.25-4.17 (m, 3H), 4.09 (d, J=15.2 Hz, 1H), 3.62-3.51 (m, 4H), 3.43-3.38 (m, 4H), 2.67-2.61 (m, 2H), 2.35-2.28 (m, 2H), 2.06-1.95 (m, 4H), 1.90-1.78 (m, 6H), 1.68-1.58 (m, 14H), 1.44-1.31 (m, 11H), 0.94 (m, 6H). HRMS (MALDI-TOF) m/z [M+H]⁺ calcd for $C_{27}H_{39}N_2O_6$: 487.2808; found: 487.2806

457

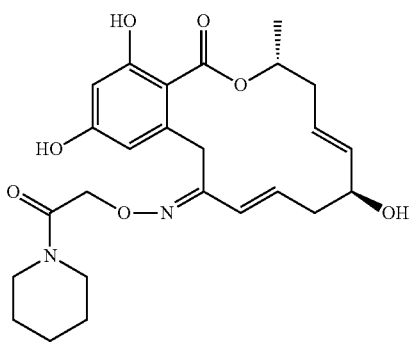

$^1$H (E-isomer, MeOD, 400 MHz, 25° C.) δ 6.26 (d, J=2.4 Hz, 1H); 6.24 (d, J=2.4 Hz, 1H); 6.05 (d, J=16.4 Hz, 1H); 5.86-5.93 (m, 1H); 5.60-5.67 (m, 1H); 5.44-5.50 (dt, 1H); 5.20-5.31 (m, 1H); 4.88 (dd, 2H); 4.44 (d, 1H); 3.95-4.01 (m, 1H); 3.53-3.67 (m, 4H); 3.45 (d, 1H); 2.58 (dd, 1H); 2.40-2.48 (m, 2H); 2.20 (dd, 1H); 1.64-1.76 (m, 6H); 1.48 (d, 3H). $^{13}$C (MeOD, 100 MHz, 25° C.) δ 170.4, 169.6, 169.3 (×2), 161.6 (×2), 159.5, 159.4, 156.7, 140.7, 139.8, 139.4, 136.9, 136.8, 135.8, 129.4, 129.3, 127.8, 121.1, 108.3, 108.1, 102.2, 102.1, 93.4, 73.8, 73.7, 72.8, 72.7, 72.6, 72.4, 72.3, 47.3, 47.2, 47.0, 44.6, 44.2, 44.1, 41.5, 41.0, 40.4, 40.1, 35.8, 29.7, 27.4, 27.3, 26.7, 26.6, 25.4, 24.4, 20.4, 20.2

476

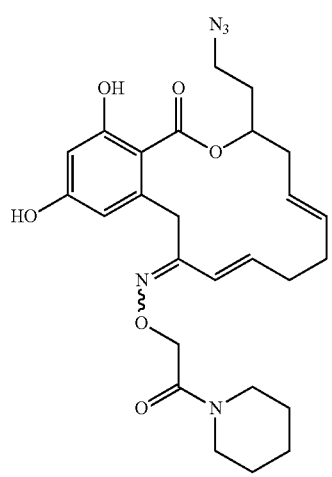

HRMS (MALDI-TOF) m/z [M+H]$^+$ calcd for C$_{26}$H$_{34}$N$_5$O$_6$: 512.2431; found: 512.2406

Example 6

Derivitization of Hydroxy-substituted Macrocycles

The preparation of compounds of the invention that contain hydroxy substituents on the macrocycle may be prepared from Weinreb amides substituted with a protected hydroxy group or by oxidation of the final macrocycle, as depicted in Scheme 9 above. Macrocycles containing hydroxy substituents may be derivatized by reagents that are reactive to hydroxy groups to produce macrocycles substituted with varying groups on the macrocyclic ring. The use of orthogonal protecting groups on Weinreb amide precursors allows the selective liberation and reaction of macrocycle hydroxy groups.

In one non-limiting embodiment of the invention, macrocycles containing hydroxy substituents may be alkylated with electrophiles to produce macrocycles substituted with varying groups on the macrocyclic ring.

Deprotection of Hydroxy Group

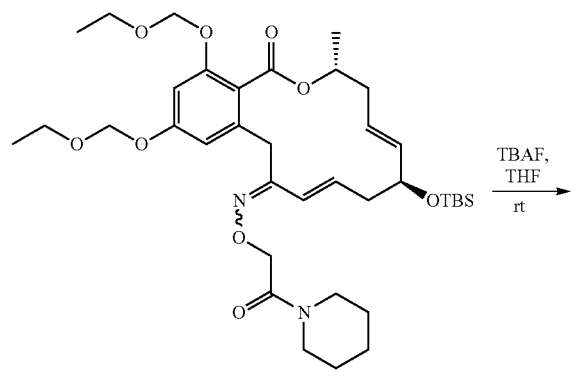

A solution of the totally protected compound (140 mg, 0.2 mmol) in THF (3 mL) was treated with the solution of TBAF in THF (0.3 mL, 1M in THF, 1.5 equiv.) at 0° C. The reaction was allowed to warm to 23° C. and for another 3 hrs. The reaction was extracted from sat. NH$_4$Cl solution with ethyl acetate (10 mL×3), washed by brine (15 mL), dried over anhydrous Na$_2$SO$_4$, and concentrated. Flash chromatography column (EA as eluent) gave desired compound (104 mg) in the yield of 88%.

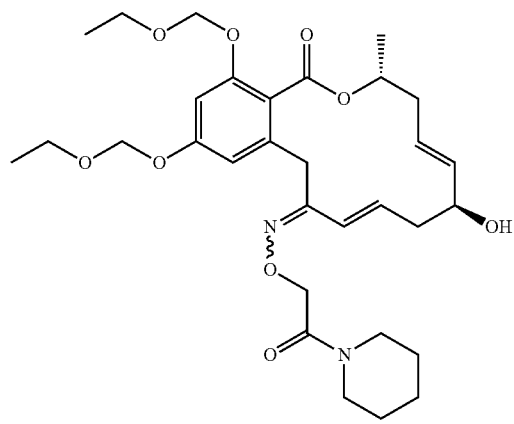
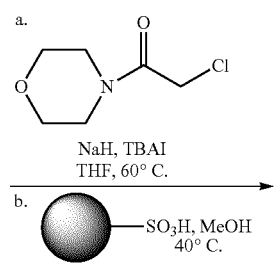
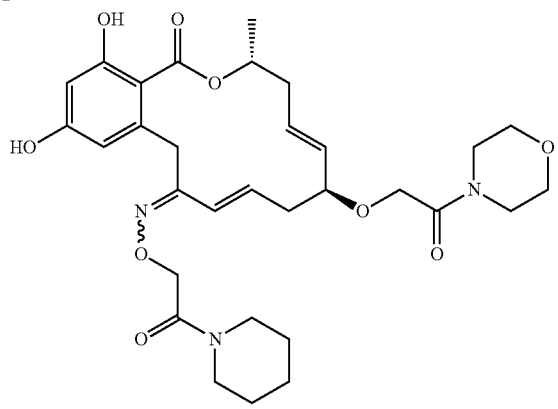

Reaction with α-halo Carbonyl Groups

To a solution of the free alcohol (50 mg, 0.085 mmol) in THF (0.6 mL) at 0° C. under nitrogen atmosphere, NaH (20 mg, 0.5 mmol, 5.8 equiv.) was added and the reaction kept stirring for another half hour. Then Bu$_4$NI (10 mg, 0.027 mmol, 0.3 equiv) and chloride (79 mg, 0.51 mmol, 6.0 equiv.) was added sequentially at the same temperature. The reaction was warmed up slowly, heated to 60° C. overnight. The mixture was extracted from sat. NH$_4$Cl and ethyl acetate, and the organic phases were combined, washed by brine, dried over anhydrous Na$_2$SO$_4$, and concentrated. Flash chromatography (PE/EA, 1/2, EA, then EA/MeOH, 20:1) afforded the desired compound (36 mg). The solution of the compound previously obtained (36 mg, 0.05 mmol) in MeOH (5 mL) was treated with sulfonic acid resin (83 mg, 3 mmol/g, 5.0 equiv.) at 40° C. After stirring for 2 hours, the reaction was diluted with CH$_2$Cl$_2$ (5 mL), filtered, rinsed with MeOH and CH$_2$Cl$_2$. The filtrate was concentrated and underwent reverse phase column (CH$_3$CN/H$_2$O, 10%, 20%, 30%) to give the desired compound (19 mg). HRMS (MALDI-TOF) m/z [M+H]$^+$ calcd for C$_{31}$H$_{41}$N$_3$O$_9$: 600.2921; found: 600.2919.

Reaction with Alkyl Halides and Formation of Azido-substituted Macrocycles

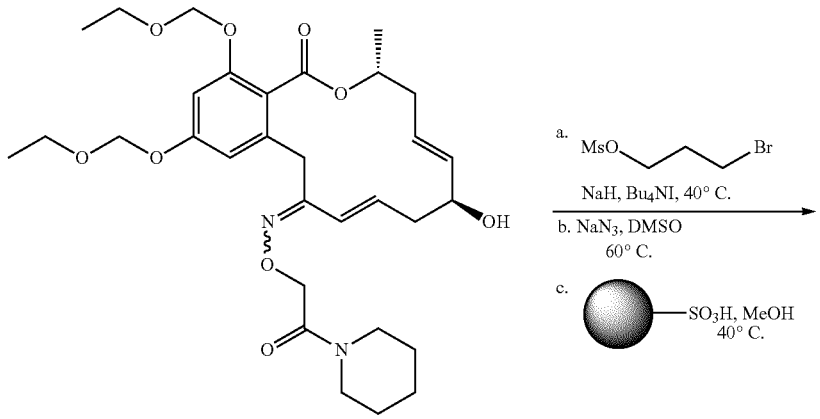

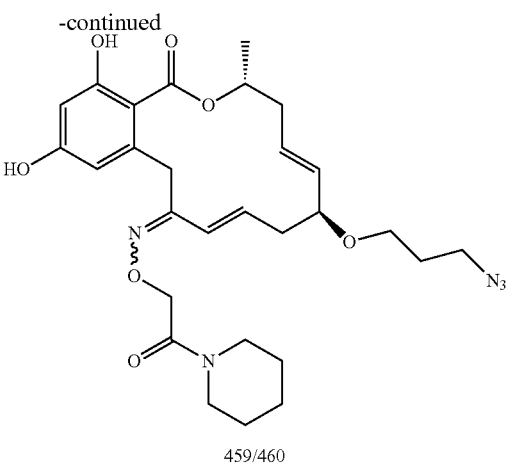

459/460

To the solution of the free alcohol (20 mg, 0.034 mmol) in THF (0.5 mL) at 0° C. under nitrogen atmosphere, NaH (9.8 mg, 0.24 mmol, 7.2 equiv.) was added and the reaction kept stirring for another half hour. Then Bu$_4$NI (13 mg, 0.038 mmol, 1.1 equiv) and bromide (35 mg, 0.16 mmol, 4.7 equiv.) was added sequentially at the same temperature. The reaction was warmed up slowly and then heated to 23° C. for 4 hrs. The mixture was extracted from sat. NH$_4$Cl and ethyl acetate, and the organic phases were combined, washed by brine, dried over anhydrous Na$_2$SO$_4$, and concentrated. The residue obtained was submitted to the next step without further purification. To a solution of the crude mixture obtained previously in DMSO (0.8 mL) was added NaN$_3$ (35 mg) at 60° C. and stirred for 2 hrs. The reaction was extracted from sat. NH$_4$Cl and ethyl acetate and the organic phases were combined, washed by brine, dried over anhydrous Na$_2$SO$_4$, and concentrated. The residue underwent flash chromatography (PE/EA, 1/1) to give the desired compound (4 mg). The solution of this compound (4 mg, 0.006 mmol) in MeOH (1 mL) was treated with sulfonic acid resin (20 mg, 3 mmol/g, 10.0 equiv.) at 40° C. After stirring for 4 hours, the reaction was diluted with CH$_2$Cl$_2$ (2 mL), filtered, rinsed with MeOH and CH$_2$Cl$_2$. The filtrate was concentrated and preparative TLC (Hex/EA, 1/2) gave the desired compound (point 1, 4.5 mg, point 2, 1.3 mg). HRMS (MALDI-TOF) m/z [M+H]$^+$ calcd for C$_{28}$H$_{38}$N$_5$O$_2$: 556.2771; found: 556.2745.

Amino-substituted Macrocycles and Derivatives

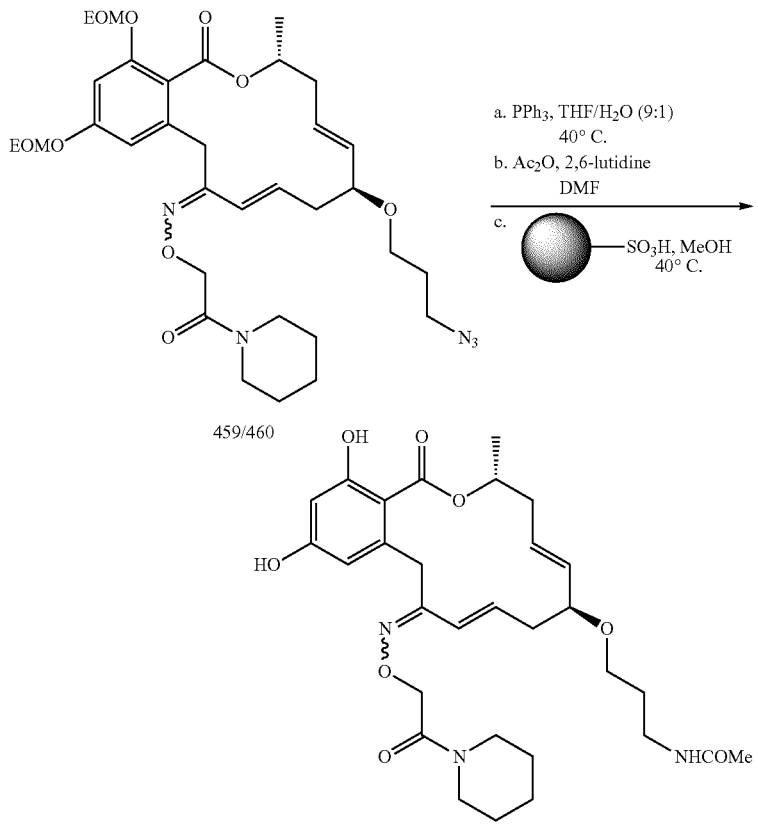

461

To the solution of the azide (30 mg, 0.044) in THF/H$_2$O (0.9/0.1 mL) was, added triphenyl phosphine (23 mg, 0.088 mmol, 2 equiv.) at 40° C. and the reaction was stirred for 1d. After evaporation to get rid of the solvent, the residue underwent flash chromatography (PE/EA, 1/1 then MeOH/NEt$_3$, 20/1) to afford the desired amine. To a solution of the amine (8 mg, 0.012 mmol) in DMF (2 mL) was added 2,6-lutidine (5 drops) and Ac$_2$O sequentially at 0° C. under nitrogen atmosphere and the reaction was warmed up to 23° C. and kept stirring for 1 hour. The mixture was extracted from sat. NH$_4$Cl and ethyl acetate, and the organic phases were combined, washed by brine, dried over anhydrous Na$_2$SO$_4$, and concentrated. The residue obtained was submitted to the next step without further purification. The solution of the crude compound obtained in MeOH (1 mL) was treated with sulfonic acid resin (30 mg, 3 mmol/g) at 40° C. After stirring for 1 hour, the reaction was filtered, rinsed with MeOH and CH$_2$Cl$_2$. The filtrate was concentrated and preparative TLC (EA/MeOH, 10/1) gave the desired compound (1.9 mg). HRMS (MALDI-TOF) m/z [M H]$^+$ calcd for C$_{30}$H$_{42}$N$_3$O$_8$: 572.2972; found: 572.2940.

sequentially at 0° C. under nitrogen atmosphere and the reaction was warmed up to 23° C. and kept stirring for 1 hour. The reaction was concentrated, and the residue underwent flash chromatography (PE/EA, 1/2, then CH$_2$Cl$_2$/MeOH, 10/1) to give the protected compound. The solution of the Cy3 labeled protected compound in MeOH (2 mL) was treated with sulfonic acid resin (30 mg, 3 mmol/g) at 40° C. After stirring for 2 hours, the reaction was filtered, rinsed with MeOH and DCM. The filtrate was concentrated and preparative TLC (CH$_2$Cl$_2$/MeOH, 10/1) gave the desired deprotected Cy3 labeled compound. MS (ES) m/z [M]$^+$ calcd for C$_{57}$H$_{72}$N$_5$O$_8$: 954.54; found: 954.53.

Example 7

Alternate Synthesis of Hydroxy-substituted Macrocycles

In addition to use of hydroxy-substituted Weinreb amides for the preparation of hydroxy substituted macrocycles,

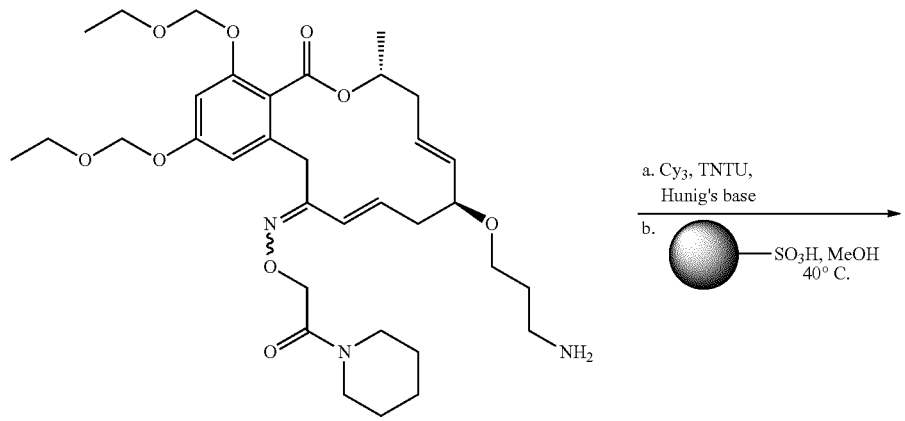

8-1

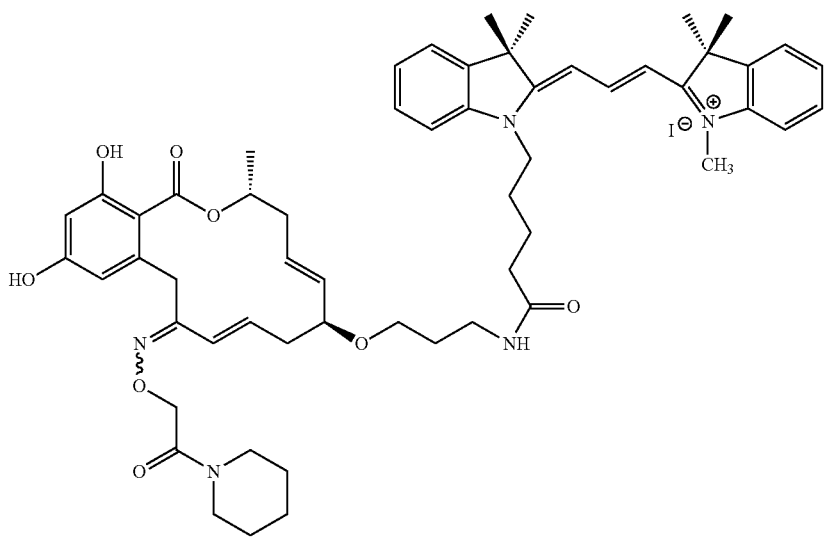

462

To the solution of the amine (11 mg, 0:017 mmol) in DMF (1 mL) was added TNTU (10 mg, 1.35 equiv.), Hunig's base (20 μL, 3.0 equiv.), and fluorophore (15 mg, 1.5 equiv.) hydroxy groups may be introduced into the macrocycle by the mild allylic oxidation of the compounds, as depicted in Scheme 9 and described below.

To a solution of bis protected macrocycle (100 mg, 0.17 mmol) in EtOH (1 mL) was added selenium dioxide (56 mg, 0.51 mmol, 3.0 equiv.). The reaction underwent microwave reaction at 110° C. for 2 h. Then the mixture was filtered and the filtrate concentrated, flash chromatography (PE/EA, 1/1, 1/2, 1/4) gave the desired compound as a mixture of isomers (70 mg). To a solution of the previously obtained mixture (15 mg, 0.025 mmol) in DMF (1.5 mL) at 0° C. under nitrogen atmosphere, NaH (6 mg, 0.15 mmol, 9.0 equiv.) was added and the reaction kept stirring for another half hour. Then Bu$_4$NI (10 mg, 0.027 mmol, 1.1 equiv) and allyl chloride (50 µL, 20 equiv.) was added sequentially at the same temperature. The reaction was warmed up to 23° C. and stirred for 1 hour. The mixture was extracted from sat. NH$_4$Cl and ethyl acetate, and the organic phases were combined, washed by brine, dried over anhydrous Na$_2$SO$_4$, and concentrated. Flash chromatography (PE/EA, 3/1) afforded the desired compound (6 mg). A solution of the allylated alcohol (6 mg, 0.009 mmol) in MeOH (1 mL) was treated with sulfonic acid resin (20 mg, 3 mmol/g, 6.7 equiv.) at 40° C. After stirring for 2 hours, the reaction was diluted with CH$_2$Cl$_2$ (3 mL), filtered, rinsed with MeOH and CH$_2$Cl$_2$. The filtrate was concentrated and underwent preparative TLC (Hex/EA, 1/2) to compound.

Example 8

Additional Azide Derivatives

The azide containing macrocycle may be modified to produce amino-substituted compounds and derivatives thereof, similarly to Example 6 above.

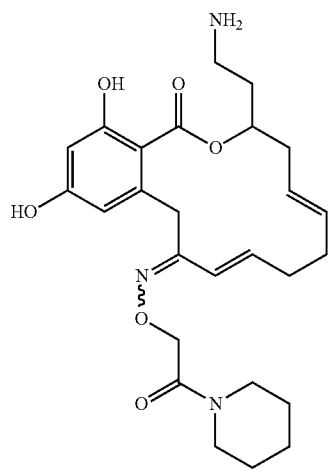

477

To a solution of the azide analog (280 mg, 0.424 mmol, 1 eq.) in THF/H$_2$O (9/1) mixture (42 mL) was added PPh$_3$ (333.6 mg, 1.272 mmol, 3 eq.). The resulting mixture was stirred overnight at 40° C. Then, the solution was evaporated to dryness without any work-up: The crude was purified on silica chromatography (CH$_2$Cl$_2$/MeOH=20/1) to yield the corresponding amine as a white solid (232.6 mg, 0.366 mmol, 86%). HRMS (MALDI-TOF) m/z [M+H]$^+$ calcd for C$_{32}$H$_{47}$ClN$_3$O$_3$: 636.3052; found: 636.3071.

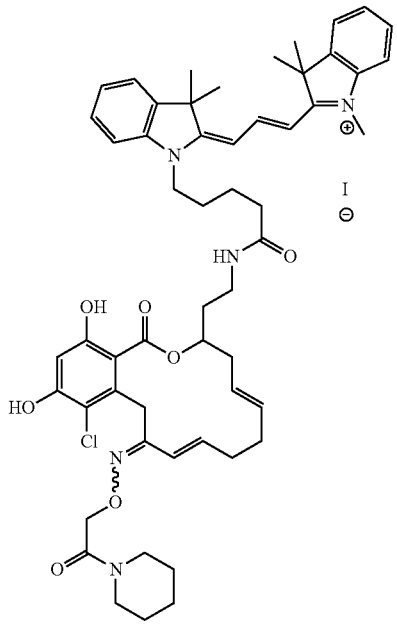

431

A solution of TNTU (8.52 mg, 23.3 µmol, 1.35 eq.), DIPEA (8.6 µL, 51.9 µmol, 3 eq.) and Cy3 (14.8 mg, 25.9 µmol, 1.5 eq.) in dry NMP (0.3 mL) was shaken 45 min at room temperature. Then, the pre-activated acid was added to a solution of the previous amine (11 mg, 17.3 mmol, 1 eq.) in 0.3 mL of NMP. After 12 hours the reaction mixture was diluted with AcOEt, washed with water (2 mL), KOH 2N (3 mL), dried with Na$_2$SO$_4$, and evaporated to dryness. The crude was purified on silica chromatography (CH$_2$Cl$_2$/MeOH=8/1) to yield the corresponding Cy3 labeled compound as a pink solid (20 mg, quantitative). MS (ES) m/z [M]$^+$ calcd for C$_{61}$H$_{79}$ClN$_5$O$_9$: 1061.56; found: 1061.25.

Example 9

Biological Activity

Compounds of the invention were assayed for cytotoxicity in HCC1954 and SK-BR-3 tumor cells. Compounds that showed significant cytotoxicity were further examined for their ability to induce degradation of known HSP90 client proteins, such as ErbB2 in SK-BR3. Thus, after 18 hrs treatment with the compounds, the whole cell protein lysates were obtained, protein concentrations were normalized and the concentration of ErbB2 was quantified by Western blotting (C. Chavany et al *J. Biol. Chem.* 271:4974-4977 (1996)). Several compounds from the library were more effective than radicicol and 17-AAG in reducing ErbB2 concentration. For example compounds 13a, 13b and 13c in the form of the E-oxime isomer were significantly more effective than both radicicol and 17-AAG.

A number of the compounds of the invention were tested for affinity to HSP90a (see Kim et al., *J. Biomol. Screen.,* 2004, 9, 375), Her-2 (HSP90 client) degradation (see Xu et al., *J. Biol. Chem.,* 2001, 276, 3702), and cytotoxicity against SKBr3 and HCC1954, two breast cancer cell lines which over express Her-2. The results of the affinity to HSP90a, Her-2 degradation and cytotoxicity are shown in Table 3.

TABLE 3

Biological Activity

| Compd. | HSP90 affinity (μM) | Client Depletion (μM) | Cytotoxicity (μM) |
|---|---|---|---|
| radicicol | 0.140 | 0.45 | |
| pochonin D | 0.36 | 3.5 | |
| 17-AAG | 0.032 | 0.050 | |
| 13a | 0.021 | 0.035 | 0.125; 0.320 |
| 13b | 0.015 | 0.050 | 0.120; 0.220 |
| 13c | 0.018 | 0.026 | 0.450; 0.630 |
| 13d | 0.220 | >10 | >10; >10 |
| 13e | >10 | >10 | >10; >10 |
| 13f | 0.068 | 2.4 | 1.3; 2.8 |
| 13g | 0.081 | nt | nt |
| 13h | 0.390 | 7.7 | 7.5; >10 |
| 13i | 1.20 | nt | >10; >10 |
| 13j | 0.11 | 5.5 | 3.5; 8.5 |
| 13k | 0.090 | 0.25 | 0.55; 0.45 |
| 13l | 0.190 | 6.5 | >10; >10 |
| 13m | >10 | >10 | >10; >10 |
| 14a | 1.8 | >10 | >10; 5.2 |
| 14b | 0.110 | 5.0 | >10; >10 |
| 336 | <0.052 | nt | |
| 349 | 0.046 | 0.105 | |
| 350 | 0.196 | 0.805 | |
| 351 | 0.204 | 0.900 | |
| 352 | 0.543 | 4.270 | |
| 353 | 3.027 | >10 | |
| 354-E | 0.543 | 2.960 | |
| 354-Z | 0.601 | 4.110 | |
| 356 | 0.511 | 9.480 | |
| 357 | 0.196 | 0.730 | |
| 358 | 0.587 | >10 | |
| 359 | 1.936 | >8.8 | |
| 361 | 0.543 | 2.960 | |
| 362 | 4.663 | >10 | |
| 363 | 0.900 | >10 | |
| 365 | 1.751 | 8.970 | |
| 366 | 0.170 | 2.040 | |
| 367 | 1.723 | >10 | |
| 368 | 0.599 | >10 | |
| 369 | 0.154 | 0.677 | |
| 370 | 0.038 | 0.097 | |
| 371 | 0.243 | 0.629 | |
| 372 | 0.886 | 3.069 | |
| 373 | 0.059 | 0.089 | |
| 374 | 0.238 | 2.030 | |
| 375 | 0.070 | 0.201 | |
| 376 | 2.240 | >10 | |
| 377 | 5.757 | >10 | |
| 378 | 0.057 | 0.929 | |
| 379 | 0.162 | 0.627 | |
| 380 | 0.124 | 0.588 | |
| 381 | 2.992 | >10 | |
| 382 | 0.022 | 0.122 | |
| 383 | 0.116 | 0.708 | |
| 384 | 0.070 | 0.512 | |
| 385 | 0.373 | 8.160 | |
| 386 | 0.128 | 0.669 | |
| 387 | 0.118 | 0.568 | |
| 388 | 0.219 | 0.509 | |
| 389 | 0.155 | 0.454 | |
| 390 | 0.094 | 0.549 | |
| 391 | 0.337 | 2.830 | |
| 392 | 0.327 | 2.870 | |
| 393 | 0.097 | nt | |
| 394 | 0.096 | 1.580 | |
| 395 | 0.097 | 0.754 | |
| 396 | 0.182 | 3.650 | |
| 397 | 0.432 | 0.980 | |
| 457 | 0.012 | nt | |

Based on the in vitro data shown in Table 3, compound 13a was further evaluated in vivo. Treatment of CB17/SCID mice with compound 13a at 100 mg/kg for five consecutive days was well tolerated with minimal weight loss observed. To investigate the in vivo efficacy of compound 13a, a xenograft bearing BT-474 (breast tumor cell line) was used, as this cell line has been shown to respond to HSP90 inhibitors in an animal model (Basso et al., *Oncogene* 2002, 21, 1159). Based on the cellular potency of compound 13a, two schedules of 100 mg every other day (q2d) or every four days (q4d) during 28 days were investigated. The treatment with compound 13a resulted in a dose-dependent inhibition of the tumor growth with an 18% regression in tumor volume using the q2d schedule. The results are shown in FIG. 1. Neither the q2d nor the q4d schedules resulted in significant weight loss, which is illustrated in FIG. 2. Histologic examination of tumors removed from animals receiving either the vehicle (DMSO) or drug for 28 days following the q2d schedule revealed a dramatic loss of cellularity in tumors obtained from drug-treated animals. Nuclei of remaining cells were uniformly condensed, suggesting the occurrence of massive apoptosis (see FIG. 4, top panels). This was confirmed by the high degree of nuclear TUNEL staining seen in tumors excised from drug treated animals, which is shown in FIG. 4, bottom panels. These data suggest that tumor regression in animals treated for 28 days according to the q2d schedule may be more dramatic than estimated with tumor volume measurements, since few to no viable cells could be identified at the end of the treatment period.

The description and examples provided herein are merely illustrative, and the invention is not so limited. Numerous variations, permutations and derivatives of these compounds, procedures and uses will occur to those of ordinary skill in the art, and are contemplated within the scope of the invention.

What is claimed is:

1. A compound, or a tautomer thereof, a pharmaceutically acceptable salt, solvate, ester or prodrug thereof, selected from

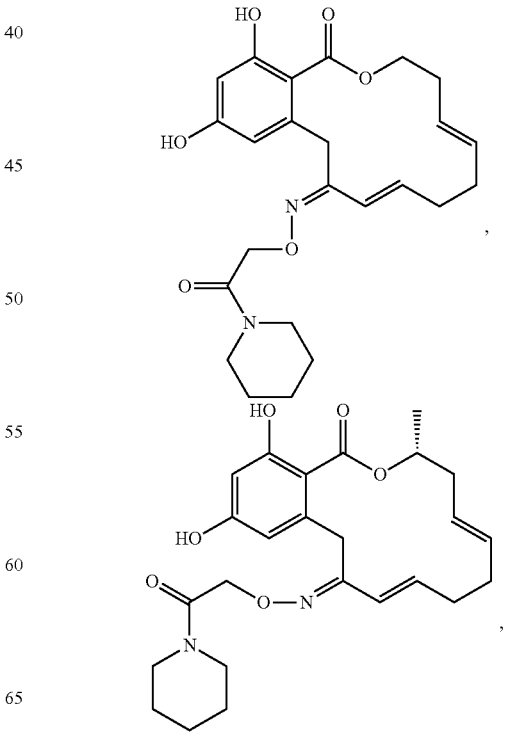

181 182

183
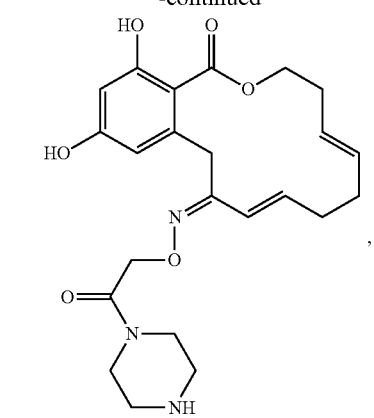
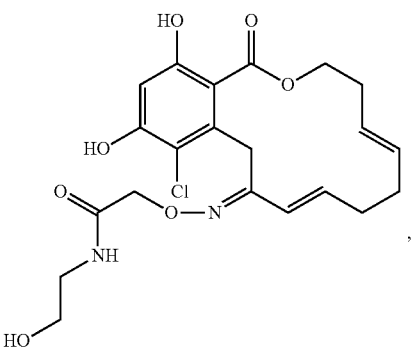
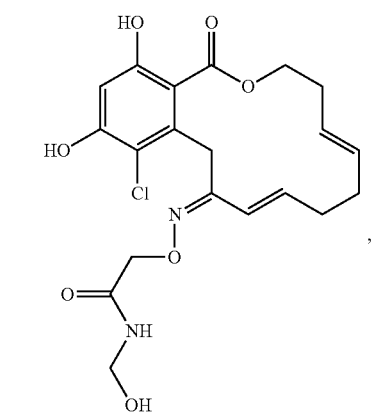
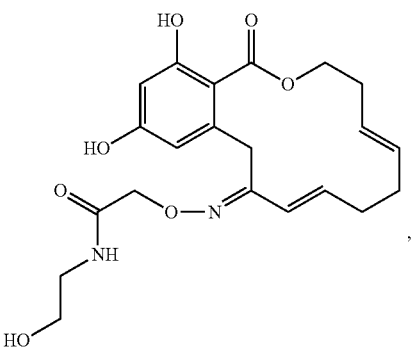
184
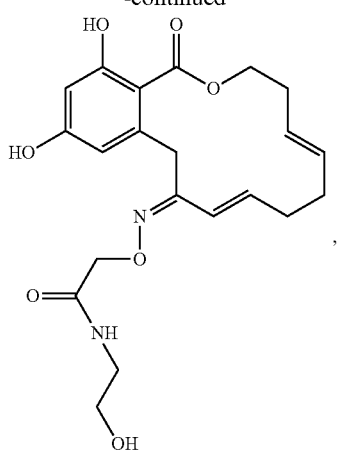
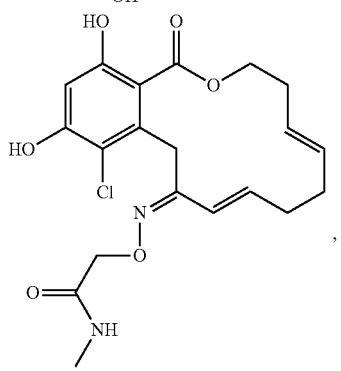
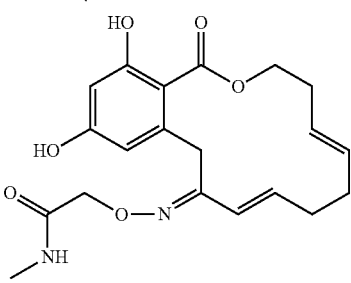
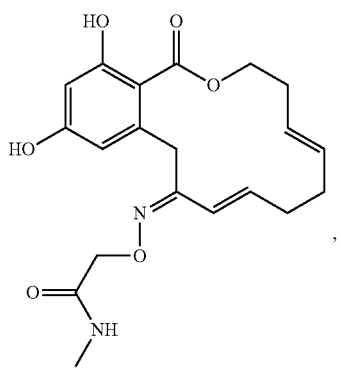
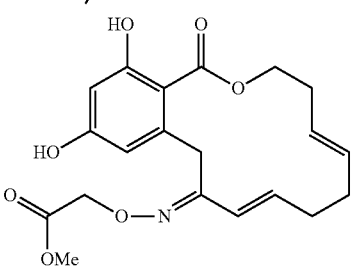

185
-continued
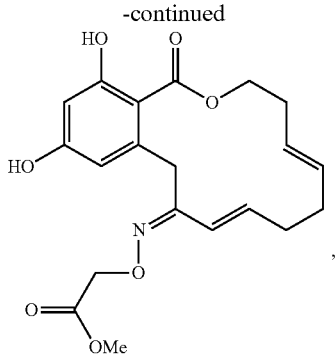
,
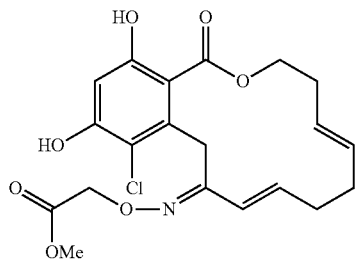
,
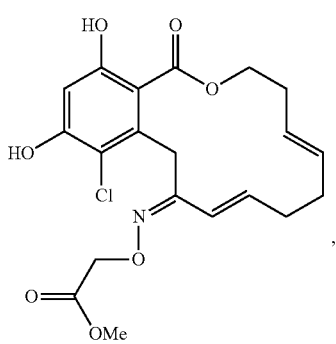
,
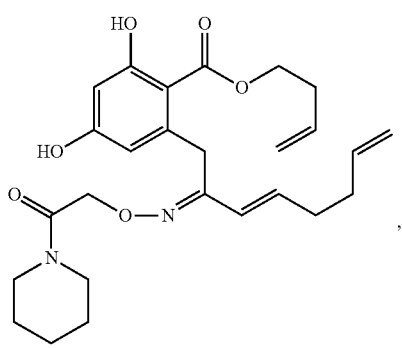
,
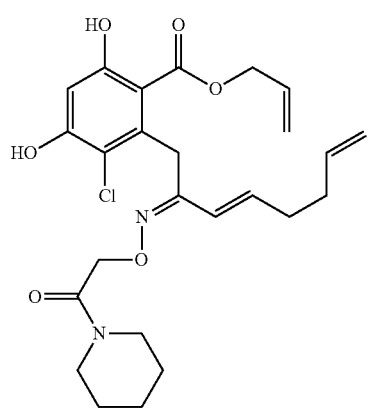
,
186
-continued
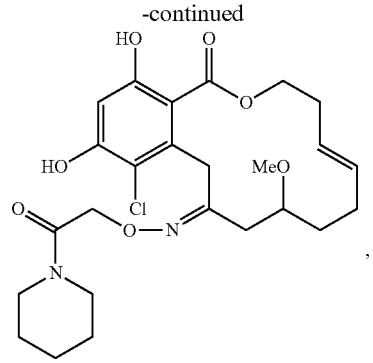
,
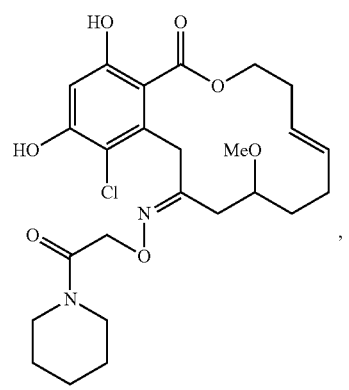
,
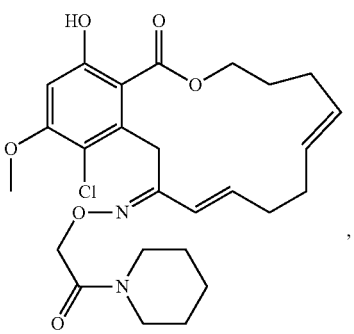
,
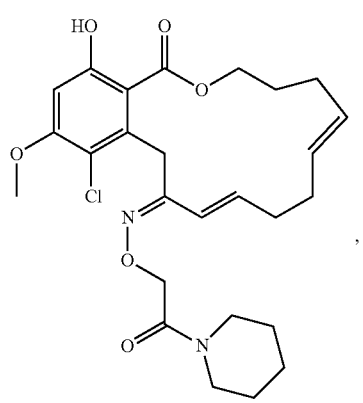
,

187

188

189 -continued

190 -continued

191
-continued
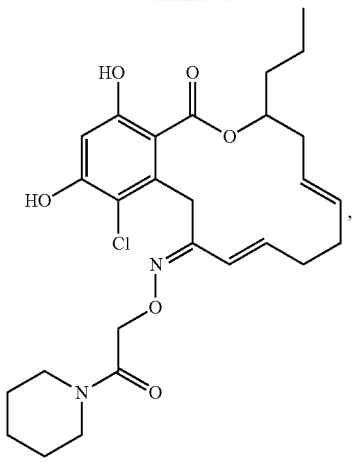
,
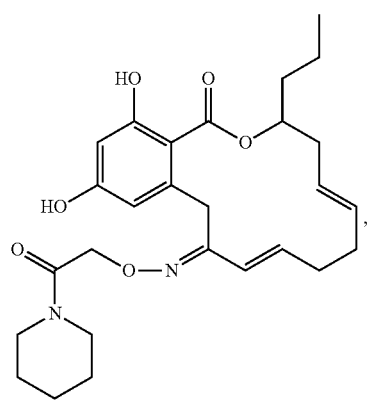
,
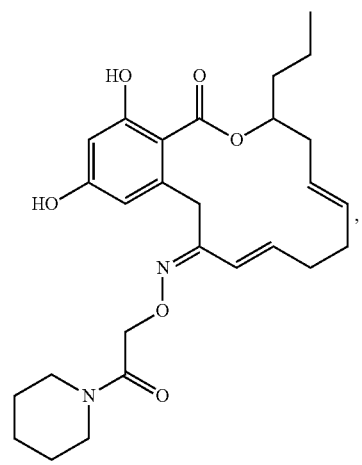
,
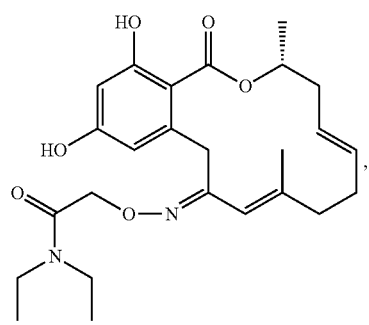
,
192
-continued
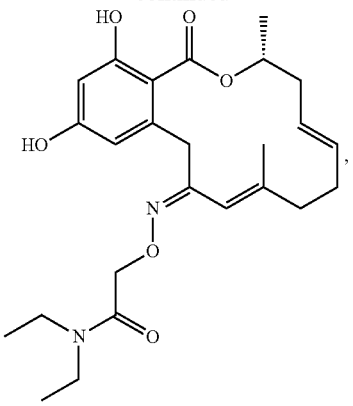
,
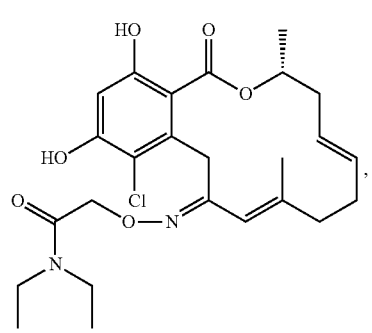
,
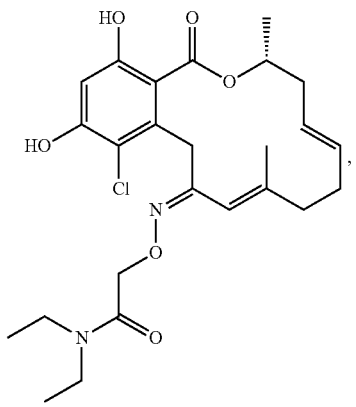
,
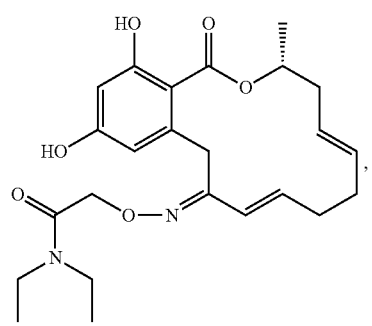
,

193
-continued
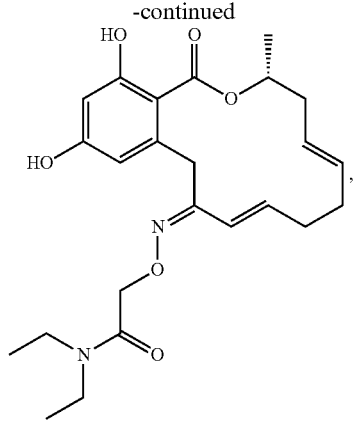
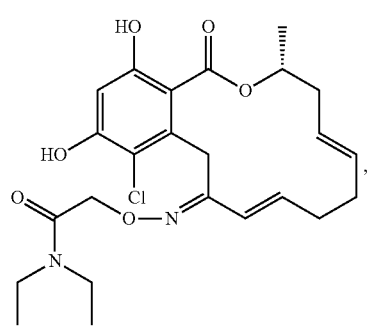
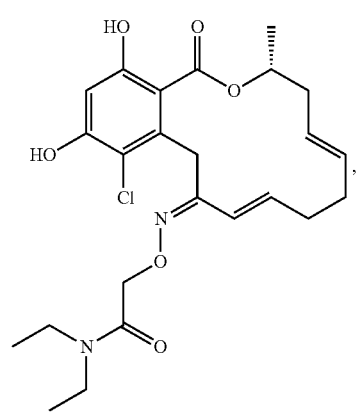
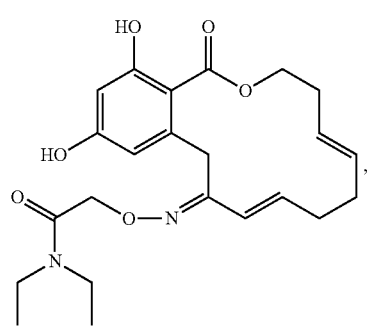
194
-continued
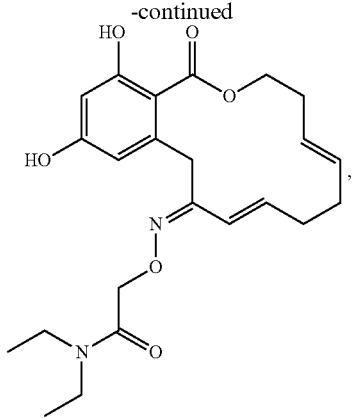
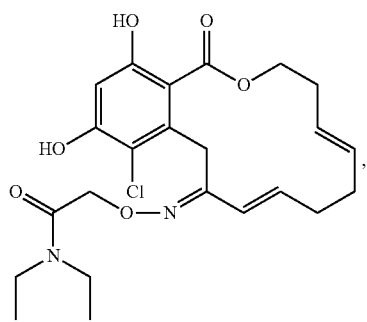
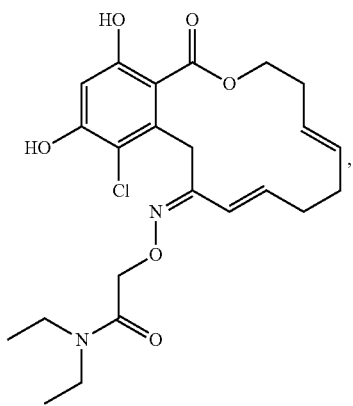
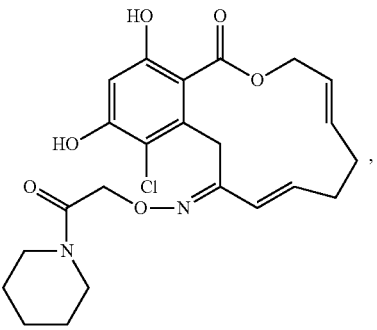

195
-continued
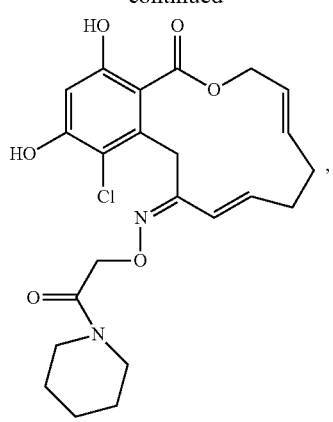
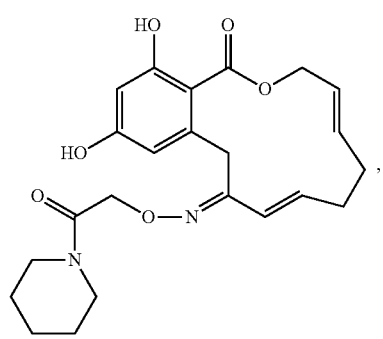
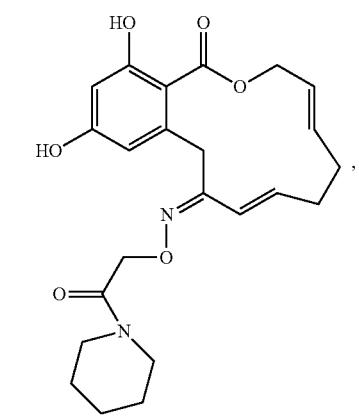
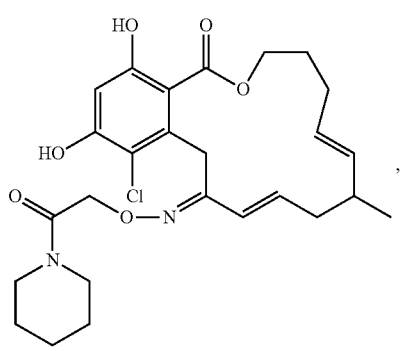
196
-continued
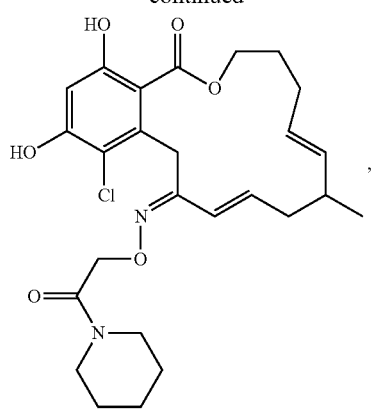
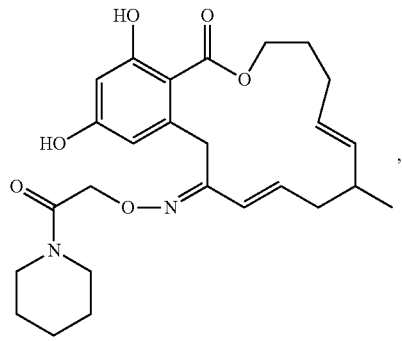
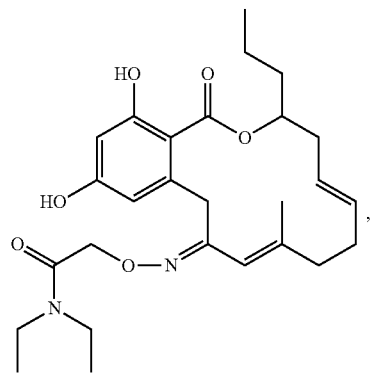

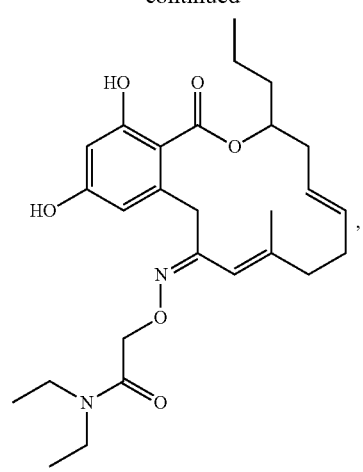
,
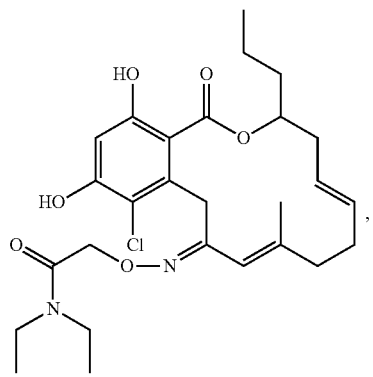
,
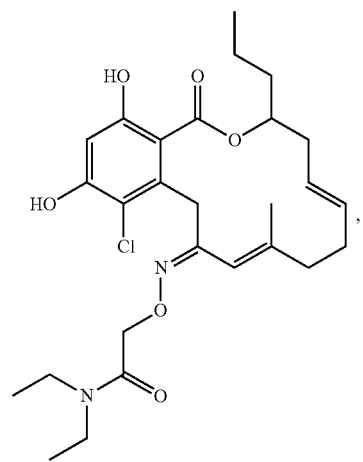
,
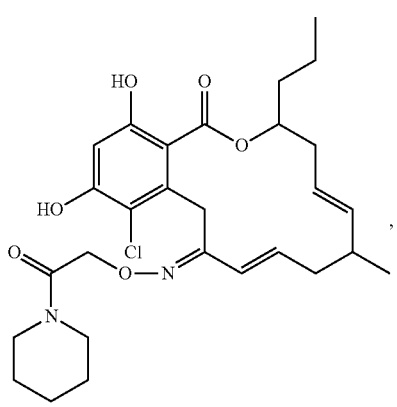
,
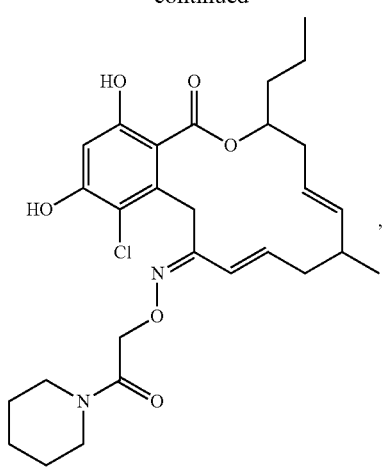
,
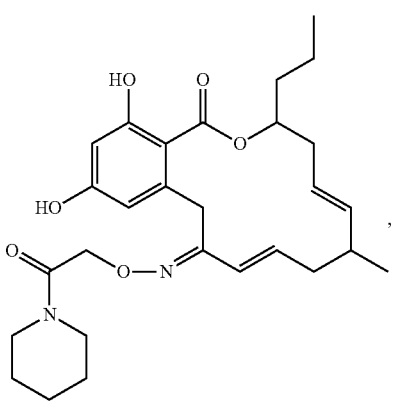
,
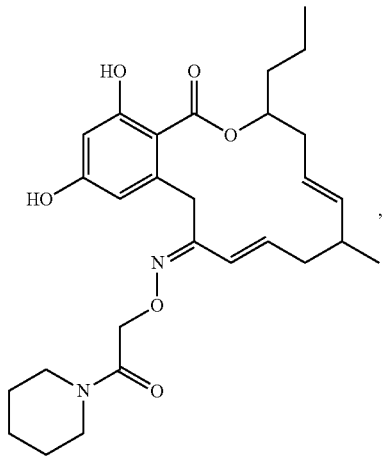
,
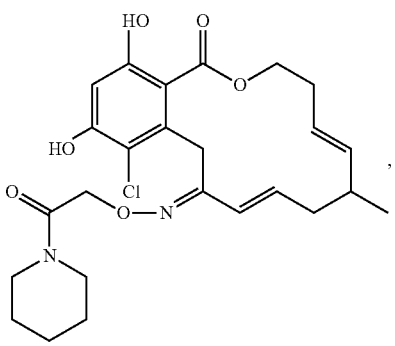
, 199
-continued
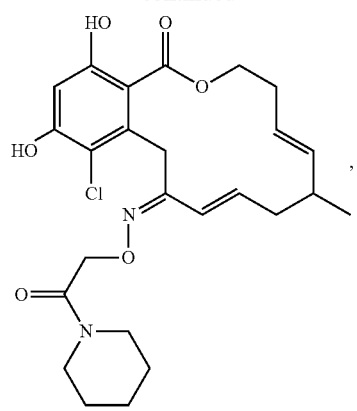,
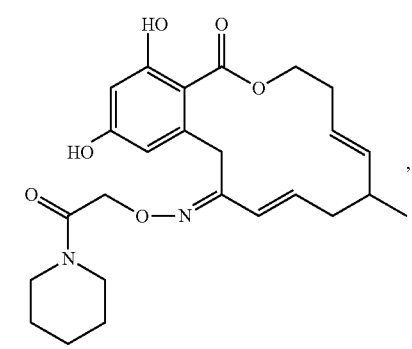,
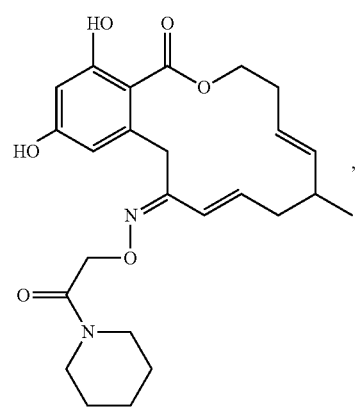,
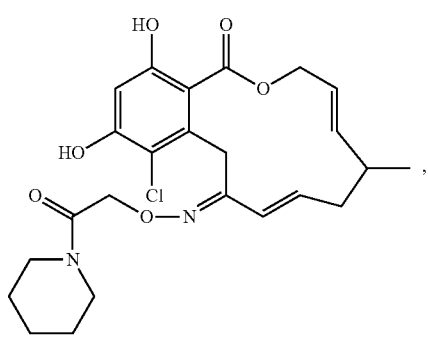,
200
-continued
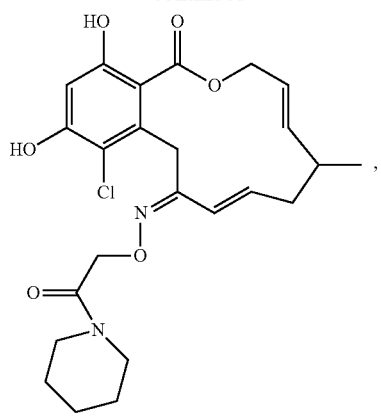,
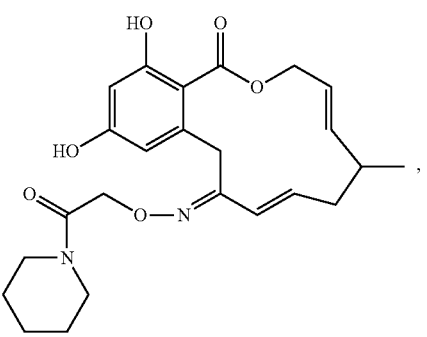,
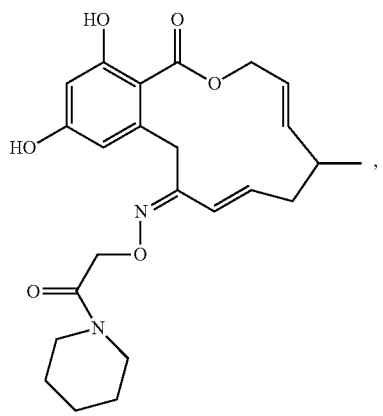,
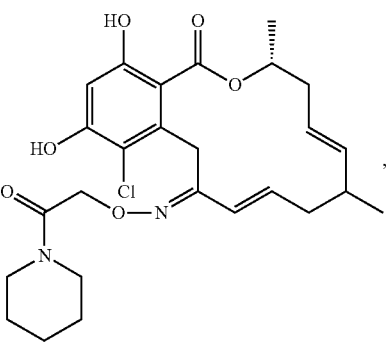, 201
-continued
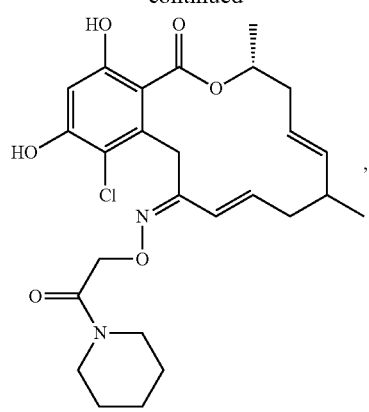
,
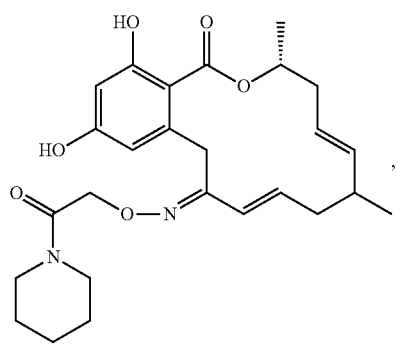
,
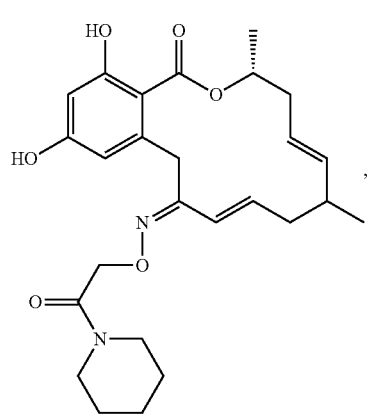
,
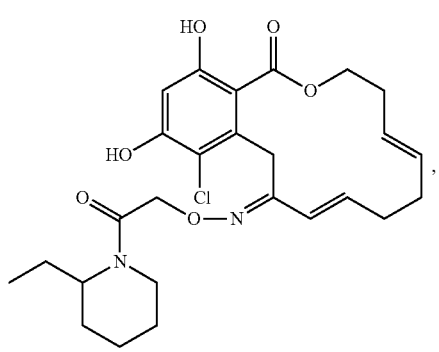
,
202
-continued
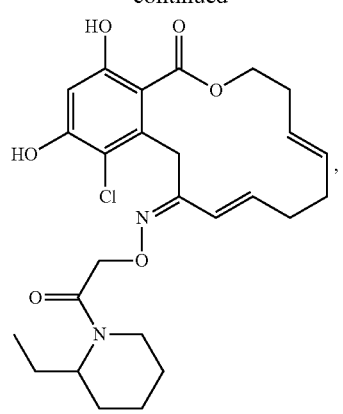
,
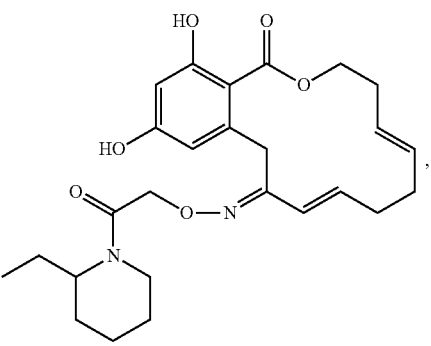
,
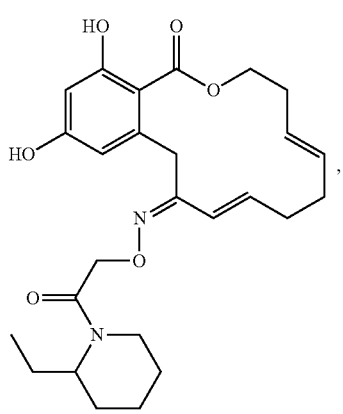
,
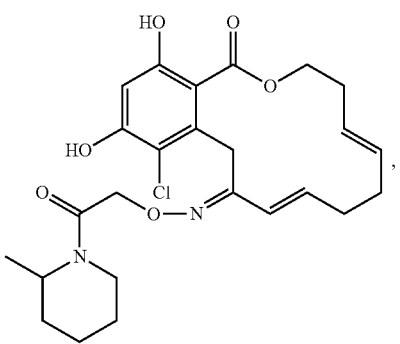
, 203
-continued
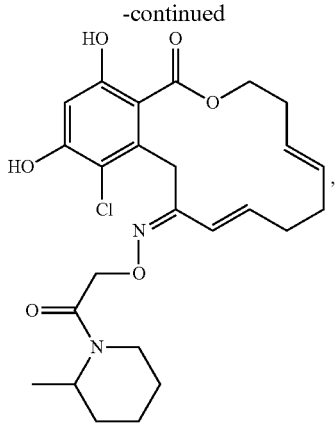
,
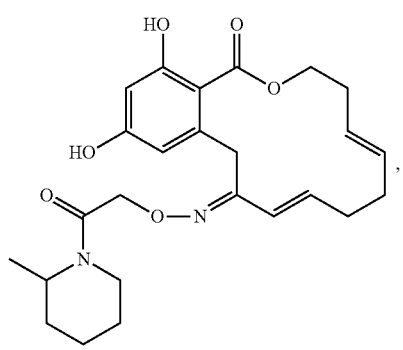
,
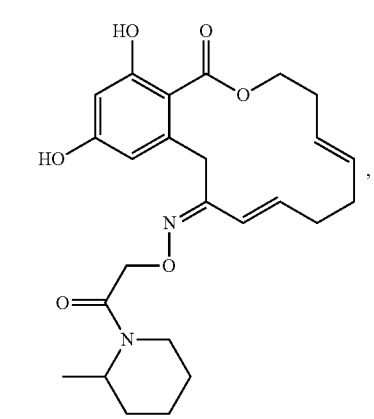
,
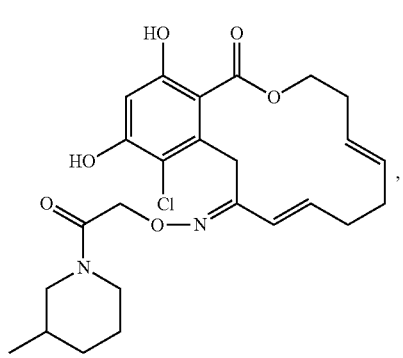
,
204
-continued
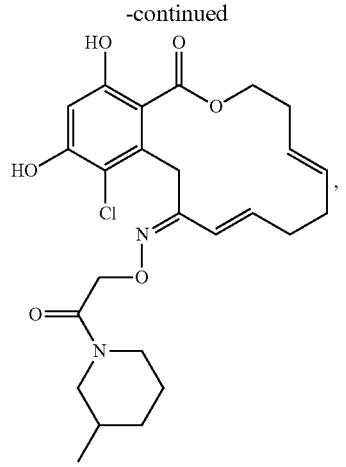
,
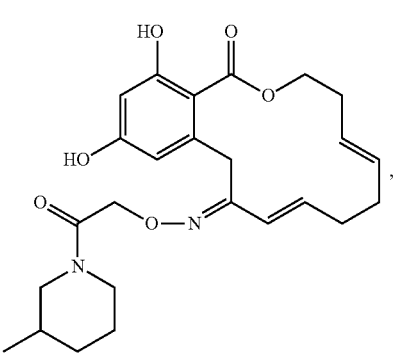
,
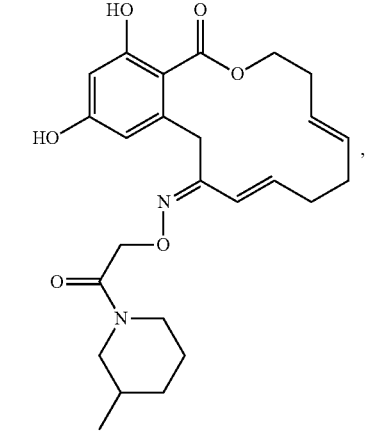
,
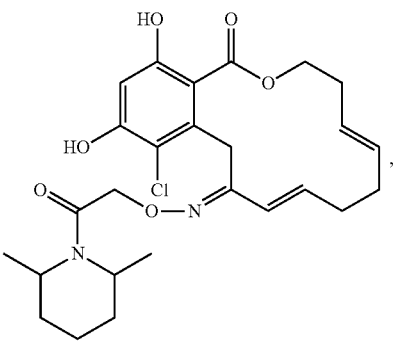
, 205
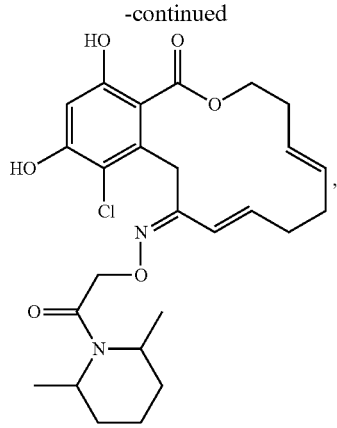
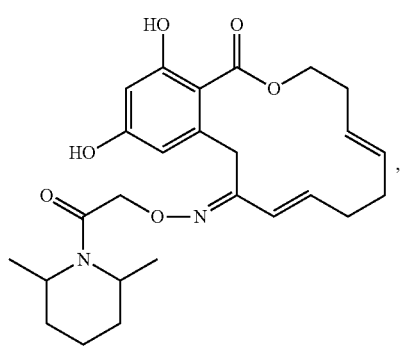
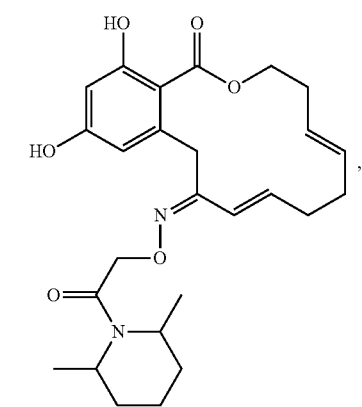
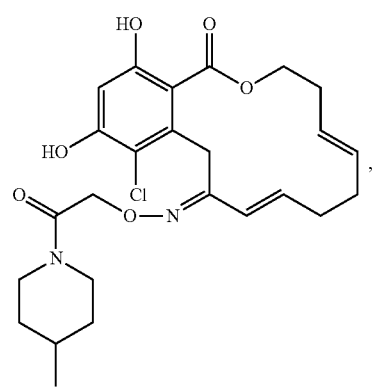
206
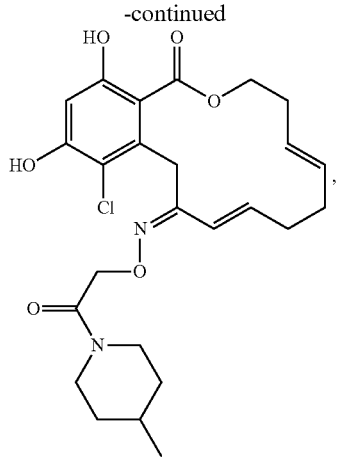
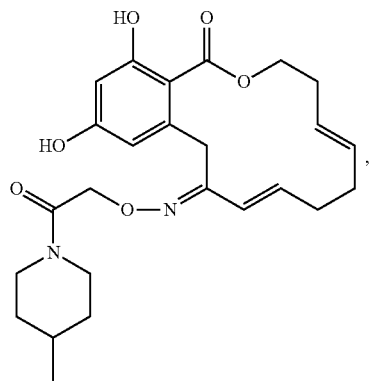
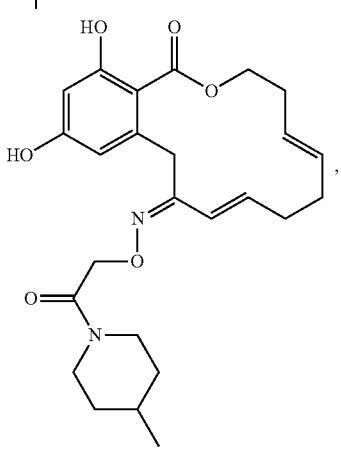
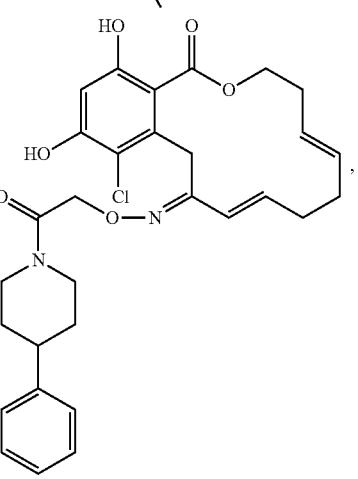

207
-continued
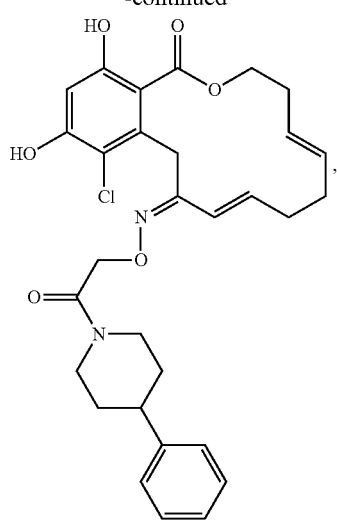
,
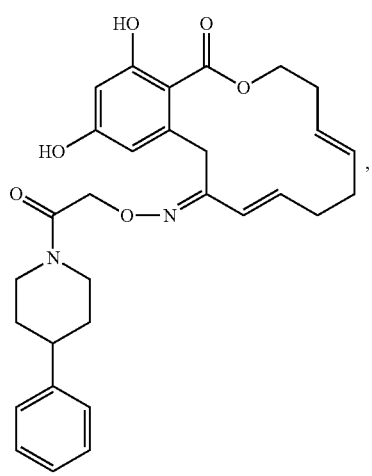
,
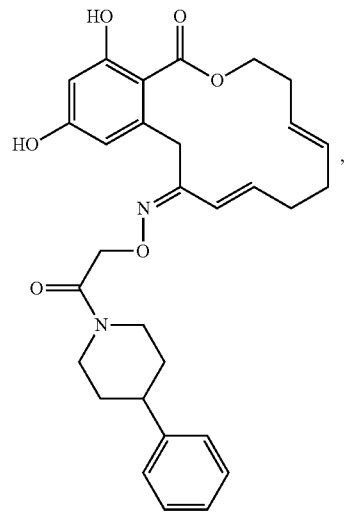
,
208
-continued
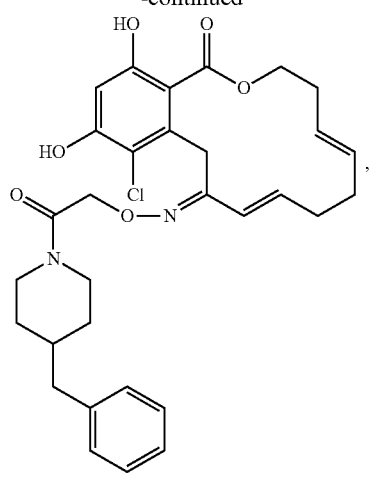
,
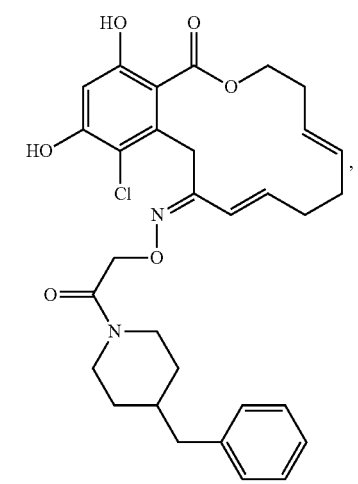
,
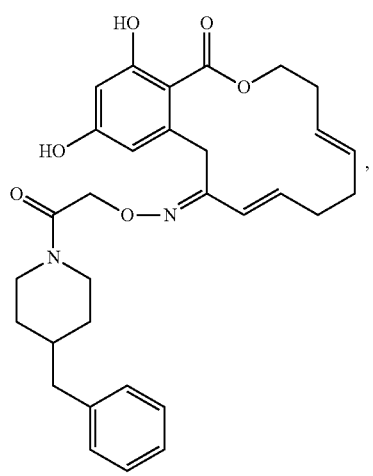
,

209
-continued
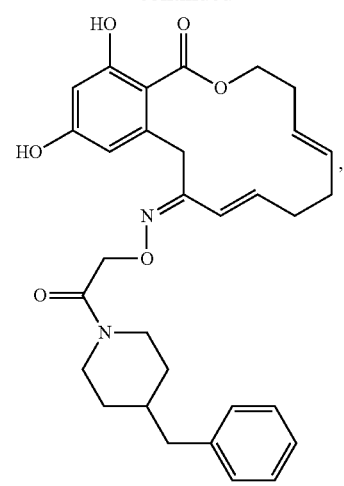
,
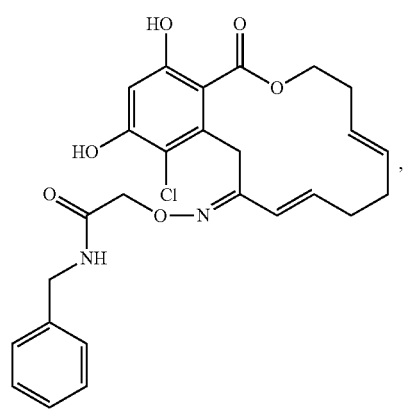
,
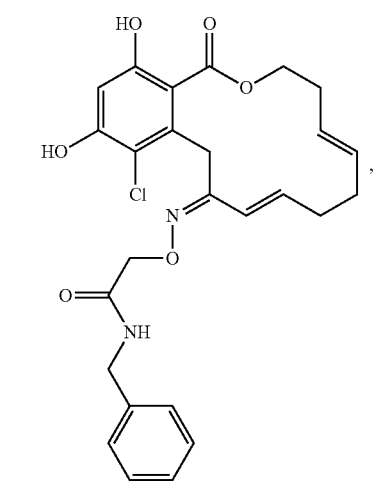
,
210
-continued
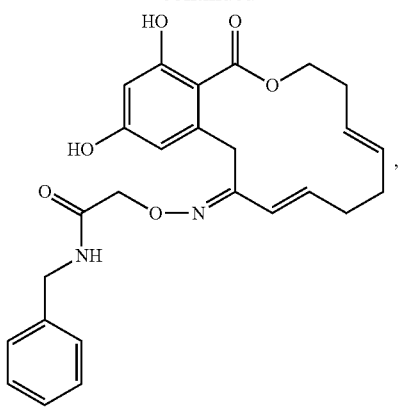
,
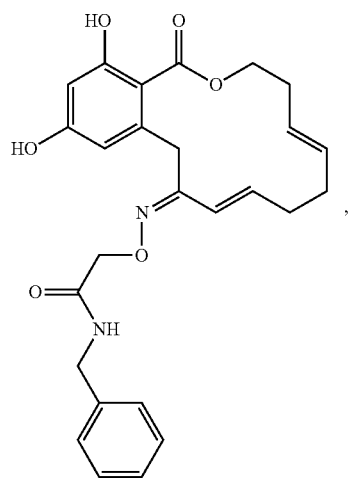
,
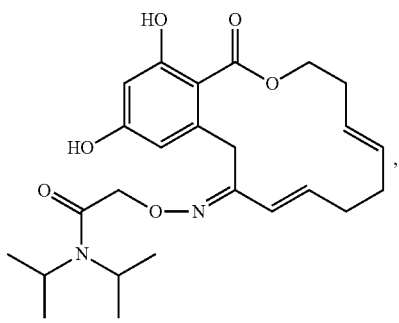
,
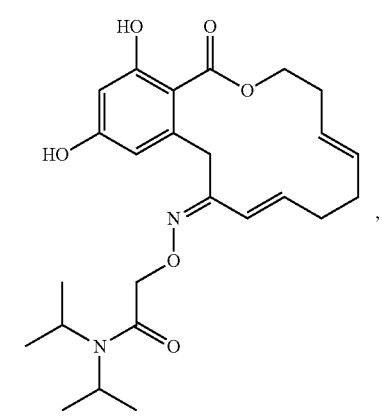
,

211
-continued
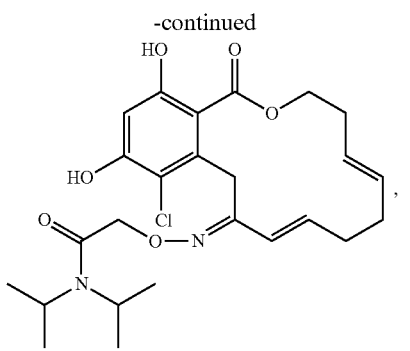
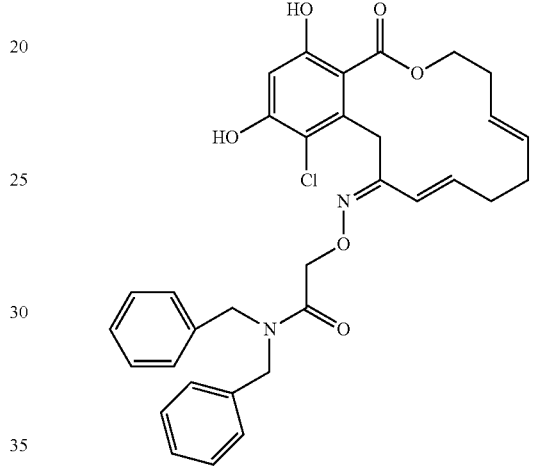
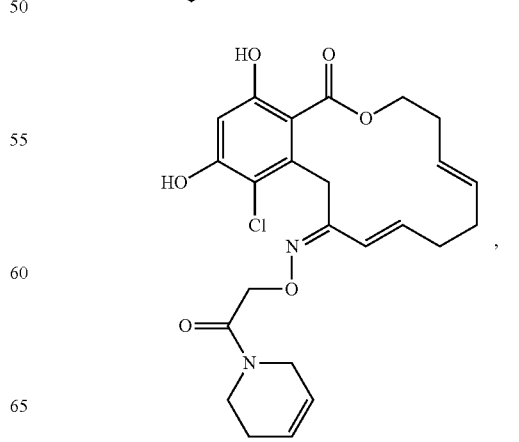
212
-continued
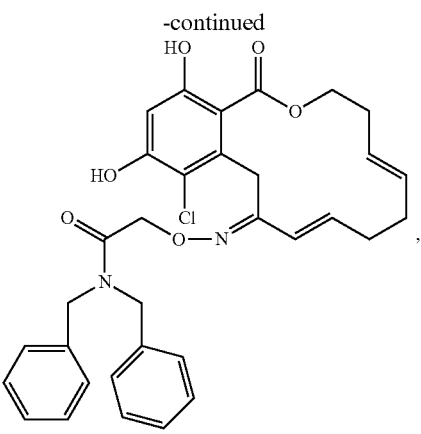
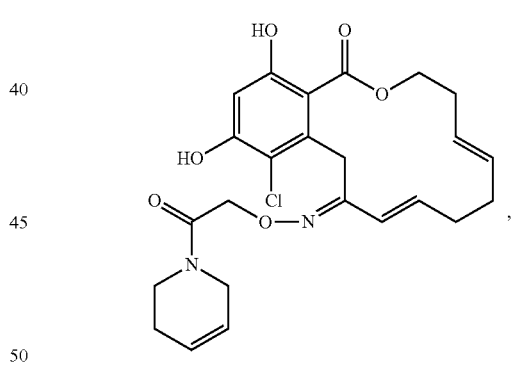

213
-continued
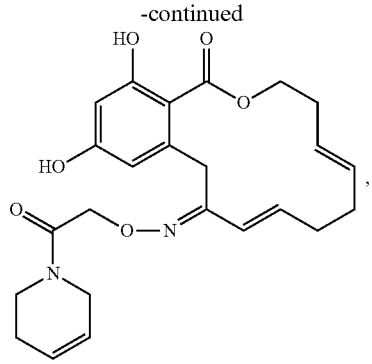
,
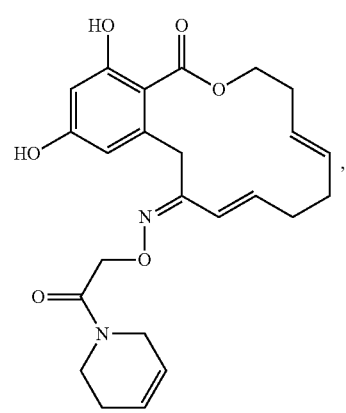
,
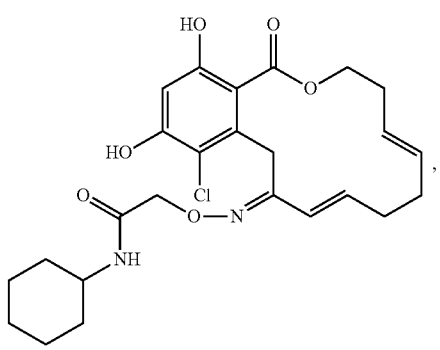
,
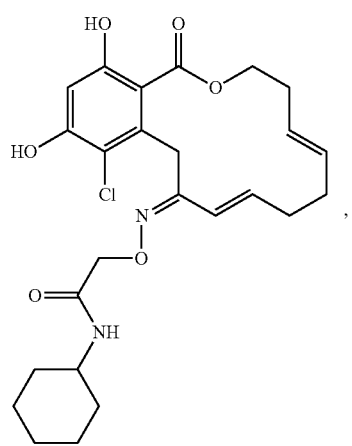
,
214
-continued
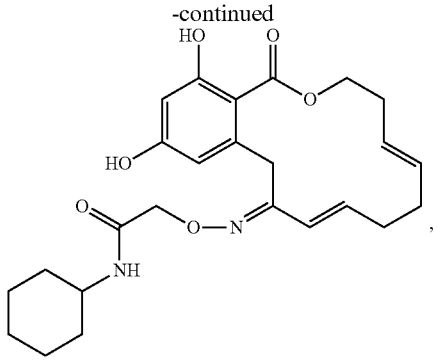
,
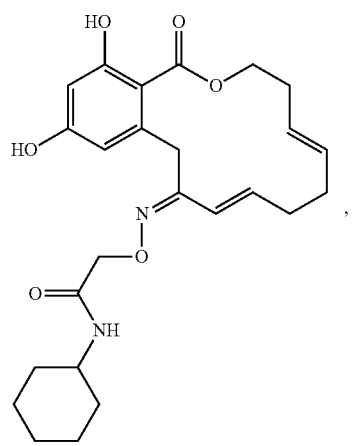
,
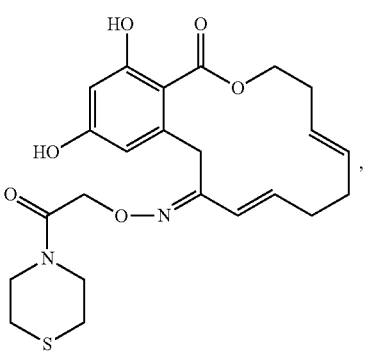
,
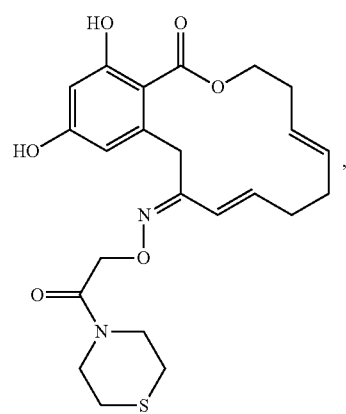
, 215
-continued
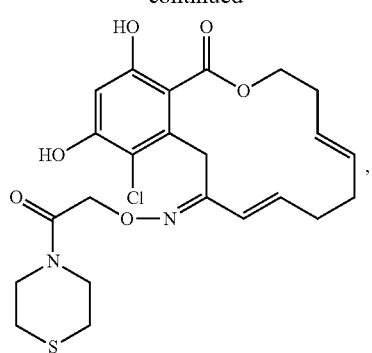,
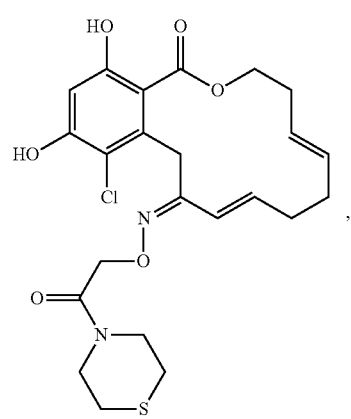,
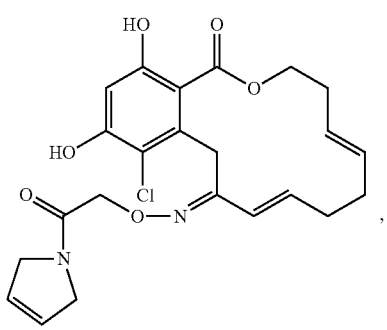,
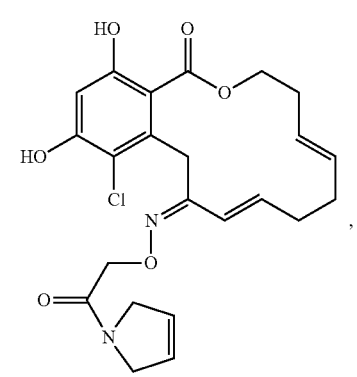,
216
-continued
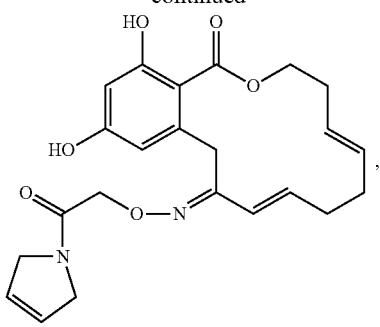,
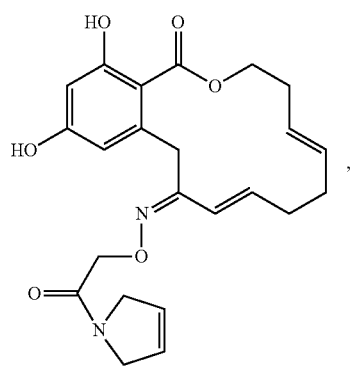,
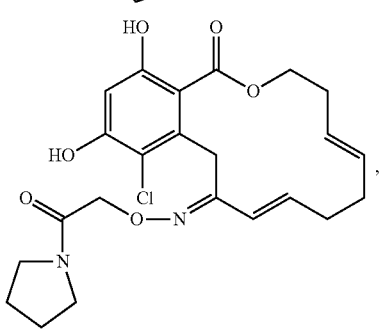,
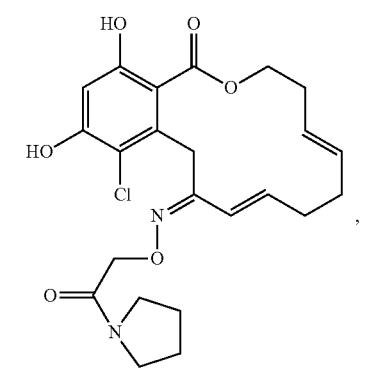,
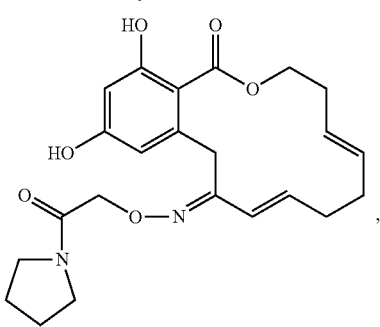, 217
-continued
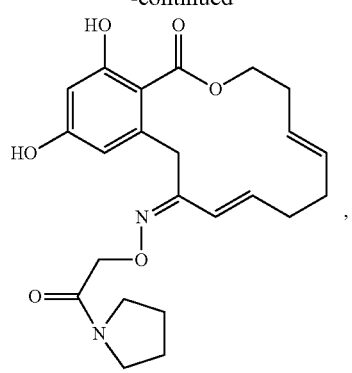
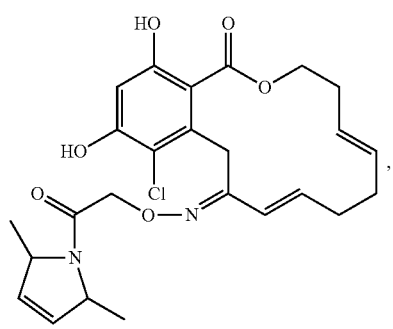
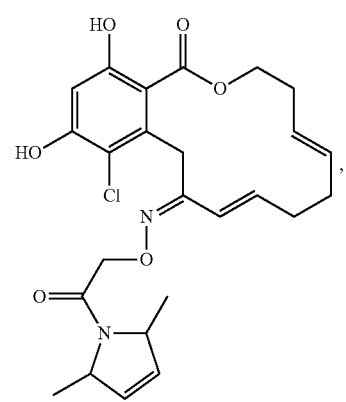
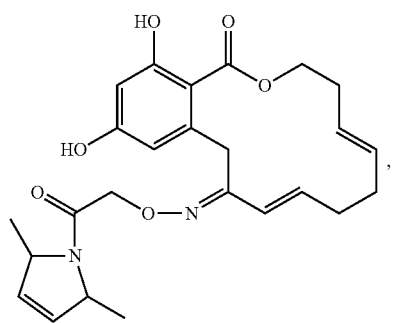
218
-continued
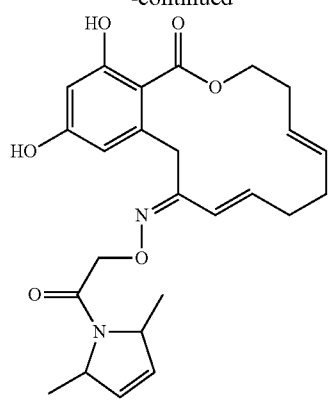
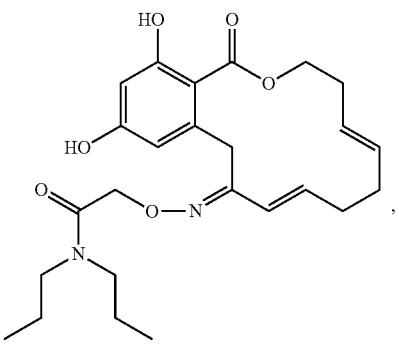
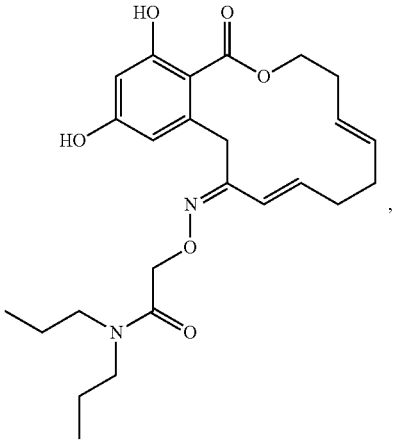 [SMILES: CCCN(CCC)C(=O)CO/N=C1\C=C\CC/C=C/CCOC(=O)c2c(O)cc(O)cc2C1]
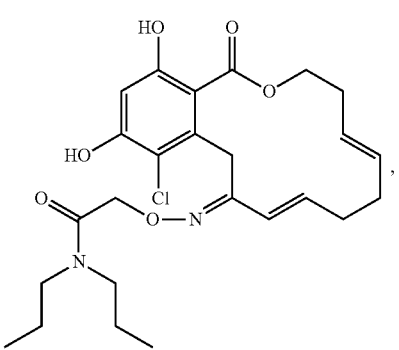

219
-continued
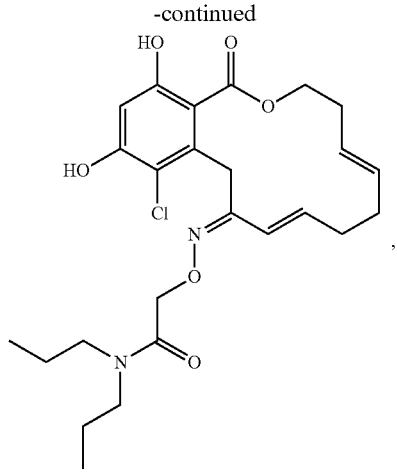
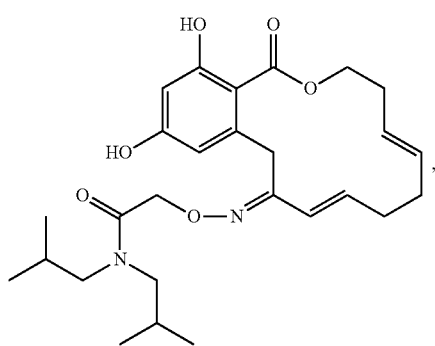
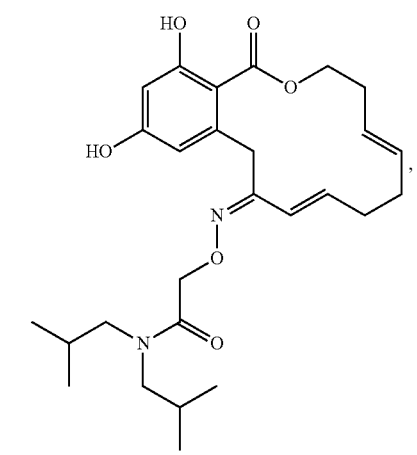
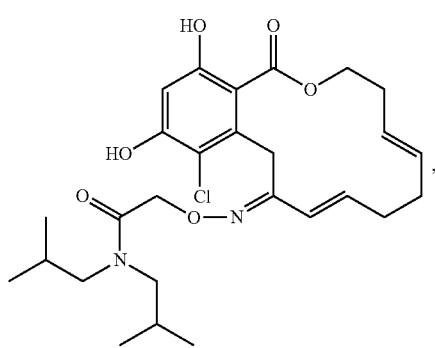
220
-continued
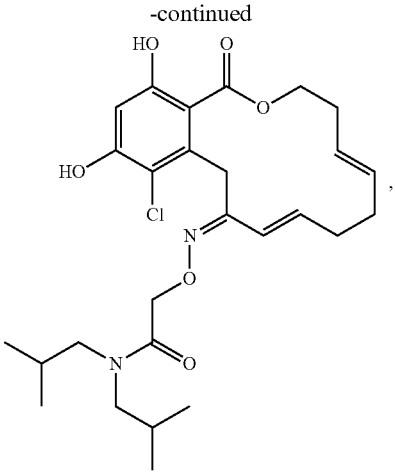
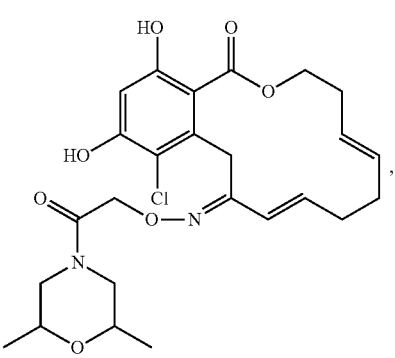
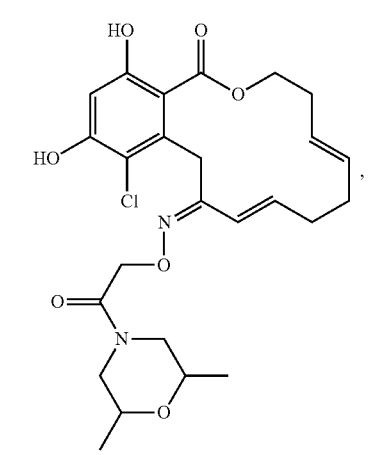
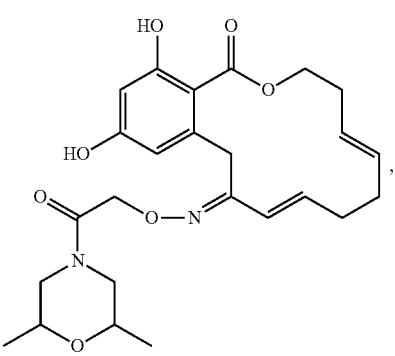

221
-continued
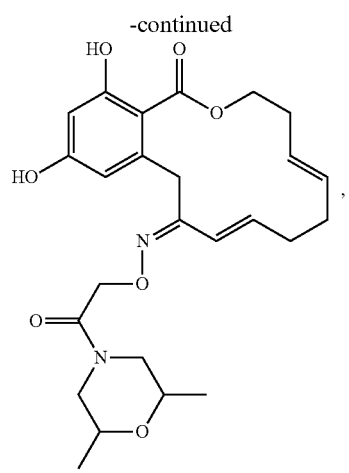
,
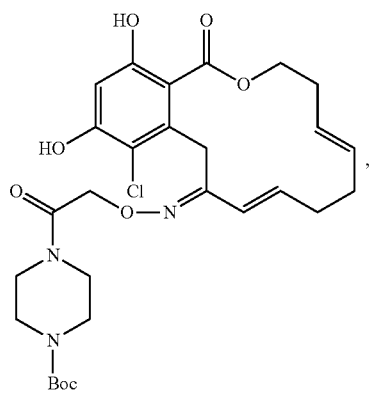
,
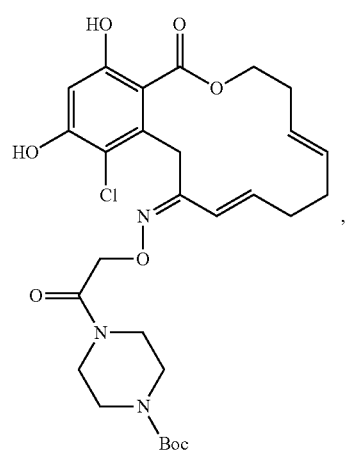
,
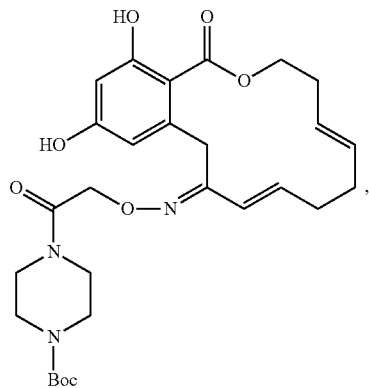
,
222
-continued
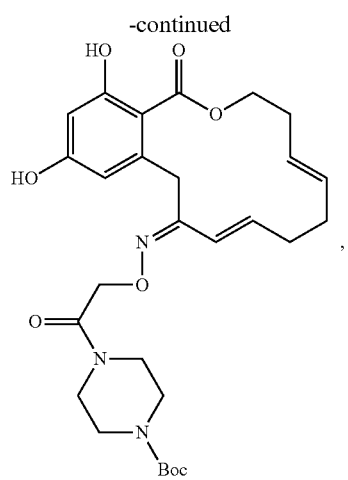
,
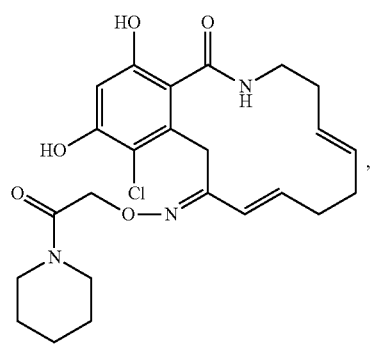
,
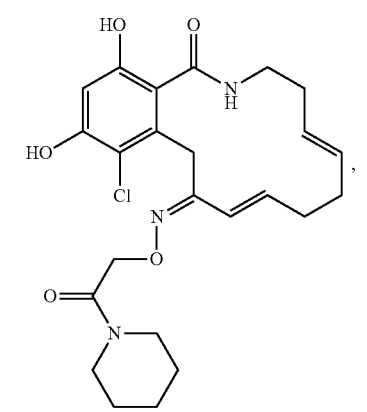
,
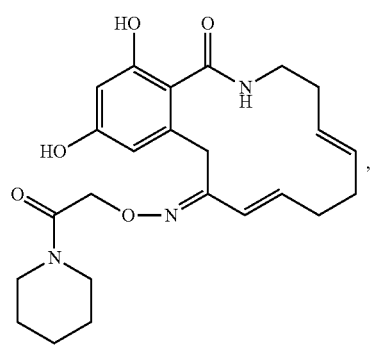
, 223
-continued
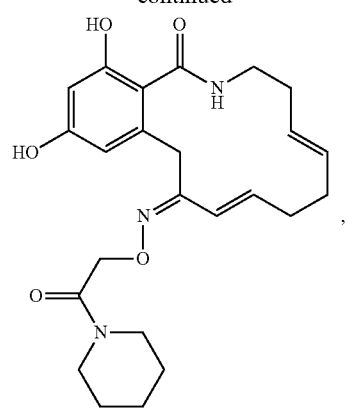,
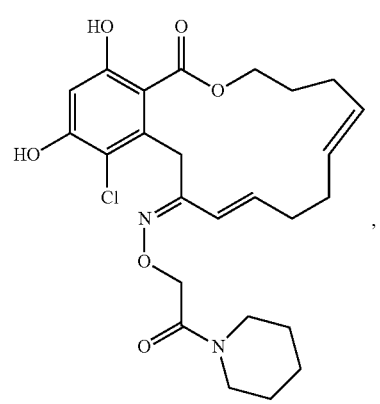,
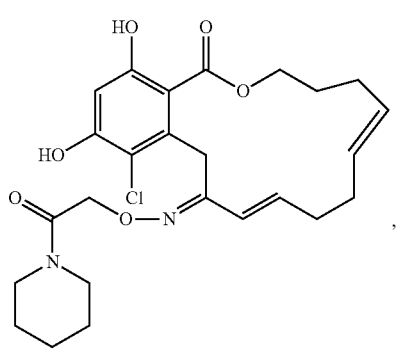,
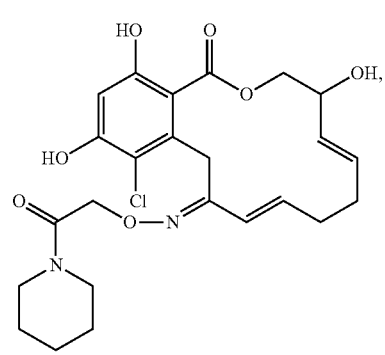,
224
-continued
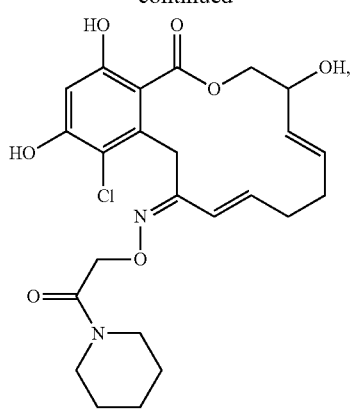,
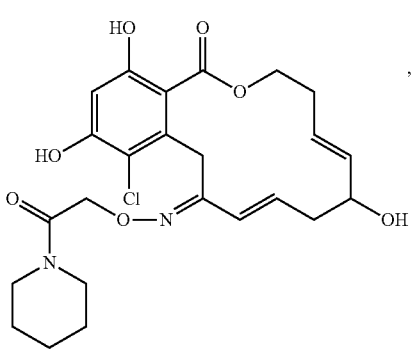,
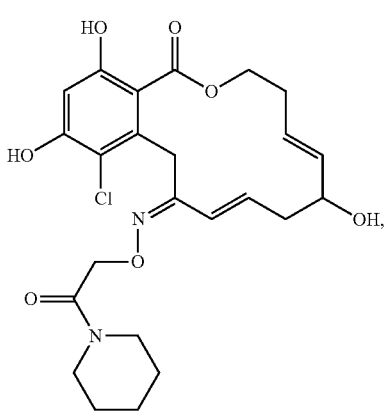,
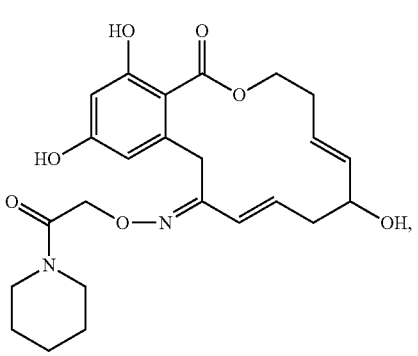, 225
-continued
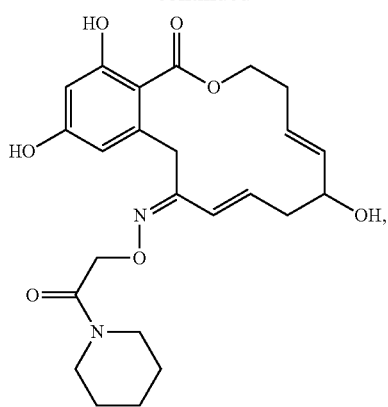
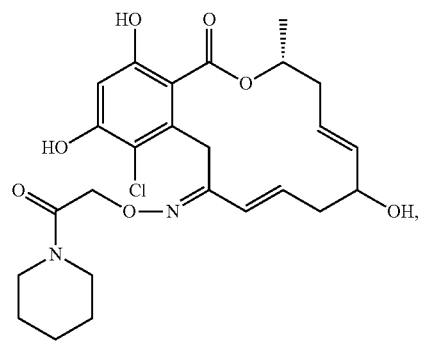
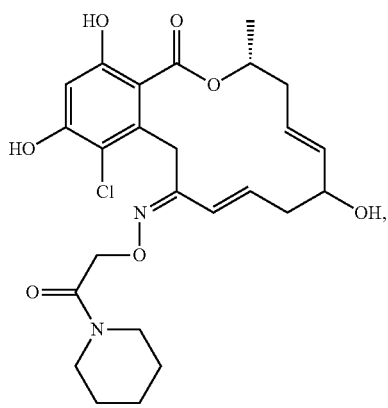
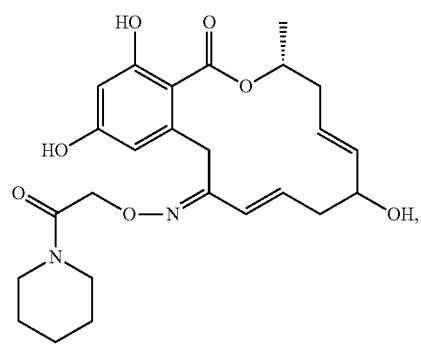
226
-continued
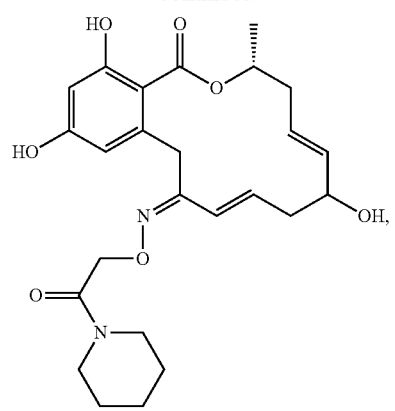
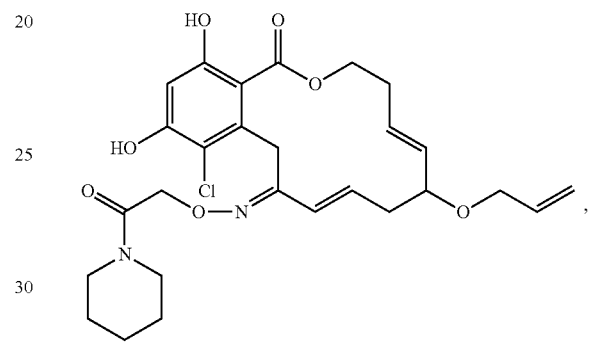
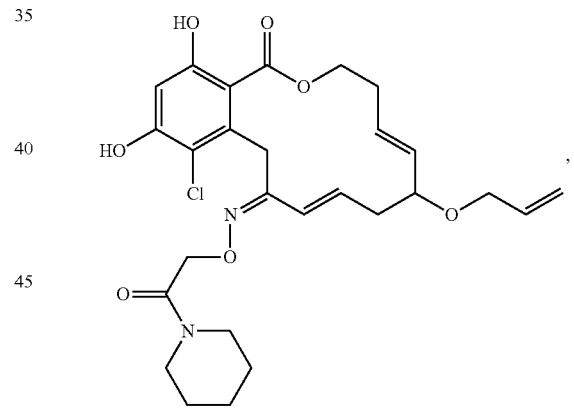
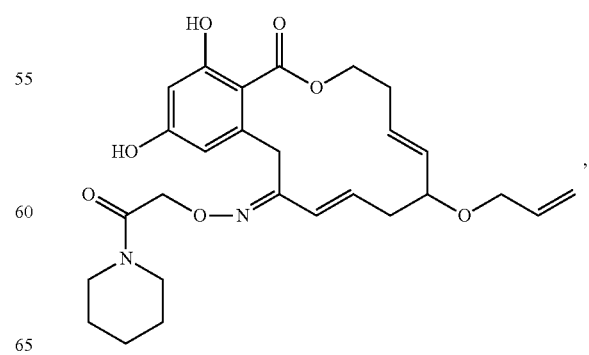

227
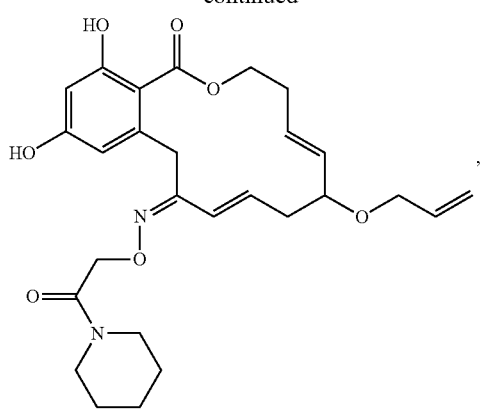
,
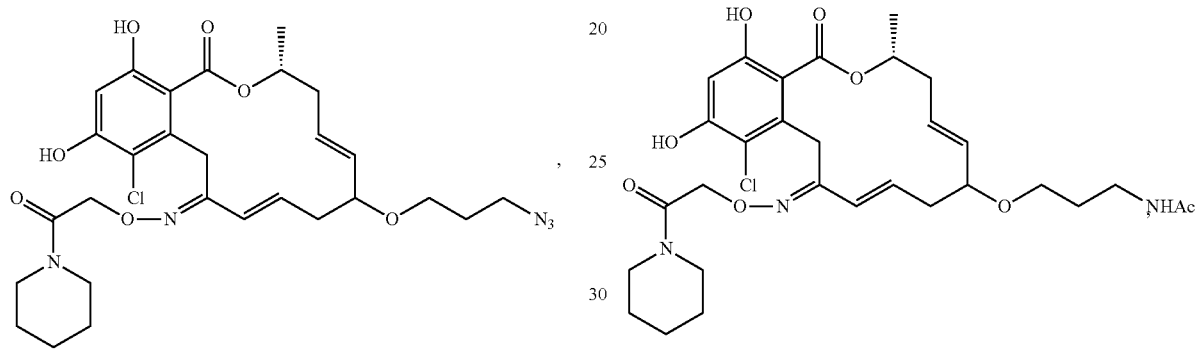
,
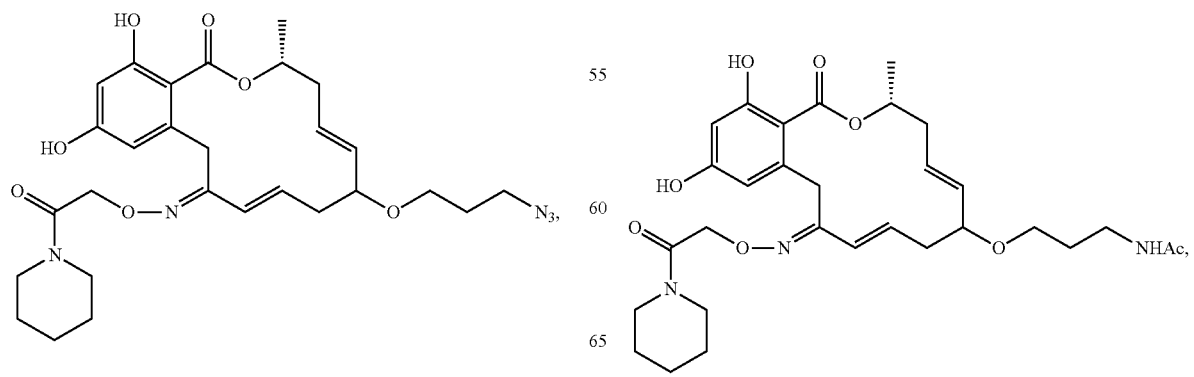
,
228
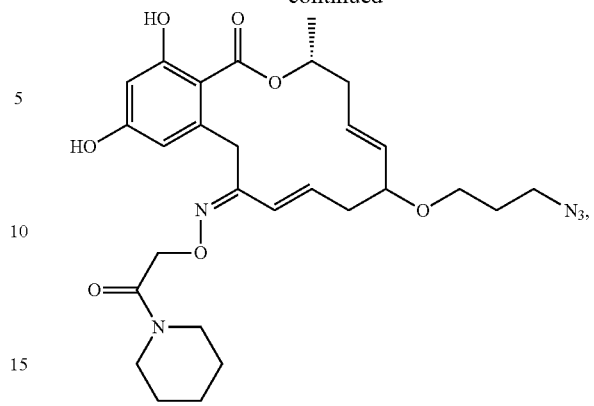
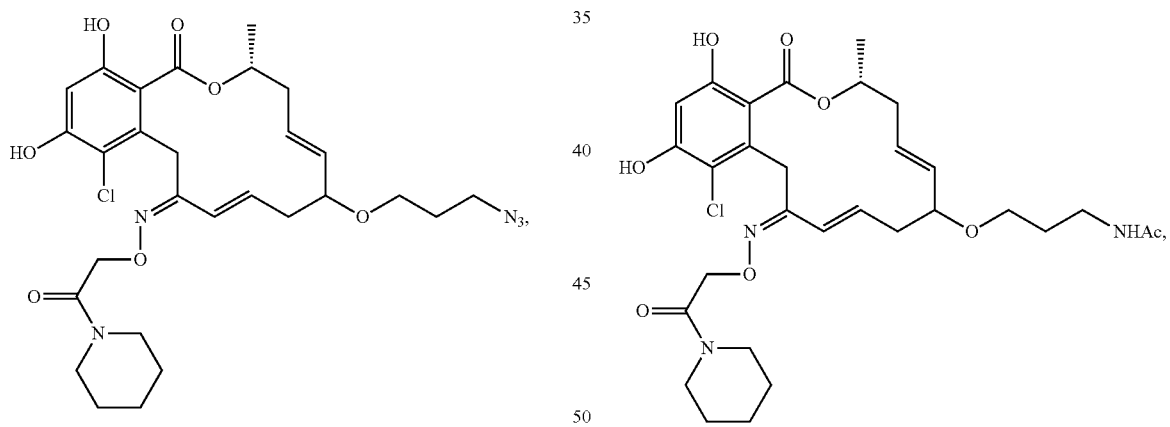

229
-continued
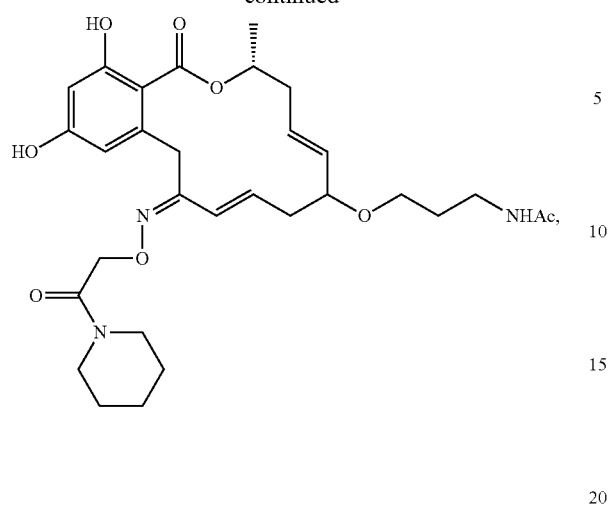
230
-continued
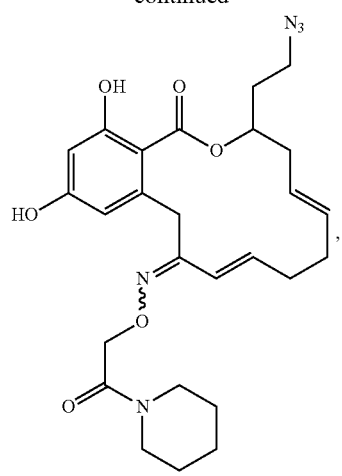
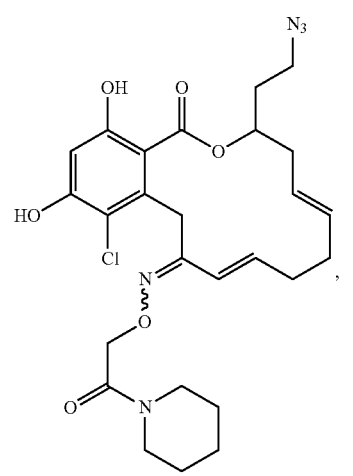
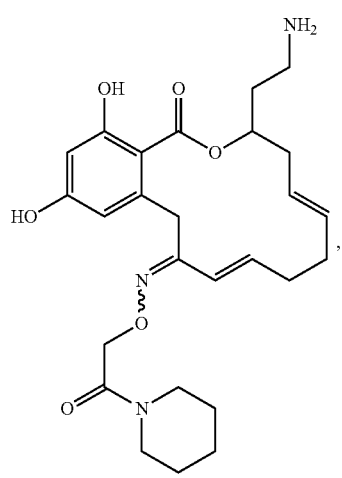 [SMILES: NCCC1C/C=C/CC/C=C/C(=NOCC(=O)N2CCCCC2)Cc2cc(O)cc(O)c2C(=O)O1]
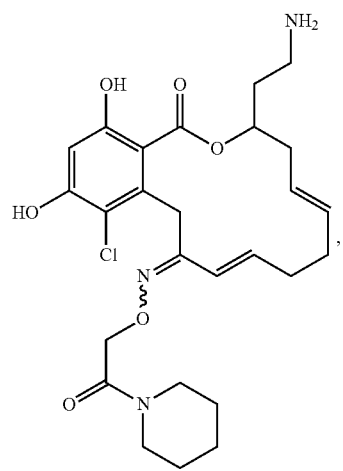
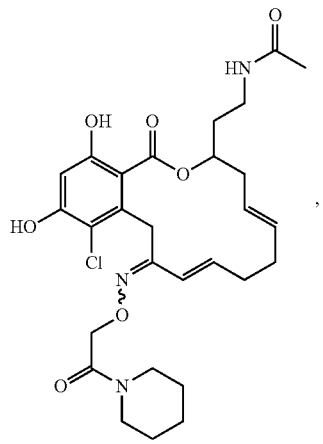

231
-continued
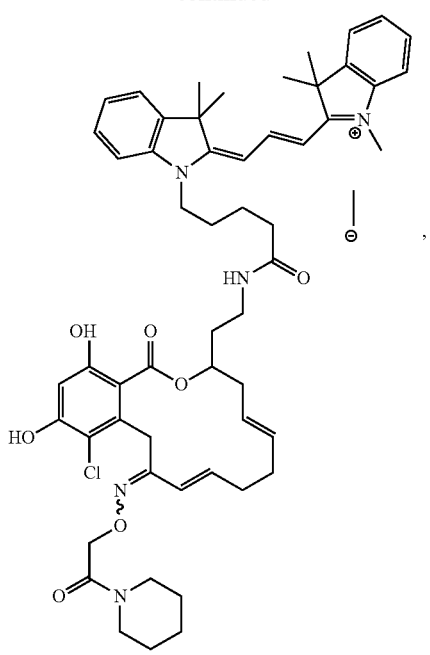
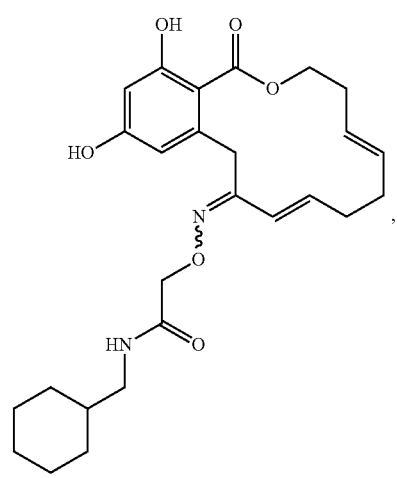
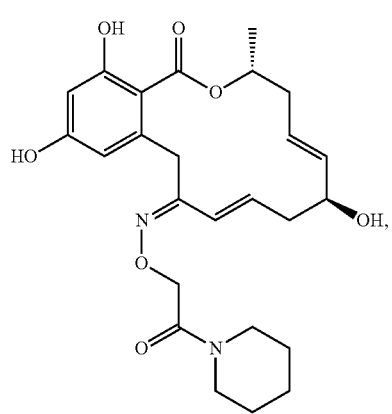
232
-continued
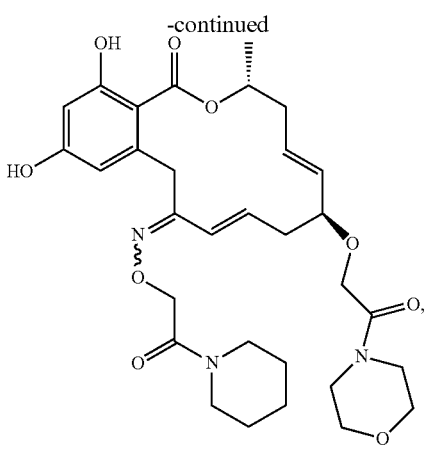
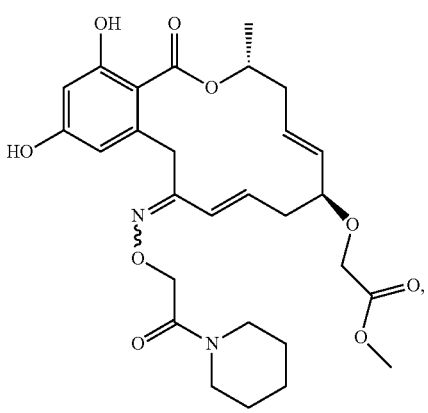
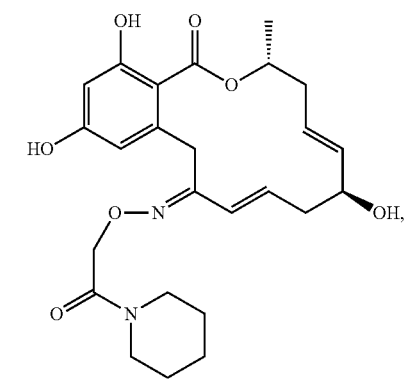
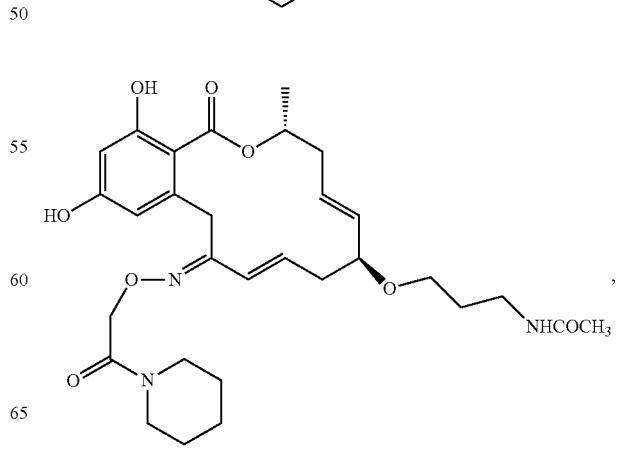

233
-continued
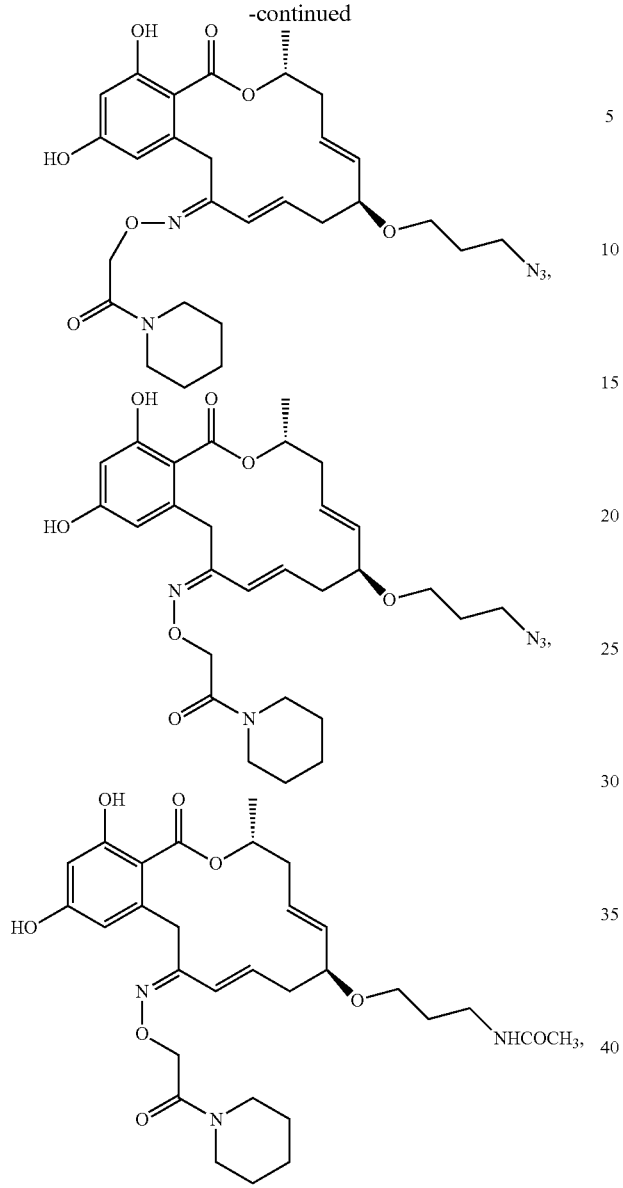
234
-continued
or
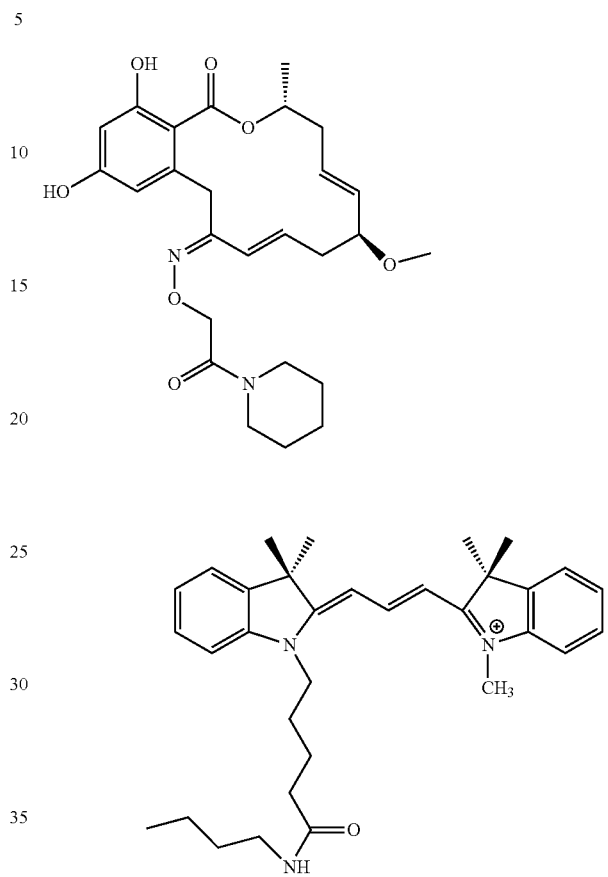
2. A pharmaceutical composition comprising an effective HSP 90-inhibiting amount of a compound of claim 1, in combination with a pharmaceutically acceptable carrier.
* * * * *